United States Patent
Black et al.

(10) Patent No.: US 10,207,853 B2
(45) Date of Patent: Feb. 19, 2019

(54) OXYGEN SCAVENGERS

(75) Inventors: D. Jeffrey Black, Akron, OH (US); Gianluca Ferrari, Portogruaro (IT); Robert Morford, Medina, OH (US); Wenxia Zhu, Akron, OH (US); Daniel Batzel, Emeryville, CA (US); Adam Safir, Emeryville, CA (US)

(73) Assignee: APG Polytech, LLC, Wilmington, DE (US)

(*) Notice: Subject to any disclaimer, the term of this patent is extended or adjusted under 35 U.S.C. 154(b) by 816 days.

(21) Appl. No.: 14/240,612

(22) PCT Filed: Jul. 18, 2012

(86) PCT No.: PCT/US2012/047259
§ 371 (c)(1),
(2), (4) Date: Feb. 24, 2014

(87) PCT Pub. No.: WO2013/028290
PCT Pub. Date: Feb. 28, 2013

(65) Prior Publication Data
US 2014/0220281 A1 Aug. 7, 2014

Related U.S. Application Data

(60) Provisional application No. 61/527,041, filed on Aug. 24, 2011, provisional application No. 61/590,321, filed on Jan. 24, 2012.

(51) Int. Cl.
*B65D 81/26* (2006.01)
*C07D 307/89* (2006.01)
(Continued)

(52) U.S. Cl.
CPC ........ *B65D 81/267* (2013.01); *C07D 307/89* (2013.01); *C08K 5/01* (2013.01);
(Continued)

(58) Field of Classification Search
CPC ............... B65D 81/267; C07D 307/89; C08K 2201/012; C08K 5/0008; C08K 5/01;
(Continued)

(56) References Cited

U.S. PATENT DOCUMENTS

2010/0051862 A1* 3/2010 Share ..................... C08K 5/01
252/188.28

FOREIGN PATENT DOCUMENTS

EP 0301719 A1 2/1989
JP 2001098300 A 4/2001
(Continued)

OTHER PUBLICATIONS

Wolfer Abate D et al., "Unsaturated Polyester Containing Myrcene-Maleic Anhydride Diels-Alder Adduct", Journal of Applied Polymer Science, Sep. 25, 1992, pp. 389-391, vol. 46, No. 3, Wiley & Sons, Inc., U.S.

*Primary Examiner* — Yan Lan
(74) *Attorney, Agent, or Firm* — Edwin A. Sisson, Attorney at Law, LLC; Jeffrey J. Banyas

(57) ABSTRACT

Described herein are oxygen scavengers, oxygen scavenging polymeric compositions, and oxygen scavenging articles. The polymeric compositions comprising the oxygen scavengers may have utility in packaging, sealing, wrapping, and storing oxygen-sensitive substances, e.g., to preserve freshness of foods, beverages, and the like.

7 Claims, 22 Drawing Sheets

(51) Int. Cl.
    *C08K 5/01*      (2006.01)
    *C08K 5/09*      (2006.01)
    *C08K 5/098*     (2006.01)
    *C08K 5/10*      (2006.01)
    *C08K 5/1539*    (2006.01)
    *C08K 5/00*      (2006.01)

(52) U.S. Cl.
    CPC ............... *C08K 5/09* (2013.01); *C08K 5/098* (2013.01); *C08K 5/10* (2013.01); *C08K 5/1539* (2013.01); *C08K 5/0008* (2013.01); *C08K 2201/012* (2013.01); *Y10T 428/13* (2015.01); *Y10T 428/1397* (2015.01)

(58) Field of Classification Search
    CPC . C08K 5/09; C08K 5/098; C08K 5/10; C08K 5/1539; Y10T 428/13; Y10T 428/1397
    See application file for complete search history.

(56) References Cited

FOREIGN PATENT DOCUMENTS

| | | |
|---|---|---|
| JP | 2008013755 A | 1/2008 |
| JP | 2010222711 A | 10/2010 |
| WO | 2008/124682 A2 | 10/2008 |

\* cited by examiner

Ex. 54: 11-40-06-39 SSP[10635+100 ppm Co/CoNeo] + 1.9% Cpd X41 (molar eq. to 1.5% Cpd D)
Ex. 55: 11-40-06-42 SSP[10635+100 ppm Co/CoNeo] + 1.75% wt Cpd 2(X41)/1(D)
Ex. 56: 11-40-06-40 SSP[10635+100 ppm Co/CoNeo] + 1.5% Cpd D (89% D assay, lot 592-82-F)
Ex. 57: 11-40-06-26 SSP[10635+100 ppm Co/CoNeo] + 1.5% wt Cpd F
Ex. 58: 11-40-06-27 SSP[10635+100 ppm Co/CoNeo] + 2.0% wt Cpd F
Control: 11-40-08-03

Table E.8

| StartMRS ID - Polymer | StartMRS ID - Bottle | Glycol Monomer 1 | Glycol Monomer 2 | "Acid" Monomer 1 | "Acid" Monomer 2 | Monomer Mole(s) | Catalyst | Stabilizer | Mole Ratio |
|---|---|---|---|---|---|---|---|---|---|
| 110040-02-05-MELTG2-001 | 110040-10-09-SMDEL-001 | EG | PEG (PA, ~600) | A | | 2.2 mole% PEG/95.8 mole% EG | TnBT-unstab | TEP | 2.2 |
| 110040-02-06-MELTG2-001 | 110040-10-10-SMDEL-001 | EG | | A | USIPA-DMBE | 2 mole% USIPA/98 mole% A | AC-869 | TEP | 2.2 |
| 110040-02-07-MELTG2-001 | 110040-10-11-SMDEL-001 | EG | | A | USIPA-DMBE | 5 mole% USIPA/95 mole% A | AC-869 | TEP | 2.2 |
| 110040-02-08-MELTG2-001 | 110040-10-12-SMDEL-001 | EG | PEG (PA, ~600) | A | | 5% mole% PEG/95% mol EG | AC-869 | TEP | 2.2 |
| 110040-02-12-MELTG2-001 | 110040-10-17-SMDEL-001 | EG | | A | | | TnBT-Stab | None | 2.2 |
| 110040-02-13-MELTG2-001 | 110040-10-18-SMDEL-001 | EG | | A | | | TnBT-Stab | None | 2.2 |
| 110040-02-16-MELTG2-001 | 110040-10-19-SMDEL-001 | EG | | A | | | AC-869 | TEP | 2.2 |
| 110040-02-17-MELTG2-001 | 110040-10-20-SMDEL-001 | EG | | A | USIPA-DMBE | 2 mole% USIPA/98 mole% A | AC-869 | TEP | 2.2 |
| 110040-02-18-MELTG2-001 | 110040-10-21-SMDEL-001 | EG | | A | USIPA-DMBE | 2 mole% USIPA/98 mole% A | AC-869 | TEP | 2.2 |
| 110040-02-19-MELTG2-001 | 110040-10-22-SMDEL-001 | EG | PEG (PA, ~600) | A | | 4.2 mole% PEG/95.8 mole% EG | AC-869 | TEP | 2.2 |
| 110040-02-20-MELTG2-001 | 110040-10-23-SMDEL-001 | EG | PEG (PA, ~600) | A | | 4.2 mole% PEG/95.8 mol% EG | AC-869 | TEP | 2.2 |
| 110040-02-21-MELTG2-001 | 110040-10-24-SMDEL-001 | EG | | C | | | AC-869 | TEP | 7.5 |
| 110040-02-23-MELTG2-001 | 110040-10-25-SMDEL-001 | EG | | C | CDET | 80mole% C/20 mol % CDET | AC-869 | TEP | 3 |

FIGURE 15A

Table E.8 cont'd

| StartiMS ID - Polymer | StartiMS ID - Bottle | Quantity (g) | Appearance | COOH | OH | GPC Mn |
|---|---|---|---|---|---|---|
| 110040-02-05-MELTGL-001 | 110040-10-09-SIDE1-001 | 46 | Transparent amber molasses | 10 | 111.5 | 9269 |
| 110040-02-06-MELTGL-001 | 110040-10-10-SIDE2-001 | 20 | Translucent yellow semisolid | 80 | 80 | 5464 |
| 110040-02-07-MELTGL-001 | 110040-10-11-SIDE1-001 | 20 | Translucent light amber semisolid | 67 | 80 | 1242 |
| 110040-02-10-MELTGL-001 | 110040-10-12-SIDE1-001 | 80 | Transparent amber honey | 352 | 102 | 1253 |
| 110040-02-12-MELTGL-001 | 110040-10-17-SIDE1-001 | 100 | Translucent light amber honey | 173 | 116.5 | 2604 |
| 110040-02-13-MELTGL-001 | | 100 | Translucent light amber honey | 49 | 134.3 | 2989 |
| 110040-02-15-MELTGL-001 | 110040-10-18-SIDE1-001 | 100 | Translucent light amber honey | 34 | 123 | 3672 |
| 110040-02-16-MELTGL-001 | | 100 | Translucent light amber honey | 23 | 86.9 | 1579 |
| 110040-02-17-MELTGL-001 | 110040-10-19-SIDE1-001 | 100 | Translucent light amber honey | 34 | 123 | 287 |
| 110040-02-18-MELTGL-001 | | 100 | Translucent light amber honey | 43 | 80 | 344 |
| 110040-02-19-MELTGL-001 | 110040-10-23-SIDE1-001 | 100 | Translucent light amber honey | 19 | 60 | 4760 |
| 110040-02-20-MELTGL-001 | | 100 | Transparent yellow honey | 72 | 127.3 | 2604 |
| 110040-02-21-MELTGL-001 | 110040-10-24-SIDE1-001 | 100 | Translucent yellow honey | 7 | 86.3 | 3425 |
| 110040-02-22-MELTGL-001 | | 100 | Translucent yellow honey | 6 | 84.5 | 5537 |
| 110040-02-23-MELTGL-001 | 110040-10-25-SIDE1-001 | 100 | Translucent yellow honey | 12 | 104 | 6394 |

OXYGEN SCAVENGERS

CROSS REFERENCE

The present application claims the benefit of priority of International application no. PCT/US2012/047259, filed Jul. 18, 2012, International application no. PCT/US2012/047257 filed Jul. 18, 2012, U.S. provisional application No. 61/527,041, filed Aug. 24, 2011 and U.S. provisional application No. 61/590,321, filed Jan. 24, 2012, the contents of each of which are hereby incorporated by reference in their entirety.

FIELD

Described herein are oxygen scavengers. The oxygen scavengers may be used as polymer compositions. The polymeric compositions comprising the oxygen scavengers may have utility in packaging, sealing, wrapping, and storing oxygen-sensitive substances, e.g., to preserve freshness of foods, beverages, and the like.

BACKGROUND

Thermoplastic resins such as polyethylene terephthalate (PET) are commonly used to make a variety of different types of packaging materials and storage containers. PET produces high strength packaging articles and has found widespread use in applications for bottling substances such as soft drinks and water. However, because PET polymers are porous to gases such as oxygen, this has limited their use in bottling beer, fruit, and other substances susceptible to degradation by oxygen. As a result, glass and metal containers continue to dominate the market for bottling of beer and juice.

To address this limitation and improve shelf life for oxygen sensitive products (e.g., certain foods, beverages and medicines), a number of strategies have been used. One of these is the use of a physical barrier. PET containers may contain multi-layer walls or one or more oxygen scavengers to prevent oxygen from reaching the contents of the container. In some instances, a passive oxygen barrier layer has been used in a polymer container to block oxygen transmission through the container wall. For example, in a multi-layer bottle, a barrier layer made from a substance that functions as a gas barrier such as ethylene vinyl alcohol (EVA), polyvinylidene dichloride (PVDC), or Nylon MXD6 may combined with one or more layers of PET. In addition to the added complexity, multi-layer constructions may lead to delamination, or increased cost, and do not fully address the problem as these may allow oxygen already present in the container material to reach contents of the container.

Another strategy is the use of an active oxygen scavenger to reduce or deplete oxygen in the environment of the oxygen-sensitive substance (whether through the environment or from the polymeric container itself). In some cases, an oxygen scavenger may be placed within a packet which is placed within the container so as to take up oxygen. However, these packets are generally limited to solid substances and solid foods as care must be taken so that the packet is not mistakenly used or ingested. In some instances, an active oxygen scavenger is incorporated into a polymer resin that forms one or more walls of a container. Examples include inorganic materials such as reduced metal powders or certain polymers. Reduced iron powder is commonly used for oxygen scavenging in food packages, where the iron reacts with oxygen and forms iron oxide. Polyamides or polyolefins may be incorporated into the backbone of a polymer forming container walls or used to make an oxygen absorbing layer in a multi-layer package wall.

A need exists for improved active oxygen scavenging additives for polymers, and active oxygen scavenging polymers. A need exists for improved organic oxygen scavengers that maintain the desired aesthetic qualities (e.g., those that can be used in clear containers without producing undesired haze or coloring). Finally, a need exists for active oxygen scavenging polymer additives and polymers that can be derived from renewable carbon sources.

SUMMARY

Described herein are oxygen scavenging molecules, oxygen scavenging polymers, oxygen scavenging compositions, and methods for making the same, and articles comprising or formed from the oxygen scavenging compositions. The oxygen scavengers are derived from isoprenoids, which in certain advantageous variations may be made by genetically modified organisms from readily renewable carbon sources such as sugars or biomass.

In some embodiments, described herein are oxygen scavenging molecules having formula (I):

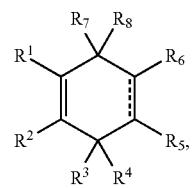

(I)

wherein the oxygen scavenging molecule is capable of removing oxygen from an environment when catalyzed by an oxidation catalyst. $R^1$, $R^2$, $R^3$, $R^4$, $R^5$, $R^6$, $R^7$ and $R^8$ are independently H, or a saturated or unsaturated, linear or branched, cyclic or acyclic, aliphatic or aryl, unsubstituted or substituted hydrocarbyl group, with the provisos that: i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tail having formula

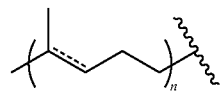

with n=1, 2, 3, 4, or 5, and/or having formula

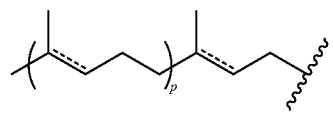

with p=0, 1, 2, 3, or 4. In some variations, $R^5$ and $R^6$ may together form a cyclic group that optionally includes one or more heteroatoms. In some variations, at least two of $R^3$, $R^4$, $R^7$ and $R^8$ are hydrogen. In some variations, at least three of $R^3$, $R^4$, $R^7$ and $R^8$ are hydrogen. In some variations, $R^3$, $R^4$, $R^7$ and $R^8$ are each hydrogen. In some variations, $R^1$ or $R^2$ is an isoprenoid tail having formula

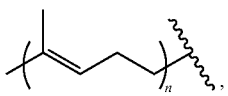

with n=1, 2, 3, 4 or 5. In some variations, $R^3$ or $R^7$ is an isoprenoid tail having formula

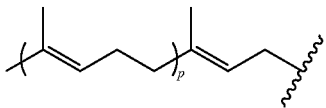

with p=0, 1, 2, 3, or 4. In some cases, when used in a composition to make a wall of a closed or sealed article used to store oxygen sensitive substances, the oxygen scavengers may consume oxygen at a sufficient rate and capacity to keep the dissolved oxygen concentration in a liquid or the total oxygen content (head space+liquid) inside the closed or sealed article at a level of 0.05 ppm or less, 0.1 ppm or less, 0.5 ppm or less, 0.8 ppm or less, 1 ppm or less, 2 ppm or less, 3 ppm or less, 5 ppm or less, or 10 ppm or less for a period of at least about 30 days, at least about 60 days, at least about 90 days, at least about 120 days, at least about 150 days, or at least about 180 days, at least about 270 days, at least about one year, or at least about 15 months under ambient conditions. Note that the total $O_2$ concentration (in ppm, mg $O_2$/L)={Caq*(33.7*Vh+Vl)}/(Vl+Vh), where Caq is the dissolved oxygen concentration in ppm as measured by an oxygen sensor and the quantities Vh and Vl are the headspace and liquid volumes, respectively (in liters). In some cases, the oxygen scavenger loading in the composition used to make the wall is at least about 0.5 wt. %, or at least about 1 wt. %. In some cases, the oxygen scavenger loading in the composition used to make the wall is about 5 wt. % or less (e.g., about 5, 4, 3, 2 or 1 wt. %).

In some variations, an oxygen scavenger has formula (I) with $R^4$ and $R^8$ each being H, and $R^2$ being an isoprenoid tail having the formula

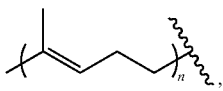

with n=1, 2, 3, 4 or 5, so that the oxygen scavenger has formula (II):

(II)

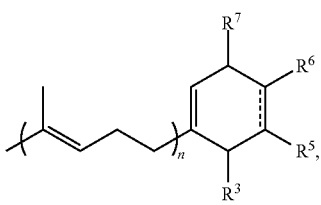

wherein $R^3$, $R^5$, $R^6$ and $R^7$ are as described for formula (I). In some variations, $R^7$ is an isoprenoid tail having formula

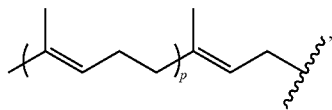

where p=0, 1, 2, 3, or 4. In some variations, $R^3$ and $R^7$ are each H. $R^5$ and $R^6$ may be the same or different. In some variations, at least one of $R^5$ and $R^6$ is a carboxylate ester group having formula —$COOR_c$, where $R_c$ is H or any suitable linear or branched, cyclic or acyclic, aliphatic or aryl, substituted or unsubstituted hydrocarbyl group. In some variations, each of $R^5$ and $R^6$ are carboxylate ester groups. In some cases, $R_c$ is a $C_1$-$C_{30}$ linear or branched, cyclic or acyclic alkyl group. In some variations, $R_c$ is methyl. In some variations, $R^5$ and $R^6$ are each carboxylate ester groups having formula —$COOCH_3$. In some variations, $R^5$ and $R^6$ together form a cyclic structure that optionally includes one or more heteroatoms.

In some variations, an oxygen scavenger has formula (I) with $R^4$ and $R^8$ each being H, $R^2$ being an isoprenoid tail having formula

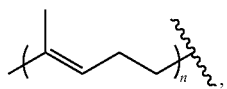

with n=1, 2, 3, 4 or 5, and $R^5$ and $R^6$ together forming a five-membered cyclic ring so that the oxygen scavenger has formula (III):

(III)

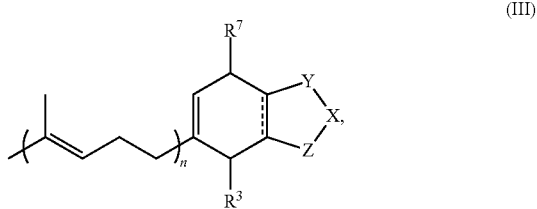

wherein: $R^3$ and $R^7$ are as described for formula (I); X is O, S, $NR^9$; PR', or PR'R"R'", and one of Y and Z is C=O and the other of Y and Z is C=O or $CR^{10}R^{11}$, wherein $R^9$, $R^{10}$, $R^{11}$, R', R", and R'" are independently H, or a saturated or unsaturated, linear or branched, cyclic or acyclic, aliphatic or aryl, unsubstituted or substituted hydrocarbyl group. In some variations, $R^7$ is an isoprenoid tail having formula

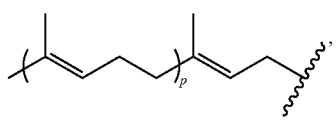

where p=0, 1, 2, 3, or 4. In some variations, $R^3$ and $R^7$ are each hydrogen. In some variations, Y and Z are each C=O. In some variations, Y and Z are each C=O and X is O. In some variations, Y and Z are each C=O and X is $NR^9$. In some variations, n=2.

In some variations, an oxygen scavenger is an oligomer or polymer having a repeat unit of formula (I). In some variations, the repeat unit having formula (I) is a side chain to a polymer main chain. In some variations, the repeat unit having formula (I) forms a portion of the polymer main chain. In some variations, the oxygen scavenging polymer is a polyester. In some variations, the oxygen scavenging polymer is a polyamide.

Described herein are oxygen scavenging compositions comprising one or more oxygen scavengers having formula (I), (II), or (III), and an accelerator, wherein the accelerator is capable of triggering or accelerating oxygen uptake by the one or more oxygen scavengers. Optionally, the compositions may comprise an effective amount of an oxidation catalyst, such as a transition metal-containing oxidation catalyst. Accelerators may or may not consume oxygen. Non-limiting examples of accelerators include polyolefins or copolymers thereof, modified polyolefins (e.g., grafted polyolefins), and molecules having formula (I″):

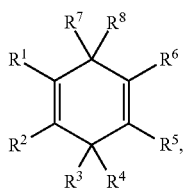
(I″)

where $R^1$, $R^2$, $R^3$, $R^4$, $R^5$, $R^6$, $R^7$, and $R^8$ are as described for formula (I). In some variations, an accelerator comprises a polybutadiene or a copolymer or an adduct thereof, e.g., a maleated polybutadiene, or a polyisoprene or a copolymer or adduct thereof, e.g., a maleated polyisoprene.

Described herein are oxygen scavenging compositions comprising a host polymer; and dispersed within the host polymer, an effective amount of one or more oxygen scavengers having formula (I):

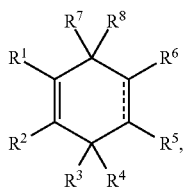
(I)

and an oxidation catalyst, wherein $R^1$, $R^2$, $R^3$, $R^4$, $R^5$, $R^6$, $R^7$ and $R^8$ are independently H, or a saturated or unsaturated, linear or branched, cyclic or acyclic, aliphatic or aryl, unsubstituted or substituted hydrocarbyl group, with the provisos that: i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tail having formula

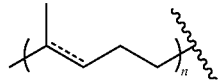

with n=1, 2, 3, 4, or 5 and/or having formula

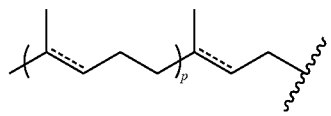

with p=0, 1, 2, 3, or 4. In some oxygen scavenging compositions, the oxygen scavengers form a homogeneous mixture with the host polymer, and in some compositions, the oxygen scavengers form phase-separated domains in the host polymer. In some variations, the oxidation catalyst comprises at least one transition metal (e.g., cobalt). In certain variations, an oxygen scavenging composition further comprises an accelerator capable of triggering or accelerating oxygen uptake by the composition. The accelerator may or may not consume oxygen. In some cases, the oxygen scavenging compositions may be used to form one or more walls of a closed or sealed article used to store oxygen sensitive substances at a sufficient rate and capacity to keep the dissolved oxygen concentration in a liquid or the total oxygen content (head space+liquid) inside the closed or sealed article at a level of 0.05 ppm or less, 0.1 ppm or less, 0.2 ppm or less, 0.5 ppm or less, 0.8 ppm or less, 1 ppm or less, 2 ppm or less, 3 ppm or less, 5 ppm or less, or 10 ppm or less for a period of at least about 30 days, at least about 60 days, at least about 90 days, at least about 120 days, at least about 150 days, or at least about 180 days, at least about 270 days, at least about one year, or at least about 15 months under ambient conditions. In some cases, the oxygen scavenger loading in the composition used to make the wall is at least about 0.5 wt. %, at least about 1 wt. %, or at least about 1.5 wt. %. In some cases, the oxygen scavenger loading in the composition used to make the wall can be about 5 wt. % or less (e.g., about 5, 4, 3, 2 or 1 wt. %).

Described herein are oxygen scavenging compositions comprising: a host polymer; and dispersed within the host polymer, an effective amount of one or more oxygen scavenging polymers comprising a repeat unit having formula (I):

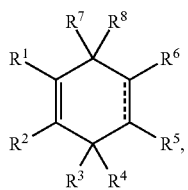
(I)

and an oxidation catalyst, wherein $R^1$, $R^2$, $R^3$, $R^4$, $R^5$, $R^6$, $R^7$ and $R^8$ are independently H, or a saturated or unsaturated, linear or branched, cyclic or acyclic, aliphatic or aryl, unsubstituted or substituted hydrocarbyl group, with the provisos that: i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tail having formula with n=1, 2, 3, 4, or 5 and/or formula

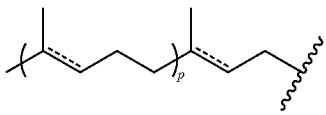

with p=0, 1, 2, 3, or 4. In some variations, the oxygen scavenging polymers form a homogeneous mixture with the host polymer, and in some variations, the oxygen scavenging polymers form phase separated domains in the host polymer. In some variations, the oxidation catalyst comprises at least one transition metal (e.g., cobalt). In certain variations, the oxygen scavenging compositions further comprise an accelerator capable of triggering or accelerating oxygen uptake by the composition. The accelerator may or may not consume oxygen.

The host polymer used in the oxygen scavenging compositions may be any suitable polymer. In some variations, the host polymer is or comprises a polyester or a copolymer or adduct thereof. In some variations, the host polymer is or comprises a polymer selected from the group consisting of polyethylene terephthalate, copolymers of polyethylene terephthalate, polyethylene naphthalate, copolymers of polyethylene napthalate, polybutylene terephthalate, copolymers of polybutylene terephthalate, polytrimethylene terephthalate, copolymers of polytrimethylene terephalate, polyethylene furanoate and copolymers of polyethylene furanoate, and poly(lactic acid) or copolymers of poly(lactic acid). In some variations, the host polymer is or comprises a polyester made by reacting at least one acid selected from the group consisting of terephthalic acid and isophthalic acid or their dimethyl esters with at least one glycol selected from the group consisting of ethylene glycol, diethylene glycol, 1,4-butanediol, 1,3-butanediol and 1,4-cyclohexanedimethanol (CHDM). In some variations, the host polymer is or comprises a homopolymer or copolymer of the reaction of terephthalic acid (or an ester thereof such as the dimethyl ester), ethylene glycol, and one or more co-acids or acid ester comonomers. In some variations, the host polymer is or comprises a homopolymer or copolymer of the reaction of terephthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a polyamide or a copolymer or adduct thereof, or a polyolefin or a copolymer or adduct thereof. In some variations, the host polymer is or comprises polyethylene furanoate or a copolymer or adduct of polyethylene furanoate, or poly(lactic acid) or a copolymer or adduct of poly(lactic acid). In some variations, the host polymer is not a polyester. In some variations, the host polymer is not polyethylene terephthalate or a copolymer thereof. In some variations, the host polymer is not polyethylene terephthalate or a copolymer or adduct thereof. In some variations, the host polymer is not a polyester made by reacting at least one acid selected from the group consisting of terephthalic acid and isophthalic acid or their dimethyl esters with at least one glycol selected from the group consisting of ethylene glycol, diethylene glycol, 1,4-butanediol, 1,3-butanediol, and 1,4-cyclohexanedimethanol (CHDM). In some variations, the host polymer is not a homopolymer or copolymer of the reaction of terephthalic acid (or ester thereof) and ethylene glycol. In some variations, the host polymer is not a homopolymer or copolymer of the reaction of terephthalic acid (or ester thereof), ethylene glycol, and one or more co-acids or acid ester co-monomers. In some variations, the host polymer is not a homopolymer or copolymer of the reaction of terephthalic acid (or ester thereof), ethylene glycol and one or more dialcohol co-monomers (e.g., 1,4-cyclohexanedimethanol, diethylene glycol, 1,4-butane diol or 1,3-butane diol). In some variations, the host polymer is not a homopolymer or copolymer of the reaction of terephthalic acid (or ester thereof), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is not a copolymer of the reaction of terephthalic acid (or ester thereof), isophthalic acid (or ester thereof) and ethylene glycol. In some variations, the host polymer is not a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol).

Described herein are oxygen scavenging compositions comprising: one or more oxygen scavenging polymers comprising a repeat unit having formula (I):

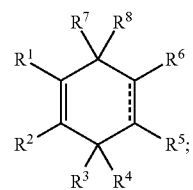

(I)

and an oxidation catalyst, wherein $R^1$, $R^2$, $R^3$, $R^4$, $R^5$, $R^6$, $R^7$ and $R^8$ are independently H, or a saturated or unsaturated, linear or branched, cyclic or acyclic, aliphatic or aryl, unsubstituted or substituted hydrocarbyl group, with the provisos that: i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tail having formula

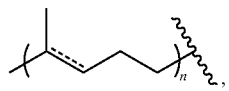

where n=1, 2, 3, 4, or 5 and/or formula

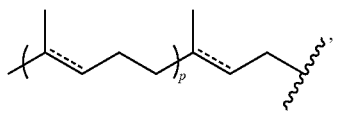

where p=0, 1, 2, 3, or 4. The repeat unit having formula (I) may be incorporated as side chains to the polymer or to form a portion of the polymer main chain. In some variations, the oxygen scavenging polymer is a polyester or a copolymer or adduct thereof. In some variations, the oxygen scavenging polymer is a polyamide or a copolymer or adduct thereof. In some variations, the oxidation catalyst comprises at least one transition metal (e.g., cobalt). In certain variations, the oxygen scavenging compositions further comprise an accelerator capable of triggering or accelerating oxygen uptake by the composition. The accelerator may or may not consume oxygen.

Various types of articles may be formed from the oxygen scavenging compositions described herein. For example, articles such as bottles, containers, films, trays, sheets, cups, jars, lids, pouches, and bags may be formed from the oxygen scavenging compositions described herein. The oxygen scavenging compositions may be used to form one or more walls of a closed or sealed article used to store oxygen sensitive substances at a sufficient rate and capacity to keep the dissolved oxygen concentration in a liquid or the total oxygen content (head space+liquid) inside the closed or sealed article at a level of 0.05 ppm or less, 0.1 ppm or less, 0.2 ppm or less, 0.5 ppm or less, 0.8 ppm or less, 1 ppm or less, 2 ppm or less, 3 ppm or less, 5 ppm or less, or 10 ppm or less for a period of at least about 30 days, at least about 60 days, at least about 90 days, at least about 120 days, at least about 150 days, at least about 180 days, at least about 270 days, at least about one year, at least about 15 months under ambient conditions. In some cases, the oxygen scavenger loading in the composition used to make the one or more walls may be at least about 0.5 wt %, at least about 1 wt. %, or at least about 1.5 wt. %. In some cases, the oxygen scavenger loading in the composition used to make the one or more walls may be about 5 wt. % or less (e.g., about 5, 4, 3, 2 or 1 wt. %). In certain variations, bottles having optical clarity may be produced, e.g., bottles exhibiting a haze value of about 8% or less. In some cases, the oxygen scavengers may cause limited or no increase in color relative to a host polymer (e.g., the oxygen scavengers may increase L* values by about 1.0 or less per mil/wall thickness, or about 0.4 or less per mil/wall thickness). The articles may be made by any suitable method, e.g., by melt forming.

Also described herein are methods for making oxygen scavengers. In some variations, the methods comprise reacting an isoprenoid having a conjugated diene with a dienophile under conditions suitable to form a Diels-Alder adduct having formula (I). In some variations, farnesene is reacted with a dienophile under conditions suitable to form a Diels-Alder adduct having formula (I), (II) or (III) that is capable of consuming oxygen at a desired rate for a desired length of time. Certain methods comprise reacting one or more oxygen scavengers of formula (I), (II), or (III) with one or more co-monomers to make an oxygen scavenging polymer, e.g., an oxygen scavenging polyester, or an oxygen scavenging polyamide.

Advantageously, any of the oxygen scavenging molecules, oxygen scavenging polymers, oxygen scavenging compositions, and articles made from the oxygen scavenging compositions may be made from renewable carbon sources. In some variations, at least about 25%, at least about 50%, or at least about 75% of the oxygen scavenger molecules, oxygen scavenging polymers, or oxygen scavenging compositions may be derived from non-petroleum sources. In some variations, essentially all of the carbon used to make the oxygen scavenging molecules, polymers, or compositions is derived from non-petroleum sources.

BRIEF DESCRIPTION OF THE DRAWINGS

FIGS. 15A-15B provides Table E.8, which shows certain oxygen scavenging polymers/oligomers formed by reacting the oxygen scavengers of Example A or Example C with ethylene glycol and one or more co-monomers.

DETAILED DESCRIPTION

I. Definitions

Figure 1:
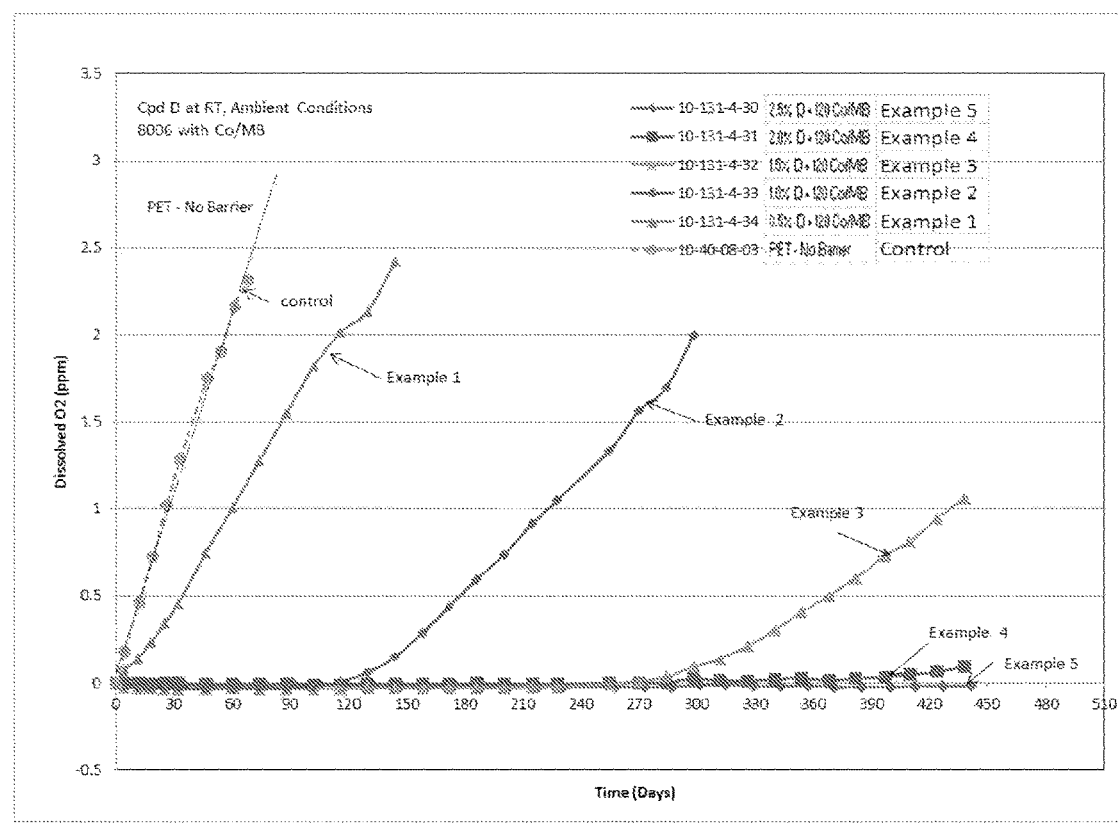
FIG. 1 provides a graph of dissolved oxygen concentration as a function of time for liquid in the interior of the capped blow molded bottles of Examples 1-5 under ambient conditions. The oxygen scavenger is Example D used at concentrations ranging from 0.5 wt % to 2.5 wt %, and the oxidation catalyst is cobalt neodecanoate (contains up to 30 wt % cobalt propionate; 20.5% wt. cobalt, available from Shepherd Chemicals).

"Alkyl" refers to a group having the general formula $C_nH_{2n+1}$ derived from a saturated, straight chain or branched aliphatic hydrocarbon, where n is an integer. In certain embodiments, n is from 1 to about 30, from 1 to about 20, or from 1 to about 10. Non-limiting examples of alkyl groups include $C_1$-$C_8$ alkyl groups such as methyl, ethyl, propyl, isopropyl, 2-methylpropyl, 2-methylbutyl, 3-methylbutyl, 2,2,-dimethylpropyl, 2-methylpentyl, 3-methylpentyl, 4-methylpentyl, 2-2-dimethylbutyl, 3,3-dimethylbutyl, 2-ethylbutyl, n-butyl, isobutyl, tert-butyl, isopentyl, n-pentyl, neopentyl, n-hexyl, isohexyl, n-heptyl, isoheptyl, n-octyl, isooctyl, n-nonyl, isononyl, n-decyl and isodecyl. An alkyl group may be unsubstituted, or may be substituted. In some embodiments, the alkyl group is straight chain having 1, 2, 3, 4, 5, 6, 7, 8, 9, 10, 11 or 12 carbons. In some embodiments, the alkyl group is branched having 1, 2, 3, 4, 5, 6, 7, 8, 9, 10, 11 or 12 carbons.

An "allylic proton" refers to a hydrogen atom that is bonded to a carbon atom that is bonded to one or more unsaturated carbon-carbon bonds. One type of allylic proton is a "multiply allylic proton," which refers to a hydrogen atom that is bonded to a carbon atom that is bonded to two or more unsaturated carbon-carbon bonds. A "doubly allylic" or "bisallylic" hydrogen refers to a hydrogen atom bonded to a carbon atom that is bonded to two unsaturated carbon-carbon bonds.

"Aryl" refers to an organic radical derived from a monocyclic or polycyclic aromatic hydrocarbon by removing a hydrogen atom. Non-limiting examples of the aryl group include phenyl, naphthyl, benzyl, or tolanyl group, sexiphenylene, phenanthrenyl, anthracenyl, coronenyl, and tolanylphenyl. An aryl group can be unsubstituted or substituted with one or more suitable substituents. Furthermore, the aryl group can be monocyclic or polycyclic. In some embodiments, the aryl group contains at least 6, 7, 8, 9, or 10 carbon atoms.

A "benzylic proton" refers to a hydrogen atom that is bonded to a carbon atom that is bonded to one or more aromatic rings.

"Container," "packaging article" and "package" refers to any form of open or closed article for containing or packaging a substance, and encompasses at least bottles, films, boxes, liners, caps, trays, bags, closures, and the like, and encompasses containers, packaging articles and packages in their final commercial form as well as any intermediate stages. For example, preforms from which bottles are formed constitute one example of an intermediate stage.

"Cycloaliphatic" encompasses "cycloalkyl" and "cycloalkenyl." Cycloaliphatic groups may be monocyclic or polycyclic. A cycloaliphatic group can be unsubstituted or substituted with one or more suitable substituents.

"Cycloalkenyl" refers to a non-aromatic carbocyclic mono- or bicyclic ring of 3 to 12 (e.g., 4 to 8) carbon atoms having one or more double bonds. Non-limiting examples of cycloalkenyl include $C_3$-$C_8$ cycloalkenyl groups such as cyclopropenyl, cyclobutenyl, cyclopentenyl, cyclohexenyl, cycloheptenyl, cyclooctenyl, and unsaturated cyclic and bicyclic terpenes. Cycloalkenyl groups may be unsubstituted or substituted.

"Cycloalkyl" refers to a saturated carbocyclic mono- or bicyclic (fused or bridged) ring of 3-12 (e.g., 5-12) carbon atoms. Non-limiting examples of cycloalkyl include $C_3$-$C_8$ cycloalkyl groups, e.g., cyclopropyl, cyclobutyl, cyclopentyl, cyclohexyl, cycloheptyl, and cyclooctyl groups and saturated cyclic and bicyclic terpenes. Cycloalkyl groups may be unsubstituted or substituted.

"Homopolymer" refers to a polymer containing repeating units of only one chemical composition.

"Hydrocarbyl" refers to a group containing one or more carbon atom backbones and hydrogen atoms, and the group may optionally contain one or more heteroatoms. Where the hydrocarbyl group contains heteroatoms, the heteroatoms may form one or more functional groups known to one of skill in the art. Hydrocarbyl groups may contain cycloaliphatic, aliphatic, aromatic, or any combination thereof. Aliphatic segments may be straight or branched. Aliphatic and cycloaliphatic groups may include one or more double and/or triple carbon-carbon bonds. Included in hydrocarbyl groups are alkyl, alkenyl, alkynyl, aryl, cycloalkyl, cycloalkenyl, alkaryl and aralkyl groups. Cycloaliphatic groups may contain both cyclic moieties and noncyclic portions. In some embodiments, the hydrocarbyl group is a saturated or unsaturated, cyclic or acyclic, unsubstituted or substituted $C_1$-$C_{30}$ hydrocarbyl group (e.g., $C_1$-$C_{20}$ alkyl, $C_1$-$C_{20}$ alkenyl, $C_1$-$C_{20}$ alkynyl, cycloalkyl, aryl, aralkyl and alkaryl).

"Interpolymer" refers to a polymer having two or more chemically different repeat units in the same macromolecules. The term interpolymer encompasses the term "copolymer" which general refers to a polymer prepared from two chemically different monomers. Interpolymer also encompasses "terpolymer," which refers to a polymer having at least three chemically distinct repeat units (e.g., a polyester made by the reaction of two different diacids with a diol). Interpolymer also encompasses polymers made by polymerizing four chemically different monomers.

"Intrinsic viscosity" or "inherent viscosity" refers to any suitable viscosity measurement of a polymer that correlates with molecular weight of that polymer. In some variations, intrinsic viscosity is measured according to ASTM D4603-86 or ASTM D4603-03 "Standard Test Method for Determining Inherent Viscosity of Poly(Ethylene Terephthalate) (PET) by Glass Capillary Viscometer," each of which is incorporated by reference herein in its entirety.

"Isoprenoid" and "isoprenoid compound" are used interchangeably herein and refer to a compound derivable from isopentenyl diphosphate.

"Oxygen scavenger" or "oxygen scavenging" refers to a substance's ability to consume or react with oxygen present in a given environment, even if it is not the primary purpose of the substance. Oxygen scavenging includes two components: i) induction time, which refers to a time delay before which oxygen scavenging activity is insufficient or not detected; and ii) capacity or lifetime, which refers to a time after which oxygen scavenging activity substantially decreases or ceases. As used herein, the term oxygen scavenger refers to any oxygen scavenging moiety, e.g., an oxygen scavenging molecule, or an oligomer or polymer that incorporates an oxygen scavenging group as a portion of the main chain and/or as a side chain. An "oxygen scavenging composition" may be used to form one or more walls of a closed or sealed article used to store oxygen sensitive substances and consume oxygen at a sufficient rate and capacity to maintain the oxygen concentration inside the closed or sealed article at a desired level for a desired length of time. In some cases, when used in reference to a closed or sealed article, an oxygen scavenging composition may be used to form one or more walls of the article and consume oxygen at a sufficient rate and capacity to maintain a dissolved oxygen concentration in a liquid or the total oxygen content (head space+liquid) inside the article at 0.05 ppm or less, 0.1 ppm or less, 0.2 ppm or less, 0.5 ppm or less, 0.8 ppm or less, 1 ppm or less, 2 ppm or less, 3 ppm or less, 5 ppm or less, or 10 ppm or less for a period of at least about 30 days, at least about 60 days, at least about 90 days, at least about 120 days, at least about 150 days, at least about 180 days, at least about 270 days, at least about one year, or at least 15 months under ambient conditions.

"Polymer" refers to any kind of synthetic or natural oligomer or polymer having two or more repeat units, including thermoplastics, thermosets, elastomers, polymer blends, polymer composites, synthetic rubbers, and natural rubbers. A synthetic oligomer or polymer can be prepared by polymerizing monomers, whether of the same or a different type. The generic term "polymer" embraces the terms "homopolymer," "copolymer," "terpolymer" as well as "interpolymer."

"Substantially all" or "essentially all" means at least about 95%; "essentially none" means at most about 5%.

A substituted group or compound refers to a group or compound in which at least one hydrogen atom is replaced with a substituent chemical moiety. A substituent chemical moiety may be any suitable substituent that imparts desired properties to the compound or group. Non-limiting examples of substituents include halo, alkyl, heteroalkyl, alkenyl, alkynyl, aryl, heteroayrl, hydroxyl, alkoxyl, amino, nitro, thiol, thioether, imine, cyano, amido, phosphonato, phosphine, carbosyl, thiocarbonyl, sulfonyl, sulfonamide, carbonyl, formyl, carbonyloxy, oxo, haloalkyl (e.g., trifluoromethyl or trichloromethyl), carbocyclic cycloalkyl (which may be monocyclic, or fused or non-fused polycyclic) such as cyclopropyl, cyclobutyl, cyclopentyl or cyclohexyl, or a heterocycloalkyl (which may be monocyclic, or fused or nonfused polycyclic such as pyrrolidinyl, piperidinyl, piperazinyl, morpholinyl or thiazinyl), carbocyclic or heterocyclic, monocyclic or fused or nonfused polycyclic aryl (e.g., phenyl, naphthyl, pyrrolyl, idolyl, furanyl, thiopenyl, imidazolyl, oxazolyl, isoxazolyl, thiazolyl, trizolyl, tetrazolyl, pyrazolyl, pyridinyl, quinolinyl, benzothiophenyl, or benzofuranyl); amino (primary, secondary or tertiary): —$CONH_2$; —$OCH_2CONH_2$; —$NH_2$; —$SO_2NH_2$; —$OCHF_2$; $CF_3$, —$CCl_3$; —$OCF_3$; —$NH_2$; —NH(alkyl); —N(alkyl)$_2$; —NH(aryl); —N(alkyl)(aryl); —N(aryl)$_2$; —CHO; —CO(alkyl); —CO(aryl); —$(OCH_2CH_2O)_n$—, where n is from 1 to about 30 (e.g., 1, 2, 3, 4, 5, 6, 7, 8, 9, 10, 11, 12, 13, 14, 15, 16, 17, 18, 19 or 20); —$(OCH_2CH(CH_3)O)_m$—, where m is from 1 to about 30 (e.g., 1, 2, 3, 4, 5, 6, 7, 8, 9, 10, 11, 12, 13, 14, 15, 16, 17, 18, 19 or 20); —Cl, —Br, or —I; and —$CO_2$(alkyl) (e.g., —$CO_2CH_3$ or —$CO_2CH_2CH_3$; —$CO_2$(aryl)). In certain embodiments, the substituents disclosed herein may be further substituted with one or more substituents.

"Thermoplastic" refers to a polymer material that softens when sufficiently heated, and can be molded to change shape in the softened state. The thermoplastic hardens to retain substantially its molded shape when cooled. Thermoplastics can undergo repeated heat/cool cycles without undergoing substantial chemical change, allowing the material to be reshaped or recycled. "Thermoset" refers to a polymer material that is cross-linked by any type of reaction and is irreversibly cured.

"Terpene" as used herein is a compound that is capable of being derived from isopentyl pyrophosphate (IPP) or dimethylallyl pyrophosphate (DMAPP), and the term terpene encompasses hemiterpenes, monoterpenes, sesquiterpenes, diterpenes, sesterterpenes, triterpenes, tetraterpenes and polyterpenes. A hydrocarbon terpene contains only hydrogen and carbon atoms and no heteroatoms such as oxygen, and in some embodiments has the general formula $(C_5H_8)_n$, where n is 1 or greater. A "conjugated terpene" as used herein refers to a terpene comprising at least one conjugated diene moiety. It should be noted that the conjugated diene moiety of a conjugated terpene may have any stereochemistry (e.g., cis or trans) and may be part of a longer conjugated segment of a terpene, e.g., the conjugated diene moiety may be part of a conjugated triene moiety. It should be understood that terpenes as used herein also encompasses monoterpenoids, sesquiterpenoids, diterpenoids, triterpenoids, tetraterpenoids and polyterpenoids that exhibit the same carbon skeleton as the corresponding terpene but have either fewer or additional hydrogen atoms than the corresponding terpene, e.g., terpenoids having 2 fewer, 4 fewer, or 6 fewer hydrogen atoms than the corresponding terpene, or terpenoids having 2 additional, 4 additional or 6 additional hydrogen atoms than the corresponding terpene. Some non-limiting examples of conjugated hydrocarbon terpenes include isoprene, myrcene, α-ocimene, β-ocimene, α-farnesene, β-farnesene, β-springene, geranylfarnesene, neophytadiene, cis-phyta-1,3-diene, trans-phyta-1,3-diene, isodehydrosqualene, isosqualane precursor I, and isosqualane precursor II. The terms terpene and isoprenoid are used interchangeably herein, and are a large and varied class of organic molecules that can be produced by a wide variety of plants and some insects. Some terpenes or isoprenoid compounds can also be made from organic compounds such as sugars by microorganisms, including bioengineered microorganisms. Because terpenes or isoprenoid compounds can be obtained from various renewable sources, they are useful monomers for making eco-friendly and renewable base oils. In certain embodiments, the conjugated hydrocarbon terpenes as described herein are derived from microorganisms using a renewable carbon source, such as a sugar.

"Isoprene" refers to a compound having the following structure:

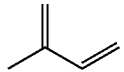

or a stereoisomer thereof.

"Myrcene" refers to a compound having the following structure:

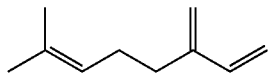

or a stereoisomer thereof.

"Ocimene" refers to α-ocimene, β-ocimene or a mixture thereof.

"α-ocimene" refers to a compound having the following formula:

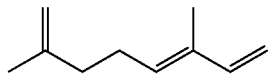

or a stereoisomer (e.g., s-cis isomer) thereof.

"β-ocimene" refers to a compound having the following formula:

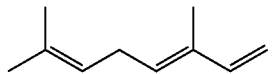

or a stereoisomer (e.g., s-cis isomer) thereof.

"Farnesene" as used herein refers to α-farnesene, β-farnesene or a mixture thereof.

"α-Farnesene" refers to a compound having the following structure:

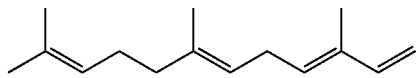

or a stereoisomer (e.g., s-cis isomer) thereof. In some embodiments, α-farnesene comprises a substantially pure stereoisomer of α-farnesene. In some embodiments, α-farnesene comprises a mixture of stereoisomers, such as s-cis and s-trans isomers. In some embodiments, the amount of each of the stereoisomers in an α-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. % or from about 20 wt. % to about 80 wt. %, based on the total weight of the α-farnesene mixture of stereoisomers.

"β-farnesene" refers to a compound having the following structure:

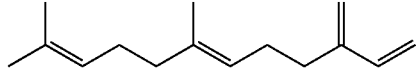

or a stereoisomer (e.g., s-cis isomer) thereof. In some embodiments, β-farnesene comprises a substantially pure stereoisomer of β-farnesene. Substantially pure β-farnesene refers to compositions comprising at least 80%, at least 90%, at least 95%, at least 97%, at least 98% or at least 99% β-farnesene by weight, based on total weight of the farnesene. In other embodiments, β-farnesene comprises a mixture of stereoisomers, such as s-cis and s-trans isomers. In some embodiments, the amount of each of the stereoisomers in a β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, or from about 20 wt. % to about 80 wt. %, based on the total weight of the β-farnesene mixture of stereoisomers.

"Farnesane" refers to a compound having the following structure:

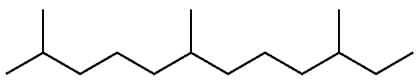

or a stereoisomer thereof.

"β-springene" or "springene" refers to a compound having the following structure:

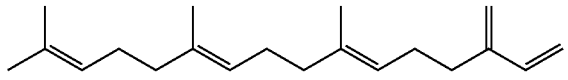 [SMILES: C=CC(=C)CC/C=C(\C)CC/C=C(\C)CCC=C(C)C]

or a stereoisomer (e.g., s-cis isomer) thereof.

"Geranylfarnesene" refers to a compound having the following structure:

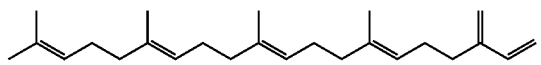 [SMILES: C=CC(=C)CC/C=C(\C)CC/C=C(\C)CC/C=C(\C)CCC=C(C)C]

or a stereoisomer (e.g., s-cis isomer) thereof.

"Farnesol" refers to a compound having the following structure:

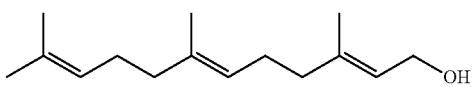 [SMILES: CC(C)=CCC/C(C)=C/CC/C(C)=C/CO]

or a stereoisomer thereof.

"Nerolidol" refers to a compound having the following structure:

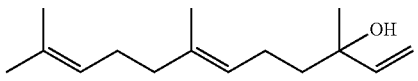 [SMILES: C=CC(C)(O)CC/C=C(\C)CCC=C(C)C]

or a stereoisomer thereof.

"Isodehydrosqualene" refers to a compound having the following structure:

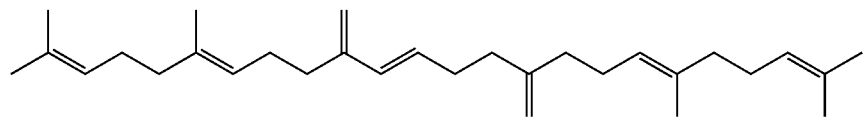 [SMILES: C=C(/C=C/CCC(=C)CC/C=C(\C)CCC=C(C)C)CC/C=C(\C)CCC=C(C)C]

or a stereoisomer thereof.

"Isosqualane precursor I" or "2,6,18,22-tetramethyl-10-methylene-14-vinyltricosa-2,6,11,17,21-pentaene" refers to a compound having the following structure:

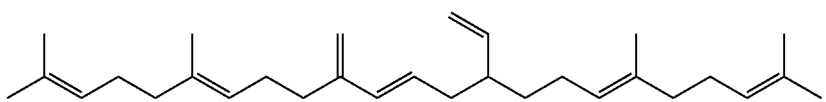 [SMILES: C=CC(C/C=C/C(=C)CC/C=C(\C)CCC=C(C)C)CC/C=C(\C)CCC=C(C)C]

or a stereoisomer thereof.

"Isosqualane precursor II" or "2,6,14,18,22-pentamethyl-10-vinyltricosa-2,6,10,14,17,21-pentaene" refers to a compound having the following structure:

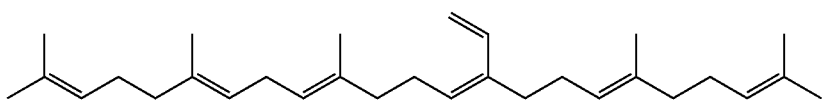 [SMILES: C=C/C(=C\CC/C(C)=C/C/C=C(\C)CCC=C(C)C)CC/C=C(\C)CCC=C(C)C]

or a stereoisomer thereof.

Farnesol or nerolidol may be converted into α-farnesene or β-farnesene, or a combination thereof by dehydration with a dehydrating agent or an acid catalyst. Any suitable dehydrating agent or acid catalyst that can convert an alcohol into an alkene may be used. Non-limiting examples of suitable dehydrating agents or acid catalysts include phosphoryl chloride, anhydrous zinc chloride, phosphoric acid, and sulfuric acid.

In the following description, all numbers disclosed herein are approximate values, regardless whether the word "about" or "approximate" is used in connection therewith. Numbers may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent or 100 percent. Moreover, any numerical range defined by two R numbers as defined in the above is also specifically disclosed.

A bond indicated by ⌇ represents a bond that may be a carbon-carbon single bond or may be a carbon-carbon double bond. For example, the bond depicted as ⌇ in compounds having formula (I) may be a carbon-carbon single bond (i.e., the compound has formula (I')) or a carbon-carbon double bond (i.e., the compound has formula (I")):

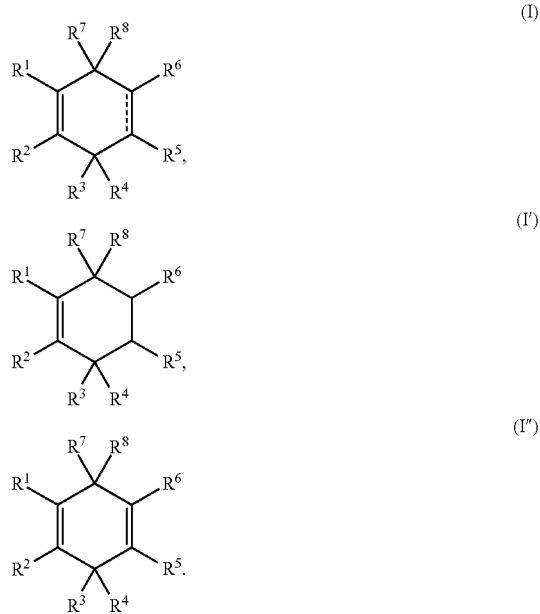

In some instances a compound having formula (I) may be a mixture of compounds having formula (I') and formula (I").

It should be noted that where stereochemistry or chirality in a structure is not specified, the structure is meant to encompass any stereoisomer or chirality.

II) Description

Described herein are isoprenoid-derived oxygen scavengers, methods for making the oxygen scavengers, oxygen scavenging compositions comprising the oxygen scavengers, methods for making the oxygen scavenging compositions, articles (e.g., containers, bottles, films, caps, jars, bags, pouches, trays, and the like) utilizing the oxygen scavenging compositions, methods for making the articles utilizing the oxygen scavenging compositions, and methods for storing oxygen-sensitive substances employing the oxygen scavenging compositions described herein.

The oxygen scavengers described herein are derived from an isoprenoid and contain at least one allylic hydrogen that is sufficiently active to scavenge oxygen from an environment. In certain variations, the isoprenoid-derived oxygen scavengers comprise at least two allylic hydrogens, e.g., 2, 3, 4 or even more allylic hydrogens. In some variations, the isoprenoid-derived oxygen scavengers comprise at least one doubly allylic (bisallylic) hydrogen. The isoprenoid-derived oxygen scavengers may be suitably functionalized to improve their effectiveness in certain applications. For example, isoprenoid-derived oxygen scavengers may be functionalized to: i) tune compatibility with the host polymer (e.g., a polyester); ii) include reactive groups that react with the host polymer; iii) inhibit or remove reactive groups that may react with the host polymer; iv) react with one or more comonomers to make an oligomer or polymer; v) increase molecular weight; vi) tune optical clarity (e.g., haziness) of a composition; and/or vii) tune color of a composition. The isoprenoid-derived oxygen scavengers may be single molecules, or comprise two or more repeat units (e.g., oligomers or polymers).

In certain variations, the oxygen scavengers comprise or include a moiety that is derived from a Diels-Alder adduct formed between a conjugated diene group of an isoprenoid and a suitable dienophile. In certain embodiments, a Diels-Alder adduct comprises at least one allylic hydrogen bonded to a carbon atom of the ring structure formed by the Diels-Alder reaction. In some cases, the oxygen scavenger adduct comprises two or more allylic hydrogens bonded to a carbon of the ring structure, e.g., 2, 3, or 4 allylic hydrogens. In some cases, Diels-Alder adducts that function as effective oxygen scavengers comprise at least one doubly allylic (bisallylic) hydrogen bonded to a carbon atom of the ring structure that is formed by the Diels-Alder reaction. In some cases, the oxygen scavenger adduct comprises two or more bisallylic hydrogen atoms bonded to a carbon of the ring structure, e.g., 2, 3, or 4 bisallylic hydrogen atoms.

One or more oxygen scavengers described herein may be incorporated into a host polymer to make an oxygen scavenging composition. It should be understood that the term host polymer encompasses a single polymer, a mixture of multiple polymers, and a mixture comprising one or more polymers and other additives. A host polymer may be a homopolymer, a copolymer, a polymer blend of two or more polymers, a polymer composite, or the like.

The oxygen scavengers may be incorporated into a host polymer in a variety of ways. For example, in a first variation, the oxygen scavengers are molecules that are dispersed into a host polymer to form a physical blend in which the oxygen scavengers undergo no or limited covalent bonding to the polymer host. In a second variation, the oxygen scavenging scavengers undergo significant amounts of covalent bonding to the polymer host, e.g., by transesterification, by grafting, or the like, to form an oxygen scavenging polymer. In such cases, the oxygen scavenging molecules can be specifically designed or derivatized to enable the desired functionalization of the host polymer. In a third variation, an oxygen scavenger functions as a monomer that is polymerized with one or more comonomers to form an oxygen scavenging polymer. An oxygen scavenging polymer made by either route (via functionalization of a host polymer or via polymerization of comonomers) may provide the major polymeric component of an oxygen scavenging composition that can be used to make oxygen scavenging articles such as bottles, trays, containers, films, and the like. Alternatively, an oxygen scavenging polymer made by either route may be dispersed in a host polymer to form a polymeric blend, and the polymeric blend is used to make oxygen scavenging articles.

Oxygen scavenging activity by the oxygen scavengers described herein may be catalyzed by an oxidation catalyst. The oxidation catalyst is dispersed in the host polymer. The concentration and dispersion of the oxidation catalyst in the host polymer is such that sufficient quantities of oxidation catalyst are in proximity to the oxygen scavengers to catalyze oxidation, and therefore facilitate oxygen uptake by the oxygen scavengers.

Optionally, certain oxygen scavenging compositions comprise one or more accelerators. An accelerator shortens induction time, or "kick starts" oxygen scavenging activity. In some cases, an accelerator also scavenges oxygen, and in some cases, an accelerator does not independently scavenge oxygen. An accelerator may generate reactive species (e.g., reactive radicals) that participate in the reaction of oxygen scavengers with oxygen by initiating and/or accelerating oxygen uptake, whether or not the accelerator itself reacts with oxygen. In some cases, an accelerator comprises one or more bisallylic hydrogens. An accelerator may provide one or both of the following functions: i) an accelerator may be used to modulate of timing of oxygen scavenging activity; and/or ii) an accelerator may be used to modulate oxygen scavenging capacity. Referring to the first function, one or more accelerators may be used in an oxygen scavenging composition to determine shelf life of an article formed from that composition. An accelerator may be selected to shorten or eliminate induction time in applications in which the article is to be used immediately. A longer-acting accelerator or no accelerator may be selected in instances in which the article is to be stored before use. Referring to the second function, an accelerator may increase oxygen scavenging capacity by consuming oxygen itself and/or by initiating or accelerating increased oxygen uptake by the oxygen scavenger. Increased oxygen scavenging capacity by an oxygen scavenger may allow use of reduced concentration of oxygen scavenger for desired oxygen scavenging performance or may extend the lifetime of an oxygen scavenging article.

Without being bound by theory, one or more moieties, for example allylic moieties, in an oxygen scavenger described herein are believed to be readily oxidized via a radical process or via direct insertion to form a hydroperoxide. The formation of the hydroperoxide may be autocatalytic or may be catalyzed by an oxidation catalyst (e.g., cobalt(II) such as cobalt neodecanoate or another suitable transition metal ion salt). The hydroperoxide undergoes homolytic cleavage to form reactive radicals that propagate, abstract hydrogen to create more reactive radicals, and cause further consumption of oxygen, e.g., as described in Zeno W. Wicks, Jr., "Drying Oils," Vol. 9, Kirk-Othmer Encyclopedia of Chemical Technology, John Wiley & Sons, 2002, pp. 142-155, Zeno W. Wicks, Jr. "Alkyd Resins," Vol. 2, Kirk-Othmer Encyclopedia of Chemical Technology, John Wiley & Sons, 2002, pp. 147-169, C. Stenberg et al., "A Study of the Drying of Linseed Oils with Different Fatty Acid Patterns using RTIR-spectroscopy and Chemiluminescence (CL)," Industrial Crops and Products 21 (2005) 263-272, and R. van Gorkum et al., "The oxidative drying of alkyd paint catalyzed by metal complexes," Coordination Chemistry Reviews 249 (2005) 1709-1728, each of which is incorporated by reference herein in its entirety. The homolytic cleavage to form reactive radicals may be catalyzed by a metal salt, e.g., salts of cobalt, copper, manganese, zirconium, and calcium salts, which may be oil-soluble salts such as cobalt neodecanoate. Suitable metals can cycle between oxidation states, e.g., Co(II) with Co(III) and Mn(II) with Mn(III). The reactive radicals formed by the activation process can abstract hydrogen (e.g., allylic hydrogen or bisallylic hydrogen) from an oxygen scavenger that reacts with oxygen to form a peroxy radical that continues the radical mechanism. In the instance that a bisallylic hydrogen is abstracted from an oxygen scavenger, a resonance stabilized radical is formed that reacts with oxygen to form conjugated peroxy radical, which can in turn abstract susceptible hydrogens (e.g., allylic or bisallylic hydrogens) and continue the radical mechanism.

Illustrative, non-limiting examples of oxygen consumption by an isoprenoid-derived oxygen scavenger having allylic or bisallylic hydrogens are provided below in Schemes I.A-I.F. Although an oxygen scavenger/accelerator having formula (II) is depicted in Schemes I.A-I.D for illustrative purposes, it is to be understood that any suitable oxygen scavenger/accelerator of formula (I) or (III) may similarly consume oxygen.

As illustrated in Schemes I.A-I.F, in some instances a hydroperoxide intermediate may be formed by reaction of oxygen with the oxygen scavenger, e.g., by direct insertion of oxygen onto the 1,4-cyclohexadiene ring to form, for example, a conjugated diene. The formation of the hydroperoxide may or may not be catalyzed by the oxidation catalyst (e.g., cobalt neodecanoate). The hydroperoxide intermediate may undergo homolytic cleavage to form a peroxy radical. As described above, a metal salt may be used to catalyze homolytic cleavage of the hydroperoxide. The peroxy radical is very reactive and abstracts a susceptible hydrogen (e.g., an allylic hydrogen or bisallylic hydrogen) on another oxygen scavenger to propagate the radical reaction and continue consumption of oxygen. It should be noted that any susceptible hydrogens, for example allylic or bisallylic hydrogens, on the isoprenoid oxygen scavengers described herein may participate in the radical mechanism and contribute to oxygen consumption. For example, allylic or bisallylic hydrogens on the six membered cyclohexene ring or 1,4-cyclohexadiene ring for oxygen scavengers of formula (I), (II) or (III) allylic hydrogens on an isoprenoid tail, and/or allylic or bisallylic hydrogens on any substituents for oxygen scavengers of formula (I), (II) or (III) may be abstracted to participate in the radical mechanism. Scheme I.B depicts one example in which a reactive radical abstracts an allylic or bisallylic hydrogen from the six-membered ring, and Scheme 1.0 depicts one example in which a reactive radical abstracts an allylic or bisallylic hydrogen from an isoprenoid tail. Scheme I.D depicts one particular example in which an oxygen scavenger/accelerator has formula (II") and "kick starts" abstraction of hydrogen from oxygen scavengers having formula (II') (monoallylic hydrogens on isoprenoid tail and/or cyclohexene ring) or from oxygen scavengers having formula (II") (monoallylic hydrogens on isoprenoid tail or bisallylic hydrogens on 1,4-cyclohexadiene ring). It should be pointed out that hydroperoxide species other than those illustrated in Schemes I.A-I.D may be formed when oxygen is consumed. For example, hydroperoxide species may be formed in which the double bonds in the six-membered ring do not rearrange, so that a hydroperoxide group is bonded to the carbon to which $R^7$ is bonded, to the carbon to which $R^3$ is bonded, or to a carbon on an isoprenoid tail, following hydrogen abstraction from any of these sites.

Scheme I.A
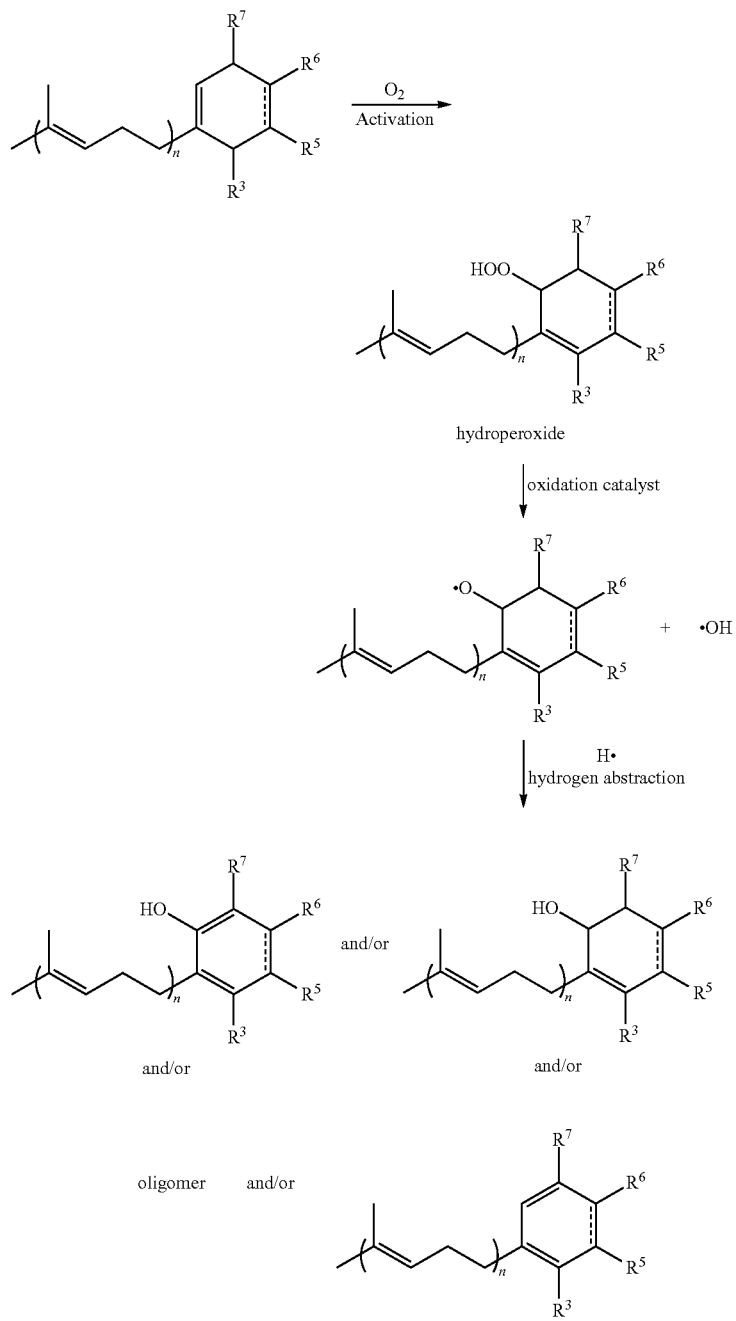
Scheme I.B
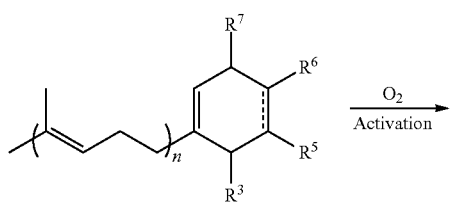

-continued
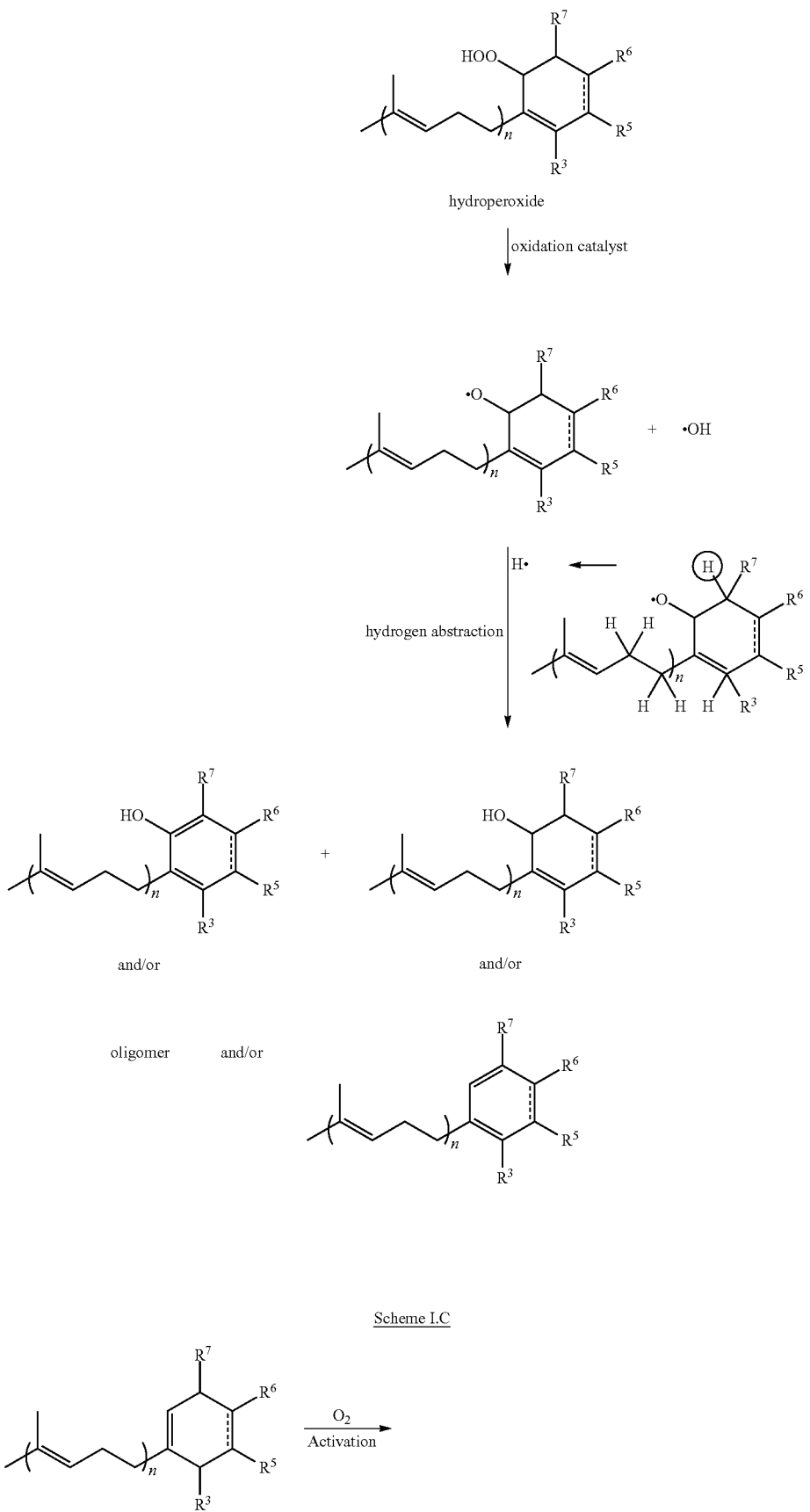
hydroperoxide
oxidation catalyst
hydrogen abstraction
and/or
and/or
oligomer and/or
Scheme I.C
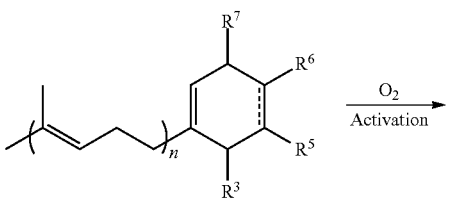

-continued
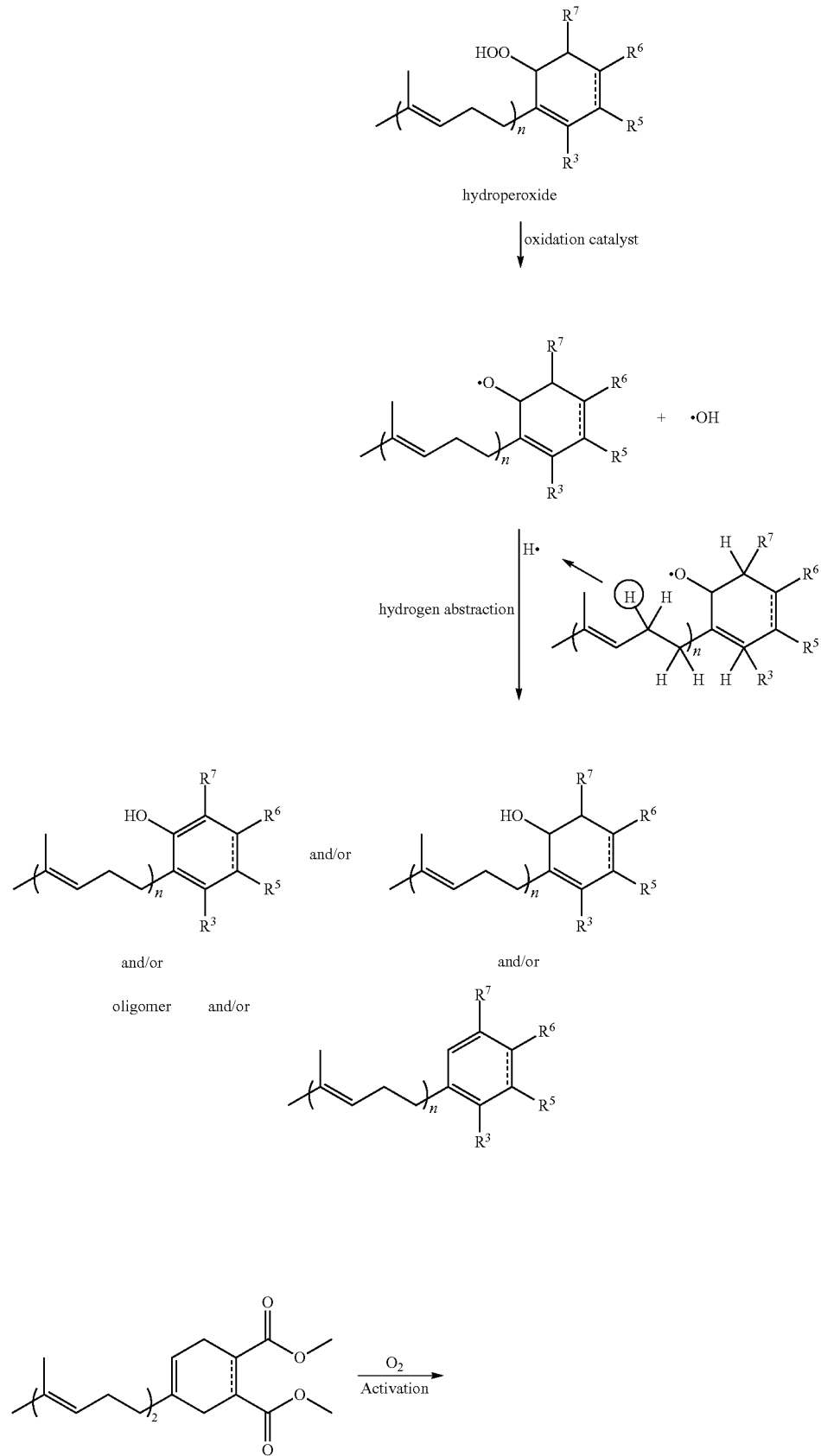

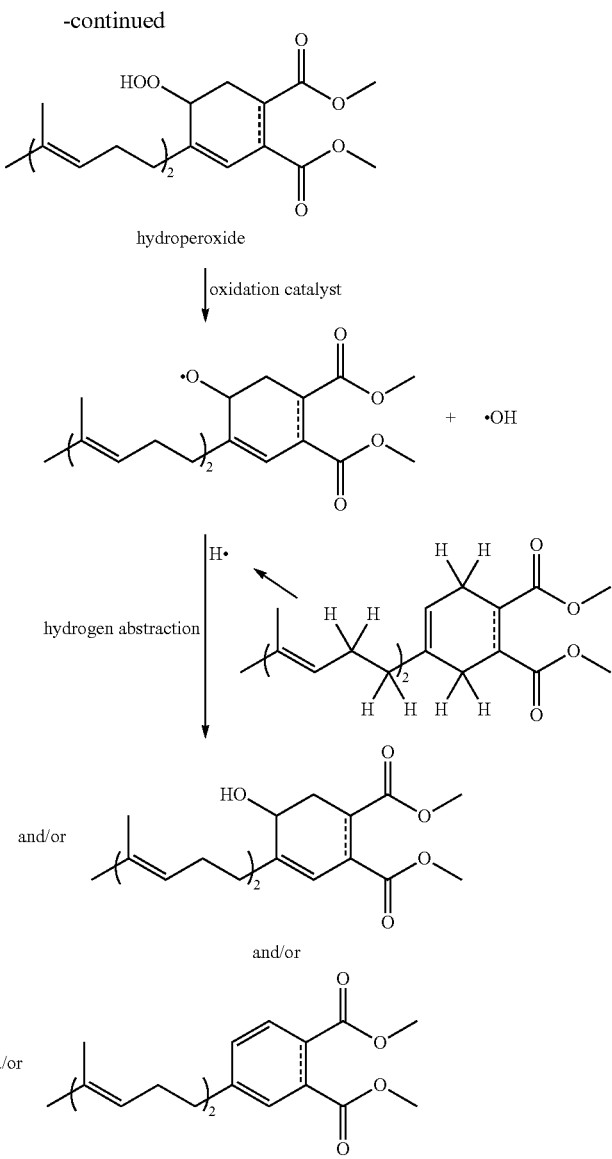

Scheme I.D Again, while not being bound by any particular theory of operation, initiation and propagation of the oxidative process can proceed through allylic hydrogen. In certain embodiments, initiation can proceed through monoallylic hydrogen. In certain embodiments, initiation can proceed through bisallylic hydrogen. Initiation and propagation of the oxidative process with monoallylic hydrogen can be slower than that with bisallylic hydrogen. Exemplary monoallylic and bisallylic mechanisms are illustrated schematically in Scheme I.E.

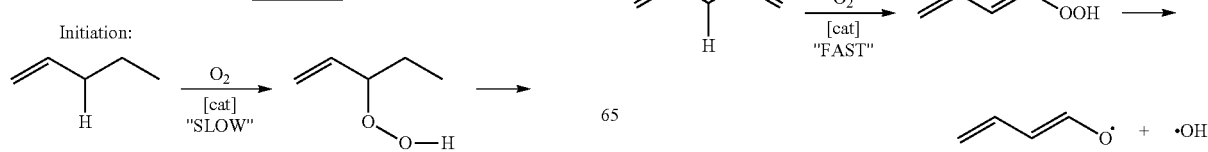

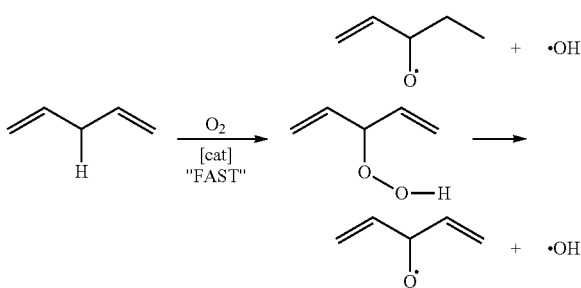

Propagation:

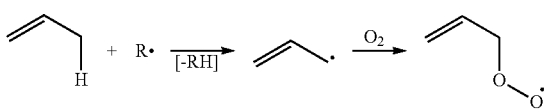

For example, the rate of abstraction of a bisallylic hydrogen may be about 100 times (or even greater) than the rate of abstraction of a monoallylic hydrogen. In some instances, an accelerator oxygen scavenger described herein or known in the art that comprises one or more bisallylic hydrogen may be initially active to create a sufficient concentration of reactive radical species to react with slower reacting monoallylic hydrogen to sustain the oxygen scavenging activity. In other instances an accelerator that has no bisallylic hydrogens and generates sufficient reactive species (e.g., reactive radicals) by another mechanism may be used to "kick start" oxygen scavenging activity by oxygen scavengers having only monoallylic hydrogens, fewer or less reactive bisallylic hydrogens, or activity by a certain portion of the molecule (e.g., abstraction of hydrogen from an isoprenoid tail). Through activating oxygen consumption by an oxygen scavenger, an accelerator may act to modulate timing of the oxygen scavenging activity (e.g., by increasing rate of oxygen uptake to reduce induction time) and/or oxygen scavenging capacity of an oxygen scavenger. Increasing oxygen scavenging capacity of an oxygen scavenger may allow less of that oxygen scavenger to be used to achieve desired oxygen scavenging capacity and lifetime, or increased capacity may allow formation of oxygen scavenging articles with extended lifetime.

In some cases, an electron-withdrawing group in a conjugated relationship with the carbon-carbon double bond of an allyl group may affect the energy required to abstract or the rate of abstraction of an allylic or bisallylic hydrogen located on the opposite end of the allyl group. This is illustrated in Scheme I.F below, where $R_w$ represents an electron-withdrawing substituent, and R represents H or any suitable hydrocarbyl group. Non-limiting examples of electron-withdrawing substituents $R_w$ that may be used to tune reactivity of allylic or bisallylic hydrogens when in a conjugated relationship with the double bond of an allyl group include ester groups and cyano groups.

Scheme I.F.

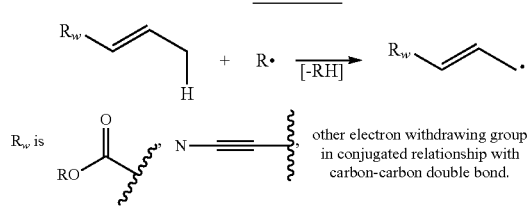

In some compositions, the oxygen scavengers (which may be single molecules, oligomers or polymers) are dispersed in a host polymer to form what is best characterized as a homogeneous mixture, i.e., without discernible phase separated domains. In other compositions, the oxygen scavenging molecules or oxygen scavenging polymers form phase separated domains in the host polymer matrix. In some cases, formation of phase separated oxygen scavenging domains in the host polymer matrix is preferred as such compositions may exhibit shortened or no induction times and/or require reduced amounts of oxygen scavenger to accomplish desired oxygen scavenging activity. Morphology of oxygen scavenging compositions may be modulated through the design of the oxygen scavenger itself (e.g., selecting chemical structure of oxygen scavenger to tune miscibility or compatibility with the host polymer) and/or through the use of additives such as surfactants, compatibilizers, or the like.

The oxygen scavenging compositions described herein may be used to produce articles (e.g., containers, bottles, jars, lids, pouches, bags, trays, films or packages) for storing oxygen sensitive substances. The oxygen scavenging compositions are capable of consuming or otherwise reducing the amount of oxygen that is transmitted through the container or package walls, and are also capable of consuming or otherwise reducing the amount of oxygen that may be initially present within the container or package (e.g., oxygen present in the headspace, oxygen present in the oxygen sensitive substance to be stored or in the container itself, and the like). Storage of oxygen sensitive substances in containers and packages described herein may increase shelf life and reduce handling requirements for oxygen sensitive substances. Certain variations of oxygen scavenging compositions described herein may be useful for making bottles, films, jars, trays, bags, pouches, lids or other containers or packaging articles for storing oxygen sensitive beverages (e.g., juice and/or beer), oxygen sensitive foods, oxygen sensitive cosmetics, oxygen sensitive pharmaceuticals, oxygen sensitive electronics, and the like.

Described below in Section A) are oxygen scavenging molecules, and methods for making the same. Described below in Section B) are polymers in which oxygen scavenging moieties are incorporated into polymeric structures, and methods for making the same. Described below in Section C) are oxygen scavenging compositions and methods for making the same. Described below in Section D) are articles utilizing the oxygen scavenging compositions and methods for making articles. It should be understood that these Section designations are for organizational purposes only and are non-limiting, e.g., any of the oxygen scavengers described in Section A may be suitable for use for making oxygen scavenging polymers described in Section B, and any of the oxygen scavenging molecules of Section A or any of the oxygen scavenging polymers of Section B may be suitable for use in making compositions using the host polymers described in Section C, and any of the compositions described in Section C may be suitable for making any of the articles described in Section D.

A. Oxygen Scavenging Molecules

The oxygen scavengers described in this section A may be physically blended with a host polymer, such that there is little or no chemical bonding with the host polymer. In other variations, the oxygen scavengers described in this Section A may be oligomerized, polymerized, or reacted with one or more coreactants to form oligomers or polymers. For example, one or more oxygen scavengers described in this Section A may be reacted with one or more comonomers to form an oxygen scavenging oligomer or polymer. In some variations, one or more oxygen scavengers described in this Section A may react to form covalent bonds with a host polymer (e.g., via reaction with polymer end groups or via grafting) to form an oxygen scavenging oligomer or polymer. Oxygen scavenging polymers are described in more detail in Section B below.

In some embodiments, described herein are oxygen scavengers having formula (I):

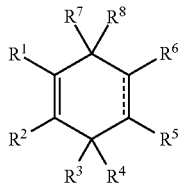

where $R^1$, $R^2$, $R^3$, $R^4$, $R^5$, $R^6$, $R^7$ and $R^8$ are independently H, or a saturated or unsaturated, linear or branched, cyclic or acyclic, aliphatic or aryl, unsubstituted or substituted hydrocarbyl group, n=1, 2, 3, 4, or 5, with the provisos that: i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tail having formula

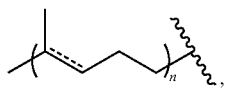

where n=1, 2, 3, 4, or 5 and/or formula

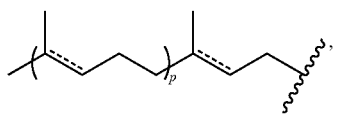

where p=0, 1, 2, 3, or 4. In some variations, one or more of the substituents $R^1$, $R^2$, $R^3$, $R^4$, $R^5$, $R^6$, $R^7$ and $R^8$ may include one or more heteroatoms, e.g., one or more of O, N, S, P, Cl, I, and Br. In some cases, there are no covalent bond bridges between carbon atoms of the six-membered ring. It should be understood that in some variations, $R^5$ and $R^6$ may together form a cyclic structure that optionally includes one or more heteroatoms. For example, $R^5$ and $R^6$ together may form a cyclic structure (e.g., a five-membered ring or a six-membered ring) that comprises one or more of O, N, S, and P. In some variations, $R^5$ and $R^6$ together form a five-membered heterocyclic ring that comprises O. In some variations, $R^5$ and $R^6$ together form a five-membered heterocyclic ring that comprises N. In some variations, an oxygen scavenger has formula (I) and at least one of $R^1$, $R^2$, $R^3$, $R^4$, $R^5$, $R^6$, $R^7$, and $R^8$ is covalently bonded to a polymer chain as portion of the main chain and/or as a side chain.

As described above, in some variations, an oxygen scavenger comprises multiple allylic or multiple bisallylic hydrogens bonded to carbons forming the six-membered ring of compounds having formula (I). In such cases, two or more of $R^3$, $R^4$, $R^7$ and $R^8$ are hydrogen. In some cases, an oxygen scavenger comprises two allylic hydrogens or two bisallylic hydrogens bonded to carbons forming the ring, so that each of $R^7$ and $R^8$ are hydrogen, each of $R^3$ and $R^4$ are hydrogen, or one of $R^3$ and $R^7$ is hydrogen and one of $R^4$ and $R^8$ is hydrogen. In some cases, an oxygen scavenger comprises three allylic hydrogens or three bisallylic hydrogens bonded to carbons forming the ring, so that any combination of three of $R^3$, $R^4$, $R^7$ and $R^8$ are hydrogen. In some cases, an oxygen scavenger comprises four allylic hydrogens or four bisallylic hydrogens bonded to carbons forming the ring, so that each of $R^3$, $R^4$, $R^7$ and $R^8$ are hydrogen.

In some embodiments, an oxygen scavenger has formula (I) wherein $R^1$, $R^4$, and $R^8$ are each hydrogen, and $R^2$ has formula

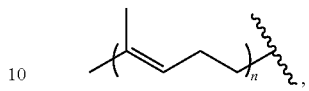

with n=1, 2, 3, 4, or 5, so that the oxygen scavenger has formula (II):

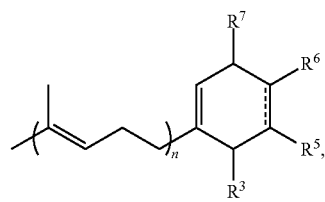

where n, p, $R^3$, $R^5$, $R^6$ and $R^7$ are as described for formula (I). In some variations, $R^7$ is an isoprenoid tail having structure

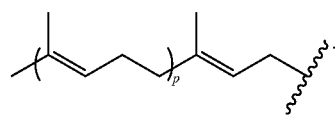

In some cases, an oxygen scavenger has formula (II) with $R^5$ and $R^6$ each being carboxylate ester groups, cyano groups, halide groups (e.g., Cl, Br or I), or acyl halide (e.g., acyl chloride) groups.

In some embodiments, an oxygen scavenger has formula (I) wherein $R^1$, $R^4$, and $R^8$ are each H, $R^2$ has formula

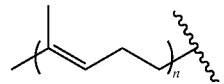

with n=1, 2, 3, 4, or 5, and $R^5$ and $R^6$ together form a five-membered ring so that the oxygen scavenger has formula (III):

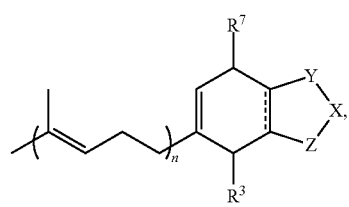

wherein: n, p, $R^3$ and $R^7$ are as described for formula (I); X is O, $NR^9$, S, PR', or PR'R''R'''; and one of Y and Z is C=O, and the other of Y and Z is C=O or $CR^{10}R^{11}$, where $R^9$, $R^{10}$, $R^{11}$, R', R'', and R''' are independently H, or a saturated or unsaturated, linear or branched, cyclic or acyclic, aliphatic or aryl, unsubstituted or substituted hydrocarbyl group. In some variations, one of Y and Z is C=O or CH$_2$, the other of Y and Z is C=O, and X is O, NR$^9$, S or PR', or PR'R"R'". In some variations, R$^7$ is an isoprenoid tail having structure

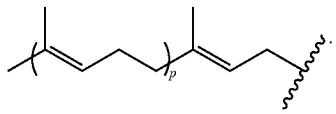

As described above, certain oxygen scavengers may comprise four allylic hydrogens or four bisallylic hydrogens bonded to carbons of a six-membered ring, which may correspond to oxygen scavengers having formula (I), (II), and (III) in which R$^3$, R$^4$, R$^7$, and R$^8$ are each H. The corresponding formulae are (I-1), (II-1), and (III-1):

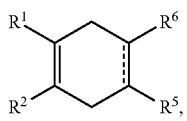

(I-1)

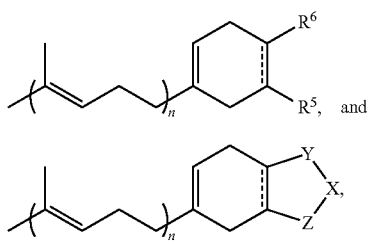

(II-1)

(III-1)

wherein R$^1$, R$^2$, R$^5$, R$^6$, n and p are independently as described for formula (I), and X, Y and Z are as described for formula (III). Formulae (I-1'), (II-1') and (III-1') correspond to oxygen scavengers having four allylic hydrogens bonded to carbons of the six-membered ring. Formula (I-1"), (II-1") and (III-1") correspond to oxygen scavengers having four bisallylic hydrogens bonded to carbons of the six-membered ring:

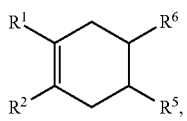

(I-1')

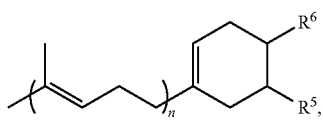

(II-1')

(III-1')

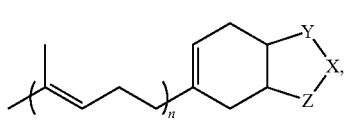

(I-1")

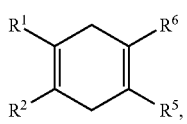

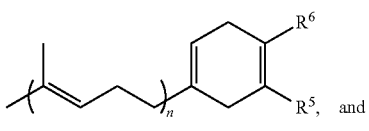

(II-1")

and (III-1")

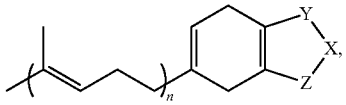

wherein R$^1$, R$^2$, R$^5$, R$^6$, n and p are independently as described for formula (I), and X, Y and Z are as described for formula (III).

In some cases, an oxygen scavenger comprises a mixture comprising two or more compounds having formula (I). For example, an oxygen scavenger may comprise a mixture comprising two or more compounds having formula (I'), two or more compounds having formula (I"), or one or more compounds having formula (I') and one or more compounds having formula (I"):

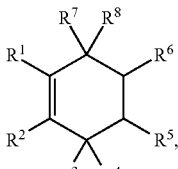

(I')

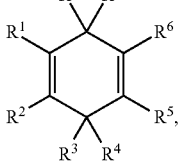

(I")

where R$^1$, R$^2$, R$^3$, R$^4$, R$^5$, R$^6$, R$^7$, R$^8$, n and p are independently as described for formula (I). It should be understood that for an oxygen scavenger comprising a mixture of two or more compounds having formula (I), the substituents R$^1$, R$^2$, R$^3$, R$^4$, R$^5$, R$^6$, R$^7$ and R$^8$, and n and p may be varied independently between each component of the mixture.

In some cases, an oxygen scavenger comprises a mixture comprising two or more compounds having formula (II), e.g., two or more compounds having formula (II'), two or more compounds having formula (II"), one or more compounds having formula (II') and one or more compounds having formula (II"):

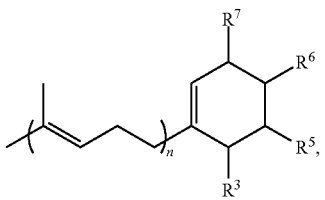

(II')

(II″)

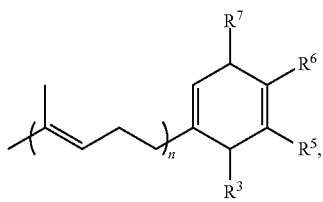

where $R^3$, $R^5$, $R^6$, $R^7$, n and p are independently as described for formula (I). It should be understood that for an oxygen scavenger comprising a mixture comprising two or more compounds having formula (II), the substituents $R^3$, $R^5$, $R^6$, $R^7$, and n and p may be varied independently between each component of the mixture.

In some cases, an oxygen scavenger comprises a mixture comprising two or more compounds having formula (III), e.g., two or more compounds having formula (III′), two or more compounds having formula (III″), or one or more compounds having formula (III′) and one or more compounds having formula (III″):

(III′)

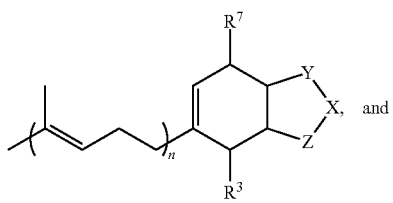 and (III″)

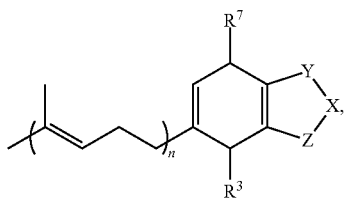

where $R^3$, $R^7$, X, Y, Z, n and p are independently as described for formula (III). It should be understood that for an oxygen scavenger comprising two or more compounds having formula (III), the substituents $R^3$, $R^7$, X, Y, Z, n and p may be varied independently between each component of the mixture.

Additional mixtures of two or more compounds of formula (I) to make an oxygen scavenger are contemplated. For example, in some variations, an oxygen scavenger comprises a mixture comprising one or more compounds having formula (II) and one or more compounds having formula (III), e.g., a mixture comprising one or more compounds of formula (II′) and one or more compounds of formula (III′), one or more compounds of formula (II′) and one or more compounds of formula (III″), one or more compounds of formula (II″) and one or more compounds of formula (III′), or one or more compounds of formula (II″) and one or more compounds of formula (III″).

In certain cases, an oxygen scavenger has formula (II) wherein $R^3$ and $R^7$ are each H and $R^5$ and $R^6$ are each carboxylate ester groups such that an oxygen scavenger has formula (II-2):

(II-2)

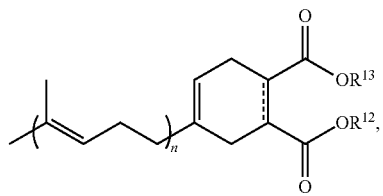

where n=1, 2, 3, 4 or 5, and $R^{12}$ and $R^{13}$ are independently H, or any saturated or unsaturated, aliphatic or aryl, linear or branched, cyclic or acyclic, unsubstituted or substituted hydrocarbyl group. $R^{12}$ and $R^{13}$ may be the same or different. In some variations, $R^{12}$ and $R^{13}$ are each independently $C_1$-$C_{20}$ linear, branched or cyclic alkyl groups. In some variations, $R^{12}$ and $R^{13}$ are each independently hydrogen, methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, one or both of $R^{12}$ and $R^{13}$ is benzyl. In some variations, one or both of $R^{12}$ and $R^{13}$ comprises an alkoxylate chain (e.g., ethoxylate or propoxylate). Alkoxylate chains may have any suitable number or average number of repeat units, e.g., 1-10 or 1-20 repeat units. The alkoxylate chains may be terminated with a hydroxyl group or an alkoxyl group (e.g., alkoxylate chains may be methoxy capped).

In some variations, an oxygen scavenger comprises a compound having formula (II-2′):

(II-2′)

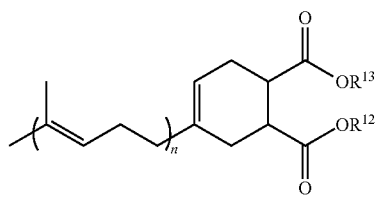

where $R^{12}$, $R^{13}$ and n are as described for formula (II-2).

In some variations, an oxygen scavenger comprises a compound having formula (II-2″):

(II-2″)

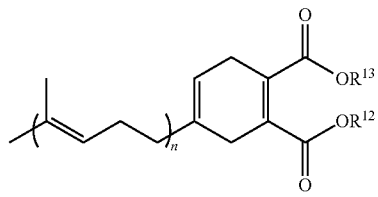

where $R^{12}$, $R^{13}$ and n are as described for formula (II-2).

In some embodiments, an oxygen scavenger comprises two or more compounds having formula (II-2). In some variations, an oxygen scavenger comprises two or more compounds having formula (II-2'), in some variations, an oxygen scavenger comprises two or more compounds having formula (II-2"), and in some variations, an oxygen scavenger comprises one or more compounds having formula (II-2') and one or more compounds having formula (II-2").

Non-limiting examples of oxygen scavengers having formulae (II-2), (II-2'), and (II-2") are shown in Tables 1A and 1B below. For each of the formulae shown in Tables 1A and 1B, n=1, 2, 3, 4, or 5. In some variations, an oxygen scavenger comprises a mixture comprising two or more compounds from Table 1A. Referring to Table 1B, in some variations, an oxygen scavenger comprises a mixture comprising two or more compounds from column 1, two or more compounds from column 2, or one or more compounds from column 1 and one or more compounds from column 2.

TABLE 1A

Non-limiting examples of oxygen scavengers having formula (II-2)

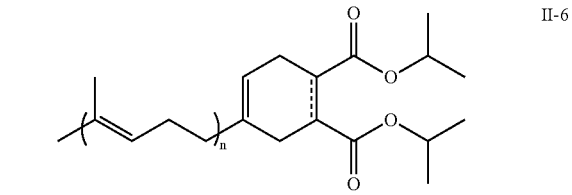
II-3

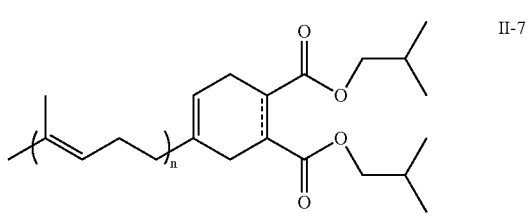
II-4

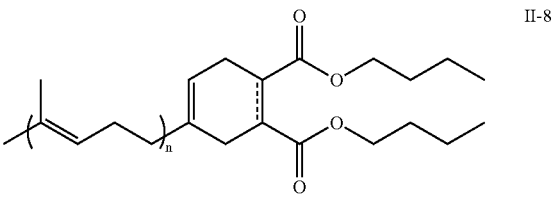
II-5

TABLE 1A-continued

Non-limiting examples of oxygen scavengers having formula (II-2)

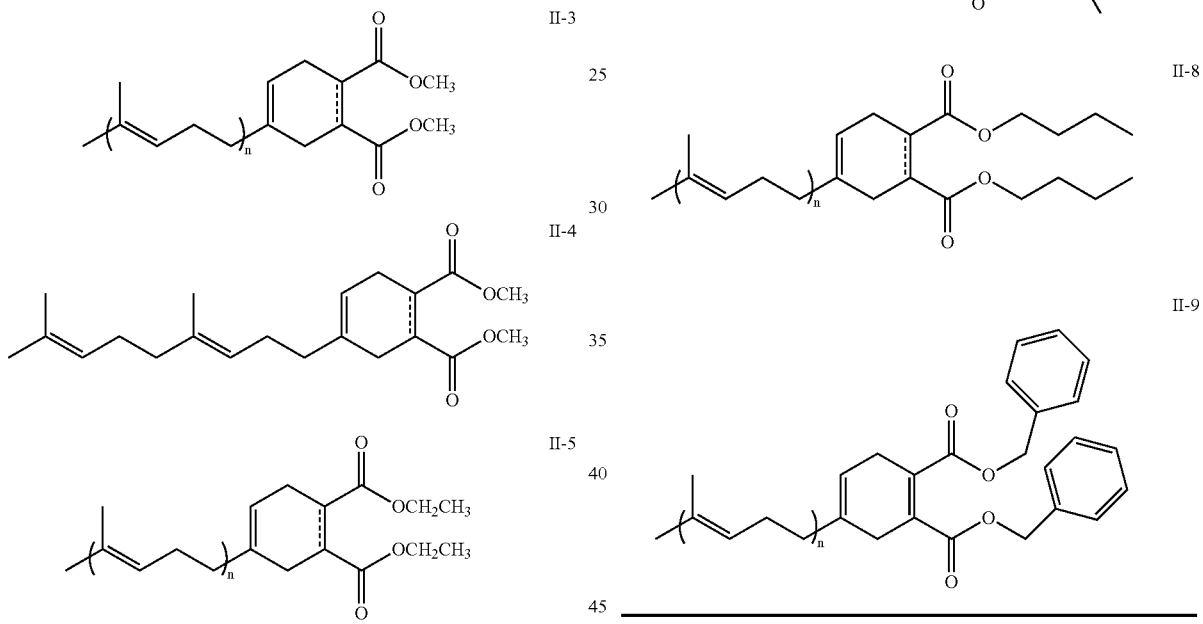

II-6

II-7

II-8

II-9

TABLE 1B

Non-limiting examples of oxygen scavengers having formula (II-2') or (II-2")

| Column 1<br>Oxygen scavengers having formula (II-2') | Column 2<br>Oxygen scavengers having formula (II-2") |
|---|---|
| II-3' | II-3" |

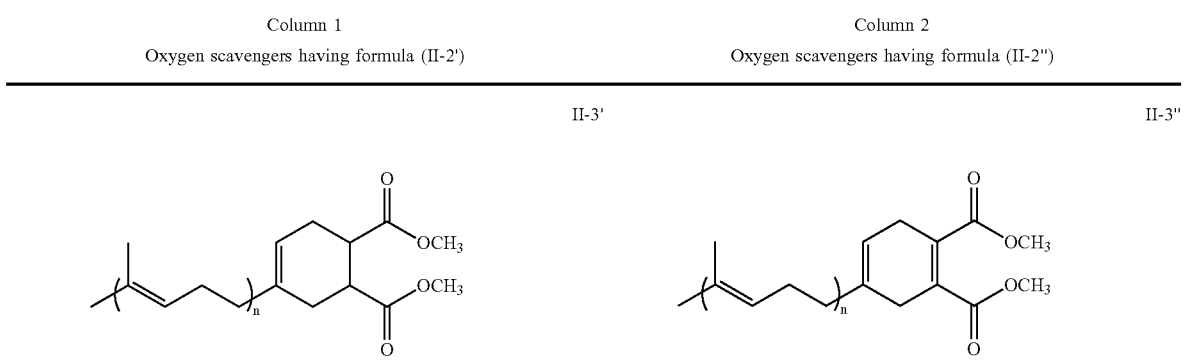

TABLE 1B-continued

Non-limiting examples of oxygen scavengers having formula (II-2') or (II-2")

| Column 1<br>Oxygen scavengers having formula (II-2') | Column 2<br>Oxygen scavengers having formula (II-2") |
|---|---|
| II-4' | II-4" |
| II-5' | II-5" |
| II-6' | II-6" |
| II-7' | II-7" |
| II-8' | II-8" |
| II-9' | II-9" |

In some cases, an oxygen has formula (II) wherein $R^3$ and $R^7$ are each H, one of $R^5$ and $R^6$ is H and the other of $R^5$ and $R^6$ is a carboxylate ester group such that the oxygen scavenger has formula (II-10):

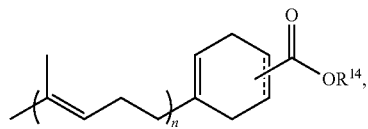
(II-10)

where n=1, 2, 3, 4, or 5 and $R^{14}$ is H, or any saturated or unsaturated, aliphatic or aryl, linear or branched, cyclic or acyclic, unsubstituted or substituted hydrocarbyl group. In some variations, $R^{14}$ is a $C_1$-$C_{20}$ linear, branched or cyclic alkyl groups. In some variations, $R^{14}$ is methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, $R^{14}$ is benzyl. In some variations, $R^{14}$ comprises an alkoxylate chain (e.g., ethoxylate or propoxylate). An alkoxylate chain may have any suitable number or average number of repeat units, e.g., 1-10 or 1-20 repeat units. An alkoxylate chain may be terminated with a hydroxyl group or an alkoxyl group (e.g., an alkoxylate chain may be methoxy capped). Formula (II-10) represents compounds having formula (II-10a), compounds having formula (II-10b), or a mixture thereof:

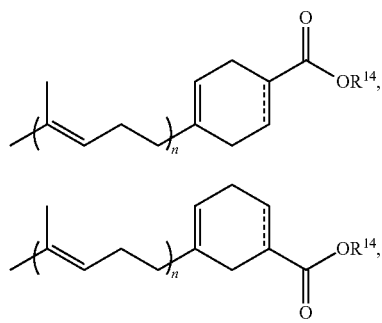
(II-10a)

(II-10b)

where any relative amounts of each may be present, e.g., limited amounts of or no (II-10a), limited amounts of or no (II-10b), or a ratio of (II-10a):(II-10b) of about 100:1, 50:1, 20:1, 10:1, 5:1, 2:1, 1:1, 1:2, 1:5, 1:10, 1:20, 1:50, or 1:100.

In some variations, an oxygen scavenger comprises a compound having formula (II-10'):

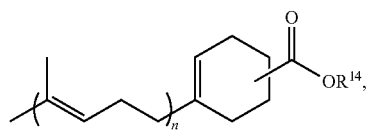
(II-10')

where $R^{14}$ and n are as described for formula (II-10). Formula (II-10') represents a compound having formula (II-10a'), a compound having formula (II-10b'), or a mixture thereof:

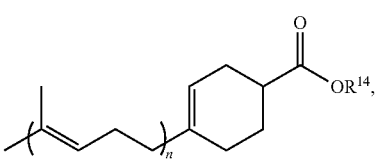
(II-10a')

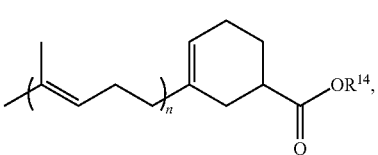
(II-10b')

where any relative amounts of each may be present, e.g., limited amounts of or no (II-10a'), limited amounts of or no (II-10b), or a ratio of (II-10a'):(II-10b') of about 100:1, 50:1, 20:1, 10:1, 5:1, 2:1, 1:1, 1:2, 1:5, 1:10, 1:20, 1:50, or 1:100.

In some variations, an oxygen scavenger comprises or is derived from a compound having formula (II-10"):

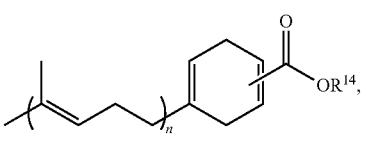
(II-10")

where $R^{14}$ and n are as described for formula (II-10). Formula (II-10") represents a compound having formula (II-10a"), a compound having formula (II-10b"), or a mixture thereof:

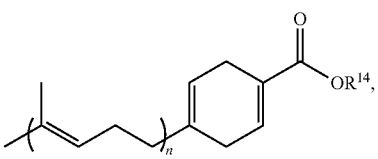
(II-10a")

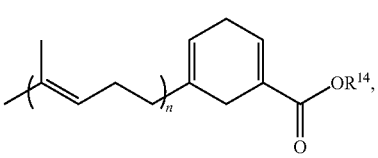
(II-10b")

where any relative amounts of each may be present, e.g., limited amounts of or no (II-10a"), limited amounts of or no (II-10b"), or a ratio of (II-10a"):(II-10b") of about 100:1, 50:1, 20:1, 10:1, 5:1, 2:1, 1:1, 1:2, 1:5, 1:10, 1:20, 1:50, or 1:100.

In some embodiments, an oxygen scavenger comprises a mixture comprising two or more compounds having formula (II-10), e.g., two or more compounds having formula (II-10'), two or more compounds having formula (II-10"), or one or more compounds having formula (II-10') and one or more compounds having formula (II-10").

Non-limiting examples of oxygen scavengers of formula (II-10), (II-10') and (II-10") are provided in Tables 2A and 2B. For each of the formulae shown in Tables 2A and 2B, n=1, 2, 3, 4, or 5. In some variations, an oxygen scavenger comprises a mixture comprising two or more compounds from Table 2A. Referring to Table 2B, in some variations, an oxygen scavenger comprises a mixture comprising two or more compounds from column 1, two or more compounds from column 2, or one or more compounds from column 1 and one or more compounds from column 2

TABLE 2A

Non-limiting examples of oxygen scavengers having formula (II-10)

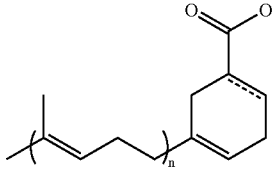

and/or II-11

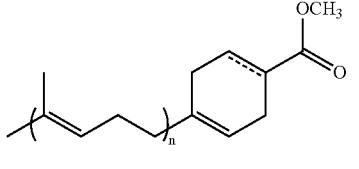

and/or II-12

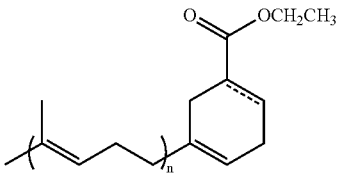

and/or II-13

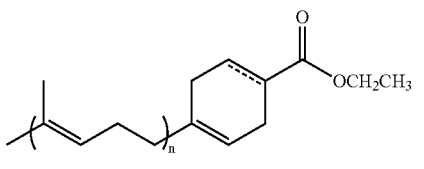

and/or II-14

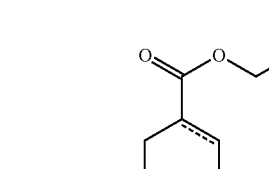

and/or II-15

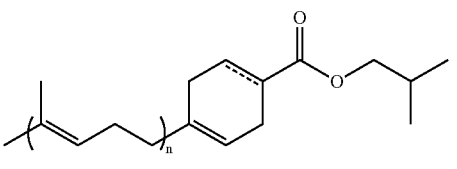

and/or II-16

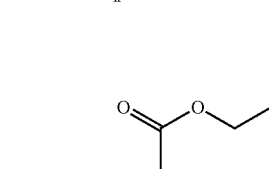

and/or II-17

TABLE 2B
Non-limiting examples of oxygen scavengers having formula (II-10') or (II-10")
| Column 1<br>Oxygen scavengers having formula (II-10') | Column 2<br>Oxygen scavengers having formula (II-10") |
|---|---|
| 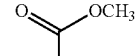 and/or <br>II-11' | 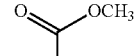 and/or <br>II-11" |
| 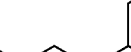 and/or 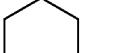<br>II-12' | 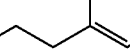 and/or 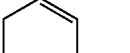<br>II-12" |
| 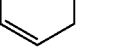 and/or <br>II-13' | 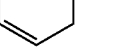 and/or 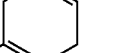<br>II-13" |
| 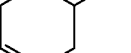 and/or <br>II-14' | 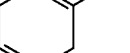 and/or <br>II-14" |

TABLE 2B-continued

Non-limiting examples of oxygen scavengers having formula (II-10') or (II-10")

| Column 1 Oxygen scavengers having formula (II-10') | Column 2 Oxygen scavengers having formula (II-10") |
|---|---|
| and/or | and/or |
| II-15' | II-15" |
| and/or | and/or |
| II-16' | II-16" |
| and/or | and/or |
| II-17' | II-17" |

In some embodiments, an oxygen scavenger has formula (II) wherein $R^3$ and $R^7$ are each H, and $R^5$ and $R^6$ are each hydroxyl groups or each comprise an ether linkage such that an oxygen scavenger has formula (II-18):

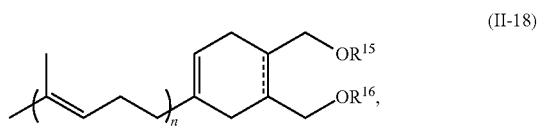

(II-18)

where n=1, 2, 3, 4 or 5, and $R^{15}$ and $R^{15}$ are independently H, or any saturated or unsaturated, aliphatic or aryl, linear or branched, cyclic or acyclic, unsubstituted or substituted hydrocarbyl group. $R^{15}$ and $R^{16}$ may be the same or different. In some variations, $R^{15}$ and $R^{16}$ are each independently $C_1$-$C_{20}$ linear, branched or cyclic alkyl groups. In some variations, $R^{15}$ and $R^{16}$ are each independently methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, one or both of $R^{15}$ and $R^{16}$ is benzyl. In some variations, one or both of $R^{15}$ and $R^{16}$ comprise an alkoxylate chain (e.g., ethoxylate or propoxylate). Alkoxylate chains may have any suitable number or average number of repeat units, e.g., 1-10 or 1-20 repeat units. The alkoxylate chains may be terminated with a hydroxyl group or an alkoxyl group (e.g., alkoxylate chains may be methoxy capped).

In some variations, an oxygen scavenger comprises a compound having formula (II-18'):

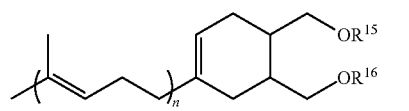

(II-18')

where $R^{15}$, $R^{16}$ and n are as described for formula (II-18).

In some variations, an oxygen scavenger comprises a compound having formula (II-18"):

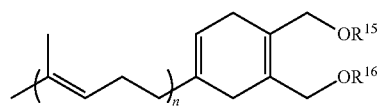

(II-18")

where $R^{15}$, $R^{16}$ and n are as described for formula (II-18).

In some embodiments, an oxygen scavenger comprises a mixture comprising two or more compounds having formula (II-18), e.g., two or more compounds having formula (II-18'), two or more compounds having formula (II-18"), or one or more compounds having formula (II-18') and one or more compounds having formula (II-18").

Non-limiting examples of oxygen scavengers of formula (II-18), (II-18') and (II-18") are provided in Tables 3A and 3B. For each of the formulae shown in Tables 3A and 3B, n=1, 2, 3, 4, or 5. In some variations, an oxygen scavenger comprises a mixture comprising two or more compounds from Table 3A. Referring to Table 3B, in some variations, an oxygen scavenger comprises a mixture comprising: (i) two or more compounds from column 1; (ii) two or more compounds from column 2; or (iii) one or more compounds from column 1 and one or more compounds from column 2

TABLE 3A

Non-limiting examples of oxygen scavengers having formula (II-18)

| | |
|---|---|
| 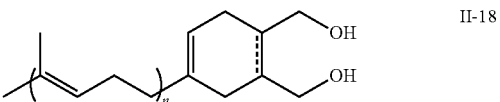 | II-18 |
| 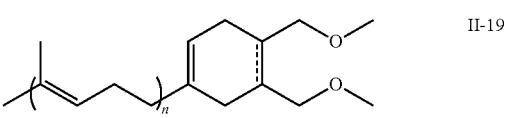 | II-19 |
| 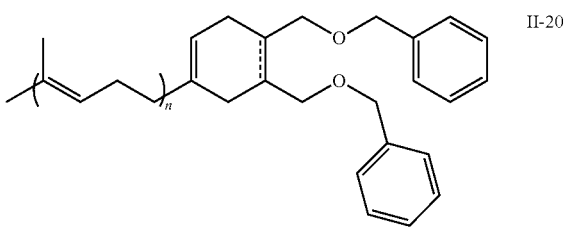 | II-20 |
| 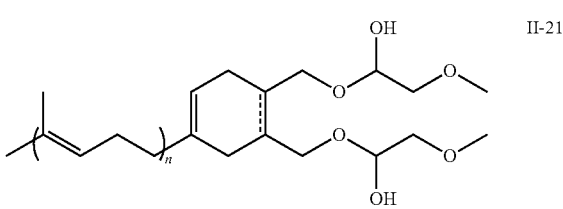 | II-21 |
| 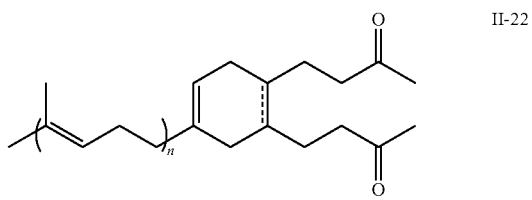 | II-22 |

TABLE 3B

Non-limiting examples of oxygen scavengers having formula (II-18') or (II-18")

| Column 1<br>Oxygen scavengers having formula (II-18') | Column 2<br>Oxygen scavengers having formula (II-18") |
|---|---|
| II-18' | II-18" |

TABLE 3B-continued

Non-limiting examples of oxygen scavengers having formula (II-18') or (II-18")

| Column 1<br>Oxygen scavengers having formula (II-18') | Column 2<br>Oxygen scavengers having formula (II-18") |
|---|---|
| 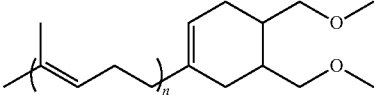<br>II-19' | 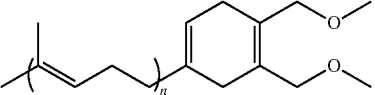<br>II-19" |
| 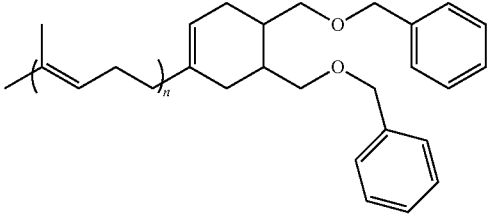<br>II-20' | 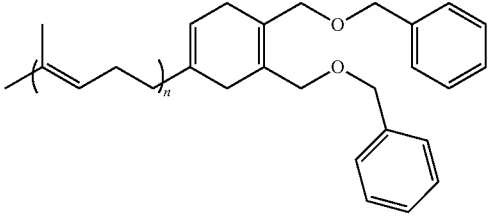<br>II-20" |
| 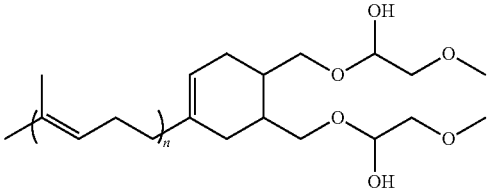<br>II-21' | 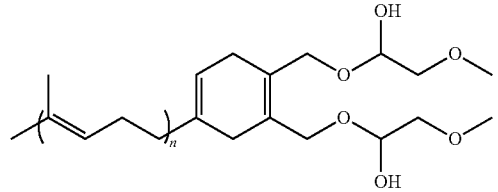<br>II-21" |
| 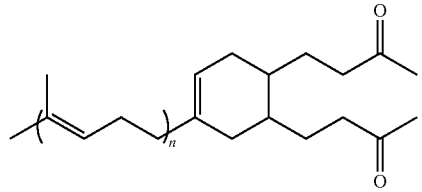<br>II-22' | 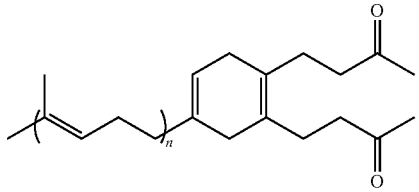<br>II-22" |

In some embodiments, an oxygen scavenger has formula (II) wherein $R^3$ and $R^7$ are each H, one of $R^5$ and $R^6$ is H, and the other of $R^5$ and $R^6$ is an amide group such that an oxygen scavenger has formula (II-23):

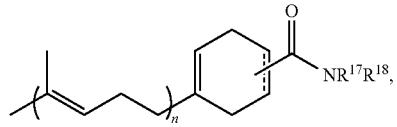

(11-23)

where n=1, 2, 3, 4, or 5, and $R^{17}$ and $R^{18}$ are independently H, or any saturated or unsaturated, aliphatic or aryl, linear or branched, cyclic or acyclic, unsubstituted or substituted hydrocarbyl group. $R^{17}$ and $R^{18}$ may be the same or different. In some variations, $R^{17}$ and $R^{18}$ are independently $C_1$-$C_{20}$ linear, branched or cyclic alkyl groups. In some variations, $R^{17}$ and $R^{18}$ are independently methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, $R^{17}$ and/or $R^{18}$ is benzyl. In some variations, $R^{17}$ and/or $R^{18}$ comprises an alkoxylate chain (e.g., ethoxylate or propoxylate). An alkoxylate chain may have any suitable number or average number of repeat units, e.g., 1-10 or 1-20 repeat units. An alkoxylate chain may be terminated with a hydroxyl group or an alkoxyl group (e.g., an alkoxylate chain may be methoxy capped). Formula (II-23) represents compounds of formula (II-23a), compounds of formula (II-23b), or a mixture thereof:

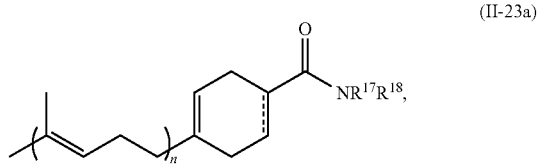

(II-23a)

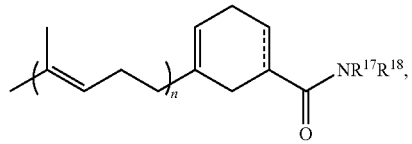
(II-23b)

where any relative amounts of each may be present, e.g., limited amounts of or no (II-23a), limited amounts of or no (II-23b), or a ratio of (II-23a):(II-23b) of about 100:1, 50:1, 20:1, 10:1, 5:1, 2:1, 1:1, 1:2, 1:5, 1:10, 1:20, 1:50, or 1:100.

In some variations, an oxygen scavenger comprises a compound having formula (II-23'):

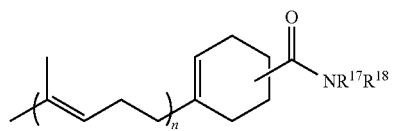
(II-23')

where $R^{17}$, $R^{18}$ and n are as described for formula (II-23). Formula (II-23') represents compounds of formula (II-23a'), compounds of formula (II-23b'), or a mixture thereof:

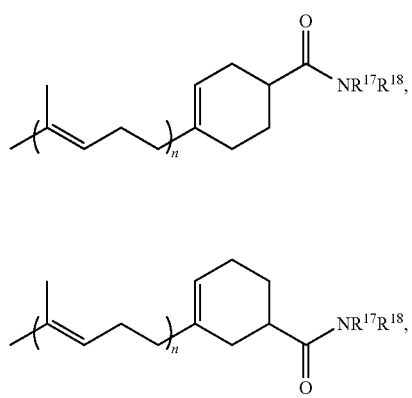
(II-23a')

(II-23b')

where any relative amounts of each may be present, e.g., limited amounts of or no (II-23a'), limited amounts of or no (II-23b'), or a ratio of (II-23a'):(II-23b') of about 100:1, 50:1, 20:1, 10:1, 5:1, 2:1, 1:1, 1:2, 1:5, 1:10, 1:20, 1:50, or 1:100.

In some variations, an oxygen scavenger comprises a compound having formula (II-23"):

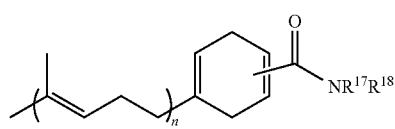
(II-23")

where $R^{17}$, $R^{18}$ and n are as described for formula (II-23). Formula (II-23") represents compounds of formula (II-23a"), compounds of formula (II-23b"), or a mixture thereof:

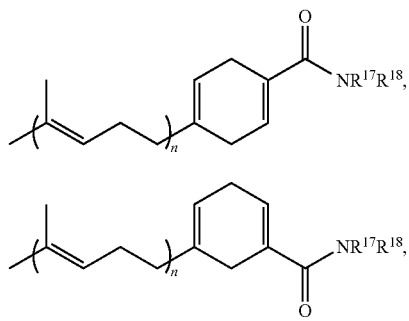
(II-23a")

(II-23b")

where any relative amounts of each may be present, e.g., limited amounts of or no (II-23a"), limited amounts of or no (II-23b"), or a ratio of (II-23a"):(II-23b") of about 100:1, 50:1, 20:1, 10:1, 5:1, 2:1, 1:1, 1:2, 1:5, 1:10, 1:20, 1:50, or 1:100.

In some embodiments, an oxygen scavenger comprises two or more compounds having formula (II-23). In some variations, an oxygen scavenger comprises two or more compounds having formula (II-23'), in some variations, an oxygen scavenger comprises two or more compounds having formula (II-23"), and in some variations, an oxygen scavenger comprises one or more compounds having formula (II-23') and one or more compounds having formula (II-23").

In some embodiments, an oxygen scavenger has formula (II) wherein $R^3$ and $R^7$ are each H, and each of $R^5$ and $R^6$ is an amide group such that an oxygen scavenger has formula (II-24):

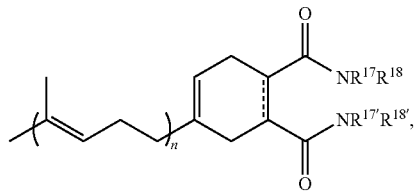
(II-24)

where n=1, 2, 3, 4, or 5, and $R^{17}$, $R^{18}$, $R^{17'}$ and $R^{18'}$ are independently H, or any saturated or unsaturated, aliphatic or aryl, linear or branched, cyclic or acyclic, unsubstituted or substituted hydrocarbyl group. $R^{17}$, $R^{18}$, $R^{17'}$, and $R^{18'}$ may be the same or different. In some variations, $R^{17}$, $R^{18}$, $R^{17'}$ and $R^{18'}$ are independently $C_1$-$C_{20}$ linear, branched or cyclic alkyl groups. In some variations, $R^{17}$, $R^{18}$, $R^{17'}$ and $R^{18'}$ are independently methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, $R^{17}$, $R^{18}$, $R^{17'}$ and/or $R^{18'}$ is benzyl. In some variations, $R^{17}$, $R^{18}$, $R^{17'}$ and/or $R^{18'}$ comprises an alkoxylate chain (e.g., ethoxylate or propoxylate). An alkoxylate chain may have any suitable number or average number of repeat units, e.g., 1-10 or 1-20 repeat units. An alkoxylate chain may be terminated with a hydroxyl group or an alkoxyl group (e.g., an alkoxylate chain may be methoxy capped).

In some embodiments, an oxygen scavenger has formula (II-24'):

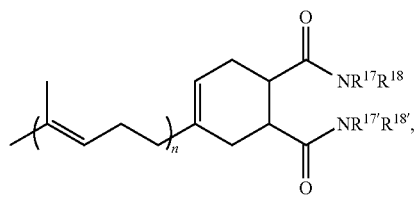
(II-24')

where n, $R^{17}$, $R^{18}$, $R^{17'}$ and $R^{18'}$ are as described for formula (II-24).

In some embodiments, an oxygen scavenger has formula (II-24"):

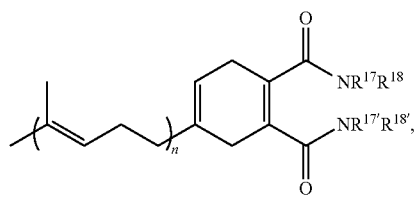
(II-24")

where n, $R^{17}$, $R^{18}$, $R^{17'}$ and $R^{18'}$ are as described for formula (II-24).

In some embodiments, an oxygen scavenger comprises two or more compounds having formula (II-24), e.g., two or more compounds having formula (II-24'), two or more compounds having formula (II-24"), and in some variations, an oxygen scavenger comprises one or more compounds having formula (II-24') and one or more compounds having formula (II-24").

In some embodiments, an oxygen scavenger has formula (II) with $R^3$ and $R^7$ each being H and each of W and $R^6$ is CN such that an oxygen scavenger has formula (II-25):

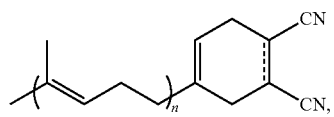
(II-25)

where n=1, 2, 3, 4 or 5.

In some embodiments, an oxygen scavenger has formula (II-25'):

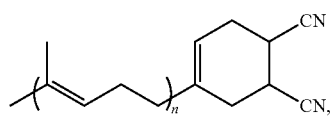
(II-25')

where n=1, 2, 3, 4 or 5.

In some embodiments, an oxygen scavenger has formula (II-25"):

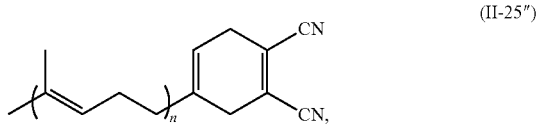
(II-25")

where n=1, 2, 3, 4 or 5.

In some embodiments, an oxygen scavenger comprises one or more compounds having formula (II-25') and one or more compounds having formula (II-25").

It should be understood that in some variations of compounds having formula (II), $R^5$ and $R^6$ may be different. For example, as illustrated in some non-limiting examples above, one of $R^5$ and $R^6$ may be H and the other of $R^5$ and $R^6$ may be any saturated or unsaturated, linear or branched, cyclic or acyclic, aliphatic or aryl, unsubstituted or substituted hydrocarbyl group, e.g., a carboxylate ester, an amide, or a cyano group. In some cases, $R^5$ and $R^6$ may be different and neither of $R^5$ and $R^6$ may be H. Non-limiting examples are provided as follows: one of $R^5$ and $R^6$ may be cyano and the other of $R^5$ and $R^6$ may be an amide (II-26a or II-26b); or one of $R^5$ and $R^6$ may be a carboxylate ester and the other of $R^5$ and $R^6$ may be —CH$_2$OH (II-27a or II-27b):

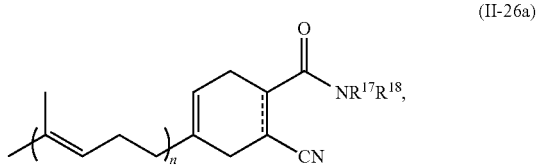
(II-26a)

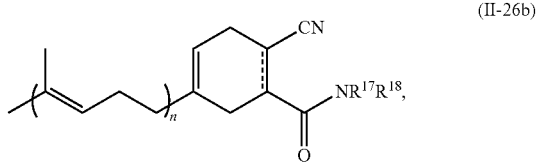
(II-26b)

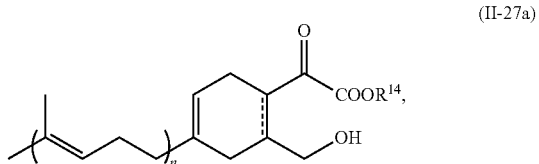
(II-27a)

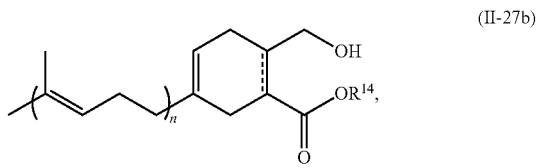
(II-27b)

where n, $R^{17}$ and $R^{18}$ are as described for formula (II-24), and n and $R^{14}$ are as described for formula (II-10).

In some cases, an oxygen scavenger has formula (III) with X being O and one of Y and Z being C=O and the other of Y and Z being C=O or CH$_2$. In some cases, an oxygen scavenger has formula (III) with X being NR$^9$ and one of Y and Z being C=O and the other of Y and Z being C=O or CH$_2$, where $R^9$ is H, or any saturated or unsaturated, aliphatic or aryl, linear or branched, cyclic or acyclic, unsubstituted or substituted hydrocarbyl group. In some variations, $R^9$ is a $C_1$-$C_{20}$ linear, branched or cyclic alkyl groups. In some variations, $R^9$ is methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylheptyl, 3-propylheptyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2 butylhexyl. In some variations, $R^9$ is benzyl. In some variations, $R^9$ comprises an alkoxylate chain (e.g., ethoxylate or propoxylate). Alkoxylate chains may have any suitable number or average number of repeat units, e.g., 1-10 or 1-20 repeat units. The alkoxylate chains may be terminated with a hydroxyl group or an alkoxyl group (e.g., alkoxylate chains may be methoxy capped).

Non-limiting examples of oxygen scavengers having formula (III), (III') and (III") are shown in Tables 4A and 4B. For the formulae shown in Tables 4A and 4B, n=1, 2, 3, 4, or 5 and n'=1, 2, 3, 4, or 5, n and n' may be the same or different for a given compound, and $R^9$ is as described in the preceding paragraph. In some cases, n=2. For compounds III-8, III-8', and III-8", n and n' may be the same or different. In some cases, n and n' are each 2. In some variations, an oxygen scavenger comprises a mixture comprising two or more compounds from Table 4A. Referring to Table 4B, in some variations, an oxygen scavenger comprises a mixture comprising two or more compounds from column 1, two or more compounds from column 2, or one or more compounds from column 1 and one or more compounds from column 2

TABLE 4A

Non-limiting examples of oxygen scavengers having formula (III)

III-2

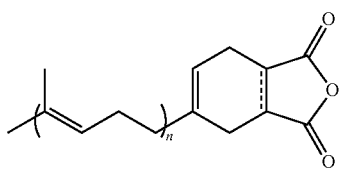

III-3

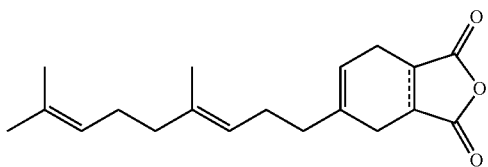

III-4

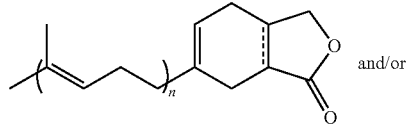

and/or

TABLE 4A-continued

Non-limiting examples of oxygen scavengers having formula (III)

III-5

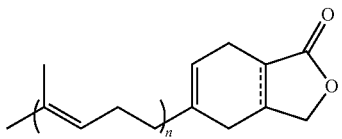

III-6

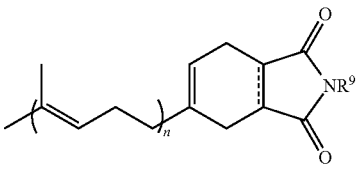

III-7

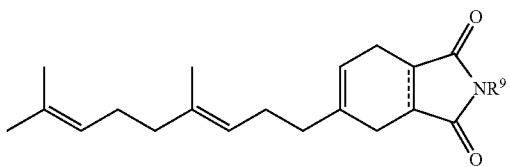

III-8

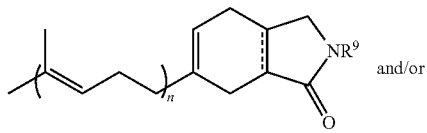

and/or

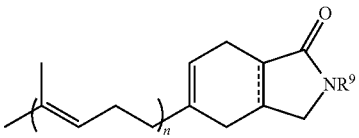

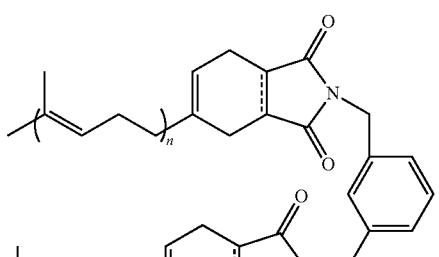

TABLE 4B
Non-limiting examples of oxygen scavengers having formula (III') or (III")
| Column 1<br>Oxygen scavengers having formula (III') | Column 2<br>Oxygen scavengers having formula (III") |
|---|---|
| 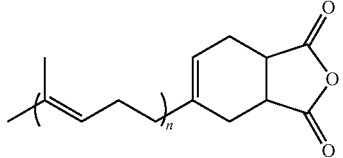<br>III-2' | 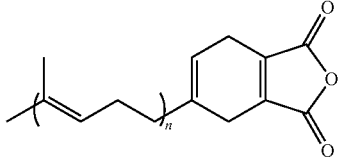<br>III-2" |
| 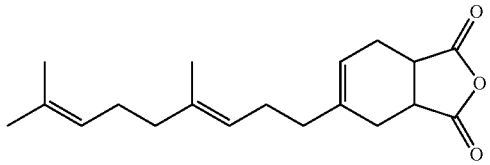<br>III-3' | 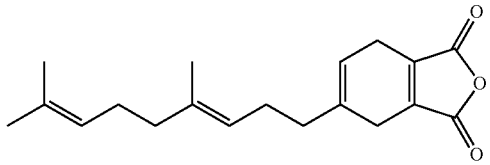<br>III-3" |
| 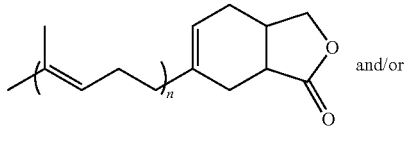 and/or<br>III-4' | 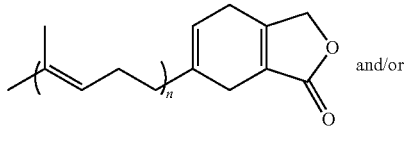 and/or<br>III-4" |
| 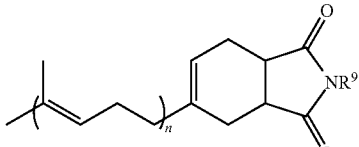<br>III-5' | 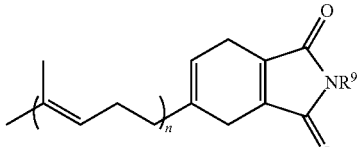<br>III-5" |
| 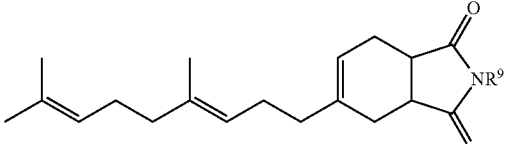<br>III-6' | 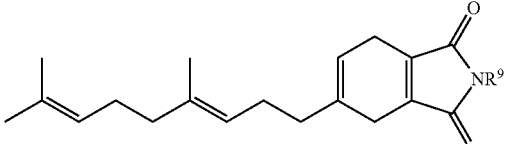<br>III-6" |
| 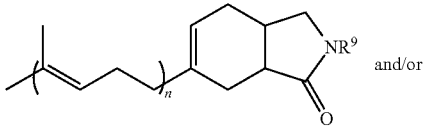 and/or<br>III-7' | 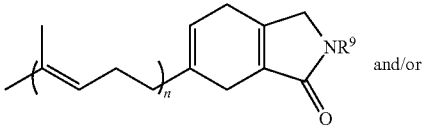 and/or<br>III-7" |

TABLE 4B-continued

Non-limiting examples of oxygen scavengers having formula (III') or (III'')

| Column 1<br>Oxygen scavengers having formula (III') | Column 2<br>Oxygen scavengers having formula (III'') |
|---|---|
| 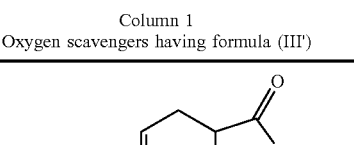<br>III-8' | 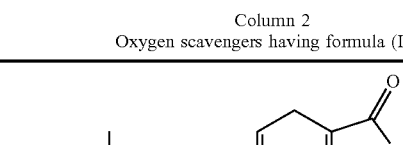<br>III-8'' |

In some cases, an oxygen has formula (II), (II'), (II''), (III), (III') or (III'') with $R^3$ being H and $R^7$ being an isoprenoid tail having formula where p=0, 1, 2, 3, or 4. Non-limiting examples are shown in Tables 5A and 5B. For compounds having formula (II-28), (II-28') and (II-28''), $R^{12}$ and $R^{13}$ are as for formula (II-2). For compounds having formula (III-9), (III-9'), or (III-9''), $R^9$ is as for formula (III-5). In some variations, an oxygen scavenger comprises a mixture of two or more compounds from Table 5A. Referring to Table 5B, in some variations, an oxygen scavenger comprises a mixture of two or more compounds from column 1, two or more compounds from column 2, or one or more compounds from column 1 and one or more compounds from column 2.

TABLE 5A

Non-limiting examples of oxygen scavengers having formula (II) or (III)

II-28

II-29

III-8

TABLE 5A-continued
Non-limiting examples of oxygen scavengers having formula (II) or (III)
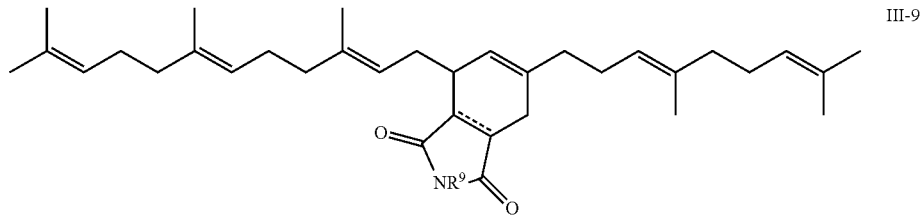
III-9
TABLE 5B
Non-limiting examples of oxygen scavengers having formula (II'), (II''), (III') or (III'')
Column 1
Oxygen scavengers having formula (II') or (III')
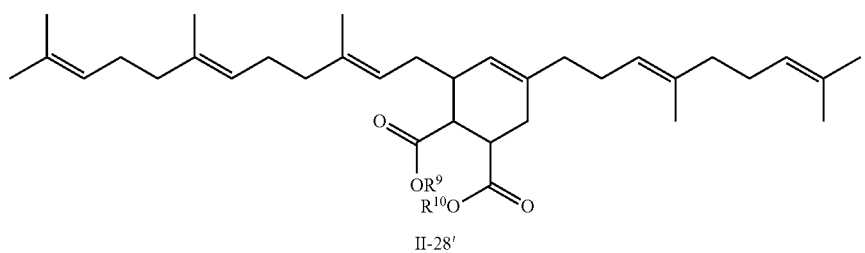
II-28'
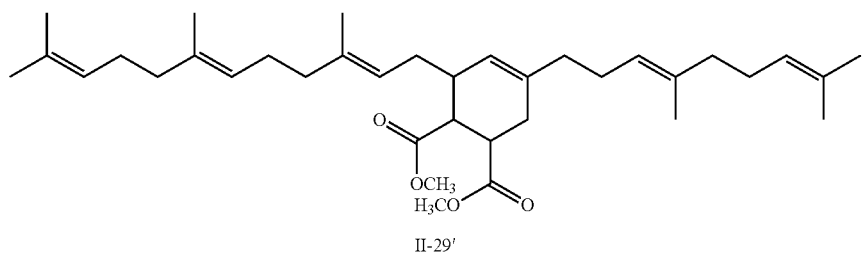 [SMILES: COC(=O)C1CC(CC/C=C(\C)CCC=C(C)C)=CC(C/C=C(\C)CC/C=C(\C)CCC=C(C)C)C1C(=O)OC]
II-29'
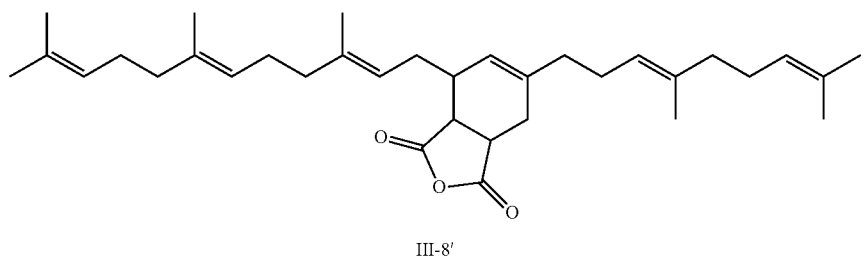 [SMILES: CC(C)=CCC/C(C)=C/CCC1=CC(C/C=C(\C)CC/C=C(\C)CCC=C(C)C)C2C(=O)OC(=O)C2C1]
III-8'
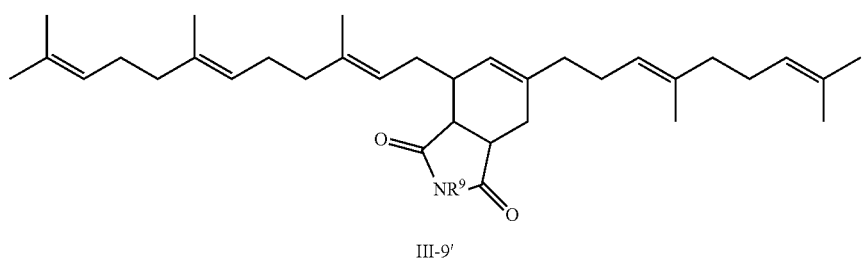
III-9'

TABLE 5B-continued

Non-limiting examples of oxygen scavengers having formula (II'), (II''), (III') or (III'')

Column 2
Oxygen scavengers having formula (II'') or (III'')

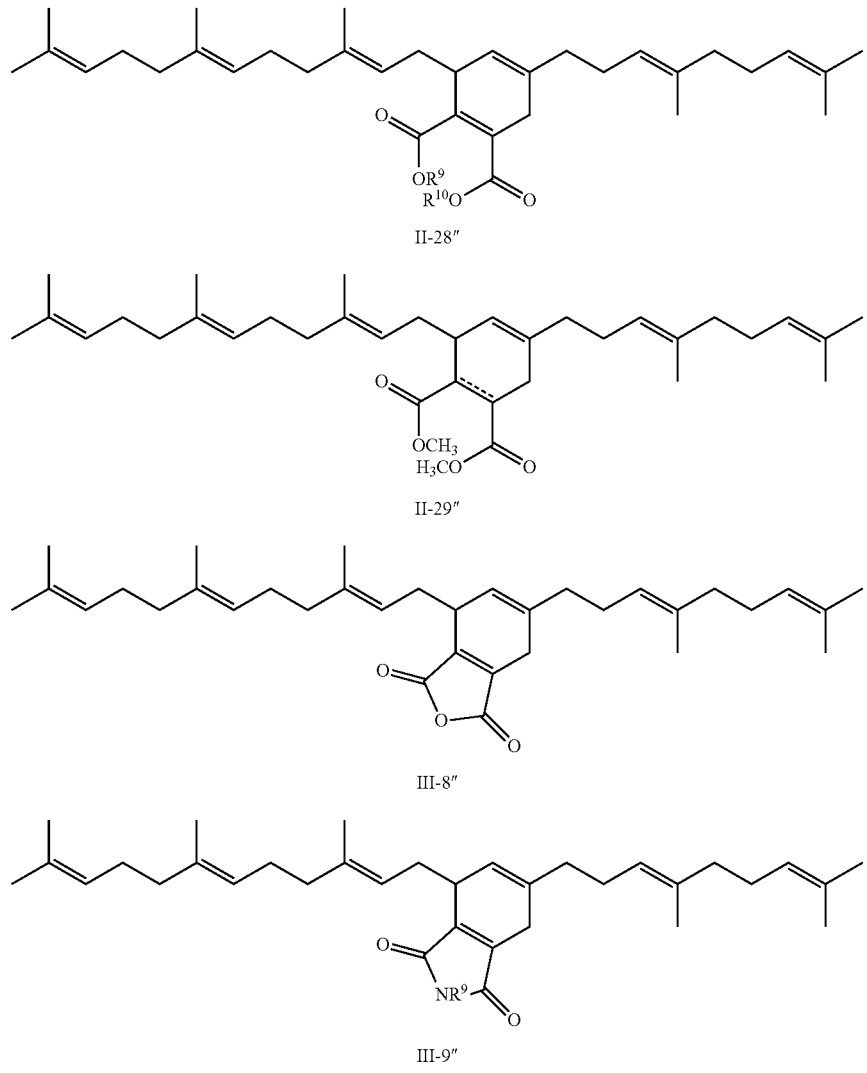

In some embodiments, an oxygen scavenger comprises two or more six-membered rings. Non-limiting examples include the oxygen scavengers of formula (IV), (V) and (VI), and Schemes A.1 and A.2 shown below.

Certain oxygen scavengers have formula (IV):

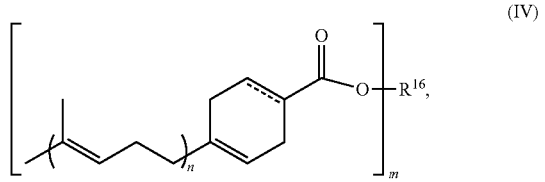

where n=2, 3, 4, or 5, m=1-20, and $R^{16}$ is any saturated or unsaturated, cyclic or acyclic, linear or branched, unsubstituted or substituted hydrocarbyl group. In some variations, $R^{16}$ is a $C_1$-$C_{10}$ alkyl group, e.g., methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylhexyl, 3-propylhexyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2-butylhexyl. In some variations, $R^{16}$ is methyl, ethyl, isopropyl, isobutyl, or benzyl. In some variations, $R^{16}$ is —$CH_2CH(OH)CH_3$, or —$(CH_2)_2C(O)CH_3$. In some variations, m=2 and $R^{16}$ is a radical of a diol. For example, and $R^{16}$ is —$CH_2CH_2$— for ethylene glycol, —$CH_2CH(CH_3)$— for propylene glycol, or

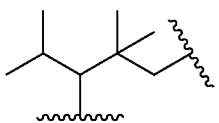

for 2,2,4-trimethyl-1,3-pentanediol. In some variations, m is greater than 2 and $R^{16}$ is a radical of a higher polyol, e.g., m=4 and $R^{16}$ is a radical for pentaerythritol.

Certain oxygen scavengers have formula (IV'):

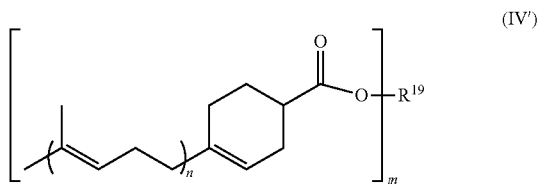

where $R^{19}$, n and m are as described above for compound (IV).

Certain oxygen scavengers have formula (IV"):

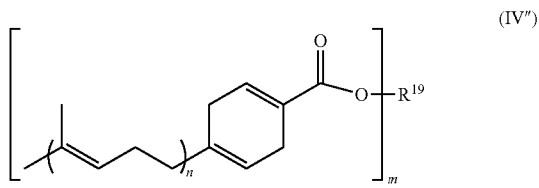

where $R^{19}$, n and m are as described above for compound (IV).

In some embodiments, an oxygen scavenger comprises a mixture comprising two or more compounds having formula (IV), e.g., an oxygen scavenger comprises two or more compounds having formula (IV), two or more compounds having formula (IV'), or one or more compounds having formula (IV) and one or more compounds having formula (IV").

Certain oxygen scavenging molecules have formula (V):

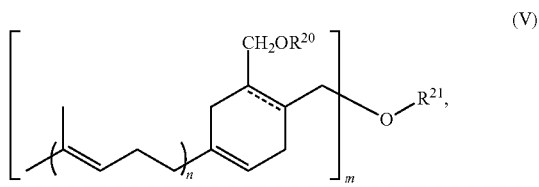

where n=1, 2, 3, 4 or 5, m=1-20, and $R^{20}$ and $R^{21}$ are independently any saturated or unsaturated, cyclic or acyclic, linear or branched, unsubstituted or substituted hydrocarbyl group. In some variations, $R^{21}$ is null. In some variations, $R^{20}$ and $R^{21}$ are independently a $C_1$-$C_{10}$ alkyl group, e.g., methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyl- octyl, 2-ethylheptyl, 3-ethylheptyl, 2-propylhexyl, 3-propylhexyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2-butylhexyl. In some variations, $R^{20}$ and $R^{21}$ are independently methyl, ethyl, isopropyl, isobutyl, or benzyl. In some variations, m=1 and $R^{20}$ and $R^{21}$ are each —$CH_2CH(OH)CH_3$, or —$(CH_2)_2C(O)CH_3$. In some variations, m=2, $R^{20}$ is null and $R^{21}$ is methyl, ethyl, isopropyl, isobutyl, benzyl, —$CH_2CH(OH)CH_3$, or —$(CH_2)_2C(O)CH_3$. In some variations, m=2 and $R^{21}$ is a radical of a diol. For example, and $R^{21}$ is —$CH_2CH_2$— for ethylene glycol, —$CH_2CH(CH_3)$— for propylene glycol, or

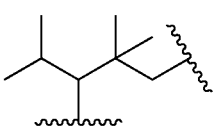

for 2,2,4-trimethyl-1,3-pentanediol. In some variations, m is greater than 2 and $R^{21}$ is a radical of a higher polyol, e.g., m=4 and $R^{21}$ is a radical for pentaerythritol.

Certain oxygen scavenging molecules have formula (V'):

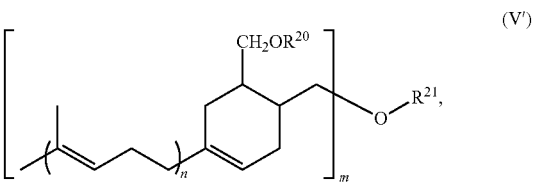

where n, m, $R^{20}$ and $R^{21}$ are as described above for formula (V).

Certain oxygen scavenging molecules have formula (V"):

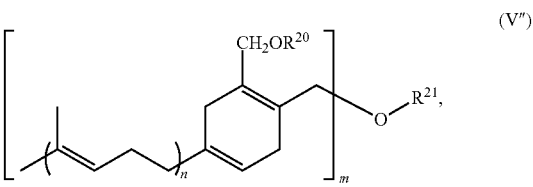

where n, m, $R^{20}$ and $R^{21}$ are as described above for formula (V).

In some embodiments, an oxygen scavenger comprises a mixture comprising two or more compounds having formula (V), e.g., two or more compounds having formula (V'), two or more compounds having formula (V"), or one or more compounds having formula (V') and one or more compounds having formula (V").

In some variations, an oxygen scavenger has formula (VI):

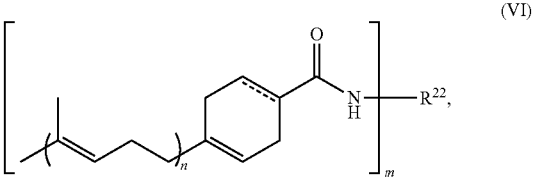

where n=1, 2, 3, 4 or 5, m=1-20 and $R^{22}$ is any saturated or unsaturated, cyclic or acyclic, unsubstituted or substituted hydrocarbyl group. In some variations, $R^{22}$ is a $C_1$-$C_{10}$ alkyl group, e.g., methyl, ethyl, n-propyl, isopropyl, n-butyl, isobutyl, t-butyl, n-pentyl, isopentyl, 2-methylbutyl, n-hexyl, isohexyl, 2-methylpentyl, 3-methylpentyl, n-heptyl, isoheptyl, 2-methylhexyl, 3-methylhexyl, 4-methylhexyl, 2-ethylpentyl, 3-ethylpentyl, n-octyl, isooctyl, 2-methylheptyl, 3-methylheptyl, 4-methylheptyl, 2-ethylhexyl, 3-ethylhexyl, n-nonyl, isononyl, 2-methyloctyl, 3-methyloctyl, 4-methyloctyl, 2-ethylheptyl, 3-ethylheptyl, 2-propylhexyl, 3-propylhexyl, n-decyl, isodecyl, 2-methylnonyl, 3-methylnonyl, 4-methylnonyl, 2-ethyloctyl, 3-ethyloctyl, 2-propylheptyl, 3-propylheptyl, or 2-butylhexyl. In some variations, $R^{22}$ is methyl, ethyl, isopropyl, isobutyl, or benzyl. In some variations, m=1 and $R^{22}$ is benzyl. In some variations, m=2 and $R^{22}$ is MXDA (meta-xylenediamine or [3-(aminomethyl)phenyl]methane). In some variations, m=2 and $R^{22}$ is a radical of a diol. For example, and $R^{22}$ is —$CH_2CH_2$— for ethylene glycol, —$CH_2CH(CH_3)$— for propylene glycol, or

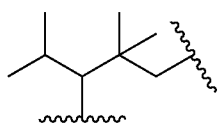

for 2,2,4-trimethyl-1,3-pentanediol. In some variations, m is greater than 2 and $R^{22}$ is a radical of a higher polyol, e.g., m=4 and $R^{19}$ is a radical for pentaerythritol.

In some variations, an oxygen scavenger has formula (VI'):

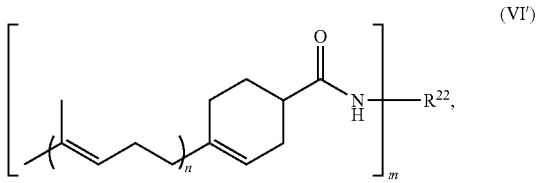

where n, m and $R^{19}$ are as described above for formula (VI).

In some variations, an oxygen scavenger has formula (VI"):

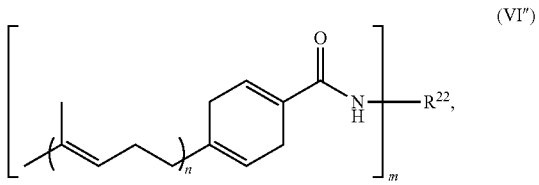

where n, m and $R^{22}$ are as described above for formula (VI).

In some embodiments, an oxygen scavenger comprises a mixture comprising two or more compounds having formula (VI), e.g., two or more compounds having formula (VI'), two or more compounds having formula (VI"), or one or more compounds having formula (VI') and one or more compounds having formula (VI").

In some embodiments, an oxygen scavenger comprises a reaction product resulting from the reaction of two or more compounds having formula (I), (II), or (III). For example, one or more compounds having formula (I), (II) or (III) and comprising anhydride or carboxylate ester groups may be esterified with one or more compounds having formula (I), (II) or (III) and comprising hydroxyl groups. The resulting product may then be subjected to any known chemical modification, e.g., alkylation (such as methylation) or amidation (e.g., using benzylamine). Non-limiting reactions are shown in Schemes A.1 and A.2 below.

SCHEME A.1

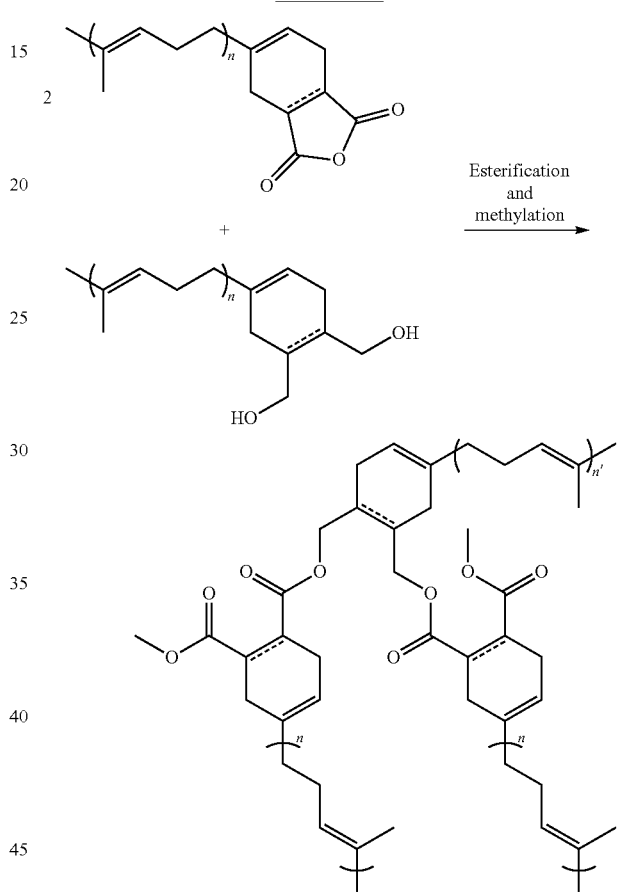

SCHEME A.2

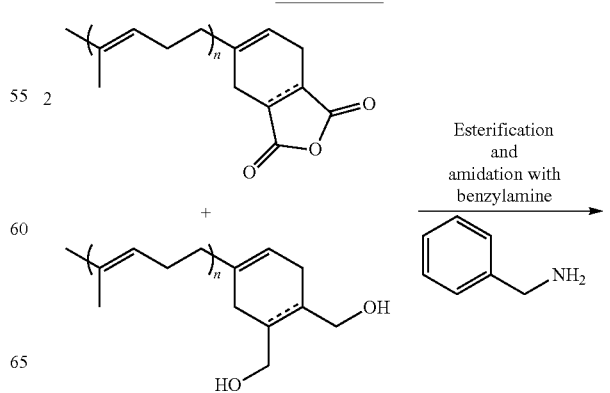

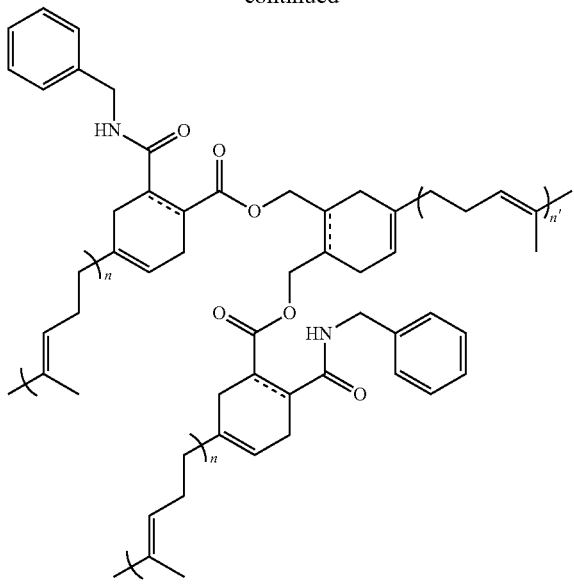

For Schemes A.1 and A.2, n and n' are independently 1, 2, 3, 4, or 5, and n and n' may be the same or different. It should be understood that any oxygen scavenger of formula (I), (II) or (III) having suitable anhydride or carboxylate ester functional groups may be substituted for the particular anhydride illustrated in Schemes A.1 and A.2, and any oxygen scavenger of formula (I), (II) or (III) having one or more hydroxyl groups may be substituted for the particular diol shown in Schemes A.1 and A.2.

The oxygen scavengers described herein may be selected or functionalized in any manner to make them more suitable for use in a desired application. For example, in some cases, it may be desired to decrease volatility of an oxygen scavenger molecule. Decreasing volatility of an oxygen scavenging molecule may permit exposure to high temperatures during processing and/or use without evaporative losses. In some cases, it may be desired to modify an oxygen scavenging molecule to reduce its tendency to migrate within or out of a host polymer. Non-limiting approaches to modifying an oxygen scavenger molecule to reduce its tendency to migrate within or out of a host polymer include increasing molecular weight and/or modifying interactions with the host polymer (e.g., increasing solubility, increasing hydrogen bonding, and the like). In some cases, it may be desired that the oxygen scavenging molecules exist in phase separated domains from the host polymer, and molecular weight of the oxygen scavenging molecules may be increased while maintaining a desired morphology that includes phase separated domains. Any known approach to increasing molecular weight without causing substantial disadvantageous modifications to interactions with the host polymer may be used. In some cases, the terpenoid side chain length and/or the chain length of other substituents may be increased. For example, for an oxygen scavenger containing carboxylate esters, the chain length of the alcohol portion of the ester may be increased. As one example, for compounds having formula (II), n, $R^{12}$ and/or $R^{13}$ may be increased in length to increase overall molecular weight of the oxygen scavenger. $R^{12}$ and $R^{13}$ may be increased in length in a manner that preserves a desired compatibility with the host matrix. For example, if solubility is limited, $R^{12}$ and/or $R^{13}$ may be selected to include branched alkyl groups (e.g., isopropyl or isobutyl), and/or heteroatoms that improve compatibility with the host polymer. If it is desired that an oxygen scavenger exist as phase separated domains within the host polymer, then $R^{12}$ and/or $R^{13}$ may be adjusted so that the desired morphology occurs. In some cases, adducts between two or more oxygen scavenging molecules may be formed to increase molecular weight while maintaining similar interactions with a host polymer. Such adducts between two or more oxygen scavenging molecules may be dimers, trimers, tetramers, and the like, and may be adducts of like oxygen scavengers or adducts between different oxygen scavengers. Non-limiting examples of trimers formed between two types of oxygen scavenging molecules are illustrated in Schemes A.1 and A.2. In some cases, oligomers or polymers are formed between oxygen scavengers and one or more co-monomers to make higher molecular weight oxygen scavengers with reduced volatility and reduced susceptibility to migration. As described in more detail below, in some cases, covalent bonding occurs between an oxygen scavenger and a host polymer which limits volatization and/or migration of oxygen scavenging moieties from a host polymer.

Described below in Section B are oxygen scavenging oligomers and polymers that can be made from oxygen scavenging molecules including appropriate chemical reactive groups. It should be understood that in some cases, it is desired that the oxygen scavenging molecule not react appreciably with the host polymer, so that an oxygen scavenging composition comprising the oxygen scavenging molecules dispersed in a host polymer is best described as a physical blend or guest-host system in which the oxygen scavenging molecules act as dopants in the host polymer. Known techniques may be used to modulate the reactivity of the oxygen scavenger molecules so that they do not undergo significant reaction with the host polymer. For example, if the host polymer comprises a polyester (e.g., PET or a copolymer of PET), the oxygen scavenger molecule may be selected or modified to not include carboxylic acid groups or hydroxyl groups to avoid transesterification or other chemical reaction with the host polymer. For example, residual hydroxyl groups may be alkylated (e.g., methylated). If an oxygen scavenging molecule includes an ester group and is to be used in a polyester host matrix, the reactivity of the ester group with the particular host polymer may be evaluated, and if an undesired level of reactivity with the host polymer is observed, the ester group may be modified (e.g., by increasing steric hindrance) to reduce or eliminate such reaction. The reactivity of the oxygen scavenging molecules can be modulated so that the oxygen scavengers exist as a physical blend with the host polymer, in which essentially none of the oxygen scavenger molecules undergo chemical reaction with the host polymer so as to be covalently bound to the host polymer. In some cases, less than about 0.001%, less than about 0.01%, less than about 0.1%, less than about 1%, or less than about 5% of the oxygen scavenging molecules are covalently bound to the host polymer. In other cases, at least about 10%, at least about 20%, at least about 30%, at least about 40%, at least about 50%, at least about 60%, at least about 70%, or at least about 80% of the oxygen scavenging molecules are covalently bound to the host polymer.

The oxygen scavengers described herein may be made by any suitable method or reaction. In some cases, the oxygen scavengers are made by Diels-Alder reaction between a conjugated terpene and a dienophile, that is, a [$2\pi+4\pi$] cycloaddition reaction between the conjugated diene moiety of the conjugated terpene and the dienophile. In some cases, the stereochemistry of the resulting compounds can be reliably predicted using orbital symmetry rules. Diels-Alder adducts can be prepared by reacting a dienophile disclosed herein with one or more conjugated isoprenoids under Diels-Alder reaction condition with or without the presence of a catalyst. The conjugated isoprenoid and a dienophile in a Diels-Alder reaction may each demonstrate stereoisomerism. Stereoisomerism of the reactants is preserved in the Diels-Alder adduct, and the relative orientation of the substituents on the reactants is preserved in the Diels-Alder adduct. For example, fumaric acid and fumaric acid esters (fumarate) exist as trans-isomers, so if a fumaric acid ester is used a dienophile, the carboxylate groups in the Diels-Alder adduct have a 1,2-anti- (also referred to as trans-) orientation relative to each other. The carboxylate groups (or anhydride) of maleic anhydride, maleic acid, and maleic acid esters (maleates) have a cis-orientation, so that the carboxylate groups in the Diels-Alder adduct have a 1,2-syn- (also referred to as cis-) orientation relative to each other. It should also be noted that enantiomers of the syn- and anti-isomers exist. For example, the 1,2-syn-isomers may be (1S,2R)- and/or (1R,2S)-enantiomers. Furthermore, isomers reflecting stereochemistry on the isoprenoid tail exist. For example, if trans-β-farnesene [(6E)-7,11-dimethyl-3-methylidenedodeca-1,6,10-triene] is used as the dienophile, the trans-stereochemistry may be preserved in the isoprenoid tail of the oxygen scavenger.

In certain embodiments, a Diels-Alder reaction between a conjugated terpene and a dienophile is thermally driven, without the need for a catalyst. In some embodiments, a Diels-Alder reaction occurs at a temperature in a range from about 50° C. to about 100° C., or from about 50° C. to about 130° C. In other embodiments, a catalyst is used, e.g., to increase reaction rate, to increase reactivity of weak dienophiles or sterically hindered reactants, or to increase selectivity of certain adducts or isomers. In some embodiments, a Diels-Alder reaction is run without solvent. In certain embodiments, reaction conditions (e.g., temperature, pressure, catalyst (if present), solvent (if present), reactant purities, reactant concentrations relative to each other, reactant concentrations relative to a solvent (if present), reaction times and/or reaction atmosphere are selected so that formation of dimers, higher oligomers and/or polymers of the conjugated terpene is suppressed or minimized. In some embodiments, the reaction conditions (e.g., temperature, catalyst (if present), solvent (if present), reactant purities, reactant concentrations, reaction times, reaction atmosphere and/or reaction pressure) are selected to produce a desired adduct or isomer. More detailed descriptions of the Diels-Alder reaction and reaction conditions for the Diels-Alder reaction are disclosed in the book by Fringuelli et al., titled "*The Diels-Alder Reaction: Selected Practical Methods,*" 1st edition, John Wiley & Sons, Ltd., New York (2002), which is incorporated by reference herein in its entirety. A suitable isomer of a conjugated terpene that is amenable to undergoing Diels-Alder reaction may be selected to prepare oxygen scavengers described herein. The hydrocarbon terpene is selected to have a stereochemistry amenable to Diels-Alder reactions. That is, the conjugated diene is able to adopt an s-cis conformer. For a hydrocarbon terpene to undergo Diels-Alder cycloaddition reaction, the double bonds exist in an s-cis conformation or conformational rotation around the single bond between the double bonds so that an s-cis conformation of the diene is adoptable. In many conjugated dienes, the s-trans conformer population is in rapid equilibrium with s-cis conformers. In some cases, steric effects due to substituents on the conjugated diene may impede a Diels-Alder reaction. Non-limiting Diels-Alder reactions of trans-β-farnesene to make pheromones are described in U.S. Pat. No. 4,546,110, which is incorporated herein by reference in its entirety. In some variations, trans-β-farnesene [(6E)-7,11-dimethyl-3-methylidenedodeca-1,6,10-triene] is selected to be reacted with a suitable dienophile to form oxygen scavengers described herein, or a Diels-Alder adduct from which the oxygen scavengers described herein are derived.

The conjugated terpenes disclosed herein may be obtained from any suitable source. In some embodiments, the conjugated terpene is obtained from naturally occurring plants or marine species. For example, farnesene can be obtained or derived from naturally occurring terpenes that can be produced by a variety of plants, such as *Copaifera langsdorfii*, conifers, and spurges; or by insects, such as swallowtail butterflies, leaf beetles, termites, or pine sawflies; and marine organisms, such as algae, sponges, corals, mollusks, and fish. Terpene oils can also be obtained from conifers and spurges. Conifers belong to the plant division Pinophya or Coniferae and are generally cone-bearing seed plants with vascular tissue. Conifers may be trees or shrubs. Non-limiting examples of suitable conifers include cedar, cypress, douglas fir, fir, juniper, kauris, larch, pine, redwood, spruce and yew. Spurges, also known as *Euphorbia*, are a diverse worldwide genus of plants belonging to the spurge family (Euphorbiaceae). Farnesene is a sesquiterpene, a member of the terpene family, and can be derived or isolated from terpene oils for use as described herein. In some embodiments, a conjugated terpene is derived from a fossil fuel (petroleum or coal), for example, by fractional distillation of petroleum or coal tar. In some embodiments, a conjugated terpene is made by chemical synthesis. For example, one non-limiting example of suitable chemical synthesis of farnesene includes dehydrating nerolidol with phosphoryl chloride in pyridine as described in the article by Anet E. F. L. J., "Synthesis of (E,Z)-α-, and (Z)-β-farnesene, Aust. J. Chem. 23(10), 2101-2108, which is incorporated herein by reference in its entirety. U.S. Pat. No. 4,546,110, which is incorporated herein by reference in its entirety, describes synthesis of a mixture of (E)-β-farnesene and (Z)-β-farnesene from nerolidol.

In some embodiments, a conjugated terpene is obtained using genetically modified organisms that are grown using renewable carbon sources (e.g., sugar cane). In certain embodiments, a conjugated terpene is prepared by contacting a cell capable of making a conjugated terpene with a suitable carbon source under conditions suitable for making a conjugated terpene. Non-limiting examples conjugated terpenes obtained using genetically modified organisms are provided in U.S. Pat. No. 7,399,323, U.S. Pat. Publ. Nos. 2008/0274523 and 2009/0137014, and International Patent Publication WO 2007/140339, and International Patent Publication WO 2007/139924, each of which is incorporated herein by reference in its entirety. Any carbon source that can be converted into one or more isoprenoid compounds can be used herein. In some embodiments, the carbon source is a fermentable carbon source (e.g., sugars), a nonfermentable carbon source or a combination thereof. A non-fermentable carbon source is a carbon source that cannot be converted by an organism into ethanol. Non-limiting examples of suitable non-fermentable carbon sources include acetate, glycerol, lactate and ethanol.

The sugar can be any sugar known to one of skill in the art. For example, in some embodiments, the sugar is a monosaccharide, disaccharide, polysaccharide or a combination thereof. In certain embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose, and combinations thereof. In some embodiments, the sugar is sucrose. In certain embodiments, the carbon source is a polysaccharide. Non-limiting examples of suitable polysaccharides include starch, glycogen, cellulose, chitin, and combinations thereof.

The sugar suitable for making a conjugated terpene can be obtained from a variety of crops or sources. Non-limiting examples of suitable crops or sources include sugar cane, bagasse, miscanthus, sugar beet, sorghum, grain sorghum, switchgrass, barley, hemp, kenaf, potato, sweet potato, cassava, sunflower, fruit, molasses, whey, skim milk, corn, stover, grain, wheat, wood, paper, straw, cotton, cellulose waste, and other biomass. In certain embodiments, suitable crops or sources include sugar cane, sugar beet and corn. In some embodiments, the sugar source is cane juice or molasses.

In certain embodiments, a conjugated terpene can be prepared in a facility capable of biological manufacture of isoprenoids. For example, for making a $C_{15}$ isoprenoid, the facility may comprise any structure useful for preparing $C_{15}$ isoprenoids (e.g., α-farnesene, β-farnesene, nerolidol or farnesol) using a microorganism capable of making the $C_{15}$ isoprenoids with a suitable carbon source under conditions suitable for making the $C_{15}$ isoprenoids. In some embodiments, the biological facility comprises a cell culture comprising a desired isoprenoid (e.g., a $C_5$, $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture. In certain embodiments, the biological facility comprises a fermentor comprising one or more cells capable of generating a desired isoprenoid. Any fermentor that can provide for cells or bacteria a stable and optimal environment in which they can grow or reproduce may be used herein. In some embodiments, the fermentor comprises a culture comprising one or more cells capable of generating a desired isoprenoid (e.g., a $C_{10}$, a $C_{15}$, a $C_{20}$, or a $C_{25}$ isoprenoid). In some embodiments, the fermentor comprises a cell culture capable of biologically manufacturing farnesyl pyrophosphate (FPP). In certain embodiments, the fermentor comprises a cell culture capable of biologically manufacturing isopentenyl diphosphate (IPP). In some embodiments, the fermentor comprises a cell culture comprising a desired isoprenoid (e.g., a $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture. The facility may further comprise any structure capable of manufacturing a chemical derivative from the desired isoprenoid (e.g., a $C_5$, $C_{10}$, a $C_{15}$, a $C_{20}$, or a $C_{25}$ isoprenoid). In some embodiments, a facility comprises a reactor for dehydrating nerolidol or farnesol to α-farnesene or β-farnesene or a combination thereof. In certain embodiments, a facility comprises a reactor for dehydrating linalool to myrcene or ocimene or a combination thereof. Any reactor that can be used to convert an alcohol into an alkene under conditions known to skilled artisans may be used. In some embodiments, the reactor comprises a dehydrating catalyst.

A variety of electron deficient dienophiles may effectively undergo the Diels-Alder reaction with conjugated terpenes to produce cyclic compounds that have utility as described herein. Any dienophile that can undergo the Diels-Alder reaction with one or more dienes may be used herein. Some non-limiting examples of suitable dienophiles are disclosed in Fringuelli et al., titled *"The Diels-Alder Reaction: Selected Practical Methods,"* 1st edition, John Wiley & Sons, Ltd., New York, pages 3-5 (2002), which is incorporated herein. Any conjugated terpene described herein or otherwise known may undergo Diels-Alder reaction with a dienophile to provide a Diels-Alder adduct having utility as described herein. Some non-limiting examples of conjugated terpenes that may be used to make the Diels-Alder adducts include suitable stereoisomers of myrcene, ocimene, α-farnesene, β-farnesene, β-springene, isodehydrosqualene, isosqualane precursor I, and isosqualane precursor II. A Diels-Alder adduct having formula (I) wherein at least one of $R^1$, $R^2$, $R^3$, $R^4$, $R^7$ and $R^8$ (e.g., $R^1$ or $R^2$) is an isoprenoid tail having formula

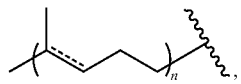

where n=2 may result when β-farnesene is the conjugated terpene. A Diels-Alder adduct having formula (I) wherein at least one of $R^1$, $R^2$, $R^3$, $R^4$, $R^7$ and $R^8$ (e.g., $R^3$ or $R^7$) is an isoprenoid tail having formula

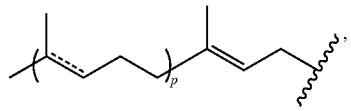

where p=1 when α-farnesene is the conjugated terpene.

The dienophile used herein can be any dienophile that undergoes a Diels-Alder reaction with a diene on the conjugated hydrocarbon terpene to form the corresponding cyclic compound. In certain embodiments, the dienophile has formula (VII) or (VIII):

wherein each of $R^{42}$, $R^{43}$, $R^{44}$, $R^{45}$, $R^{46}$, and $R^{47}$ is independently H, a saturated or unsaturated, cyclic or acyclic, unsubstituted or substituted $C_1$-$C_{30}$ hydrocarbyl group (e.g., $C_1$-$C_{20}$ alkyl, $C_1$-$C_{20}$ alkenyl, $C_1$-$C_{20}$ alkynyl, cycloalkyl, aryl, aralkyl and alkaryl), hydroxyalkyl (e.g., —CH$_2$OH), aminoalkyl (e.g., —CH$_2$NH$_2$), carboxylalkyl (e.g., —CH$_2$CO$_2$H), thioalkyl (e.g., —CH$_2$SH), epoxyalkyl (e.g., glycidyl), hydroxyaryl, aminoaryl, carboxylaryl, thioaryl, hydroxyl, amino, halo, cyano, nitro, acyl (e.g., formyl and acetyl), —CO$_2$R$^{48}$, —(CH$_2$)$_n$CO$_2$R$^{49}$, —(CH$_2$)$_m$COO$^-$M$_1^+$, —(CH$_2$)$_m$COO$^-$M$_2^+$, —C(=O)NR$^{50}$R$^{51}$, —OR$^{52}$ or —C(=O)X where X is halo; or $R^{44}$ and $R^{45}$ together or $R^{46}$ and $R^{47}$ together form a —C(=O)—O—C(=O)— group, a —C(=O)—S—C(=O)— group, a —C(=O)—NR$^{53}$—C(=O)— group, a —C(=O)—CR$^{54}$=CR$^{55}$—C(=O)— group, or a —C(=O)—C(=O)—CR$^{26}$=CR$^{27}$— group; or R$^{44}$ and R$^{45}$ together or R$^{46}$ and R$^{47}$ together form a —CH$_2$—C(=O)—O—C(=O)— group, where each of M$_1^+$ and M$_2^+$ is independently a monovalent cation such as Fr$^+$, Cs$^+$, Rb$^+$, K$^+$, Na$^+$, Li$^+$, Ag$^+$, Au$^+$, Cu$^+$, NH$_4^+$, primary ammonium, secondary ammonium, tertiary ammonium, or quaternary ammonium; each of R$^{48}$, R$^{49}$, R$^{50}$, R$^{51}$, R$^{52}$, R$^{53}$, R$^{54}$, R$^{55}$, R$^{56}$, and R$^{57}$ is independently H, hydrocarbyl, hydroxyalkyl, aminoalkyl, carboxylalkyl, thioalkyl, epoxyalkyl, hydroxyaryl, aminoaryl, carboxylaryl, thioaryl, hydroxyl, amino, halo, cyano, nitro or acyl, or R$^{54}$ and R$^{55}$ together or R$^{56}$ and R$^{57}$ together form a benzo ring or a substituted or unsubstituted —CH$_2$(CH$_2$)$_k$CH$_2$— group; and each of m, n and k is independently an integer from 1 to 20 or from 1 to 12, with the proviso that at least one of R$^{44}$, R$^{45}$, R$^{46}$ and R$^{47}$ is not H, and the proviso that at least one of R$^{42}$ and R$^{43}$ is not H. In some variations, at least one of R$^{42}$ and R$^{43}$ is a COOH group, or a carboxylate ester group. In some cases, each of R$^{42}$ and R$^{43}$ is a COOH group or a carboxylate ester group. In some cases, one of R$^{42}$ and R$^{43}$ is H and the other of R$^{42}$ and R$^{43}$ is a COOH group or a carboxylate ester group.

Some non-limiting specific examples of dienophiles that can react with a conjugated terpene (e.g., farnesene or myrcene) to produce oxygen scavenging compounds useful as described herein include dienophiles in groups (A)-(Y) below:

(A) maleic anhydride and substituted maleic anhydrides;
(B) citraconic anhydride and substituted citraconic anhydrides;
(C) itaconic acid and substituted itaconic acids;
(D) itaconic anhydride and substituted itaconic anhydrides;
(E) acrolein and substituted acroleins;
(F) crotonaldehyde and substituted crotonaldehydes;
(G) dialkyl maleates or dialkyl fumarates (e.g., linear or branched, cyclic or acyclic, C$_1$-C$_{30}$ dialkyl maleates or dialkyl fumarates such as dimethyl maleate, dimethyl fumarate, diethyl maleate, diethyl fumarate, di-n-propyl maleate, di-n-propyl fumarate, di-isopropyl maleate, di-isopropyl fumarate, di-n-butyl maleate, di-n-butyl fumarate, di(isobutyl) maleate, di(isobutyl) fumarate, di-tert-butyl maleate, di-tert butyl fumate, di-n-pentyl maleate, di-n-pentyl fumarate, di(isopentyl) maleate, di(isopentyl) fumarate, di-n-hexyl maleate, di-n-hexyl fumarate, di(2-ethylhexyl) maleate, di(2-ethylhexyl) fumarate, di(isohexyl) maleate, di(isohexyl) fumarate, di-n-heptyl maleate, di-n-heptyl fumarate, di(isoheptyl) maleate, di(isoheptyl) fumarate, di-n-octyl maleate, di-n-octyl fumarate, di(isooctyl) maleate, di(isooctyl) fumarate, di-n-nonyl maleate, di-n-nonyl fumarate, di(isononyl) maleate, di(isononyl) fumarate, di-n-decyl maleate, di-n-decyl fumarate, di(isodecyl) maleate), and di(isodecyl) fumarate;
(H) dialkyl itaconates (e.g., linear or branched, cyclic or acyclic, C$_1$-C$_{30}$ dialkyl itaconates such as dimethyl itaconate, diethyl itaconate, di-n-propyl itaconate, di-isopropyl itaconate, di-n-butyl itaconate, di(isobutyl) itaconate, di-tert-butyl itaconate, di-n-pentyl itaconate, di(isopentyl) itaconate, di-n-hexyl itaconate, di(2-ethylhexyl) itaconate, di(isohexyl) itaconate, di-n-heptyl itaconate, di(isoheptyl) itaconate, di-n-octyl itaconate, di(isooctyl) itaconate, di-n-nonyl itaconate, di(isononyl) itaconate, di-n-decyl itaconate and di(isodecyl) itaconate);
(I) acrylic acid esters (e.g., linear or branched, cyclic or acyclic, C$_1$-C$_{30}$ alkyl acrylates, such as methyl acrylate, ethyl acrylate, n-propyl acrylate, isopropyl acrylate, n-butyl acrylate, isobutyl acrylate, tert-butyl acrylate, n-pentyl acrylate, isopentyl acrylate, n-hexyl acrylate, isohexyl acrylate, 2-ethylhexyl acrylate, n-heptyl acrylate, isoheptyl acrylate, n-octyl acrylate, isooctyl acrylate, n-nonyl acrylate, isononyl acrylate, n-decyl acrylate, isodecyl acrylate, n-undecyl acrylate, isoundecyl acrylate, n-dodecyl acrylate, isododecyl acrylate, n-tridecyl acrylate, n-tetradecyl acrylate, n-pentadecyl acrylate, n-hexadecyl acrylate, n-heptadecyl acrylate, n-octadecyl acrylate, n-nonadecyl acrylate, n-eicosyl acrylate, and n-tricosyl acrylate);
(J) methacrylic acid esters (e.g., linear or branched, cyclic or acyclic, C$_1$-C$_{30}$ alkyl methacrylates, such as methyl methacrylate, ethyl methacrylate, n-propyl methacrylate, isopropyl methacrylate, n-butyl methacrylate, isobutyl methacrylate, tert-butyl methacrylate, n-pentyl methacrylate, isopentyl methacrylate, n-hexyl methacrylate, isohexyl methacrylate, 2-ethylhexyl methacrylate, n-heptyl methacrylate, isoheptyl methacrylate, n-octyl methacrylate, isooctyl methacrylate, n-nonyl methacrylate, isononyl methacrylate, n-decyl methacrylate, isodecyl methacrylate, n-undecyl methacrylate, isoundecyl methacrylate, n-dodecyl methacrylate, isododecyl methacrylate, n-tridecyl methacrylate, n-tetradecyl methacrylate, n-pentadecyl methacrylate, n-hexadecyl methacrylate, n-heptadecyl methacrylate, n-octadecyl methacrylate, n-nonadecyl methacrylate, n-eicosyl methacrylate, and n-tricosyl methacrylate);
(K) cinnamic acid and cinnamic acid esters (e.g., linear or branched, cyclic or acyclic, C$_1$-C$_{30}$ alkyl cinnamate, such as methyl cinnamate and ethyl cinnamate);
(L) mesityl oxide and substituted mesityl oxides;
(M) hydroxyalkyl acrylates (e.g., 2-hydroxymethyl acrylate and 2-hydroxyethyl acrylate);
(N) carboxyalkyl acrylates (e.g., 2-carboxyethyl acrylate);
(O) (dialkylamino)alkyl acrylates (e.g., 2-(diethylamino) ethyl acrylate);
(P) dialkyl acetylene dicarboxylates (e.g., linear or branched, cyclic or acyclic, C$_1$-C$_{30}$ dialkyl acetylene dicarboxylates such as dimethyl acetylene dicarboxylate, diethyl acetylene dicarboxylate, di-n-propyl acetylene dicarboxylate, di(isopropyl)acetylene dicarboxylate, di-n-butyl acetylene dicarboxylate, di(isobutyl)acetylene dicarboxylate, di(tert-butyl)acetylene dicarboxylate, di-n-pentyl acetylene dicarboxylate, di(isopentyl)acetylene dicarboxylate, di-n-hexyl acetylene dicarboxylate, di(2-ethylhexyl)acetylene dicarboxylate, di(isohexyl)acetylene dicarboxylate, di-n-heptyl acetylene dicarboxylate, di(isoheptyl)acetylene dicarboxylate, di-n-octyl acetylene dicarboxylate, di(isooctyl)acetylene dicarboxylate, di-n-decyl acetylene dicarboxylate, and di(isodecyl)acetylene dicarboxylate); an alkyl propiolate, e.g., an alkyl propiolate incorporating any C$_1$-C$_{20}$ alkyl group such as methyl propiolate, ethyl propiolate, or butyl propiolate; an alkyl 2-butynoate, e.g., an alkyl 2-butynoate incorporating any C$_1$-C$_{20}$ alkyl group such as methyl 2-butynoate, ethyl 2-butynoate, propyl 2-butynoate, or propyl 2-butynoate; an alkyl 2-pentynoate, e.g., an alkyl 2-pentynoate incorporating any C$_1$-C$_{20}$ alkyl group such as methyl 2-pentyne, ethyl 2-pentanoate, propyl 2-pentynoate or butyl 2-pentynoate; an alkyl 2-hexynoate, e.g., an alkyl 2-hexynoate incorporating any C$_1$-C$_{20}$ alkyl group such as methyl 2-hexynanoate, ethyl 2-hexynoate, propyl 2-hexynoate or butyl 2-hexynoate; 2-butynoic acid; 2-pentynoic acid; 2-hexynoic acid; dicyanoacetylene; and cyanoacetylene.
(Q) vinyl ketones (e.g., linear or branched, cyclic or acyclic, aliphatic or aromatic, C$_1$-C$_{30}$ vinyl ketones, such as methyl vinyl ketone, ethyl vinyl ketone, n-propyl vinyl ketone, n-butyl vinyl ketone, isobutyl vinyl ketone, tert-butyl vinyl ketone, n-pentyl vinyl ketone, n-hexyl vinyl ketone, 2-ethylhexyl vinyl ketone, n-heptyl vinyl ketone, n-octyl vinyl ketone, n-nonyl vinyl ketone, n-decyl vinyl ketone, n-undecyl vinyl ketone, n-dodecyl vinyl ketone, n-tridecyl vinyl ketone, n-tetradecyl vinyl ketone, n-pentadecyl vinyl ketone, n-hexadecyl vinyl ketone, n-heptadecyl vinyl ketone, n-octadecyl vinyl ketone, n-nonadecyl vinyl ketone, n-eicosyl vinyl ketone, and n-tricosyl vinyl ketone);
(R) maleamides, fumaramides, maleimide and substituted maleimides (e.g., maleic acid diamide, or $C_1$-$C_{30}$ alkyl or aryl N- or N,N'-substituted maleamides such as N-methyl maleamide, N-ethyl maleamide, N-n-butyl maleamide, N,N'-dimethyl maleamide, N,N'-methyl ethyl maleamide, or N,N'-tetramethyl maleamide; fumaramide, or $C_1$-$C_{30}$ alkyl or aryl N- or N,N'-substituted fumaramides such as N-methyl fumaramide, N-isopropyl fumaramide, N,N'-diethyl fumaramide, N,N'-di-n-butyl fumaramide, N,N'-tetraethyl fumaramide; linear or branched, cyclic or acyclic, $C_1$-$C_{30}$ alkyl or aryl N-substituted maleimides, such as N-methylmaleimide, N-ethyl maleimide, N-n-propyl maleimide, N-isopropyl maleimide, N-n-butyl maleimide, N-tert-butyl maleimide, N-n-pentyl maleimide, N-isopentyl maleimide, N-n-hexyl maleimide, N-isohexyl maleimide, N-(2-ethylhexyl) maleimide, N-n-heptyl maleimide, N-n-octyl maleimide, N-n-decyl maleimide, N-n-undecyl maleimide, N-n-dodecyl maleimide, N-n-tridecyl maleimide, N-n-tetradecyl maleimide, N-n-pentadecyl maleimide, N-n-hexadecyl maleimide, N-n-heptadecyl maleimide, N-n-octadecyl maleimide, N-n-nonadecyl maleimide, N-n-eicosyl maleimide, and maleimides in which the nitrogen is substituted with —COOR, where R represents any linear or branched, cyclic or acyclic $C_1$-$C_{30}$ alkyl group, for example, N-methoxycarbonylmaleimide);
(S) dialkyl azidocarboxylates, e.g. linear or branched, cyclic or acyclic, $C_1$-$C_{30}$ dialkyl azidocarboxylates, such as dimethyl azidocarboxylate, and diethyl azidocarboxylate;
(T) azidocarboxylic acid and azidodicarboxylic acid diesters containing two ester groups which may be the same or different ester groups;
(U) sulfur dioxide;
(V) 1,4-benzoquinone and substituted 1,4-benzoquinones (e.g., 2-(3-methyl-2-butenyl)benzo-1,4-quinone), 1,2-benzoquinone and substituted 1,2-benzoquinones;
(W) naphthoquinones such as 1,4-naphthoquinone, 1,2-naphthoquinone, plumbagin, and juglone;
(X) phosphorus trihalide (e.g., phosphorus tribromide); and
(Y) vinyl sulfonates, vinyl sulfinates, or vinyl sulfoxides.

In some cases in which the dienophile has formula (VII), the Diels-Alder adduct may be suitably oxidized to form a 1,4-cyclohexadienyl group. Any suitable oxidation conditions known in the art may be used, with the proviso that the oxidation does not proceed to form an aromatic ring for a usable portion of molecules.

An appropriate dienophile may be selected so that the Diels-Alder adduct may be used as-is in making an oxygen scavenging composition. In other cases, a Diels-Alder adduct may undergo one or more chemical modifications known in the art to form the desired oxygen scavenger.

B. Oxygen Scavenging Oligomers or Polymers

As described above, it is possible to incorporate oxygen scavenging compounds having formula (I), (II), or (III) into a polymer to make an oxygen scavenging polymer. Formation of oxygen scavenging polymers can be accomplished by a variety of routes. For example, in a first route, one or more oxygen scavengers described herein are reacted with an existing polymer to functionalize that polymer to make it capable of scavenging oxygen. In a second route, an oxygen scavenger described herein functions as a monomer that is polymerized to make an oxygen scavenging polymer. In a third route, one or more oxygen scavengers described herein function as a monomer that is copolymerized with one or more comonomers to make an oxygen scavenging polymer. As described in more detail in Sections C and D below, an oxygen scavenging polymer made by any route (via functionalization of a host polymer or via polymerization, or copolymerization) may provide the major polymeric component of an oxygen scavenging composition that can be used to make oxygen scavenging articles such as bottles, trays, containers, films, and the like. Alternatively, an oxygen scavenging polymer made by any route may be dispersed in a host polymer to form a polymeric blend, and the polymeric blend is used to make oxygen scavenging articles.

B.1 Functionalization of Polymer to Make an Oxygen Scavenging Polymer

For a first route to making an oxygen scavenging polymer, one or more oxygen scavengers of formula (I), (II) or (III) may be suitably functionalized to react to form covalent bonds with a host polymer. Such functionalization of host polymers may be conducted using any known technique for functionalizing polymers.

In some variations, a host polymer is functionalized so that oxygen scavenging activity is present on side chains of the host polymer. For example, one or more oxygen scavengers may be grafted onto the host polymer using known techniques. Oxygen scavengers that are grafted onto the host polymer may be individual molecules or may be oxygen scavenging polymers that are grafted to a host polymer. In one example, a host polymer contains unsaturated bonds, and an oxygen scavenger is suitably functionalized to graft onto an unsaturated bond. Grafting of the oxygen scavenger to the unsaturated bond of the host polymer can occur via a variety of mechanisms, e.g. a radical mechanism, an addition to a double bond, or an ene reaction As one non-limiting example, a host polymer such as polybutadiene containing unsaturated bonds may be reacted with an oxygen scavenger of formula (I), (II) or (III), where the oxygen scavenger is suitably functionalized to undergo the desired grafting reaction to the host polymer containing unsaturated bonds. In those instances in which a polybutadiene is functionalized with an oxygen scavenger described herein, any suitable polybutadiene may be used, e.g., trans-1,4-polybutadiene, cis-1,4-polybutadiene, 1,2-polybutadiene, or a mixture of any two or more of the foregoing. In some cases, a polybutadiene comprising substantial amounts of 1,4-polybutadiene is used, e.g., at least about 70% 1,4-polybutadiene, or at least about 50% 1,4-polybutadiene.

In some variations, one or more oxygen scavengers is reacted with a host polymer in such a way to form a portion of the main chain of the polymer so that the oxygen scavenging activity is imparted to the main chain or end group of the host polymer. In some cases, an oxygen scavenger may be reacted with a host polymer via a transesterification reaction. For example, an oxygen scavenging compound (which may be an individual molecule or an oxygen scavenging polymer) having an anhydride, a carboxylic acid, a hydroxyl, or certain suitable carboxylate reactive groups may be reacted with a polyester under suitable conditions via transesterification. In some cases, an oxygen scavenger may be reacted with a reactive end group of the host polymer.

B.2. Polymerization of Oxygen Scavenging Monomer to Make an Oxygen Scavenging Polymer In a second route to making an oxygen scavenging polymer, an oxygen scavenger of formula (I), (II), or (III) functions as a monomer that is oligomerized or polymerized to make an oxygen scavenging polymer. Any of the oxygen scavengers described herein having reactive groups known to undergo polymerization under certain thermal or catalytic conditions may be polymerized to form an oxygen scavenging polymers. In some cases, one or more unsaturated bonds on the isoprenoid tail provides a reactive center for polymerization, one or more unsaturated bonds in the six-membered ring provides a reactive center for polymerization, and in some cases other reactive groups on an oxygen scavenger provides a reactive center for polymerization (e.g., alcohol, carboxylate, anhydride, amine, amide, and the like). In some cases, oxygen scavengers of formula (III-2'), formula (III-2"), formula (II-3'), or formula (II-3") may undergo thermal and/or catalytic polymerization under certain conditions.

B.3 Copolymerizing Oxygen Scavenging Mononomer with One or More Comonomers to Make an Oxygen Scavenging Polymer For a third route to making an oxygen scavenging polymer, one or more oxygen scavengers of formula (I), (II), or (III) has suitable reactive groups so that it functions as a monomer that is copolymerized with one or more comonomers. Oxygen scavenging monomers may be selected to undergo any type of polymerization reaction, e.g., condensation polymerization or addition polymerization. In some cases, an oxygen scavenger has reactive groups which undergo a condensation reaction with one or more comonomers to form a polyester or a polyamide. For example, an oxygen scavenging compound described herein having anhydride, carboxylic acid, hydroxyl, or certain carboxylate reactive groups may undergo condensation polymerization with one or more comonomers to make an oxygen scavenging polyester, or an oxygen scavenging compound described herein having anhydride, carboxylic acid, hydroxyl, amino, or certain suitable carboxylate reactive groups may undergo condensation polymerization with one or more comonomers to make an oxygen scavenging polyamide.

In one non-limiting example, an oxygen scavenger having formula (I), (II), or (III) that is an anhydride or dicarboxylate (dicarboxylic acid or suitable ester of dicarboxylic acid) is reacted with one or more polyols to form an oxygen scavenging polyester. One non-limiting reaction of an oxygen scavenger having formula (III) that is an anhydride with ethylene glycol to form an oxygen scavenging polyester is shown below in Scheme B.1:

SCHEME B.1

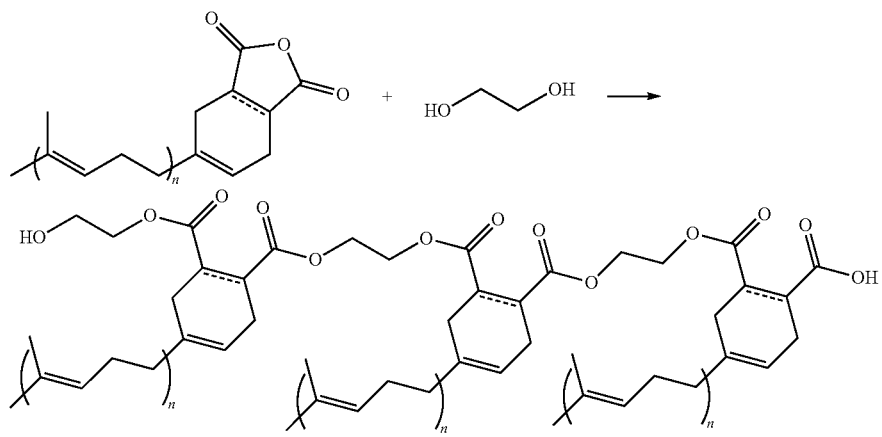

For the reaction shown in Scheme B.1, n=1, 2, 3, 4 or 5, and q is 1 or greater. In some cases, n=2. It should be understood that any suitable polyol may be substituted for the ethylene glycol in Scheme B.1, and any suitable compound of formula (I), (II), or (III) that is an anhydride or a dicarboxylate may be substituted for the particular anhydride illustrated in Scheme B.1. For example, a compound of formula (II-3') or (II-3") may be substituted for the anhydride. In some variations, more than one compound of formula (I), (II) or (III) that is an anhydride or a dicarboxylate is used in place of the particular anhydride illustrated in Scheme B.1. For example, any combination of two or more of the following may be used in place of the anhydride in Scheme B.1: a compound of formula (II-3'), a compound of formula (II-3"), a compound of formula (II-4'), a compound of formula (II-4"), a compound of formula (III-3'), and a compound of formula (III-3"). In some variations, a compound of formula (I) or (II) that is a polyol (e.g., a diol) is substituted for ethylene glycol and/or for the poly(propylene glycol) in Scheme B.1. In some variations, one or more additional comonomers may be included in the reaction shown in Scheme B.1, e.g., a dicarboxylic acid or a phthalate such as dimethyl terephthalate (DMT). The reaction may be allowed to progress for any desired molecular weight of the reaction product. In some applications, the oxygen scavenger is oligomeric and is dispersed in a host polymer to make an oxygen scavenging composition. In some applications, the oxygen scavenger is polymeric to make an oxygen scavenging polymer which may be used as the sole polymeric component or is dispersed in a host polymer to make an oxygen scavenging composition. In some variations, q is about 100 or less, or about 10 or less. In some variations, q is greater than 100, e.g., at least about 200, at least about 500, at least about 1000, at least about 5000, or at least about 10,000. In some variations, q is much greater than 10,000, e.g., about 50,000 or about 100,000. It should be understood that any suitable polyol may be substituted for ethylene glycol shown in Scheme B.1, e.g., propylene glycol, a polyalkylene glycol, or a compound having formula (I) or (II) that is a polyol. Further, any suitable anhydride or dicarboxylate may be substituted for the particular anhydride illustrated in Scheme B.1.

In some variations, an oxygen scavenger of formula (I), (II), or (III) is reacted with two or more different comonomers to make an oxygen scavenging polymer. For example, an oxygen scavenger of formula (I), (II), or (III) that is an anhydride or a dicarboxylate may be reacted with two or more different polyols to make an oxygen scavenging polyester. A non-limiting reaction of an oxygen scavenger having formula (III-2) with ethylene glycol and a poly(propylene glycol) (PPG) to form an oxygen scavenging polyester is shown in Scheme B.2:

dimethyl terephthalate (DMT). The reaction may be allowed to progress to produce any desired molecular weight of the reaction product. In some applications, the oxygen scavenger is oligomeric and is dispersed in a host polymer to make an oxygen scavenging composition. In some applications, the oxygen scavenger is polymeric to make an oxygen scavenging polymer which may be used the primary polymeric component, or an oxygen scavenging polymer may be dispersed in a host polymer to make an oxygen scavenging composition. Any suitable combination of r and q may be selected to form an oxygen scavenger having desired physical and chemical properties. For example, the ratio r:q may be about 100:1, 50:1, 20:1, 10:1, 5:1, 2:1, 1:1, 1:2, 1:5, 1:10, 1:50, or 1:100. In some variations, r is about 10 or less, or about 100 or less. In some variations, q is about 100 or less, or about 10 or less. In some variations, q is greater than 100, e.g., at least about 200, at least about 500, at least about

SCHEME B.2

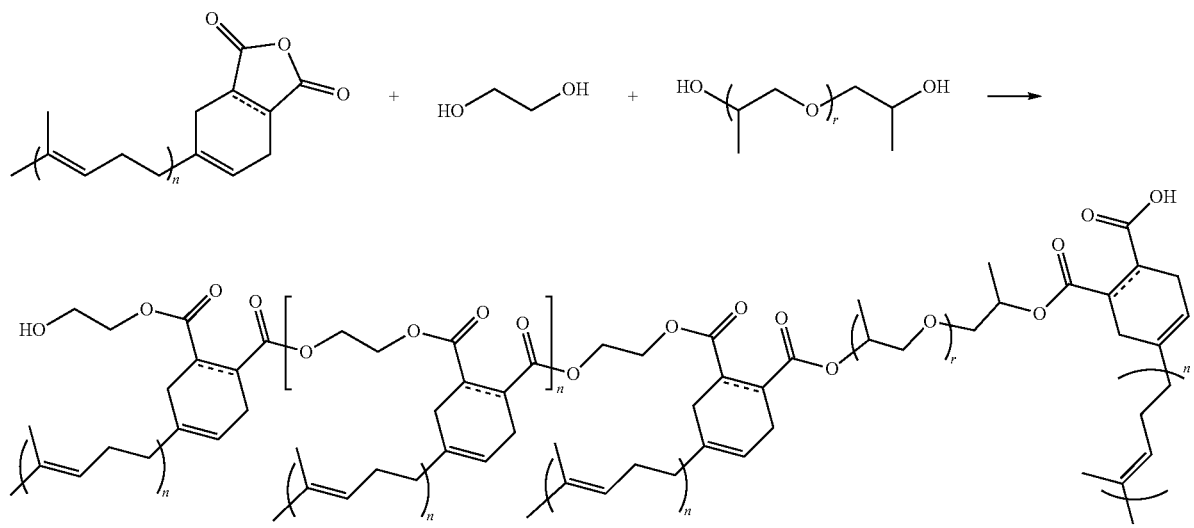

For the reaction shown in Scheme B.2, n=1, 2, 3, 4 or 5, q is 1 or greater, and r is 0 or greater. In some cases, n=2. It should be understood that any suitable polyol may be substituted for the ethylene glycol in Scheme B.2, any suitable polyol may be substituted for the poly(propylene glycol) in Scheme B.2, and any suitable compound of formula (I), (II), or (III) that is an anhydride or a dicarboxylate may be substituted for the particular anhydride illustrated in Scheme B.2. For example, a compound of formula (II-3') or (II-3") may be substituted for the anhydride. In some variations, more than one compound of formula (I), (II) or (III) that is an anhydride or a dicarboxylate is used in place of the particular anhydride illustrated in Scheme B.2. For example, any combination of two or more of the following may be used in place of the anhydride in Scheme B.2: a compound of formula (II-3'), a compound of formula (II-3"), a compound of formula (III-3'), and a compound of formula (III-3"). In some variations, a compound of formula (I) or (II) that is a polyol (e.g., a diol) is substituted for ethylene glycol and/or for the poly(propylene glycol) in Scheme B.2. In some variations, one or more additional comonomers may be included in the reaction shown in Scheme B.2, e.g., a dicarboxylic acid or a phthalate such as 1000, at least about 5000, or at least about 10,000. In some variations, q is much greater than 10,000, e.g., about 50,000 or about 100,000.

In some cases, an oxygen scavenging monomer having formula (I), (II), or (III) is selected to undergo condensation polymerization with one or more comonomers to make a polyamide. A non-limiting reaction of an oxygen scavenger having formula (III) with a diamine to form an oxygen scavenging polyamide is shown in Scheme B.3:

SCHEME B.3

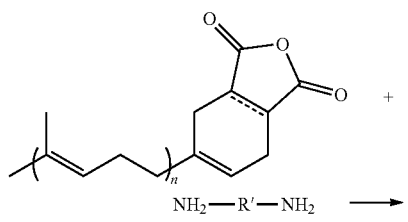

-continued

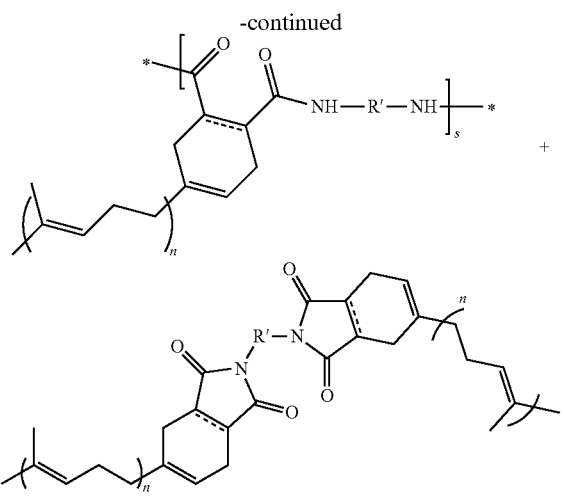

For the reaction shown in Scheme B.3, n=1, 2, 3, 4 or 5, and s is 1 or greater. In some cases, n=2. For the diamine, R' may be any suitable hydrocarbyl group selected impart desired physical and/or chemical properties to the resulting oligomer or polymer. In some variations, R' is a $C_1$-$C_{20}$ alkyl group. For example, R' may be —$(CH_2)_6$— so that the diamine is hexamethylenediamine or R' may be —$(CH_2)_5$— so that the diamine is pentamethylenediamine. In some variations, R' comprises one or more ether linkages. For example, the diamine may be a polyoxyalkyleneamine comprising primary amino groups on the terminal ends of a polyether backbone may be used, e.g., a polyoxyalkyleneamine having the formula

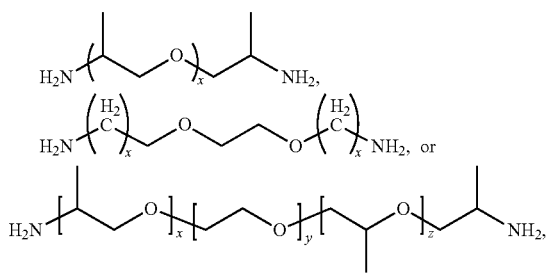

where x, y, and z are independently about 1-50. In some variations, a Jeffamine® polyetheramine available from Huntsman, such as Jeffamine HK/511 is used. In some variations, a compound having formula (I) or (II) that is a diamine is used in the reaction shown in Scheme B.3. It should be understood that any oxygen scavenger having formula (I), (II) or (III) that is a dicarboxylate or an anhydride may be substituted for the particular anhydride of formula (III) illustrated in Scheme B.3. For example, a compound of formula (II-3") or (II-3') may be substituted for the anhydride. In some variations, more than one compound of formula (I), (II) or (III) that is an anhydride or a dicarboxylate is used in place of the particular anhydride illustrated in Scheme B.3. For example, any combination of two or more of the following may be used in place of the anhydride in Scheme B.3: a compound of formula (II-3'), a compound of formula (II-3"), a compound of formula (III-3'), and a compound of formula (III-3"). In some variations, a compound of formula (I), (II) or (III) that is a diamine is used as the diamine in Scheme B.3. In some variations, one or more additional comonomers may be included in the reaction shown in Scheme B.3, e.g., a dicarboxylic acid or a phthalate such as dimethyl terephthalate (DMT). The reaction may be allowed to progress for any desired molecular weight of the reaction product. In some applications, it is desired that the oxygen scavenger is oligomeric and is dispersed in a host polymer to make an oxygen scavenging composition. In some applications, it is desired that the oxygen scavenger is polymeric to make an oxygen scavenging polymer which may be used as-is or is dispersed in a host polymer to make an oxygen scavenging composition. In some variations, s is about 10 or less, or about 100 or less. In some variations, s is greater than 100, e.g., at least about 200, at least about 500, at least about 1000, at least about 5000, or at least about 10,000. In some variations, s is much greater than 10,000, e.g., about 50,000 or about 100,000.

In some cases, an oxygen scavenging monomer having formula (I), (II), or (III) is selected to undergo condensation polymerization with an aromatic or aliphatic diamine to form an oxygen scavenging polyamide. One non-limiting example is a reaction of an oxygen scavenger having formula (III) with meta xylylene diamine to form an oxygen scavenging polyamide as shown in Scheme B.4:

SCHEME B.4

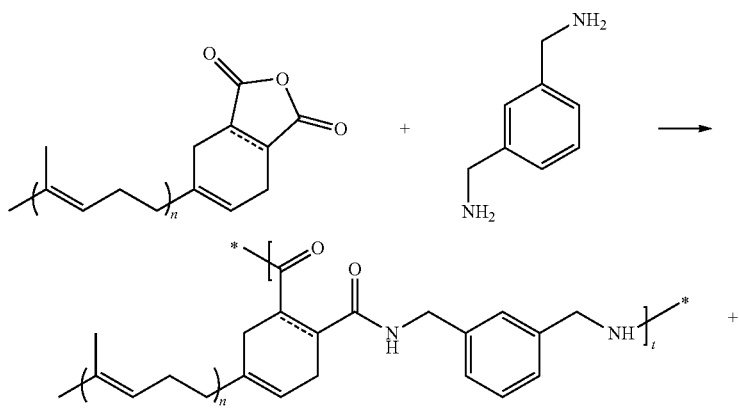

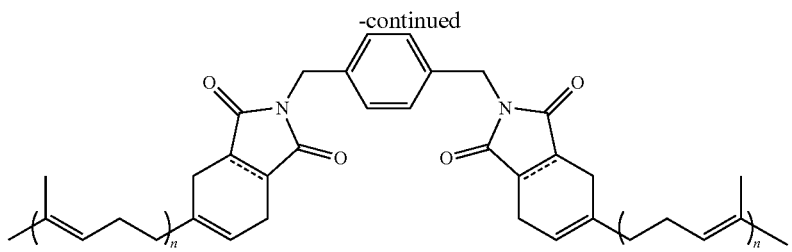

For the reaction shown in Scheme B.4, n=1, 2, 3, 4 or 5 and t is 1 or greater. In some cases, n=2. It should be understood that any oxygen scavenger having formula (I), (II), or (III) and being a dicarboxylate (or anhydride) may be substituted for the particular anhydride shown in Scheme B.4 any suitable aromatic diamine may be substituted for meta xylylene diamine in Scheme B.4. The dicarboxylate (or anhydride) and the aromatic diamine may be selected to impart desired physical and/or chemical properties to the resulting oligomer or polymer. The reaction may be allowed to progress for any desired molecular weight of the reaction product. In some applications, it is desired that the oxygen scavenger is oligomeric and is dispersed in a host polymer to make an oxygen scavenging composition.

Additional combinations of oxygen scavengers of formula (I), (II), or (III) with one or more comonomers to make oxygen scavenging polymers, e.g., polyesters or polyamides, are contemplated. For example, an oxygen scavenger may be a diol which is reacted with a dicarboxylic acid to make a polyester including a terephthalate repeat unit, as shown in Scheme B.5:

SCHEME B.5

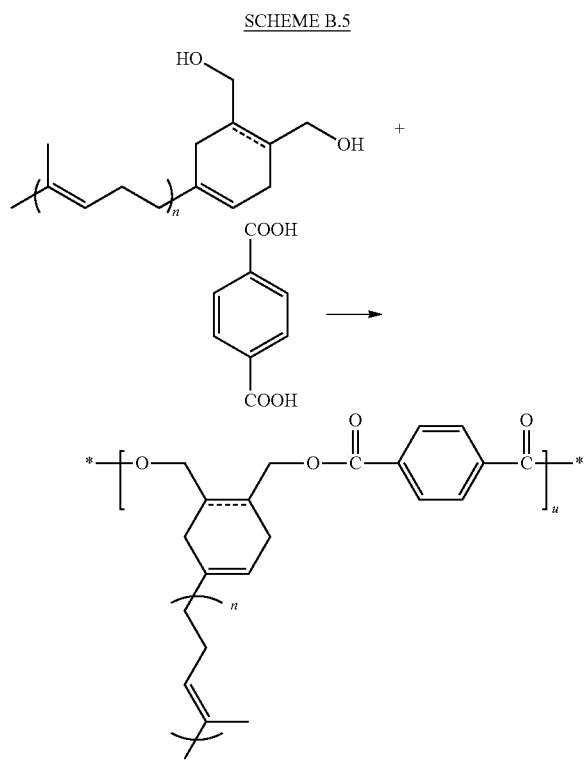

For the reaction shown in Scheme B.5, n=1, 2, 3, 4 or 5, and u is 1 or greater. The reaction is allowed to progress to achieve any desired molecular weight product. It should be understood that any oxygen scavenger of formula (I) or (II) that is a polyol (e.g., diol) may be substituted for the particular diol shown in Scheme B.5, and any suitable dicarboxylate or anhydride may be substituted for terephthalic acid as shown in Scheme B.5 to form other variations of oxygen scavenging polyesters. In some cases, isophthalic acid, or naphthalene dicarboxylic acid or their esters are used in the reaction illustrated in Scheme B.5. In some cases, a compound of formula (I), (II), or (III) that is an anhydride or dicarboxylate is substituted for terephthalic acid in Scheme B.5.

In some variations, a compound having formula (I), (II) or (III) that is a diamine is reacted with a compound of formula (I), (II), or (III) that is an anhydride or dicarboxylate to make an oxygen scavenging polyamide. In some variations, a compound having formula (I) or (II) that is a polyol (e.g., a diol) is reacted with a compound of formula (I), (II), or (III) that is an anhydride or dicarboxylate to make an oxygen scavenging polyester.

C. Oxygen Scavenging Compositions

A variety of polymeric oxygen scavenging compositions can be made using the oxygen scavenging molecules described in Section A and/or oxygen scavenging polymers described in Section B. The oxygen scavenging compositions may be used to make articles, as described in Section D below. In some variations, the oxygen scavengers are molecules that are dispersed into a host polymer to form a physical blend in which the oxygen scavengers undergo no or limited covalent bonding to the polymer host. In some variations, the oxygen scavenging molecules are dispersed in a host polymer matrix and the oxygen scavengers undergo significant covalent bonding to the host polymer, e.g., by transesterification, by grafting, by reaction with polymer end groups, or the like. In some variations, an oxygen scavenging polymer functions as the primary polymeric component of an oxygen scavenging composition. In some variations, an oxygen scavenging oligomer or polymer is blended with a host polymer to form a polymer blend in which the oxygen scavenging oligomer or polymer is dispersed in the host polymer. It should be understood that the term host polymer encompasses single polymers and mixtures of multiple polymers, or mixtures comprising polymers and other additives. A host polymer may be a homopolymer, a copolymer, a polymer blend of two or more polymers, a polymer composite, or the like.

In some variations, one or more oxygen scavenging molecules described above in Section A may be incorporated into a host polymer to form a polymeric oxygen scavenging composition. Such an oxygen scavenging composition comprises a host polymer, and dispersed within the host polymer: i) an effective quantity of one or more oxygen scavenging molecules having formula (I), (II) or (III); and ii) an effective amount of an oxidation catalyst. The host polymer, oxygen scavenging molecules, and oxidation catalyst are each selected to provide a polymeric composition having desired physical properties and desired oxygen scavenging properties. Non-limiting examples of oxygen scavenging properties include induction time and oxygen scavenging capacity. In some cases, the effective quantities of oxygen scavenger and oxidation catalyst are such that the physical properties of the host polymer are not significantly altered. For example the intrinsic viscosity of the host polymer and the composition comprising the oxygen scavenger and oxidation catalyst may differ by about 0.05 or less.

In some variations, one or more oxygen scavenging polymers described above in Section B may be incorporated into a host polymer to form a polymeric oxygen scavenging composition. Such an oxygen scavenging composition comprises a host polymer, and dispersed within the host polymer: i) an effective quantity of one or more oxygen scavenging polymers including a repeat unit of formula (I), (II) or (III); and ii) an effective amount of an oxidation catalyst. The host polymer, oxygen scavenging polymers, and oxidation catalyst can each be selected to provide a polymeric composition having desired physical properties and desired oxygen scavenging properties. Non-limiting examples of oxygen scavenging properties include induction time and oxygen scavenging capacity. In some cases, the effective quantities of oxygen scavenger and oxidation catalyst are such that the physical properties of the host polymer are not significantly altered. For example the intrinsic viscosity of the host polymer and the composition comprising the oxygen scavenging polymer and oxidation catalyst may differ by about 0.05 or less.

In some variations, a polymeric oxygen scavenging composition comprises: i) one or more oxygen scavenging polymers having a repeat unit having formula (I), (II), or (III); and ii) an effective amount of an oxidation catalyst dispersed within the oxygen scavenging polymer. The oxygen scavenging polymer and oxidation catalyst can each be adjusted to provide a polymeric composition having desired physical properties and desired oxygen scavenging properties.

Any of the polymeric oxygen scavenging compositions may further comprise one or more additional oxygen scavengers described herein or known in the art. For example, a polymeric oxygen scavenging composition comprising one or more oxygen scavenging molecules having formula (I), (II) or (III) may additionally comprise one or more oxygen scavenging oligomers or polymers having one or more repeat units of formula (I), (II), or (III) and/or one or more additional oxygen scavengers (molecules or polymers) known in the art. A polymeric oxygen scavenging composition comprising one or more oxygen scavenging oligomers or polymers having one or more repeat units of formula (I), (II) or (III) may additionally comprise one or more oxygen scavenging molecules having formula (I), (II), or (III) and/or one or more oxygen scavengers (molecules or polymers) known in the art.

Non-limiting examples of certain properties for which the compositions may be tuned include one of or any combination of the following: i) molecular weight and intrinsic viscosity; ii) crystallinity, iii) optical clarity (e.g., haziness); iv) color (e.g., colorless); v) temperature stability during processing and/or during continuous use; vi) induction time for onset of oxygen scavenging activity; vii) shelf life; viii) oxygen scavenging capacity; ix) UV absorptivity; x) suitability for hot fill applications; xi) suitability for contact with food; and xii) suitability for contact with oils. For example, molecular weight (e.g., as measured by intrinsic viscosity) may be adjusted so that the compositions is suitable for certain downstream processing conditions, such as solid state polymerization, melt blending, injection molding and/or blow molding. In some cases, molecular weight (e.g., intrinsic viscosity) of an oxygen scavenging composition is adjusted so that the composition may be melt blended and blow molded to form bottles.

The relative compatibility of the components of the polymeric oxygen scavenging composition is an important consideration in designing an oxygen scavenging composition utilizing the oxygen scavengers described herein. In some variations, an oxygen scavenger may be selected to modulate its dispersion within the host polymer to result in a desired morphology. In some cases, a desired morphology may be one in which the oxygen scavenging components are phase separated from the host polymer, and in some cases, it may be desired that the oxygen scavenging component not phase separate from the host polymer, and instead form a relatively homogeneous solution. In cases in which a phase-separated morphology results, domain size may be affected by: i) tuning the compatibility of the oxygen scavenging component with that of the host polymer and oxidation catalyst; ii) mixing conditions; and/or iii) use of dispersants, compatibilizers, surfactants, and the like. As an example, an oxygen scavenger having extensive hydrocarbon content (e.g., due to the isoprenoid tail or due to other medium or long chain hydrocarbon substituents) may readily undergo phase separation when used in a polar polymer such as a polyester (e.g., a polyethylene terephthalate or a copolymer or adduct thereof). Domain size may be adjusted by varying mixing conditions and/or use of appropriate compatibilizers, dispersants, or surfactants known in the art. As another example, an oxygen scavenger as described herein having relatively low hydrocarbon content and increased polar character may be selected to be compatible with a polar host polymer such as a polyethylene terephthalate or a copolymer or adduct thereof such that a relatively homogeneous blend results. Without being bound by theory, in some cases, an effective amount of oxygen scavenger may be lower in some phase-separated blends than in some homogeneous mixtures, as the domains present in a phase separated blend may provide a higher local concentration of oxygen scavengers within the domains that initiate and/or enables propagation of radical species that consume oxygen. In some cases, it may be desired to form a phase separated composition in which the average domain size is sufficiently small so that the resulting polymer blend does not exhibit an undesired level of haze.

The oxygen scavengers may be incorporated into and dispersed in a host polymer using several methods. The oxygen scavenging molecules may or may not be covalently bound to the host polymer. In some variations, the oxygen scavenging molecules exist as a physical blend with the host polymer, in which essentially none of the oxygen scavenger molecules undergo chemical reaction with the host polymer so as to be covalently bound to the host polymer. In some cases, less than about 0.001%, less than about 0.01%, less than about 0.1%, less than about 1%, or less than about 5% of the oxygen scavenging molecules are covalently bound to the host polymer. In other cases, at least about 10%, at least about 20%, at least about 30%, at least about 40%, at least about 50%, at least about 60%, at least about 70%, or at least about 80% of the oxygen scavenging molecules are covalently bound to the host polymer.

In some variations, oxygen scavenging molecules may be specifically designed to have functionality to enable them to undergo a reaction with the host polymer so as to be covalently bound thereto. In other cases, an oxygen scavenging molecule may be designed to be a monomer to undergo a polymerization reaction to form at least a portion of the host polymer. Here, the oxygen scavengers are incorporated into the host polymer by copolymerizing an oxygen scavenger or a derivative thereof with one or more chemically different monomers to form an oxygen scavenging polymer. The oxygen scavenging polymer can be used as-is to form articles, or the oxygen scavenging polymer can be blended with the host polymer before use. In some cases, the oxygen scavengers are chemically incorporated into oligomers. The oligomers, in turn, can be physically blended with the host polymer before use, or copolymerized with one or more chemically different monomers to make an oxygen scavenging polymer. An oxygen scavenging polymer derived from oligomers incorporating the oxygen scavengers may be used as is, or blended with the host polymer before use.

Any effective amount of oxygen scavenger may be present in an oxygen scavenging composition. In some variations, an oxygen scavenging composition comprises about 0.1 wt % to about 30 wt % of one or more oxygen scavengers described herein. In some variations, about 5 wt % or less oxygen scavenger is used, e.g., about 0.1 wt %, 0.5 wt %, 1 wt %, 1.5 wt %, 2 wt %, 2.5 wt %, 3 wt %, 3.5 wt %, 4 wt %, 4.5 wt % or 5 wt %. In some cases, an effective amount of oxygen scavenger is in a range from 1 wt % to 3 wt %, e.g., about 1 wt %, 1.5 wt %, 2 wt %, 2.5 wt %, or 3 wt %. In some cases, an effective amount of oxygen scavenger that is used in a polymeric composition is low enough so that the composition substantially retains the physical properties of the host polymer (e.g., retains one or more of intrinsic viscosity, melt temperature, or glass transition temperature of the host polymer). By using an oxygen scavenging in which an effective amount allows the oxygen scavenging composition to substantially retain physical properties of the host polymer, processing equipment and processing conditions for the oxygen scavenging compositions are similar to that of the neat host polymer.

One or more oxidation catalysts are present in the oxygen scavenging compositions described herein. In some cases, a single oxidation catalyst is present and in other cases, more than one oxidation catalyst is present, e.g., 2 or 3 oxidations catalysts. A variety of metallic or organic compounds may be used as an oxidation catalyst for the compositions described herein. Any appropriate oxidation catalyst known in the art may be used, and selection of the catalyst may be influenced by any combination of factors including but not limited to compatibility with one or more components of the composition, compatibility with the end use of the product (e.g., appropriate for use in food grade materials), compatibility with processing conditions, and effect on final aesthetics of the product (e.g., optical clarity (haze) and/or color). Non-limiting examples of suitable oxidation catalysts include transition metals, complexes of transition metals, photoinitiators, and combinations of the foregoing.

In some variations, an oxidation catalyst comprises one or more transition metals, e.g., one or more transition metals in a positive oxidation state. Non-limiting examples of suitable transition metal metals that may be used as oxidation catalysts include cobalt, iron, nickel, aluminum, ruthenium, rhodium, palladium, antimony, osmium, iridium, platinum, copper, manganese, zinc, vanadium, complexes of any of the foregoing, oxides of any of the foregoing, and mixtures of any of the foregoing. In some cases, a metal fatty acid salt catalyst is used, e.g., a metal fatty acid salt comprising cobalt, manganese, or copper. Non-limiting examples of suitable counterions to transition metal cations in an oxidation catalyst include carboxylates (e.g., neodecanoates, octanoates, acetates, lactates, napthalates, malates, stearates, acetylacetanates, linolates, oleates, palmitates, 2-ethylhexanoates, or ethylene glycolates), oxides, borates, carbonates, chlorides, dioxides, hydroxides, nitrates, phosphates, sulfates, or silicates. Suitable metal fatty acid salt catalysts may have one of the following counterions: acetate, stearate, propionate, hexanoate, neodecanoate, octanoate, benzoate, salicylate, cinnamate, or any combination of two or more of the foregoing. In some variations, cobalt (II) salts may be used as oxidation catalysts. Non-limiting examples of cobalt catalysts that may be used include cobalt salts of acetic acid, terephthalic acid, propionic acid, benzoic acid, salicylic acid, cinnamic acid, neodecanoic acid, stearic acid, 2-ethyl hexanoic acid, or octenyl succinic acid. In some variations, salts of inorganic acids (e.g., antimony chloride III, antimony chloride V, or cobalt chloride) are used as oxidation catalysts. In some variations, cobalt neodecanoate or a mixture of salts that includes cobalt neodecanoate is used as an oxidation catalyst. In some variations, an oxidation catalyst is selected from the group consisting of cobalt neodecanoate, cobalt propionate, cobalt acetate, cobalt stearate, and cobalt octanoate.

Any effective amount of an oxidation catalyst may be used. For example, an oxidation catalyst may be present in an amount in a range from about 10 ppm to about 10000 ppm (by weight of elemental metal, based on the total composition). In some variations, a cobalt-containing oxidation catalyst (e.g., cobalt neodeconoate) is present at about 10 ppm, 20 ppm, 50 ppm, 100 ppm, 200 ppm, 300 ppm, 400 ppm, 500 ppm, 600 ppm, 700 ppm, 800 ppm, 900 ppm, 1000 ppm, 2000 ppm, 3000 ppm, 4000 ppm, 5000 ppm, 6000 ppm, 7000 ppm, 8000 ppm, 9000 ppm, or 10000 ppm.

The oxidation catalyst may be incorporated into the polymeric composition using any suitable method. In some variations, the oxidation catalyst may be added directly as a neat substance or in a liquid or waxy carrier to an extruder, blender, pelletizer, or any other equipment used in mixing or blending the components of the oxygen scavenging composition. In some variations, the oxidation catalyst may be premixed with the oxygen scavenger component before mixing with the host polymer. In some variations, the oxidation catalyst may be premixed with the host polymer, e.g., mixed with pellets, incorporated into a master batch premix. In some variations, an oxidation catalyst (e.g., a cobalt oxidation catalyst such as cobalt neodecanoate) is incorporated into a compartment of a compartmentalized host polymer pellet such as described in U.S. Patent Publication 2011/0266704, which is incorporated herein by reference in its entirety. For example, cobalt neodecanoate may be mixed in an extruder with a PET, or PET copolymer, and incorporated into a central core of a pellet having a polyester (e.g., PET or copolymer of PET) shell. In some variations, all of or at least a portion of the oxidation catalyst (e.g., cobalt neodecanoate) may be dispersed in a polyethylene terephthalate or copolymer thereof with intrinsic viscosity typically ranging from 0.40-0.65 dl/g. Such PET or copolymer thereof is subsequently solid state polymerized to achieve an intrinsic viscosity typically ranging from 0.70-90 dl/g. The higher molecular weight polymer so obtained may be used as the host polymer (e.g., PET) used to make an oxygen scavenging composition.

Optionally, any of the oxygen scavengers described herein may be used in combination with an accelerator. An accelerator is any substance that triggers or accelerates oxygen uptake by an oxygen scavenger. An accelerator may be used in a composition to: i) modulate timing of oxygen scavenging activity; and/or ii) modulate capacity or lifetime of oxygen scavenging activity. An accelerator may or may not be capable of scavenging oxygen. In some cases, an accelerator itself reacts with oxygen and in other cases, an accelerator generates reactive species that initiates initiates or accelerates reaction of the oxygen scavengers with oxygen so that the rate of oxygen uptake and/or the amount of oxygen uptake is increased. In some cases, an accelerator may be used eliminate or shorten induction time. In compositions in which the accelerator takes up oxygen, a capacity of the oxygen scavenger to take up oxygen may in some cases exceed a capacity of the accelerator to take up oxygen for the amounts of oxygen scavenger and accelerator present. For example, a composition comprising only the accelerator (and no other oxygen scavenger) may scavenge oxygen at a desired rate for an initial time period, but may lose activity before the desired lifetime of the oxygen scavenging composition. The presence of the oxygen scavenger with the accelerator may extend the lifetime of the composition to a useful range. In some variations, an accelerator may be an auxiliary oxygen scavenger that is present in addition to one or more primary oxygen scavengers. An auxiliary oxygen scavenger may be more reactive to oxygen or have a shorter induction time than the primary oxygen scavenger. In some cases, the auxiliary oxygen scavenger may be present in a smaller amount than the primary oxygen scavenger. Without being bound by theory, as an accelerator that acts as an auxiliary oxygen scavenger begins scavenging oxygen, radicals or other reactive species may be created which trigger or accelerate oxygen scavenging activity in the primary oxygen scavenger. Non-limiting examples of oxygen scavenging accelerators include photoinitiators, peroxides, radical initiators, and one or more auxiliary oxygen scavengers. In some cases, an accelerator may be created in situ in a polymer composition or article by irradiation, e.g., by actinic radiation (radiation having a wavelength of 750 nm or shorter), electron beam radiation, or gamma radiation.

In some cases, an accelerator comprises one or more allylic hydrogens, bisallylic hydrogens, or benzylic hydrogens that can be abstracted during use to provide a desired oxygen consumption rate. In some cases, an accelerator forms a resonance-stabilized radical after abstraction of a hydrogen, e.g., as is the case for bisallylic hydrogens and benzylic hydrogens. In some variations, an oxygen scavenger of formula (I), (II) or (III) and comprising a 1,4-cyclohexadiene ring that includes one or more bisallylic hydrogens (e.g., one, two, three, or four bisallylic hydrogens) functions as an accelerator. For example, an oxygen scavenger having four bisallylic hydrogens such as those having formula (I-1"), (II-1") or (III-1") may function as an accelerator. In some variations, an oxygen scavenger of formula (I") having a cyclohexadiene ring and having one or more bisallylic hydrogens (e.g., two, three or four bisallylic hydrogens) may function as an accelerator for a primary oxygen scavenger of formula (I') having a cyclohexene ring. Other non-limiting examples of accelerators for use with certain oxygen scavengers described herein (e.g., oxygen scavengers having formula (I) comprising a cyclohexene ring) include oxygen scavenging polyolefins (e.g., polyethylenes or copolymers thereof, cyclohexene copolymers, polybutadienes or copolymers or adducts thereof, polyisoprenes or copolymers or adducts thereof), oxygen scavenging copolymers of polyethylene terephthalate (e.g., copolymers of polyethylene terephthalate with 5-sulfoisophthalic acid, copolymers of polyethylene terephthalate with polybutadiene, or copolymers of polyethylene terephthalate with polyisoprene), or oxygen scavenging polyamides (e.g., meta-xylylamine-base polyamides or copolymers thereof, or poly(meta-xylylamine)-based adipamide), AMOSORB® oxygen scavengers available from ColorMatrix® (e.g., as described in U.S. Pat. No. 6,083,585, which is incorporated herein by reference in its entirety), Oxbar® oxygen scavengers available from Constar (e.g., as described in U.S. Pat. No. 5,952,066, which is incorporated herein by reference in its entirety), suitable photoinitiators (e.g., Rose Bengal containing or Rose Bengal derived photoinitiators), oxidizable unsaturated polyolefins such as grafted polybutadiene homopolymers or copolymers of polybutadienes that have functionality to improve compatibility with a host polymer (e.g., PET). A functionalized polybutadiene homopolymer may be a 1,4- and/or 1,2-polybutadiene, and a polybutadiene copolymer may include 1,4-polybutadiene and/or 1,2-polybutadiene. In some cases, a polybutadiene copolymer may comprise a substantial amount of 1,4-polybutadiene (e.g., about 30% or more, about 40% or more, about 50% or more, about 60% or more, about 70% or more, about 80% or more, or about 85% or more). In some cases, a functionalized polybutadiene may have a 1,2-vinyl content of about 70% or less (e.g., about 70%, about 60%, about 50%, about 40% or less, about 30%, about 25%, about 20%, about 15%, or about 10% 1,2-vinyl content). A functionalized polybutadiene homopolymer or copolymer may have an average molecular weight in a range from about 1000 to about 50,000, in a range from about 1000 to about 20,000, or in a range from about 1000 to about 10,000, e.g., a molecular weight of about 1500, about 2500, about 3000, about 5000, about 8000, about 9000, about 10,000 (units g/mol). Non-limiting examples of functionalized polybutadienes containing less than about 25-30 parts 1,2-vinyl content that may function as accelerators include carboxylic acid or maleic anhydride adducted polybutadienes, such as the Ricon® Resins family of maleic anhydride adducted polybutadienes, e.g., Ricon® 131MA5, Ricon® 131MA10, Ricon® 131MA12, Ricon® 131MA17, and Ricon® 131MA20, each available from Cray Valley Polymers) or Lithene® polybutadiene resins (e.g., Lithene® N4-5000-15MA, Lithene® N4-9000-10MA, or Lithene® PM4-7.5MA maleic anhydride polybutadiene resin, each available from Synthomer). If a maleic anhydride adducted polybutadiene resin is used, any suitable molecular weight of polybutadiene and any suitable maleic anhydride content may be used, e.g., about 5 wt % or parts, about 8 wt % or parts, about 10 wt % or parts, about 12 wt % or parts, about 15 wt % or parts, about 17 wt % or parts, about 20 wt % or parts, or about 25 wt % or parts functional group. In some cases, an average number of functional groups per polymer chain may be in a range from about 1 to about 20 or from about 1 to about 11, e.g., about 1, 2, 5, 9, 10, 11, 15, or 20 functional groups/chain. In some cases, a maleic anhydride adducted polybutadiene having a molecular weight in a range from about 1000 to about 10,000, a functional group content in a range from about 2 to about 20 wt %, and optionally a 1,2-vinyl content of about 50 wt % or less. Non-limiting examples of maleic anhydride adducted polybutadienes that may be used are described in U.S. Pat. No. 5,300,569, which is incorporated herein by reference in its entirety. Other suitable radical accelerators or photoinitiators may be used as accelerators with the oxygen scavengers described herein.

Some oxygen scavenging compositions may comprise two or more oxygen scavengers. The multiple oxygen scavengers may be selected to have complementary properties. For example, a first oxygen scavenger having little or no induction time may be used in combination with a second oxygen scavenger that may have a longer induction time. As desired, a third or subsequent oxygen scavenger having an even longer induction time may be used. Oxygen scavenging composition comprising scavengers with staged induction times may be employed in a variety of applications. For example, the compositions may be used in application in which the article will be stored for an unknown period of time that may be very short or very long, or the compositions may be used in the event that the first oxygen scavenger has limited capacity and stops scavenging after some period of time. Combinations of two or more oxygen scavengers described herein may be used, or combinations of one or more oxygen scavengers described herein and one or more oxygen scavengers known in the art may be used. For example, an oxygen scavenging composition may comprise one or more oxygen scavengers described herein in combination with one or more of the following known oxygen scavengers: oxidizable polyolefins (e.g., polyethylenes or copolymers thereof, cyclohexene copolymers, polybutadienes or copolymers or adducts thereof such as grafted polybutadienes, polyisoprenes or copolymers or adducts thereof), oxygen scavenging copolymers of polyethylene terephthalate (e.g., copolymers of polyethylene terephthalate with 5-sulfoisophthalic acid, or copolymers of polyethylene terephthalate with polybutadiene), or oxygen scavenging polyamides (e.g., meta-xylylamine-base polyamides or copolymers thereof, or poly(meta-xylylamine)-based adipamide), AMOSORB® oxygen scavengers available from ColorMatrix®, or Oxbar® oxygen scavengers available from Constar.

Optionally, a polymer composition comprises one or more additives in addition to one or more oxygen scavengers, where the additives do not undesirably impact oxygen scavenging capabilities. For example, any one of or any combination of heat stabilizers, antioxidants, pigments or colorants, impact modifiers, surface lubricants, stabilizers, UV absorbers, metal deactivators, nucleating agents, blowing agents, inorganic fillers, accelerants, crystallization agents, surfactants, and compatibilizers may be added. In some polyester-based compositions intended for use as bottles, one or more reheat additives may be added for those processes in which preforms are made which are subsequently reheated prior to undergoing stretch blow molding into a bottle. Non-limiting examples of reheat additives include carbon black, activated carbon, black iron oxide, glassy carbon, silicon carbide, antimony, silica, and red iron oxide. Non-limiting examples of impact modifiers that may be added in some compositions include ethylene/acrylate/glycidyl terpolymers, ethylene/acrylate copolymers, ethyl methacrylate, butyl acrylate, and styrene-based block copolymers. Ultraviolet absorbers may be added in those instances in which a substance that is sensitive to light as well as to oxygen is to be stored. In some variations, the total weight of additives other than oxygen scavengers, accelerators and oxidation catalysts is about 25 wt % or less, or about 10 wt % or less (based on the total weight of the composition).

In some variations, one or more antioxidants (e.g., butylated hydroxytoluene (BHT) or 4-tert-butyl catechol (TBC) is added to the composition prior to or during processing to stabilize the oxygen scavenging composition. In some variations in which an antioxidant is present, the induction time of oxygen scavenging activity may be increased. In some variations, it may be desired to incorporate one or more antioxidants or radical inhibitors into an oxygen scavenging composition to modulate oxygen scavenging activity. Such antioxidants or radical inhibitors may be used to increase induction time, which may for example be employed to inhibit oxygen scavenging activity during storage or to control shelf life of a composition or article. Nonlimiting examples of antioxidants or radical inhibitors that may be used to modulate oxygen scavenging activity include phenolic antioxidants (e.g., sterically hindered phenolic antioxidants such as Irganox® 1010, Irganox® 1076, or Irganox® 1098, available from BASF), butylated hydroxytoluene (BHT), TBC, and the like. If it is desired to decrease induction time, any known technique may be implemented to reduce induction time to a desirable range. For example, irradiation (e.g., using light having a wavelength of 750 nm or shorter, using electron beam radiation, or using gamma radiation) may be used to treat a composition or an article formed from a composition, or a composition may be treated with a peroxide to reduce induction time. Antioxidants may be selected to be compatible with the processing and use conditions employed for the oxygen scavenging compositions, resistant to discoloration, suitable for use with food in appropriate applications, and may provide added benefits of improving thermo-oxidative stability and/or improving UV stability of a composition.

In some cases, one or more compatibilizers or surfactants may be used in a polymeric composition comprising oxygen scavengers as described herein. A compatibilizer or surfactant may be used to control dispersion of domain size of oxygen scavenger composition within a host polymer. Any suitable compatibilizer or surfactant that is known in the art may be used to control dispersion and domain size to result in morphology in an article that does not exhibit an undesirable amount of haze for its intended application and/or to exhibit sufficient oxygen scavenging activity. In some cases, a compatibilizer or surfactant is employed in an oxygen scavenging composition so that crystallites or phase separated domains have an average size of about 300 nm or less, or to produce a haze value of about 8% or less.

An oxygen scavenging composition comprising any suitable relative amounts of one or more oxygen scavengers, one or more oxidation catalysts, one or more accelerators (if present), and one or more additional additives (if present) may be designed to meet requirements for performance (e.g., oxygen scavenging, aesthetics such as optical clarity (e.g., haze), color, physical properties, food contact suitability, taste, odor), cost, and manufacturability (e.g., effect on intrinsic viscosity during melt blending, ease of extrusion, suitability for injection molding and blow molding, and the like).

Suitable host polymers for the oxygen scavengers include any polymer that can be formed into a container, bottle, tray, film or the like, and may be thermoplastics, elastomers, or thermosets. Suitable thermoplastic polymers include any thermoplastic homopolymer or copolymer. Non-limiting examples of suitable host polymers include polyamides (e.g., nylon 6, nylon nylon 11, 6,6, nylon 6,12, nylon 12, MXD-6 Nylon (meta-xylylene diamine/adipic Acid)); linear polyesters (e.g., polyethylene terephthalate (PET), polybutylene terephthalate (PBT), polytrimethylene terephthalate, polyethylene napthalate (PEN), polybutylene napthalate (PBN)); branched polyesters; poly(lactic acid) (PLA) and copolymers thereof; polyethylene furanoate and copolymers thereof; polystyrenes; polycarbonates; polyvinylchloride (PVC); polyvinylidene dichloride; polyacrylamide; polyacrylonitrile; polyvinyl acetate; polyacrylic acid; polyvinyl methyl ether; ethylene vinyl acetate copolymer; ethylene methyl acrylate copolymer; acrylics and acrylic copolymers such as acrylonitrile-butadiene-styrene; polyolefins (e.g., polyethylene, polypropylene, ethylene-propylene copolymers, polybutadiene, polyisoprene, poly(1-hexene), poly(4-methyl-1-pentene), poly(1-butene), poly(3-methyl-1-butene), poly(3-phenyl-1-propene)); poly(ethylene oxides) (PEO); poly(ε-caprolactams); thermoplastic fluoropolymers (e.g., polytetrafluoroethylenes such as TEFLON® and polyvinylidenefluoride); polyurethanes; polyepoxides; polylactones (e.g., polycaprolactones); polymethyl methacrylates; polystyrenes; polyarylates; polyphenylene oxides (PPO); styrene/maleic anhydrides; polyoxymethylnes; imides such as polyimide, polyetherimide, and polyamideimide; polyphthalamides; sulfones such as polysulfone, polyarylsulfone and polyethersulfone; polyaminoacids; polydimethylsiloxanes; styrenes such as polystyrene; hydrogenated polystyrene; cellulosic resins such as cellulose proprionate, cellulose acetate, and cellulose nitrate; poly a-methyl styrene and styrene/acrylonitrile; vinyls such as polyvinyl chloride and polyvinylnaphthalene; ketone polymers such as polyetheretherketone and polyarylether ketone; any interpolymer or copolymer of the foregoing; any mixture or polymer blend of the foregoing; any derivatives of the foregoing. In some variations, the host polymer is not a polyester. In some variations, the host polymer is not PET or a copolymer or adduct thereof.

Host polymers described herein may be made by any means and by methods known in the art and those which have not yet been invented. In some variations, melt phase polymerization involving the reaction of a diol with a carboxylic acid or its corresponding diester is used to prepare a polyester.

Suitable dicarboxylic acids and esters that can be used to make suitable polyesters may comprise about 6 to about 40 carbon atoms. Non-limiting examples of specific dicarboxylic acids include terephthalic acid, isophthalic acid, naphthalene 2,6-dicarboxylic acid, cyclohexanedicarboxylic acid, cyclohexanediacetic acid, 1,2-phenylenediacetic acid, 1,4-phenylenedioxydiacetic acid, succinic acid, glutaric acid, adipic acid, azelaic acid, sebacic acid, furan dicarboxylic acid, and the like. Also included are the dimethyl esters of the preceding dicarboxylic acids. Non-limiting examples of specific esters that can be used to make suitable polyesters include the diesters of phthalic acid diesters and naphthalic diesters.

Suitable acids or esters may be reacted with an aliphatic diol having from about 2 to about 30 carbon atoms, a cycloaliphatic diol having from about 7 to about 15 carbon atoms, an aromatic diol having from about 6 to about 15 carbon atoms, or a glycol ether having from about 4 to about 10 carbon atoms. Non-limiting examples of suitable diols include ethylene glycol, 1,4-butanediol, 1,3-butane diol, trimethylene glycol, 1,6-hexanediol, 1,4-cyclohexanedimethanol, diethylene glycol, resorcinol, and hydroquinone. In some instances polyfunctional comonomers are used (e.g., in an amount from 0.1 to about 3 mole percent) to make polyesters. Non-limiting examples of suitable comonomers include trimellitic anhydride, trimethylolpropane, pyromellitic dianhydride (PMDA), and pentaerythritol. Polyacids or polyols may also be used.

The host polymer used in the oxygen scavenging compositions may be any suitable polymer. In some variations, a host polymer is or comprises a polyester or a copolymer or adduct thereof. One non-limiting example of a suitable polyester is polyethylene terephthalate (PET) formed from the approximate 1:1 stoichiometric reaction of terephthalic acid (or a corresponding ester such as dimethyl terephthalic acid), with ethylene glycol. Another non-limiting example of a suitable polyester is polyethylene(2,6-naphthalate) (PEN) formed from the approximate 1:1 to 1:6 (e.g., 1:1, 1:2, 1:3, 1:4, 1:5, or 1:6) stoichiometric reaction of naphthalene 2,6-dicarboxylic acid (or its corresponding ester, e.g., dimethyl ester) with ethylene glycol. Another non-limiting example of a suitable polyester is polybutylene terephthalate (PBT). In some variations, a copolymer of PET, PEN, or PBT is used. In some variations, a polyester is made from a reaction of isophthalic acid or a corresponding diester with 2,6-napthalic acid and/or a corresponding diester and 1,4-cyclohexane dimethanol. A further non-limiting example of a suitable polyester is polytrimethylene terephthalate (PTT), which may be prepared by reacting 1,3-propanediol with at least one aromatic diacid or a corresponding alkyl ester. Non-limiting examples of suitable diacids and esters that can be used to make PTT include terephthalic acid (PTA) and dimethyl terephthalate (DMT). In some variations, PTA or DMT makes up at least about 80% of a PTT polyester. Non-limiting examples of diols that may be used in place of or in addition to 1,3-propanediol to make PTT include ethylene glycol, diethylene glycol, 1,4-cyclohexane dimethanol, and 1,4-butanediol. In some variations, another aromatic or aliphatic acid (e.g., isophthalic acid or sebacic acid) is co-reacted to make a copolymer.

In certain variations, the host polymer is or comprises a crystallizable polyester. Crystallizable or semicrystalline polyesters may be made by reacting one or more diols with one or more dicarboxylic acids or its corresponding diester, e.g., a crystallizable polyester made by reacting an acid selected from the group consisting of terephthalic acid and 2,6-naphthalene dicarboxylic acid (or their corresponding dimethyl esters) with a diol selected from the group consisting of ethylene glycol, diethylene glycol, 1,4-butane diol and 1,3-butane diol. In some variations, the sum of the number of moles of the carboxylic acid and the number of moles of the diol divided by the total quantity of acids and polyols in the polymer is at least about 85%. In some variations, the host polymer is or comprises a copolymer of PET or PEN. For example, a host polymer may comprise a copolymer made by reacting terephthalic acid (or its corresponding dimethyl ester) with ethylene glycol and one or more the group consisting of isopthalic acid, 2,6-naphthalene dicarboxylic acid, cyclohexanedimethanol, 1,4-butane diol, 1,3-butane diol, diethylene glycol, and 1,3-propane diol.

For clarification the unmodified term PET refers to polyethylene terephthalate or copolyethylene terephthalate. The modifier crystallizable refers to the ability of the polymer to be crystallized to some extent as measured by differential scanning calorimetry (D.S.C.). Typical crystallinity levels range from 5 to as high as 65 percent depending upon the type of thermal treatment and nucleation techniques used. Typically a polymer will be considered amorphous when it has less than 5% crystallinity.

There are two types of crystalline structures: one is strain induced crystallinity which orders the moelcules by exposing the material to force at an elevated temperature below the melt point. This type of crystallinity is also known as orientation and occurs when fibers are drawn or when bottles are stretch blown. Because of the order and orientation of the crystals, the materials with strain induced crystallinity are generally clear. Non-strain induced crystallinity occurs when the amorphous material is heated in the absence of a stress. The material will become white. This crystallinity is random in nature and is very brittle. The embodiments of this invention can be conducted on amorphous pellets (those with less than 5% crystallinity), strain induced crystalline pellets, non-strain induced crystalline pellets and pellets with both strain induced and non-strain induced crystallinity. Pellets with both types of crystallinity would come from orienting the strand during the extrusion process and then exposing the cut pellets or strand to heat sufficient to convert some of the remaining amorphous material in the pellet to a non-strain induced crystalline morphology.

In some variations, the host polymer is or comprises a polymer selected from the group consisting of polyethylene terephthalate, copolymers of polyethylene terephthalate, polyethylene naphthalate, copolymers of polyethylene napthalate, polybutylene terephthalate, copolymers of polybutylene terephthalate, polytrimethylene terephthalate, copolymers of polytrimethylene terephalate, polyethylene furanoate and copolymers of polyethylene furanoate, and poly(lactic acid) and copolymers of poly(lactic acid). In some variations, the host polymer is or comprises a polyester made by reacting at least one acid selected from the group consisting of terephthalic acid and isophthalic acid or their dimethyl esters with at least one glycol selected from the group consisting of ethylene glycol, diethylene glycol, 1,4-butane diol, 1,3-butanediol, and 1,4-cyclohexanedimethanol (CHDM). In some variations, the host polymer is or comprises a homopolymer or copolymer of the reaction of terephthalic acid (or an ester thereof such as the dimethyl ester), ethylene glycol, and one or more co-acids or acid ester comonomers. In some variations, the host polymer is or comprises a homopolymer or copolymer of the reaction of terephthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a polyamide or a copolymer or adduct thereof, or a polyolefin or a copolymer or adduct thereof. In some variations, the host polymer is or comprises polyethylene furanoate or a copolymer or adduct of polyethylene furanoate or poly(lactic acid) or a copolymer or adduct of poly(lactic acid). In some variations, the host polymer is not a polyester. In some variations, the host polymer is not polyethylene terephthalate or a copolymer thereof. In some variations, the host polymer is not a polyester made by reacting at least one acid selected from the group consisting of terephthalic acid and isophthalic acid or their dimethyl esters with at least one glycol selected from the group consisting of ethylene glycol, diethylene glycol, 1,4-butanediol, 1,3-butanediol and 1,4-cyclohexanedimethanol (CHDM). In some variations, the host polymer is not polyethylene terephthalate or a copolymer or adduct thereof. In some variations, the host polymer is not a homopolymer or copolymer of the reaction of terephthalic acid (or an ester thereof such as the dimethyl ester) and ethylene glycol. In some variations, the host polymer is not a homopolymer or copolymer of the reaction of terephthalic acid (or an ester thereof such as the dimethyl ester), ethylene glycol, and one or more co-acids or acid ester co-monomers. In some variations, the host polymer is not a homopolymer or copolymer of the reaction of terephthalic acid (or an ester thereof such as the dimethyl ester), ethylene glycol and one or more dialcohol co-monomers (e.g., 1,4-cyclohexanedimethanol, diethylene glycol, 1,4-butane diol or 1,3-butane diol). In some variations, the host polymer is not a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is not a copolymer of the reaction of terephthalic acid (or an ester thereof such as the dimethyl ester), isophthalic acid (or an ester thereof such as the dimethyl ester) and ethylene glycol. In some variations, the host polymer is not a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol).

In some variations, the host polymer comprises polytrimethylene terephthalate (PTT) or a copolymer or adduct thereof. PTT can be made by reacting 1,3-propanediol with at least one aromatic diacid or alkyl ester thereof (e.g, terephthalic acid or dimethyl terephthalate (DMT)). Optionally, a host polymer may be a copolymer of PTT made by reacting 1,3-propane diol with terephthalic acid or DMT and one or more comonomers selected from the group consisting of ethylene glycol, diethlene glycol, 1,4-cyclohexane dimethanol, 1,4-butanediol, isophthalic acid, and sebacic acid.

In forming a polyester, a catalyst may be used in the esterification or polycondensation reaction. Non-limiting examples of suitable catalysts for forming polyesters include antimony oxide, antimony triacetate, antimony ethylene glycolate, organomagnesium, tin oxide, titanium alkoxides, dibutyl tin dilaurate, and germanium oxide. Any of these catalysts may be used in combination with zinc, manganese, magnesium acetates or benzoates. In some variations, a catalyst comprising titanium or zirconium is used, e.g., titanium or zirconium alkylates and their derivatives, titanium or zirconium complex salts, titanium or zirconium complexes with hydroxycarboxylic acids, titanium dioxide-silicon dioxide co-precipitates or zirconium dioxide-silicon dioxide co-precipitates, and hydrated alkaline-containing titanium dioxide or zirconium dioxide. Some non-limiting examples include tetra-(2-ethylhexyl)titanate, tetrastearyl titanate, diisopropoxy-bis(acetylacetonato)titanium, di-n-butoxy-bis(triethanolaminato)titanium, tributylmonoacetyltitanate, triisopropylmonoacetyltitanate, tetrabenzoic acid titanate, alkali titanium oxalates and malonates, potassium hexafluortitanate, and titanium complexes with tartric acid, citric acid or lactic acid, titranium tetrabutylate, and titanium tetraisopropylate. For any of the preceding, corresponding zirconium compounds may be used. Residue of the polymerization catalyst may be present in the resulting polymer, and in those cases in which color of the oxygen scavenging article or composition is important, a polymerization catalyst may be selected that does not react with oxygen scavenging species to impart undesired color. In some variations, a titanium containing polymerization catalyst is used.

In some variations, a host polymer may contain a colorant or compound that provides a certain color tint.

It is desired that the polymer have an intrinsic viscosity necessary for manufacture of the desired article (e.g., a bottle). Any suitable method for preparing polymers with a desired intrinsic viscosity may be used. In some cases, a melt phase polymerization employed for polyester polymers is followed by crystallization, which is followed by solid state polymerization step (solid stating or SSP). The crystallization may be carried out at a temperature in a range from about 100° C. to about 150° C. A crystallization step may increase the overall crystallinity content of a polymer by at least about 5%. The solid phase polymerization may be carried out at a temperature in a range from about 200° C. to about 1° C. less than the melting point of the polymer. For certain commercial crystallizable polyesters that melt at 242-248° C., a SSP reaction may be carried out from about 200° C. to about 235° C., or from about 215° C. to about 235° C. The solid state polymerization may be carried out for a time sufficient to raise the molecular weight and intrinsic viscosity to a desired value, which depends on the end application for the polymer. The time necessary for the SSP depends on the initial intrinsic viscosity of the polyester. In some cases, an intrinsic viscosity in a range from about 0.54 dl/g to about 1.0 dl/g, or from about 0.54 dl/g to about 0.88 dl/g may be reached by solid state polymerization reaction carried out for a time in a range from about 8 to about 45 hours. Typical increases in intrinsic viscosity by SSP are at least about 0.04 dl/g, e.g., about 0.2 to 0.4 dl/g. The crystallization and solid phase polymerization step may be performed in a tumbler dryer reaction in a batch-wise or continuous solid state process in which the polymer flows from one reactor to another after undergoing designated thermal treatment in each reactor.

In some variations, compartmentalized polyester pellets may be used in an SSP reaction. In one preferred embodiment, a compartmentalized pellet may include an interior core and an exterior sheath, that may, for example, be prepared by coextrusion, e.g., as described in U.S. Patent Publication 2007/0093616, which is incorporated herein by reference in its entirety. In some variations, the interior core comprises one or more oxidation catalysts, e.g, cobalt neo-decanoate. In some variations, the interior core comprises one or more oxygen scavengers having formula (I), (II), or (III). In certain variations, the oxygen scavenger is specifically designed to have suitably low volatility and suitably high thermo-oxidative stability to be used in a compartmentalized pellet.

The desired intrinsic viscosity of the polymer depends on the application. In some cases in which the polymer will be used to make bottles, the intrinsic viscosity may be in a range from about 0.6 deciliter/gram to about 1.0 deciliter/gram (e.g., about 0.6, 0.65, 0.7, 0.75, 0.8, 0.85, 0.9, 0.95, or 1 dl/g), where the intrinsic viscosity is determined by the method described in ASTM D-4603-86 or ASTM D4603-03 "Standard Test Method for Determining Inherent Viscosity of Poly(Ethylene Terephthalate) (PET) by Glass Capillary Viscometer" (which is incorporated herein by reference in its entirety) carried out at 30° C. for a 0.5 wt % solution in a 60/40 by weight mixture of phenol and 1,1,2,2,-tetrachlorethane using a glass capillary viscometer. Solution viscosity and melt viscosity of the polymeric compositions described herein may be measured using a variety of techniques. For example, melt viscosity can be measured using a rheometer. In some cases, solution viscosity is measured by dissolving a known amount of the polymeric composition into an appropriate solvent. In some cases, melt viscosity is measured by following a procedure described in ASTM D3835-08 "Standard Test Method for Determination of Properties of Polymeric Materials by Means of a Capillary Rheometer," which is incorporated herein by reference in its entirety.

In some cases, processing associated with the addition of an oxygen scavenger as described herein leads to a drop in intrinsic viscosity in a host polymer (e.g., a polyester). It may be desirable to limit the amount of water, carboxylic acid, amine, and hydroxyl content in an oxygen scavenger, accelerator, and/or oxidation catalyst to limit undesired decrease in intrinsic viscosity. In some cases, it is desired that for oxygen scavengers or compositions comprising oxygen scavengers, the water content be limited to about 500 ppm or less and/or the total acid and anhydride content be limited to about 0.1 mg KOH/g or less to limit reduction in intrinsic viscosity. Total acid number may be measured by any suitable technique, e.g., according to ASTM D974 "Standard Test Method for Acid and Base Number by Color-Indicator Titration," which is incorporated herein by reference in its entirety. Water content may be measured by any suitable method, e.g., by Karl Fischer titration. It may be desirable to use a polymer that has an intrinsic viscosity that is higher than that desired for forming of bottles or other containers to compensate for the intrinsic viscosity drop and so that the composition that is to be formed has the desired intrinsic viscosity. For example, in some cases, a polymer may be selected to have an intrinsic viscosity that is about 25%, 20%, 15%, 10% or 5% higher than would be selected for a particular forming operation (e.g., forming into bottles) in the absence of addition of the oxygen scavenger.

In some cases, a chain extender or cross-linking agent may be used to counteract molecular weight degradation that may occur with the addition of the oxygen scavenger. Sufficient chain extender or crosslinking agent may be added to maintain the glass transition temperature of the polymeric substance in a desired range to allow for melt blending and melt processing of the polymer into the desired shape. In some cases, pyromellitic dianhydride (PMDA) is used as a chain extender. PMDA-modified PET is approved by the US FDA for contact with food. Any suitable amount of chain extender or crosslinking agent may be used, e.g., about 0.1 to about 3 wt %. In some variations, sufficient chain extender or crosslinking agent is added such that a change in intrinsic viscosity upon addition of the oxygen scavenger is about 0.1 dl/g or less, about 0.05 dl/g or less, or about 0.02 dl/g or less. In some cases, sufficient PMDA is added such that the intrinsic viscosity of the polymer blend including the oxygen scavenger is not appreciably different than the intrinsic viscosity of the host polymer without the oxygen scavenger. In instances in which a polyester (e.g., PET, PEN, or a copolymer or terpolymer thereof) is used as the host polymer, PMDA may be added in an amount of about 0.1 wt % to about 3 wt %. In some cases, a maleic anhydride adducted polybutadiene as described herein may be used as a chain extender or cross-linking agent. In some cases, a maleic anhydride adducted polybutadiene may function as both an accelerator and as a chain extender or a cross-linking agent.

In some cases, a host polymer may comprise recycled polyester or materials derived from recycled polyester, e.g., polyester monomers, catalysts, and/or oligomers. In some variations, post-consumer recycled polyester is used, e.g., post-consumer recycled PET having an intrinsic viscosity in a range from about 0.6 dl/g to about 0.85 dl/g. In some cases, postconsumer recycled polyester that is suitable for use in food packaging as laid out in the applicable regulations promulgated by the relevant governing bodies, e.g., by the Food Drug and Cosmetic Act in the United States. In some cases, suitable polyesters that can be used herein are listed in Code of Federal Regulations Title 21 Part 177 (as revised as of Apr. 1, 2011) as acceptable for use in containers that will contact food.

The oxygen scavenging compositions in which the oxygen scavenging molecules or polymers are physically blended with a host polymer may be made using any known blending process using any suitable scheme for adding the components. In some variations, the oxidation catalyst is combined with the host polymer prior to mixing with the oxygen scavenging molecules. In some variations, the oxidation catalyst and the oxygen scavengers are directly mixed with a host polymer. In some variations, one or both of the oxidation catalyst and the oxygen scavengers are injected into a port of an extruder. In some variations, one or both of the oxidation catalyst is premixed with the host polymer by tumbling in a hopper or blender prior to undergoing melt blending.

Any suitable polymerization method may be used to make the oxygen scavenging polymer described herein. In some variations, an oxygen scavenging polymer may be formed via polymerization in a reactor (batch-wise or continuous). In other variations, an oxygen scavenging polymer may be formed via reactive extrusion. In reactive extrusion, the reactants are fed into the mixing zone of an extruder. The components may be premixed prior to introduction into the extruder, or the components may be fed separately into the extruder.

Oxygen scavenging capability of a polymer composition described herein may be measured by a variety of methods using a variety of oxygen sensing techniques. In some cases, a procedure described in ASTM D3985-05 (2010) entitled "Standard Test Method for Oxygen Gas Transmission Rate Through Plastic Film and Sheeting Using a Coulometric Sensor," which is incorporated herein by reference in its entirety, is used to measure oxygen scavenging capability of a polymer composition described herein. In some cases, a method described in ASTM F1927-07 "Standard Test Method for Determination of Oxygen Gas Transmission Rate, Permeability and Permeance at Controlled Relative Humidity Through Barrier Materials Using a Coulometric Detector," which is incorporated herein by reference in its entirety, is used to measure oxygen scavenging capability. In some variations, oxygen permeation through a container wall is measured using an oxygen permeation testing apparatus made by MOCON (www.mocon.com, Minneapolis, Minn.), such as an OpTech® O2 Platinum analyzer that uses fluorescence detection, or using one of the Ox-Tran® family of oxygen permeation testing apparatus that utilize coulometric sensors. In some variations, oxygen concentration in a closed or sealed container wall is analyzed using a fiber optic oxygen sensor, e.g., fiber optic oxygen sensors available from Ocean Optics, Dunedin, Fla. Fiber optic oxygen sensors are phase fluorometer-coupled chemical sensors that allow spectral analysis of dissolved and gaseous oxygen pressure, where fluorescence is used to measure the partial pressure of dissolved or gaseous oxygen. In some variations, a FIBOX 3 fiber optic oxygen sensor made by PreSens GmbH (Regensburg, Germany) is used to measure the partial pressure of dissolved or gaseous oxygen in a container.

Polymer compositions comprising the oxygen scavengers can be formed directly into articles, or stored, or further processed. In some cases, polymer compositions comprising the oxygen scavengers are pelletized, e.g., chopped or ground into pieces or flakes. In some cases, polymer compositions comprising the oxygen scavengers are used in solid stating formulations. In solid stating, the host polymer (e.g., a polyester such as PET or PEN) is formed by a polymerization process that is stopped when a desired molecular weight or intrinsic viscosity is reached. Pellets are formed from the polymer at this stage. The pellets are stored pending final use. During the final use, the pellets are heated and tumbled so that the polymerization continues in the solid state until the desired final molecular weight is reached.

If a polymer composition is to be stored before use, it may be desirable to stored in a sealed container under an inert atmosphere until use.

In some variations, an oxygen scavenging composition comprises one or more compounds of Group A1 having formula (I'), (II'), (III'), (IV'), (V'), or (VI') and optionally an accelerator. In some variations, one or more compounds of Group B1 having formula (I"), (II"), (III"), (IV"), (V"), or (VI") functions as an accelerator for an oxygen scavenger of Group A1. In some preferred variations, the accelerator of Group B1 has at least 2 (e.g., 2, 3, or 4) bisallylic hydrogens attached to carbons of the six-membered ring. In some variations, an oxygen scavenging composition comprises an oxygen scavenger of Group A1 and an accelerator of Group B1, wherein the accelerator comprises a 1,4-cyclohexadiene ring comprising one or more bisallylic hydrogens bonded thereto and the primary scavenger has a corresponding structure with a cyclohexene ring substituted for the 1,4-cyclohexadiene ring, and singly allylic hydrogens substituted for the bisallylic hydrogens. For example, in some variations, an oxygen scavenging composition comprises a primary oxygen scavenger having structure (II') and an accelerator having structure (II"). Table A.1 provides non-limiting combinations of oxygen scavengers (shown in rows) and accelerators (shown in columns). Each "X" in Table A.1 specifically discloses that combination of primary oxygen scavenger and accelerator. In the oxygen scavenging compositions, any relative amount of oxygen scavenger of Group A1 to accelerator of Group B1 may be present to achieve an oxygen scavenging composition having desirable properties. For example, a mass ratio (A1):(B1) may be about 1000:1, 500:1, 200:1, 100:1, 50:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:50, 1:100, 1:200, 1:500, or 1:1000.

TABLE A.1.

| Group B1 Accelerator formula | Group A1 oxygen scavenger formula | | | | | |
| --- | --- | --- | --- | --- | --- | --- |
| | (I') | (II') | (III') | (IV') | (V') | (VI') |
| (I") | X | X | X | X | X | X |
| (II") | X | X | X | X | X | X |
| (III") | X | X | X | X | X | X |
| (IV") | X | X | X | X | X | X |
| (V") | X | X | X | X | X | X |
| (VI") | X | X | X | X | X | X |

Any suitable oxidation catalyst and any suitable host polymer described herein or otherwise known may be used with the combinations disclosed in Table A.1. In some variations, a transition-metal containing oxidation catalyst such as a salt of cobalt or manganese may be used. In some cases, a cobalt containing catalyst (e.g., cobalt neodecanoate, cobalt propionate, cobalt stearate, cobalt octoate, or cobalt acetate) is used. In some variations, the host polymer is or comprises a polyester (such as PET, PBT, PEN, or PBN) or a copolymer or adduct thereof. In some variations, the host polymer is or comprises a polymer selected from the group consisting of polyethylene terephthalate, copolymers of polyethylene terephthalate, polyethylene naphthalate, copolymers of polyethylene napthalate, polybutylene terephthalate, copolymers of polybutylene terephthalate, polytrimethylene terephthalate, copolymers of polytrimethylene terephalate, polyethylene furanoate and copolymers of polyethylene furanoate, poly(lactic acid) and copolymers of poly(lactic acid). In some variations, the host polymer is or comprises a polyester made by reacting at least one acid selected from the group consisting of terephthalic acid and isophthalic acid or their dimethyl esters with at least one glycol selected from the group consisting of ethylene glycol, diethylene glycol, 1,4-butanediol, 1,3-butanediol and 1,4-cyclohexanedimethanol (CHDM). In some variations, the host polymer is or comprises a homopolymer or copolymer of the reaction of terephthalic acid (or an ester thereof such as the dimethyl ester), ethylene glycol, and one or more co-acids or acid ester comonomers. In some variations, the host polymer is or comprises a homopolymer or copolymer of the reaction of terephthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a polyamide or a copolymer or adduct thereof, or a polyolefin or a copolymer or adduct thereof. In some variations, the host polymer is or comprises polyethylene furanoate or a copolymer or adduct of polyethylene furanoate, or poly(lactic acid) or a copolymer or adduct of poly(lactic acid). In some variations, the host polymer is not a polyester. In some variations, the host polymer is not or does not comprise PET. In some variations, the host polymer is not polyethylene terephthalate or a copolymer or adduct thereof. In some variations, the host polymer is not a polyester made by reacting at least one acid selected from the group consisting of terephthalic acid and isophthalic acid or their dimethyl esters with at least one glycol selected from the group consisting of ethylene glycol, diethylene glycol, 1,4-butanediol, 1,3-butanediol, and 1,4-cyclohexanedimethanol (CHDM). In some variations, the host polymer is not a homopolymer or copolymer of the reaction of terephthalic acid (or an ester thereof such as the dimethyl ester) and ethylene glycol. In some variations, the host polymer is not a homopolymer or copolymer of the reaction of terephthalic acid (or an ester thereof such as the dimethyl ester), ethylene glycol, and one or more co-acids or acid ester co-monomers. In some variations, the host polymer is not a homopolymer or copolymer of the reaction of terephthalic acid (or an ester thereof such as the dimethyl ester), ethylene glycol and one or more dialcohol co-monomers (e.g., 1,4-cyclohexanedimethanol, diethylene glycol, 1,4-butane diol or 1,3-butane diol). In some variations, the host polymer is not a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is not a copolymer of the reaction of terephthalic acid (or an ester thereof such as the dimethyl ester), isophthalic acid (or an ester thereof such as the dimethyl ester) and ethylene glycol. In some variations, the host polymer is not a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol).

In some variations, an oxygen scavenging composition comprises one or more compounds of Group A2 having formula (II-1'), (II-2'), (II-3'), (II-4'), (II-5'), (II-6'), (II-7'), (II-7'), (II-9'), (II-10'), (II-11'), (II-12'), (II-13'), (II-14'), (II-15'), (II-16'), (II-17'), (II-18'), (II-19'), (II-20'), (II-21'), (II-22'), (II-23'), (II-24'), (II-25'), (III-1'), (III-2'), (III-3'), (III-4'), (III-5'), (III-6'), (III-7'), (III-8'), or (III-9') and optionally an accelerator. In some variations, one or more compounds of Group B2 having formula (II-1"), (II-2"), (II-3"), (II-4"), (II-5"), (II-6"), (II-7"), (II-7"), (II-9"), (II-10"), (II-11"), (II-12"), (II-13"), (II-14"), (II-15"), (II-16"), (II-17"), (II-18"), (II-19"), (II-20"), (II-21"), (II-22"), (II-23"), (II-24"), (III-25"), (III-1"), (III-2"), (III-3"), (III-4"), (III-5"), (III-6"), (III-7"), (III-8") or (III-9") functions as an accelerator for an oxygen scavenger of Group A2. In some variations, an oxygen scavenging composition comprises an oxygen scavenger of Group A2 and an accelerator of Group B2, wherein the accelerator comprises a 1,4-cyclohexadiene ring comprising one or more bisallylic hydrogens bonded thereto and the primary scavenger has a corresponding structure with a cyclohexene ring substituted for the 1,4-cyclohexadiene ring, and singly allylic hydrogens substituted for the bisallylic hydrogens. For example, in some variations, an oxygen scavenging composition comprises a primary oxygen scavenger having structure (II-2') and an accelerator having structure (II-2"). Table A.2 provides non-limiting combinations of primary oxygen scavengers (shown in rows) and accelerators (shown in columns). Each "X" in Table A.2 specifically discloses that combination of primary oxygen scavenger and accelerator. In the oxygen scavenging compositions, any relative amount of oxygen scavenger of Group A2 to accelerator of Group B2 may be present to achieve an oxygen scavenging composition having desirable properties. For example, a mass ratio (A2): (B2) may be about 1000:1, 500:1, 200:1, 100:1, 50:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:50, 1:100, 1:200, 1:500, or 1:1000. In some variations, an oxygen scavenging composition comprises compound (II-4') and compound (II-4"). In some instances, the mass ratio of (II-4'):(II-4") may be about 1:1, 2:1, 3:1, or 4:1.

TABLE A.2

| Group B2 Accelerator | \multicolumn{17}{c}{Group A1 oxygen scavenger} |
|---|---|---|---|---|---|---|---|---|---|---|---|---|---|---|---|---|---|
| | II-1' | II-2' | II-3' | II-4' | II-5' | II-6' | II-7' | II-8' | II-9' | II-10' | II-11' | II-12' | II-13' | II-14' | II-15' | II-16' | II-17' | II-18' |
| II-1" | X | X | X | X | X | X | X | X | X | X | X | X | X | X | X | X | X | X |
| II-2" | X | X | X | X | X | X | X | X | X | X | X | X | X | X | X | X | X | X |
| II-3" | X | X | X | X | X | X | X | X | X | X | X | X | X | X | X | X | X | X |
| II-4" | X | X | X | X | X | X | X | X | X | X | X | X | X | X | X | X | X | X |
| II-5" | X | X | X | X | X | X | X | X | X | X | X | X | X | X | X | X | X | X |
| II-6" | X | X | X | X | X | X | X | X | X | X | X | X | X | X | X | X | X | X |
| II-7" | X | X | X | X | X | X | X | X | X | X | X | X | X | X | X | X | X | X |
| II-8" | X | X | X | X | X | X | X | X | X | X | X | X | X | X | X | X | X | X |
| II-9" | X | X | X | X | X | X | X | X | X | X | X | X | X | X | X | X | X | X |
| II-10" | X | X | X | X | X | X | X | X | X | X | X | X | X | X | X | X | X | X |
| II-11" | X | X | X | X | X | X | X | X | X | X | X | X | X | X | X | X | X | X |
| II-12" | X | X | X | X | X | X | X | X | X | X | X | X | X | X | X | X | X | X |
| II-13" | X | X | X | X | X | X | X | X | X | X | X | X | X | X | X | X | X | X |
| II-14" | X | X | X | X | X | X | X | X | X | X | X | X | X | X | X | X | X | X |
| II-15" | X | X | X | X | X | X | X | X | X | X | X | X | X | X | X | X | X | X |
| II-16" | X | X | X | X | X | X | X | X | X | X | X | X | X | X | X | X | X | X |
| II-17" | X | X | X | X | X | X | X | X | X | X | X | X | X | X | X | X | X | X |
| II-18" | X | X | X | X | X | X | X | X | X | X | X | X | X | X | X | X | X | X |
| II-19" | X | X | X | X | X | X | X | X | X | X | X | X | X | X | X | X | X | X |
| II-20" | X | X | X | X | X | X | X | X | X | X | X | X | X | X | X | X | X | X |
| II-21" | X | X | X | X | X | X | X | X | X | X | X | X | X | X | X | X | X | X |
| II-22" | X | X | X | X | X | X | X | X | X | X | X | X | X | X | X | X | X | X |
| II-23" | X | X | X | X | X | X | X | X | X | X | X | X | X | X | X | X | X | X |
| II-24" | X | X | X | X | X | X | X | X | X | X | X | X | X | X | X | X | X | X |
| II-25" | X | X | X | X | X | X | X | X | X | X | X | X | X | X | X | X | X | X |
| III-1" | X | X | X | X | X | X | X | X | X | X | X | X | X | X | X | X | X | X |
| III-2" | X | X | X | X | X | X | X | X | X | X | X | X | X | X | X | X | X | X |
| III-3" | X | X | X | X | X | X | X | X | X | X | X | X | X | X | X | X | X | X |
| III-4" | X | X | X | X | X | X | X | X | X | X | X | X | X | X | X | X | X | X |
| III-5" | X | X | X | X | X | X | X | X | X | X | X | X | X | X | X | X | X | X |
| III-6" | X | X | X | X | X | X | X | X | X | X | X | X | X | X | X | X | X | X |
| III-7" | X | X | X | X | X | X | X | X | X | X | X | X | X | X | X | X | X | X |
| III-8" | X | X | X | X | X | X | X | X | X | X | X | X | X | X | X | X | X | X |
| III-9" | X | X | X | X | X | X | X | X | X | X | X | X | X | X | X | X | X | X |

| Group B2 Accelerator | \multicolumn{15}{c}{Group A1 oxygen scavenger} |
|---|---|---|---|---|---|---|---|---|---|---|---|---|---|---|---|
| | II-19' | II-20' | II-21' | II-22' | II-23' | II-24' | II-25' | III-1' | III-2' | III-3' | III-4' | III-5; | III-6' | III-7' | III-8' | III-9' |
| II-1" | X | X | X | X | X | X | X | X | X | X | X | X | X | X | X | X |
| II-2" | X | X | X | X | X | X | X | X | X | X | X | X | X | X | X | X |
| II-3" | X | X | X | X | X | X | X | X | X | X | X | X | X | X | X | X |
| II-4" | X | X | X | X | X | X | X | X | X | X | X | X | X | X | X | X |
| II-5" | X | X | X | X | X | X | X | X | X | X | X | X | X | X | X | X |
| II-6" | X | X | X | X | X | X | X | X | X | X | X | X | X | X | X | X |
| II-7" | X | X | X | X | X | X | X | X | X | X | X | X | X | X | X | X |
| II-8" | X | X | X | X | X | X | X | X | X | X | X | X | X | X | X | X |
| II-9" | X | X | X | X | X | X | X | X | X | X | X | X | X | X | X | X |
| II-10" | X | X | X | X | X | X | X | X | X | X | X | X | X | X | X | X |
| II-11" | X | X | X | X | X | X | X | X | X | X | X | X | X | X | X | X |
| II-12" | X | X | X | X | X | X | X | X | X | X | X | X | X | X | X | X |
| II-13" | X | X | X | X | X | X | X | X | X | X | X | X | X | X | X | X |
| II-14" | X | X | X | X | X | X | X | X | X | X | X | X | X | X | X | X |
| II-15" | X | X | X | X | X | X | X | X | X | X | X | X | X | X | X | X |
| II-16" | X | X | X | X | X | X | X | X | X | X | X | X | X | X | X | X |
| II-17" | X | X | X | X | X | X | X | X | X | X | X | X | X | X | X | X |
| II-18" | X | X | X | X | X | X | X | X | X | X | X | X | X | X | X | X |
| II-19" | X | X | X | X | X | X | X | X | X | X | X | X | X | X | X | X |
| II-20" | X | X | X | X | X | X | X | X | X | X | X | X | X | X | X | X |
| II-21" | X | X | X | X | X | X | X | X | X | X | X | X | X | X | X | X |
| II-22" | X | X | X | X | X | X | X | X | X | X | X | X | X | X | X | X |
| II-23" | X | X | X | X | X | X | X | X | X | X | X | X | X | X | X | X |
| II-24" | X | X | X | X | X | X | X | X | X | X | X | X | X | X | X | X |
| II-25" | X | X | X | X | X | X | X | X | X | X | X | X | X | X | X | X |
| III-1" | X | X | X | X | X | X | X | X | X | X | X | X | X | X | X | X |
| III-2" | X | X | X | X | X | X | X | X | X | X | X | X | X | X | X | X |
| III-3" | X | X | X | X | X | X | X | X | X | X | X | X | X | X | X | X |
| III-4" | X | X | X | X | X | X | X | X | X | X | X | X | X | X | X | X |
| III-5" | X | X | X | X | X | X | X | X | X | X | X | X | X | X | X | X |
| III-6" | X | X | X | X | X | X | X | X | X | X | X | X | X | X | X | X |

TABLE A.2-continued

| | | | | | | | | | | | | | | | | |
|---|---|---|---|---|---|---|---|---|---|---|---|---|---|---|---|---|
| III-7" | X | X | X | X | X | X | X | X | X | X | X | X | X | X | X | X |
| III-8" | X | X | X | X | X | X | X | X | X | X | X | X | X | X | X | X |
| III-9" | X | X | X | X | X | X | X | X | X | X | X | X | X | X | X | X |

Any suitable oxidation catalyst and any suitable host polymer may be used with the combinations disclosed in Table A.2. In some variations, a cobalt catalyst such as cobalt neodecanoate is used. In some variations, the host polymer is or comprises a polyester (such as PLA, PET, PBT, PEN, or PBN) or a copolymer or adduct thereof. In some variations, the host polymer is or comprises a polymer selected from the group consisting of polyethylene terephthalate, copolymers of polyethylene terephthalate, polyethylene naphthalate, copolymers of polyethylene napthalate, polybutylene terephthalate, copolymers of polybutylene terephthalate, polytrimethylene terephthalate, copolymers of polytrimethylene terephalate, polyethylene furanoate and copolymers of polyethylene furanoate, and poly(lactic acid) and copolymers of poly(lactic acid). In some variations, the host polymer is or comprises a homopolymer or copolymer of the reaction of terephthalic acid (or an ester thereof such as the dimethyl ester), ethylene glycol, and one or more co-acids or acid ester comonomers. In some variations, the host polymer is or comprises a homopolymer or copolymer of the reaction of terephthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol). In some variations, the host polymer is or comprises a homopolymer or copolymer of the reaction of terephthalic acid (or an ester thereof such as the dimethyl ester), isophthalic acid (or an ester thereof such as the dimethyl ester), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is or comprises a polyamide or a copolymer or adduct thereof, or a polyolefin or a copolymer or adduct thereof. In some variations, the host polymer is or comprises polyethylene furanoate or a copolymer or adduct of polyethylene furanoate, or poly(lactic acid) or a copolymer or adduct of poly(lactic acid). In some variations, the host polymer is not a polyester. In some variations, the host polymer is not PET. In some variations, the host polymer is not polyethylene terephthalate or a copolymer or adduct thereof. In some variations, the host polymer is not a homopolymer or copolymer of the reaction of terephthalic acid (or ester thereof) and ethylene glycol. In some variations, the host polymer is not a homopolymer or copolymer of the reaction of terephthalic acid (or ester thereof), ethylene glycol, and one or more co-acids or acid ester co-monomers. In some variations, the host polymer is not a homopolymer or copolymer of the reaction of terephthalic acid (or ester thereof), ethylene glycol and one or more dialcohol co-monomers (e.g., 1,4-cyclohexanedimethanol, diethylene glycol, 1,4-butane diol or 1,3-butane diol). In some variations, the host polymer is not a homopolymer or copolymer of the reaction of terephthalic acid (or ester thereof), ethylene glycol, one or more co-acid or acid ester co-monomers, and one or more dialcohol co-monomers (e.g., 1,4-cyclohexanedimethanol, diethylene glycol, 1,4-butane diol or 1,3-butane diol). In some variations, the host polymer is not a copolymer of the reaction of terephthalic acid (or ester thereof), isophthalic acid (or ester thereof) and ethylene glycol. In some variations, the host polymer is not a homopolymer or copolymer of the reaction of terephthalic acid (or an ester thereof such as the dimethyl ester), isophthalic acid (or an ester thereof such as the dimethyl ester), ethylene glycol, and one or more dialcohol co-monomers (e.g., 1,4-cyclohexanedimethanol, diethylene glycol, 1,4-butane diol or 1,3-butane diol).

The oxygen scavenging compositions described herein comprise: i) a host polymer; and ii) dispersed in the host polymer, an effective amount of one or more oxygen scavengers having formula (I); (II) or (III) and an effective amount of an oxidation catalyst. In some cases, an oxygen scavenging composition comprises: i) a host polymer; ii) about 0.1 wt %-30 wt % (wt % refers to weight scavenger/weight host polymer×100%) of one or more oxygen scavengers having formula (I), (II), or (III); and iii) about 10-5000 ppm oxidation catalyst. In some cases, the dispersion of the components in the host polymer is such that the composition has a phase separated morphology.

In some cases, an oxygen scavenging composition comprises: i) a host polymer; and ii) at least about 0.5 wt. %, at least about 1 wt. %, or at least about 1.5 wt. % of an oxygen scavenger described herein. In some cases, an oxygen scavenging composition comprises at most about 5 wt. % of an oxygen scavenger described herein. In some cases, an oxygen scavenger composition comprises at least about 0.5 wt % and at most about 5 wt % of an oxygen scavenger described herein.

In some variations, an oxygen scavenging composition comprises: i) a host polymer; and ii) dispersed in the host polymer, about 0.1 wt %-10 wt % (e.g., 0.1 wt %, 0.2 wt %, 0.5 wt %, 1 wt %, 1.5 wt %, 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt %, 9.5 wt % or 10 wt %, wt % refers to weight scavenger/weight host polymer×100%) of one or more oxygen scavengers having formula (I), (II), (III), (IV), (V) or (VI) and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm or 1000 ppm, where ppm refers to weight of elemental metal in the catalyst per weight of host polymer).

In some variations, an oxygen scavenging composition comprises: i) a host polymer; and ii) dispersed in the host polymer, about 0.1 wt %-10 wt % (e.g., 0.1 wt %, 0.2 wt %, 0.5 wt %, 1 wt %, 1.5 wt %, 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt %, 9.5 wt % or 10 wt %, wt % refers to weight scavenger/weight host polymer×100%) of one or more oxygen scavengers having formula (I'), (II'), or (III'), (IV'), (V') or (VI') and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer).

In some variations, an oxygen scavenging composition comprises: i) a host polymer; and ii) dispersed in the host polymer, about 0.1 wt %-10 wt % (e.g., 0.1 wt %, 0.2 wt %, 0.5 wt %, 1 wt %, 1.5 wt %, 2 wt %, 2.5 wt %, 3 wt %, 3.5 wt %, 4 wt %, 4.5 wt %, 5 wt %, 5.5 wt %, 6 wt %, 6.5 wt %, 7 wt %, 7.5 wt %, 8 wt %, 8.5 wt %, 9 wt %, 9.5 wt % or 10 wt %, wt % refers to weight scavenger/weight host polymer×100%)) of one or more oxygen scavengers having formula (I"), (II"), (III"), (IV"), (V"), or (VI") and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer).

In some cases, an oxygen scavenging composition comprises: i) a host polymer; and ii) dispersed in the host polymer about 0.5 wt %-5 wt % (e.g., 0.5 wt %, 1 wt %, 1.5 wt %, 2 wt %, 2.5 wt %, 3 wt %, 3.5 wt %, 4 wt %, 4.5 wt %, or 5 wt %, wt % refers to weight scavenger/weight host polymer×100%) of one or more compounds having formula (II-2"), and about 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer). In some cases, the oxidation catalyst comprises cobalt, e.g., as cobalt neodecanoate.

In some cases, an oxygen scavenging composition comprises: i) a host polymer; and ii) dispersed in the host polymer about 0.5 wt %-3 wt % (e.g., 0.5 wt %, 1 wt %, 1.5 wt %, 2 wt %, 2.5 wt % or 3 wt %) compound having formula (III-2") and about 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer). In some cases, the oxidation catalyst comprises cobalt, e.g., as cobalt neodecanoate.

In some cases, an oxygen scavenging composition comprises: i) a host polymer; and ii) dispersed in the host polymer, an effective amount of one or more oxygen scavengers having formula (I), (II), or (III), an effective amount of an oxidation catalyst, and an effective amount of an accelerator that triggers or accelerates oxygen uptake by the composition. In some cases, an oxygen scavenging composition comprises: i) a host polymer; and ii) dispersed in the host polymer, about 0.1 wt %-30 wt % of an oxygen scavenger having formula (I), (II), or (III), about 10-5000 ppm oxidation catalyst, and an accelerator. The accelerator can be present in any effective amount and may be any accelerator described herein or otherwise known, e.g., an oxygen scavenger of formula (I") having one or more bisallylic hydrogens, or a grafted polybutadiene such as a maleic anhydride adducted polybutadiene.

In some cases, an oxygen scavenging composition comprises: i) a host polymer; and ii) dispersed in the host polymer, about 0.5 wt %-5 wt %, or 0.5 wt %-3 wt % of a mixture comprising a compound of formula (II') and compound of formula (II"), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm catalyst refers to weight of elemental metal in the catalyst per weight of host polymer, and wt % refers to combined weight of (II') and (II")/weight of host polymer×100%). In some cases, the oxidation catalyst comprises cobalt, e.g., as cobalt neodecanoate. In these compositions, a mass ratio of (II'):(II") may be about 1:1, 2:1, 3:1, 4:1, 5:1, 6:1, 7:1, 8:1, 9:1 or 10:1. In some variations, the mass ratio of (II'):(II") is about 80:20, 75:25, 70:30, 65:35, 60:40, or 50:50.

In some cases, an oxygen scavenging composition comprises: i) a host polymer; and ii) dispersed in the host polymer, about 0.5 wt %-5 wt %, or 0.5 wt %-3 wt % of a mixture comprising a compound of formula (II-3') and compound of formula (II-3"), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer, and wt % refers to combined weight of (II-3') and (II-3")/weight of host polymer×100%).). In some cases, the oxidation catalyst comprises cobalt, e.g., as cobalt neodecanoate. In these compositions, a mass ratio of (II-3'):(II-3") may be about 1:1, 2:1, 3:1, 4:1, 5:1, 6:1, 7:1, 8:1, 9:1 or 10:1. In some variations, the mass ratio of (II-3'):(II-3") is about 80:20, 75:25, 70:30, 65:35, 60:40, or 50:50.

In some cases, an oxygen scavenging composition comprises: i) a host polymer; and ii) dispersed in the host polymer, about 0.5 wt %-5 wt %, or 0.5 wt %-3 wt % of a mixture comprising a compound of formula (II-4') and compound of formula (II-4"), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer, and wt % refers to combined weight of (II-3') and (II-3")/weight of host polymer×100%).). In some cases, the oxidation catalyst comprises cobalt, e.g., as cobalt neodecanoate. In the compositions, a mass ratio of (II-4'): (II-4") may be about 1:1, 2:1, 3:1, 4:1, 5:1, 6:1, 7:1, 8:1, 9:1 or 10:1. In some variations, the mass ratio of (II-4'):(II-4") is about 80:20, 75:25, 70:30, 65:35, 60:40, or 50:50.

In some cases, an oxygen scavenging composition comprises: i) a host polymer; and ii) dispersed in the host polymer, about 0.5 wt %-5 wt %, or 0.5 wt %-3 wt % of a mixture comprising a compound of formula (III-2') and compound of formula (III-2"), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer, and wt % refers to combined weight of (III-2') and (III-2")/weight of host polymer×100%). In some cases, the oxidation catalyst comprises cobalt, e.g., as cobalt neodecanoate. In the compositions, a mass ratio of (III-2'): (III-2") may be about 1:1, 2:1, 3:1, 4:1, 5:1, 6:1, 7:1, 8:1, 9:1 or 10:1. In some variations, the mass ratio of (III-2'):(III-2") is about 80:20, 75:25, 70:30, 65:35, 60:40, or 50:50.

In some cases, an oxygen scavenging composition comprises: i) a host polymer; and ii) dispersed in the host polymer, about 0.5 wt %-5 wt %, or 0.5 wt %-3 wt % of an oxygen scavenger having formula (II') and an accelerator comprising a polybutadiene or a copolymer or adduct thereof (e.g., maleic anhydride adducted polybutadiene), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer, and wt % refers to weight of (II')/weight of host polymer×100%). Any effective amount of polybutadiene or copolymer or adduct thereof (e.g., maleic anhydride adducted polybutadiene) may be used, e.g., about 0.01-1 wt % (such as about 0.01, 0.05, 0.1, 0.15, 0.2, 0.25, 0.5, 0.75, or 1 wt %, where wt % refers to weight accelerator/weight host polymer×100%).

In some cases, an oxygen scavenging composition comprises: i) a host polymer; and ii) dispersed in the host polymer, about 0.5 wt %-5 wt %, or 0.5 wt %-3 wt % of an oxygen scavenger having formula (II-3') and an accelerator comprising a polybutadiene or a copolymer or adduct thereof (e.g., maleic anhydride adducted polybutadiene), and 10-1000 ppm oxidation catalyst (e.g., about 10 ppm, 50 ppm 100 ppm, 120 ppm, 150 ppm, 180 ppm, 200 ppm, 300 ppm, 400 ppm, 500 ppm, 600 ppm, 700 ppm, 800 ppm, 900 ppm, or 1000 ppm, where ppm refers to weight of elemental metal in the catalyst per weight of host polymer, and wt % refers to weight of (II-3')/weight of host polymer×100%). Any effective amount of polybutadiene or copolymer or adduct thereof (e.g., maleic anhydride adducted polybutadiene) may be used, e.g., about 0.01-1 wt % (such as about 0.01, 0.05, 0.1, 0.15, 0.2, 0.25, 0.5, 0.75, or 1 wt %, where wt % refers to weight accelerator/weight host polymer× 100%).

The host polymer for the oxygen scavenging compositions described herein may be any suitable polymer from which bottles, containers, trays, films, lids, cups, jars, trays, pouches, bags, and the like may be formed. In some variations, the host polymer is or comprises a polyester such as PET, PBT, PEN, PBN, or PLA. In some variations, the host polymer is not a polyester. In some variations, the host polymer is not PET or a copolymer or adduct thereof.

Also described herein are oxygen scavenging compositions comprising: i) one or more oxygen scavengers of formula (I), (II), or (III); and ii) one or more accelerators. Optionally, the compositions may comprise one or more oxidation catalysts as described herein. Some non-limiting examples of compositions comprising one or more oxygen scavengers and one or more accelerators are provided in Tables 1A, 1B, 2A, 2B, 3A, 3B, 4A, and 4B. In other non-limiting examples, the compositions comprise one or more accelerators that do not have formula (I), (II) or (III) as described herein or are otherwise known. Non-limiting examples of such accelerators include polybutadienes and copolymers and adducts thereof (e.g., maleic anhydride adducted polybutadienes), and polyamides and copolymers thereof (e.g., meta-xylylamine based polyamides) and polyisoprenes and copolymers and adducts thereof (e.g. maleic anhydrive adducted polyisoprene).

In some cases, an oxygen scavenging composition comprises: i) an oxygen scavenger having formula (II'); and ii) and 1 wt %-50 wt % (e.g., 10 wt %-50 wt %, or 20 wt %-50 wt %, or 30 wt %-40 wt %) accelerator having formula (II"), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (II-3'); and ii) and 1 wt %-50 wt % (e.g., 10 wt %-50 wt %, or 20 wt %-50 wt %, or 30 wt %-40 wt %) accelerator having formula (II-3"), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (II-4'); and ii) and 1 wt %-50 wt % (e.g., 10 wt %-50 wt %, or 20 wt %-50 wt %, or 30 wt %-40 wt %) accelerator having formula (II-4"), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (I), (II), or (III); and ii) and 0.1 wt %-50 wt % (e.g., 0.1 wt %-10 wt %, 1 wt %-10 wt %, or 10 wt %-50 wt %) accelerator comprising a polybutadiene or a copolymer or adduct thereof (e.g., a maleic anhydride adducted polybutadiene), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (II'); and ii) and 0.1 wt %-50 wt % (e.g., 0.1 wt %-10 wt %, 1 wt %-10 wt %, or 10 wt %-50 wt %) accelerator comprising a polybutadiene or a copolymer or adduct thereof (e.g., a maleic anhydride adducted polybutadiene), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (II-3'); and ii) and 0.1 wt %-50 wt % (e.g., 0.1 wt %-10 wt %, 1 wt %-10 wt %, or 10 wt %-50 wt %) accelerator comprising a polybutadiene or a copolymer or adduct thereof (e.g., a maleic anhydride adducted polybutadiene), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

In some cases, an oxygen scavenging composition comprises: i) an oxygen scavenger having formula (II-4'); and ii) and 0.1 wt %-50 wt % (e.g., 0.1 wt %-10 wt %, 1 wt %-10 wt %, or 10 wt %-50 wt %) accelerator comprising a polybutadiene or a copolymer or adduct thereof (e.g., a maleic anhydride adducted polybutadiene), where wt % refers to weight accelerator/combined weight oxygen scavenger and accelerator. Optionally, the composition may comprise about 10-100000 ppm oxidation catalyst (e.g., about 10 ppm, 100 ppm, 1000 ppm, 2000 ppm, 3000 ppm, 4000 ppm, 5000 ppm, 6000 ppm, 7000 ppm 7500 ppm, 8000 ppm, 8500 ppm, 9000 ppm, 9500 ppm, 10000 ppm, 15000 ppm, 20000 ppm, 50000 ppm, 75000 ppm, or 100000 ppm, where ppm refers to weight of elemental metal in the catalyst per combined weight of oxygen scavenger and accelerator). Any suitable oxidation catalyst may be used, e.g., a transition metal containing oxidation catalyst. In some cases, an oxidation catalyst comprising cobalt is used (e.g., as cobalt neodecanoate).

It should be understood that in some cases, a composition comprises one or more oxygen scavengers described herein and one or more oxygen scavengers known in the art, and the one or more oxygen scavengers described herein shortens induction time, or "kick starts" oxygen scavenging activity and/or increases oxygen scavenging capacity or lifetime of the composition. For example, an oxygen scavenger described herein having one or more bisallylic hydrogens (e.g., an oxygen scavenger of formula (I") comprising a 1,4-cyclohexadiene ring) may be used as an accelerator for other oxygen scavengers known in the art. In some cases, an oxygen scavenger described herein that includes allylic hydrogens but does not include bisallylic hydrogens (e.g., an oxygen scavenger of formula (I') comprising a cyclohexene ring) may be used to increase oxygen scavenging capacity or lifetime of the composition.

D. Articles Comprising the Oxygen Scavengers

Articles having one or more walls comprising the oxygen scavengers may be made according to a variety of methods known in the art. Non-limiting examples of articles that may be formed include packages (rigid, semi-rigid, collapsible, flexible, lidded, and the like), containers (e.g., bottles, cups, jars, cartons, totes, boxes, and the like), trays, and films. The articles may be used to store substances that are sensitive to oxygen, such as food, beverages, cosmetics, pharmaceuticals, electronic products, and the like. In some variations, the oxygen scavenging compositions are used to make bottles that are used to store juices, beer or other beverages or food substances in which any one of flavor, fragrance, color, or composition degrades in the presence of oxygen. In some variations, the compositions are used to make sheets, trays or films (rigid or flexible). Non-limiting examples of rigid packages that can be made using the oxygen scavengers include food trays and lids. Non-limiting example of flexible packages that can be made using the oxygen scavengers include flexible films for coverings, bags, pouches, and the like.

It should be understood that a container wall refers to any surface of a container that divides the contents of the container from its environment. That is, a wall may refer to a sidewall, a base surface, or a top surface, and encompasses caps, lids and the like, and bases, bottoms and the like. The containers may be sealed in any suitable manner, e.g., using lids, caps, thin film coverings, and the like that may be made from the same or different material than the container itself. In some variations, a seal such as a cap, lid, or thin film covering is made from a different composition than the container. In some variations, a seal is made from an identical or similar composition than the container. In some variations, a seal comprises the same oxygen scavenger as the container, and in some variations, a seal comprises a different oxygen scavenger than the container.

The oxygen scavenging walls of the articles may be of single layer or multilayer construction. In some variations, an article may be of single layer construction. In some variations, oxygen scavengers as described herein are incorporated into one or more layers of a multilayer construction. In some variations, an oxygen scavenging layer is sandwiched between two external layers (e.g., external layers comprising a polyolefin, a polyester, or a polyvinyl alcohol). A multilayer construction may be produced by any suitable method, including lamination, co-extrusion, and the like. In some variations, an article make comprise one or more walls that are of single layer construction and one or more walls of multilayer construction. In some variations, multiple walls of an article may comprise an oxygen scavenging composition as described herein, and in other variations only a single wall of an article may comprise an oxygen scavenging composition as described herein.

Any suitable method may be used for forming single or multilayer containers, films, and other articles from polymeric materials incorporating the oxygen scavengers described herein. Non-limiting examples of methods that may be used to form articles using the polymeric compositions comprising the oxygen scavengers include: molding, rotational molding, compression molding, injection molding, stretch blow molding, extrusion blow molding, extrusion, co-extrusion, thermoforming, and lamination. In some variations, a stretch blow molding process is used with a phthalate containing polyester host polymer, as the stretch blow molding process provides orientation of crystalline regions, providing improved mechanical properties for certain applications (such as bottles).

A container may comprise stretched or unstretched films or sheets. In some cases, a container may comprise a bottle that is expanded from a preform, referring to a formed structure that is expanded in a mold to form a bottle. In some cases, a container may comprise a tray, film, pouch, sack, or the like.

In some cases, polyester bottles are prepared by forming a preform, heating the preform above the glass transition temperature of the polyester, and expanding the heated preform by injecting air into the preform to force the preform into a shape of a mold of the desired bottle shape. Once formed, the bottle is cooled so that it maintains the shape of the mold. In those variations in which low haze is desired, the blow mold conditions (heating temperature, time, and cooling conditions) may be selected to reduce haze.

The oxygen scavengers may be melt blended with packaging resins such as PET for use in monolayer packages. In some cases, the oxygen scavengers may be blended into a desired layer of a multilayer container. For example, in some cases, the oxygen scavengers described herein may be used in a multilayer construction in which one of the other layers is designed to act as a barrier against $CO_2$ permeation. Such multilayer bottles may be useful for storage of beer, carbonated juices, or other carbonated oxygen sensitive substances.

Processing conditions, such as barrel temperature, injection speed and cycle time, for forming containers comprising the oxygen scavengers may be similar to those used for the corresponding host polymer (e.g., PET) without the oxygen scavenger. In some variations, a master batch approach may be used, in which an oxygen scavenger as described herein is blended with a host polymer (e.g., PET) at a concentration higher than will be used in the final article to form a master batch. The master batch is then melt blended with the host polymer to achieve the desired concentration of oxygen scavenger in the blend. In some cases, an oxygen scavenger is injected directly into molten host polymer. For example, in the case of certain PET polymers or copolymers, the oxygen scavenger may be injected into a PET polymer or copolymer at a temperature of about 285° C. prior to blow molding.

In some cases, a container (e.g., a bottle) is fabricated by injection stretch blow molding (ISBM). In some variations, ISBM may be carried out using a two step process. In a two step process, the host polymer and the oxygen scavenger are heated in a chamber to a temperature at which flow occurs under shear. The hot polymer blend is then forced into a mold cavity under pressure. Upon cooling the polymer blend solidifies to form a preform in the shape of the mold. The mold cavity is opened and the molded preform is removed. The preform is transferred to a second machine in which the preform is placed in the interior space of a mold in the shape of the desired container. The preform is heated above its glass transition temperature and gas is pumped into an interior cavity of the hot preform to expand the polymer blend against the interior surface of the container mold such that it forms a hollow, thin-walled article in the shape of the container mold. Upon cooling, the polymer solidifies. The mold is opened and the formed container is removed. In some variations, ISBM may be accomplished in a one step process in which injection and blow molding are carried out on a single piece of equipment. The one step process is carried out in a similar manner to the two step process, except that the preform is not cooled completely between the steps of making the preform and expanding the preform. Gas is injected into an interior cavity of the preform while its temperature is still about the glass transition temperature so that the polymer blend expands against the interior surface of the container mold to acquire the shape of the mold. Upon cooling and solidifying, the finished container is removed from the mold.

Containers described herein advantageously exhibit effective oxygen scavenging function and acceptable optical properties. The optical properties of the polymeric substance are related to degree of crystallinity, domain size of crystalline particles, polymer structure and presence of species that exhibit color detectable by human eyes. Transmittance is a measure of light that is transmitted through an article, and refers to the ratio (light radiation that is transmitted through an article)/light radiation incident on the article. Light radiation that is absorbed, scattered, reflected, or lost by any other means is not transmitted. Haze is a measure of the amount of light radiation that deviates from the direction of transmittance through the object by at least 2.5 degrees. In some variations, articles (e.g., bottles) are formed that exhibit a haze value of about 8%, about 6%, about 5% or less. In some variations, the addition of effective amounts of oxygen scavenging composition does not substantially alter the color of the host polymer resin. The color and brightness of a polyester article can be observed visually, and can be quantitatively measured by any suitable spectrometer. Any suitable metric may be used to quantify color and brightness. For example, 1976 CIE (Commission on Illumination) a*, b* and L* designations of color and brightness may be used. L*=0 represents a specimen that appears black to the human eye, L*=100 represents a specimen that appears diffuse white, a* represents a value between red and green (with negative values indicating green and positive values indicating red), and b* represents a value between yellow and blue (with negative values indicating blue and positive values indicating yellow). See, e.g., Commission Internationale de L'Eclairage at www.cie.co.at. The observer may be positioned at 10°, and the illuminant may be a CIE standard D65 illuminant to simulant standard daylight illumination. An Color-Eye® 7000A spectrophotometer (available from XRite Corp., Grand Rapids, Mich.), a HunterLab Color Quest Spectrometer, or similar apparatus may be used to evaluate color of the samples relative to the standard. The coordinates L*, a*, and b* can be measured for each sample. The difference between each of the coordinates L*, a* and b* of a sample and that of the reference can be calculated, and a color parameter DE*=sqrt{[(L*(sample)−L*(ref)]²+ [a*(sample)−a*(ref)]²+[b*(sample)−b*(ref)]²} can be calculated. For example, in some cases, the transmission L* of a wall of an article formed from the oxygen scavenging compositions described herein changes by about 1.0 per mil of the wall, about 0.8 per mil of the wall, about 0.6 per mil of the wall, or about 0.4 per mil of the wall or less when compared to a control formed from the host polymer that does not contain oxygen scavengers. In some cases, an L* of about 80 or greater, or about 85 or greater is acceptable, e.g., an L* value of about 80, about 85, or about 90.

In those variations in which the oxygen scavengers are physically blended with the host polymer, it is desired that migration of the oxygen scavengers within or out of an article be minimized. In some variations, a container for storing oxygen sensitive substances comprises or is formed from the compositions described herein, and migration of oxygen scavenging components of the compositions to the oxygen sensitive substances is about 50 ppb or less under applicable use conditions (environment and temperature) over an applicable storage time of the substance.

In certain variations, an interior volume of closed monolayer containers (e.g., bottles) formed from the oxygen scavenging compositions described herein exhibit a dissolved oxygen concentration or total oxygen concentration of about 10 ppm or less, about 5 ppm or less, about 3 ppm or less, about 2 ppm or less, about 1.5 ppm or less, about 1 ppm or less, about 0.8 ppm or less, about 0.5 ppm or less, about 0.4 ppm or less, about 0.3 ppm or less, about 0.2 ppm or less, about 0.1 ppm or less, or about 0.05 ppm or less during a time period extending at least 30 days under ambient conditions. In some variations, the interior volume of closed monolayer containers (e.g., bottles) formed from the oxygen scavenging compositions described herein exhibit a dissolved oxygen concentration or total oxygen concentration of about 10 ppm or less, about 5 ppm or less, about 3 ppm or less, about 2 ppm or less, about 1.5 ppm or less, about 1 ppm or less, about 0.8 ppm or less, about 0.5 ppm or less, about 0.4 ppm or less, about 0.3 ppm or less, about 0.2 ppm or less, about 0.1 ppm or less, or about 0.05 ppm or less during a time period extending at least 60 days under ambient conditions. In some variations, the interior volume of closed monolayer containers (e.g., bottles) formed from the oxygen scavenging compositions described herein exhibit a dissolved oxygen concentration or total oxygen concentration of about 10 ppm or less, about 5 ppm or less, about 3 ppm or less, about 2 ppm or less, about 1.5 ppm or less, about 1 ppm or less, about 0.8 ppm or less, about 0.5 ppm or less, about 0.4 ppm or less, about 0.3 ppm or less, about 0.2 ppm or less, about 0.1 ppm or less, or about 0.05 ppm or less during a time period extending at least 90 days, at least 120 days, at least 150 days, at least 180 days, at least 210 days, at least 240 days, at least 270 days, at least one year, or at least 15 months. Bottles suitable for storing juices can tolerate a few ppm oxygen (e.g., up to about 1.5-2 ppm) in the total package for a desired storage time (e.g., 1 month to about 15 months), whereas total oxygen concentration in a beer container is below 0.5 ppm. Total $O_2$ concentration (in ppm, mg $O_2$/L)={Caq*(33.7*Vh+Vl)}/(Vl+Vh), where Caq is the dissolved oxygen concentration in ppm as measured by an oxygen sensor and the quantities Vh and Vl are the headspace and liquid volumes, respectively (in liters).

Advantageously, in some cases, one or more oxygen scavengers and/or host polymers may be derived from non-petroleum renewable carbon sources such as sugars or other recently grown biomass. For example, in some cases, a polymer (e.g., a polyester may contain at least about 25%, at least about 50%, at least about 75%, or about 100% of the carbon atoms that are derived from non-petroleum carbon sources. In some cases, an oxygen scavenger may contain at least about 25%, at least about 50%, at least about 75%, or about 100% renewable carbon atoms. Non-petroleum carbon content may be measured using any suitable technique. In some cases, an oxygen scavenging composition may contain at least about 25%, at least about 50%, at least about 75%, or about 100% renewable carbon atoms.

Renewable carbon content can be measured using any suitable method. For example, renewable carbon content can be measured according to ASTM D6866-11, "Standard Test Methods for Determining the Biobased Content of Solid, Liquid, and Gaseous Samples Using Radiocarbon Analysis," published by ASTM International, which is incorporated herein by reference in its entirety. Some carbon in atmospheric carbon dioxide is the radioactive $^{14}C$ isotope, having a half life of about 5730 years. Atmospheric carbon dioxide is utilized by plants to make organic molecules. The atmospheric $^{14}C$ becomes part of biologically produced substances. As the biologically produced organic molecules degrade to produce carbon dioxide into the atmosphere, no net increase of carbon in the atmosphere is produced as a result, which may control or diminish undesired climate effects that may result when molecules produced from fossil fuels degrade to produce carbon dioxide to increase carbon in the atmosphere.

Isotope fractionation occurs during physical processes and chemical reactions, and is accounted for during radiocarbon measurements. Isotope fractionation results in enrichment of one isotope over another isotope. Exemplary processes that can affect isotope fractionation include diffusion (e.g., thermal diffusion), evaporation, and condensation. In some chemical reactions, certain isotopes may exhibit different equilibrium behaviors than others. In some chemical reactions, kinetic effects may affect isotope ratios. In the carbon cycle of plants, isotope fractionation occurs. During photosynthesis, the relative amounts of different carbon isotopes that are consumed are $^{12}C>^{13}C>^{14}C$, due to slower processing of heavier isotopes. Plants species exhibit different isotope fractionation due to isotopic discrimination of photosynthetic enzymes and diffusion effects of their stomata. For example $C_3$ plants exhibit different isotope fractionation than $C_4$ plants. The international reference standard for isotope fractionation between $^{13}C$ and $^{12}C$ is PDB (Pee Dee Belemnite standard) or VPDB (Vienna Pee Dee Belemnite standard, replacement for depleted PDB standard). For a given sample, isotope fractionation can be expressed as $\delta\ ^{13}C$ (per mil)={[R(sample)/R(VPDB standard)]−1}×1000%, where R(sample)=$^{13}C/^{12}C$ and R(VPDB standard)=$^{13}C/^{12}C$ for the VPDB standard. Instead of a $^{13}C/^{12}C$ ratio, $\delta^{13}C$ is the relative change of the $^{13}C/^{12}C$ ratio for a given sample from that of the VPDB standard. Carbon isotopic ratios are reported on a scale defined by adopting a $\delta^{13}C$ value of +0.00195 for NBS-19 limestone (RM 8544) relative to VPDB. "New IUPAC guidelines for the reporting of stable hydrogen, carbon, and oxygen isotope-ratio data," Letter to the Editor, J. Res. Natl. Stand. Technol. 100, 285 (1995). Most naturally occurring materials exhibit negative $\delta^{13}C$ values. In general, for atmospheric $CO_2$ $\delta^{13}C$ ranges between −11 to −6%, for $C_3$ plants, $\delta C^{13}$ varies between −22 and −32% and for $C_4$ plants $\delta^{13}C$ varies between −8 to −18%. The $^{14}C$ fractionation factor can be approximated as the square of the $^{13}C$ fractionation factor. See, e.g., M. Stuiver and S. W. Robinson, Earth and Planetary Science Letters, vol. 23, 87-90.

$^{14}C$ content of a sample can be measured using any suitable method. For example, $^{14}C$ content can be measured using Accelerator Mass Spectrometry (AMS), Isotope Ratio Mass Spectrometry (IRMS), Liquid Scintillation Counting (LSC), or a combination of two or more of the foregoing, using known instruments. Activity refers to the number of decays measured per unit time and per unit mass units. To compare activity of a sample with that of a known reference material, isotope fractionation effects can be normalized. If an activity of a sample is measured to be $A_S$, the sample activity normalized to the reference is $A_{SN}$ and can be expressed as:

$$A_{SN}=A_S\{[(^{13}C/^{12}C)\ \text{reference}]/[(^{13}C/^{12}C)\text{sample}]\}^2.$$

Radiocarbon measurements are performed relative to a standard having known radioactivity. SRM 4990B is an oxalic acid dehydrate Standard Reference Material provided by the U.S. National Bureau of Standards (now National Institute of Standards and Technology, NIST) in the late 1950s having $\delta^{13}C$=−19% (PDB). SRM 4990B has been depleted so another standard is used, such as SRM 4990C, a second oxalic acid standard from NIST having $\delta^{13}C$=−17.8% (VPDB). Modern carbon, referenced to AD1950, is 0.95 times $^{14}C$ concentration of SRM 4990B, normalized to $\delta^{13}C=-19\%$ (PDB). The factor 0.95 is used to correct the value to 1950 because by the late 1950s, $^{14}C$ in the atmosphere had artificially risen about 5% above natural values due to testing of thermonuclear weapons. Fraction of modern ($f_M$) refers to a radiocarbon measured compared to modern carbon, referenced to AD1950. Modern carbon as defined above has $f_M=1$. For current living plant material not more than a few years old (such as corn), $f_M$ is approximately 1.1. Percent modern carbon (pMC) is $f_M \times 100\%$. The AD1950 standard had 100 pMC. Fresh plant material may exhibit a pMC value of about 107.5. Biobased carbon content is determined by setting 100% biobased carbon equal to the pMC value of freshly grown plant material (such as corn), and pMC value of zero corresponds to a sample in which all of the carbon is derived from fossil fuel (e.g., petroleum). A sample containing both modern carbon and carbon from fossil fuels will exhibit a biobased carbon content between 0 and 100%. In some cases, a sample that is more than several years old but containing all biobased carbon (such as wood from a mature tree trunk) will exhibit a pMC value to yield a biobased carbon content >100%.

Renewable carbon content or biobased carbon content as used herein refers to fraction or percent modern carbon determined by measuring $^{14}C$ content, e.g., by any of Method A, Method B, or Method C as described in ASTM D6866-11 "Standard Test Methods for Determining the Biobased Content of Solid, Liquid, and Gaseous Samples Using Radiocarbon Analysis." Counts from 14C in a sample can be compared directly or through secondary standards to SRM 4990C. A measurement of 0% $^{14}C$ relative to the appropriate standard indicates carbon originating entirely from fossils (e.g., petroleum based). A measurement of 100% $^{14}C$ indicates carbon originating entirely from modern sources. A measurement of >100% $^{14}C$ indicates the source of carbon has an age of more than several years.

In some variations, at least about 25%, at least about 30%, at least about 40%, at least about 50%, at least about 60%, at least about 70%, at least about 80%, at least about 90%, or about 100% of the carbon atoms in the oxygen scavengers originate from renewable carbon sources. In some variations, the oxygen scavengers have a $\delta^{13}C$ of from about −11 to about −6%, from about −15 to about −10%, from about −22 to about −15%, from about −22 to about −32%, from −8 to about −18%, from about −14 to about −12%, or from about −13 to about −11%. In some variations, the oxygen scavengers have a $f_M$ greater than about 0.3, greater than about 0.4, greater than about 0.5, greater than about 0.6, greater than 0.7, greater than about 0.8, greater than about 0.9, or greater than about 1.0. In some variations, the oxygen scavengers have a $f_M$ of about 1.0 to about 1.05, about 1.0 to about 1.1, or about 1.1 to about 1.2. In some variations, the oxygen scavengers have a $\delta^{13}C$ from about −15 to about −10% and a $f_M$ greater than about 0.5, greater than about 0.7, or greater than about 1.0. In some variations, the oxygen scavengers have a $\delta^{13}C$ from about −8 to about −18% and a $f_M$ greater than about 0.5, greater than about 0.7, or greater than about 1.0. In some variations, the oxygen scavengers are derived from a conjugated hydrocarbon terpene (e.g., myrcene, β-farnesene, or α-farnesene) that is made by genetically modified microorganisms using renewable carbon sources such as a sugar (e.g., sugar cane). In some variations, one or more alcohols, diols (e.g, 1,4-butane diol), glycols (e.g., ethylene glycol or propylene glycol) made from renewable carbon sources may be used to make oxygen scavengers described herein. In some cases, a host polymer used in making an oxygen scavenging composition is at least partially derived from renewable carbon sources, e.g., so that at least about 10%, at least about 25%, at least about 30%, at least about 40%, at least about 50%, at least about 60%, at least about 70%, at least about 80%, at least about 90%, or about 100% of the carbon atoms in the oxygen scavenging composition originate from renewable carbon sources Provided below are examples to illustrate various embodiments of oxygen scavengers and oxygen scavenging compositions described herein. The examples are illustrative and not limiting.

EXAMPLES

Example A: Preparation of Compound II'-2'

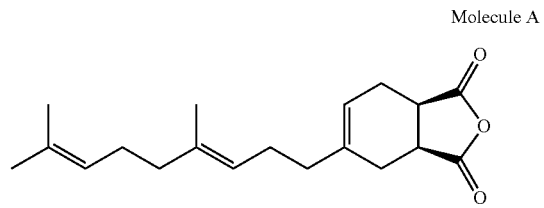 [SMILES: CC(C)=CCC/C(C)=C/CCC1=CC[C@H]2C(=O)OC(=O)[C@H]2C1]

Molecule A rac-3a,7a-syn-((E)-5-(4,8-dimethylnona-3,7-dien-1-yl)-3a,4,7,7a-tetrahydroisobenzofuran-1,3-dione)

A 50 gallon GLS reactor which was purged with argon was charged first with ethyl acetate (80 L) followed by BHT (9.8 g) and trans-beta-farnesene (26.3 kg, 129 mol). Maleic anhydride (12.0 kg, 122 mol) was added in portions over 1.5 hours while the temperature was maintained through water cooling <25° C. The reaction was then allowed to proceed at ambient temperature under an atmosphere of Ar for 21.5 hours once the addition of maleic anhydride was complete. Ethyl acetate was removed at 35 torr where the reactor jacket temperature was raised to 65° C. An analysis of this product mixture by GC indicated 3.0 wt % EtOAc. Excluding EtOAc, the product was shown to be 96.9 wt % pure with 1.55 wt % unreacted beta-farnesene. The product was a clear and colorless viscous liquid. The product was further purified by vacuum distillation using a shortpath distillation apparatus. The fraction boiling between 185° C. and 200° C. at 1 torr was collected as the purified product. Analyses were performed on the product which had been purified by distillation: GC-MS (m/z=302); $^1H$ NMR (400 MHz, CDCl$_3$): δ 5.63-5.65 (m, br, 1H), 5.03-5.10 (m, 2H), 3.32-3.42 (m, 2H), 2.51-2.64 (m, 2H), 2.24-2.29 (m, 2H), 1.94-2.10 (m, 8H), 1.68 (s, 3H), 1.60 (s, 3H), 1.58 (s, 3H).

Example B: Preparation of Compound (III-2″) According to Scheme 3

Scheme 3

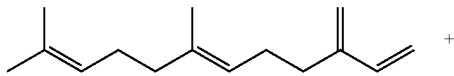

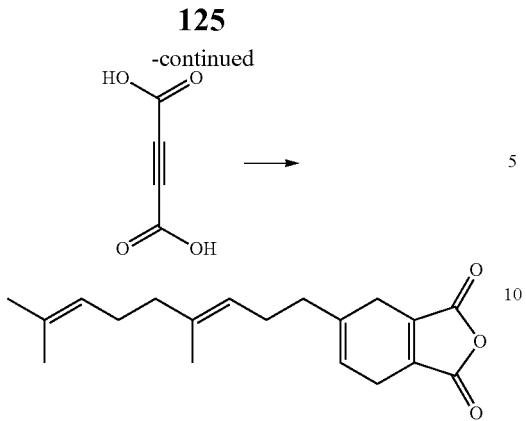

Trans-β-farnesene-Acetylenedicarboxylic acid Diels Alder Adduct (ID 497-90-1). Using a round bottom flask equipped with a distillation head and nitrogen blanketing, a stirred suspension of xylenes (600 mL, Fisher X5S-4, Lot 105919), acetylenedicarboxylic acid (126.0 g, 97.8% GC, 1.080 contained moles, Sigma-Aldrich A15207, Lot BCBC9689V) and trans-β-farnesene (221.1 g, 98% est., 1.060 contained moles, Amyris, Inc., alumina treated, Lot 10025-125_20L) was protected from direct light, heated from room temperature to reflux over the course of three hours (collecting ~14 mL aqueous distillate) and kept at 110° C. for an additional five hours to give a stirred solution. The solution was cooled to room temperature and the protection from light and nitrogen blanketing were discontinued. A GCMS analysis of the solution indicated that all of the trans-β-farnesene had reacted and that the product, not counting the xylenes, was composed of compound (VIId) (300 m/z M+, 80%) and six smaller components (each 300 m/z M+, each between 1.5-4%). The solution was combined with a similarly prepared solution (1000 mL) to give a solution. To the combined solution was added magnesium sulfate (42.98 g, anhydrous, JT Baker 2506-01) and after 12 hours the resulting suspension was filtered (5 μm, nylon tortuous path, Sterlitech) to give a light yellow filtrate. The filtrate was rotary evaporated in batches under low light (17 Torr, 105-110° C., ~2 hours) and a portion (375 g) of the distilland from one of the batches was subjected to simple vacuum distillation under protection from direct light giving a transparent yellow oil (282.1 g, fraction collected between 179-184° C./1.2 mm Hg). The NMR was consistent with the proposed structure.

Example C. Preparation of rac-1,2-syn-(dimethyl 4-((E)-4,8-dimethylnona-3,7-dien-1-yl)cyclohex-4-ene-1,2-dicarboxylate) (syn isomer of compound (II-4')) according to Scheme 4

Scheme 4

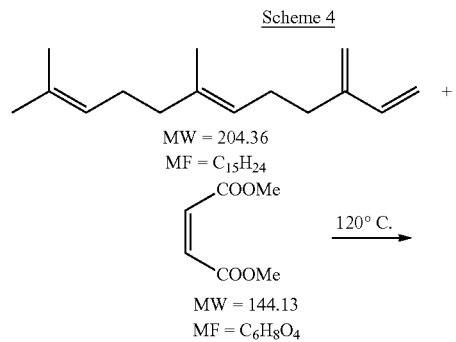

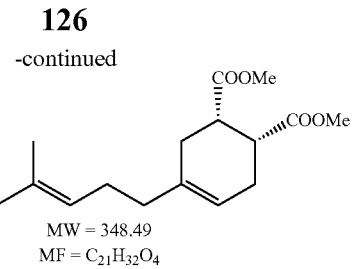

Although only one syn enantiomer is depicted in Scheme 4, as discussed below, a racemic mixture of two syn enantiomers is formed by the reaction. A 2000 mL round-bottom flask was equipped with a magnetic stirring bar and was charged with dimethyl maleate (461.1 g, 3199 mmol, available from TCI America) and trans-β-farnesene (653.7 g, 3199 mmol, available from Amyris, Inc. as described in Examples 1 and 2). The reaction mixture was initially heterogeneous, but on heating to 120° C., the mixture became homogeneous. Heating with stirring was continued for 19 h under nitrogen, and then the reaction mixture was allowed to cool to ambient temperature. The reaction mixture was distilled using a shortpath condenser. The hotplate temperature was set to 150° C. and a forerun was collected (~110° C. at 14 mm Hg). Once the forerun had distilled, the vacuum was reduced to 0.4 mm Hg and the fraction distilling between 154-165° C. was collected as the product. The product was obtained as a colorless liquid in 3 fractions of 397.4 g, 446.9 g and 18.6 g for a total of 861.9 g (77%). Some material remained in the pot as non-volatile components after distillation. Note that it is possible to prepare the composition of Example C for use as a diluent or solvent for the reaction of Example D to prepare a mixture of the compositions of Example C and Example D.

A scaled up procedure is as follows. In a 15 gallon stainless steel batch reactor which was purged with nitrogen, xylenes (10.85 kg, 12.62 L) were charged followed by dimethyl maleate (8.53 kg, 7.42 L, 59.2 mol). The resulting mixture was stirred and was heated to 140° C. at a rate of 1° C./min. Trans-beta-farnesene (11.00 kg, 13.75 L, 53.8 mol) was then added by feed pump to the reactor at a rate of 19.3 g/min (total feed time 10.8 hours). The reaction mixture was then cooled to 25° C. and held at that temperature for 13 hours. The reaction mixture was then brought back to 140° C. for 8 hours. The reaction mixture was then cooled to 25° C. and was held at that temperature for 73 hours. The reaction mixture was then brought back to 140° C. for 6.5 hours at which point analysis of the reaction mixture by GC-MS showed a satisfactory conversion to the desired product. The reaction mixture was cooled. The product was obtained in this manner as a slightly yellow mixture. (16.30 kg uncorrected yield based on GC analysis of the mixture, 87% yield). Analyses were performed on a product purified by distillation: GC-MS (m/z=348); $^1$H NMR (400 MHz, CDCl$_3$): δ 5.37 (s, br, 1H), 5.06-5.10 (m, 2H), 3.69 (s, 3H), 3.68 (s, 3H), 2.98-3.06 (m, 2H), 2.23-2.58 (m, 4H), 2.01-2.12 (m, 4H), 1.94-2.01 (m, 4H), 1.68 (s, 3H), 1.60 (s, 3H), 1.59 (s, 3H). Optionally, the quantity of farnesene in the reaction mixture may be kept to about 14% or less to reduce formation of thermal dimers from farnesene.

An alternative preparation for Example C is as follows. A reactor is purged with nitrogen, and a nitrogen blanket is maintained throughout reaction. Dimethyl maleate (0.71 kg, 12.17 L) is charged into the reactor vessel. BHT is charged into the reactor vessel. Stirring at 250-300 rpm is initiated. The reactor contents are heated to 140+/−5° C. (heating rate 1.0° C./min). Trans-β-farnesene (distilled and containing 300 ppmw butylated hydroxytoluene (BHT)) stabilizer, 1.00 kg, 1.25 L) is charged to the reactor using a feed pump. The feed rate is 17.6-25.4 g/min. Reaction is monitored hourly and feed rate of farnesene is adjusted as necessary. The feed rate of farnesene is controlled to minimize pooling of farnesene in vessel and to control the exothermic reaction. Limiting the amount of farnesene in the reaction mixture by controlled addition rate favors the Diels-Alder reaction over the formation of thermal dimers. If the temperature begins to increase by greater than or equal to 5° C./2 min, the feed rate is reduced or feed is stopped until the temperature is stabilized at 140+/−5° C. Reactor contents are sampled hourly to determine area % (by GC-FID) for dimethyl maleate, farnesene and product. Reactor contents are maintained at 140+/−5° C. until GC-FID indicates reaction completion (approximately 20 hours). When the amount of dimethyl maleate remaining is about 2 area % or less by GC-FID, temperature can be increased to 160° C. Reaction is complete when the area % by GC-FID of dimethyl maleate is about 1.0% or less. For non-continuous operation, the reactor contents may be held for up to 62 hours at ambient temperature (20+/−5° C.) while stirring under nitrogen. Optionally, additional BHT may be added to the reaction to control formation of high boiling side products. Example C is sensitive to air and is stored under nitrogen or other inert atmosphere. Optionally, the reaction products may be distilled to isolate the desired Example C from any residual reactants and higher boiling byproducts (oligomers) that may have been formed. The presence of oligomers may contribute to undesired haziness in some oxygen scavenging compositions. Distillation conditions take into account sensitivity of Example C to air. A wiped film evaporator operating at 260° C. (top and bottom heating zones), pressure of 2 torr, feed flow rate of 15 mL/min, wiper blade rotation at 60% may be used to distill Example C to about 94-95 wt % purity.

In a scaled up procedure for preparing Example C, a reactor is purged with nitrogen, and a nitrogen blanket is maintained throughout reaction. Dimethyl maleate (DMM) (651 kg, 4523 mol) is charged into the reactor vessel. The DMM is sparged with nitrogen for 30 minutes. Trans-β-farnesene (distilled and containing 300 ppmw butylated hydroxytoluene (BHT)) stabilizer) (924 kg, 4523 mol) is staged to be charged to the reactor using a feed pump. The reactor is heated to 160° C.+/−5° C. and stirred at 85 rpm. Farnesene is delivered into the reactor over a period of approximately 28 hours using a metered pump at a feed rate of 33 kg/hr. The reaction mixture and farnesene delivery is monitored during the reaction by in process control GC-FID. The flow rate is adjusted so that the farnesene area % as measured by GC-FID is below 4% during addition. Once product area % by GC-FID is greater than 90%, farnesene area % and DMM area % are monitored. Reaction is complete when DMM area % is less than 1% and farnesene area % is less than 1.5% (approximately 36 hours). The reactor is cooled to 30° C. The product is filtered through a 1 micron filter and stored under nitrogen blanket in a container that has been purged with nitrogen. Theoretical yield: 1575 kg Example C.

The reaction of trans-β-farnesene with dimethyl maleate produces a racemic mixture of two enantiomoers of the syn-Diels-Alder product:

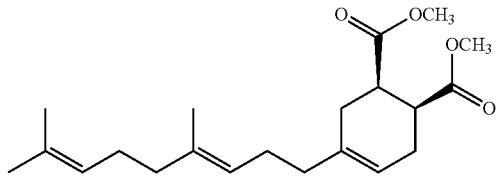 [SMILES: COC(=O)[C@H]1CC=C(CC/C=C(\C)CCC=C(C)C)C[C@H]1C(=O)OC]

(1S,2R)-dimethyl-4-((E)-4,8-dimethylnona-3,7-dien-1-yl)cyclohex-4-ene-1,2-dicarboxylate; and

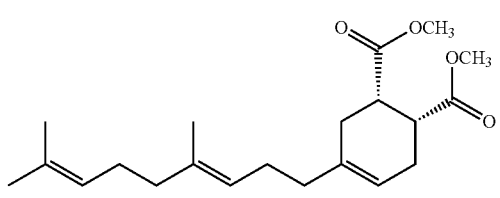 [SMILES: COC(=O)[C@H]1CC(CC/C=C(\C)CCC=C(C)C)=CC[C@H]1C(=O)OC]

(1R,2S)-dimethyl-4-((E)-4,8-dimethylnona-3,7-dien-1-yl)cyclohex-4-ene-1,2-dicarboxylate. The formation of the syn-Diels-Alder product was confirmed by $^1$H NMR analysis. The syn-enantiomers were resolved by a two step process. First, by silica gel chromatography to remove impurities in Example C, and second, by chiral HPLC chromatography to provide the ratio of each enantiomer. First, a 20" long by 1" diameter column of silica was equilibrated with hexanes and Example C (2.3 g as prepared above) was added and eluted with 9:1 hexanes/ethyl acetate to yield the pure syn racemic Example C (1.7 g). Next in order to establish the ratio of enantiomers, a sample of the syn racemic Example C was analyzed by chiral HPLC using a CHIRALPAK AY-3 (150×4.6 mm i.d., 3 micron) column, a mobile phase of hexane/ethanol 95:5 (about 3.0 mg sample/mL in 20% ethanol in hexane), injection volume of 5 microL, a flow rate of 0.70 mL/min, and a UV detector, 220 nm, reference 450 nm. The chromatograph showed two peaks (3.881 min and 4.256 minutes) representing the two enantiomers. The respective area counts of 1981 and 1991 support the conclusion that Example C is comprised of about 1:1 mixture of the syn enantiomers, (1S,2R)-dimethyl-4-((E)-4,8-dimethylnona-3,7-dien-1-yl)cyclohex-4-ene-1,2-dicarboxylate, and (1R,2S)-dimethyl-4-((E)-4,8-dimethylnona-3,7-dien-1-yl)cyclohex-4-ene-1,2-dicarboxylate.

Typical constituents include: 48 wt % (1S,2R)-dimethyl 4-((E)-4,8-dimethylnona-3,7-dien-1-yl)cyclohex-4-ene-1,2-dicarboxylate, 48 wt % (1R,2S)-dimethyl 4-((E)-4,8-dimethylnona-3,7-dien-1-yl)cyclohex-4-ene-1,2-dicarboxylate, about 1.4 wt % DMM, about 1 wt % (2E,6E)-3,7,11-trimethyldodeca-2,6,10-trien-1-ol (farnesol), about 0.1 wt % (6E)-7,11-dimethyl-3-methylenedodeca-1,6,10-triene (trans-β-farnesene), about 0.1 wt % of a first diastereomer of Example C, and about 0.8 wt % of a second diastereoisomer of Example C.

Example D. Preparation of Compound (II-4") According to Scheme I

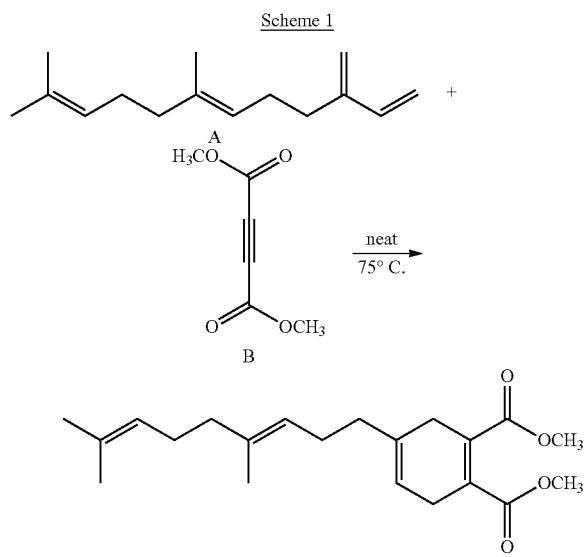

To a 1 L 3-necked round bottom flask fitted with two temperature probes (one recording, one readout), water condenser and an addition funnel was charged with 217.5 g (1500 mmol) dimethylacetylene dicarboxylate (DMAD) (98% pure, available from TCI Chemicals). The DMAD was sparged with nitrogen gas for 15 minutes. 1500 mmol trans-β-farnesene (Amyris, Inc., distilled and filtered through alumina, containing 100 ppm TBC (4-tert butyl catechol) as a stabilizer, having a purity of 99%) was sparged with nitrogen gas. DMAD was heated to 75° C. and held for 5 minutes. β-farnesene (306.5 g, 372.9 ml, 1500 mmol) was added dropwise to the flask containing DMAD at a rate of 0.5-2 drops/second to result in an average rate of 83 ml/hour over a period of 4.5 hours, with addition rate controlled to maintain temperature at 75° C. (temperature maintained at or below 77° C. with addition rate of 0.5 drops/sec, momentary temperature spike to 90.1° C. observed when addition rate was increased to 2 drops/sec). The reaction mixture was allowed to cool to room temperature overnight. The following day, the reaction mixture was reheated to 75° C. to allow remaining (approximately 2%) DMAD to react for approximately 31 hours. The reaction mixture was observed to be a clear yellow liquid containing no crystals. The product was filtered through a 4 micron nylon filter. Yield was estimated to about 93%. The product was analyzed by GC-MS, proton NMR, and $^{13}$C NMR to be Example D, and purity analyzed by HPLC to be 91% and by GC-FID to be 90-91%.

In an alternative scheme for making Example D, a reactor system is purged with nitrogen and charged with dimethylacetylenedicarboxylate (1.1 molar equivalent, relative to farnesene). Vigorous stirring is initiated and 3 vacuum/nitrogen purge cycles are repeated (to greater than or equal to 28 in. Hg vacuum and greater than or equal to 0 psig nitrogen) to strip dissolved oxygen out of the liquid, and then a pressure of 1-5 psig nitrogen is added to prevent potential ingress of atmospheric oxygen. Farnesene is distilled and stabilized with 300 ppmw BHT. Farnesene is stripped with nitrogen by sparging the material in a feed tank with ten times the volume of the vessel while stirring. The reactor contents are heated to 85+/–3° C. Reactor vessel pressure is monitored. Temperature of the reactor is maintained at 85+/–3° C. using the reactor coolant system. Farnesene (1 molar equivalent) is delivered at a rate such that the temperature is maintained at 85+/–3° C. An excess of dimethylacetylenedicarboxylate may result in reduced formation of farnesene dimers. Reaction completion is monitored based on analytic analysis. Optionally, a final charge of farnesene may be added to consume residual dimethylacetylenedicarboxylate. After cooling, the reactor contents are filtered through a 5 micron PTFE filter. The product is stored in containers that have been sparged with nitrogen and sealed under nitrogen atmosphere.

In a scaled up synthesis for Example D, a reactor system is purged with nitrogen. 8.85 kg trans-β-farnesene (distilled and stabilized with 300 ppmw BHT) (15% total amount) is charged to the reactor. Agitation is started and the reactor is heated to 80-90° C. 6.21 kg dimethylacetylenedicarboxylate (DMAD) (15% total amout) is delivered to the reactor over a period of 3 hours using at an addition rate of 2.1 kg/hr. DMAD is monitored using in process control HPLC and flow rate is adjusted so that area % DMAD is less than 4%. Agitation is continued for 30 minutes. Temperature is increased to 100-110° C. Over the next 3-5 hours, 35.21 kg DMAD and 50.13 kg farnesene are charged in parallel to the reactor. The DMAD addition rate is 7.04-11.34 kg/hr and the farnesene addition rate is 10.03-16.71 kg/hr. The reaction is agitated for 5-10 hours. The reaction is complete when HPLC area % for DMAD is less than 0.65%, HPLC area % for farnesene is less than 1.3%, HPLC area % for Example D is greater than 93%. When the reaction is complete the reactor is cooled to 20-30° C. The product is filtered and stored in containers that have been sparged with nitrogen and sealed under nitrogen atmosphere.

Typical product yield is 89 wt %, with 5 wt % farnesene, 0.6 wt % trimethyl 5-methoxyfuran-2,3,4-tricarboxylate, 0.5 wt % dimethyl but-2-ynedioate, 0.2 wt % (E)-dimethyl 4-(4,8-dimethylnona-3,7-dien-1-yl)phthalate. Other impurities that have not been conclusively identified but may be present include: about 0.1 wt % (E)-dimethyl 4-(4,8-dimethylnona-3,7-dien-1-yl)-3-hydroxycyclohexa-1,4-diene-1,2-dicarboxylate, about 0.4 wt % farnesol, about 1 wt % (E)-dimethyl 5-(4,8-dimethylnona-3,7-dien-1-yl)-5-(2-methoxy-5-(methoxycarbonyl)furan-3-yl)cyclohexa-1,3-diene-1,2-dicarboxylate, about 0.2 wt % (E)-trimethyl 5-(1-(4,8-dimethylnona-3,7-dien-1-yl)-4,5-bibs(methoxycarboonyl)cyclohexa-2,4-dien-1-yl)-6-methoxy-4H-pyran-2,3,4-tricarboxylate, about 1 wt % dimethyl 5-((Z)-1,4-dimethoxy-1,4-dioxobut-2-en-2-yl)-5-((E)-4,8-dimethylnona-3,7-dien-1-yl)cyclohexa-1,3-diene-1,2-dicarboxylate, about 0.2 wt % (Z)-tetramethyl 2,2'-(4-((E)-4,8-dimethylnona-3,7-dien-1-yl)-1,2-bis(methoxycarbonyl)cyclohexa-2,5-diene-1,4-diyl)dimaleate, and about 1.8 wt % trimethyl 5-(4-((Z)-1,4-dimethoxy-1,4-dioxobut-2-en-2-yl)-1-((E)-4,8-dimethylnona-3,7-dien-1-yl)-3,4-bis(methoxycarbonyl)cyclohexa-2,5-dien-1-yl)-6-methoxy-4H-pyran-2,3,4-tricarboxylate.

Example E. Preparation of Compounds Having Formula (II-11") with n=2 According to Scheme 2

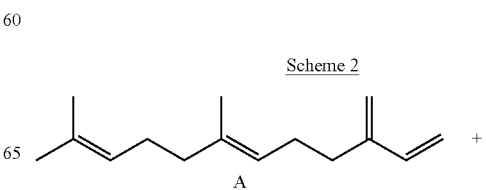

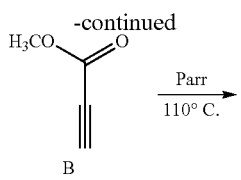

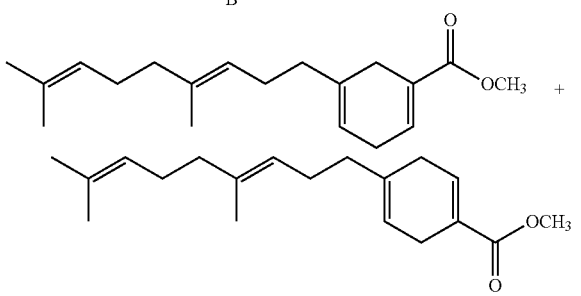

372.9 ml (306.53 g, 1500 mmol) trans-β-farnesene (Amyris, Inc., distilled, filtered through alumina, containing 100 ppm TBC as a stabilizer, 99% pure) and 133.44 ml (126.11 g, 1500 mmol) methyl propiolate (Alpha Aeser, 99.7% pure) were combined in a 1 L Parr reaction vessel. The mixture was sparged with nitrogen gas for 10 minutes before heating to 110° C. over 30 minutes. The reaction temperature was maintained at 110° C. for 20 hours and then allowed to cool to room temperature. The slightly yellow clear liquid was filtered through a 5 micron nylon filter. The filtered liquid was sparged with ultrahigh purity nitrogen gas for 7 hours, providing 415 g (theoretical yield 432.6 g). The structure of compound (II-11″) was confirmed by GC-MS, proton NMR and $^{13}$C NMR.

Example F. Preparation of Compound Having Formula II-6″ with n=2. Diisopropyl Analog of Example D Example F

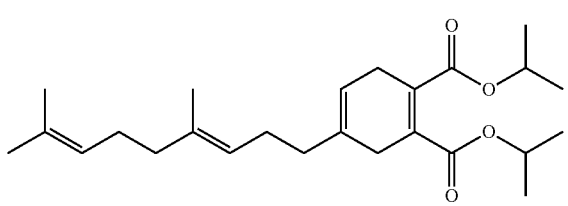

Step one: Preparation of diisopropyl diacetylene carboxylate. At 0° C., a 2 liter round bottom flask which was purged with nitrogen was charged first with isopropanol (1 L, 26.20 mol) followed by cold concentrated sulfuric acid (300 g, 3.06 mol). Then, acetylene dicarboxylic acid monopotassium salt (100 g, 0.66 mol) was added to the mixture in portions over 1 hour while the temperature was maintained by ice-water bath (0° C.). The reaction was then allowed to proceed at 0° C. under an atmosphere of nitrogen for 3 hours. Then, the reaction temperature was warmed to room temperature naturally without extra heating. After another 5 days at room temperature, the mixture was concentrated under reduced pressure. The residue was diluted by cold water (1.5 L) and extracted with diethyl ether 3×1 L. The combined organic layers were washed with water and brine, dried over anhydrous sodium sulfate, and concentrated under reduced pressure to give crude diisopropyl diacetylene carboxylate 49 g. The crude product was purified by distillation. The pure diisopropyl diacetylene carboxylate was collected around 90-140° C. (21 g, 15.4%). This synthesis was scaled up by running parallel reactions for multiple times.

Step two: Preparation of diisopropyl analog of Example D. Under nitrogen, at room temperature, a 2 liter round bottom flask with 3 necks was added with a solution of trans-beta-farnesene (40.62 g) and toluene (300 mL). This flask was charged a dropping funnel which was filled with diisopropyl diacetylene carboxylate (39.38 g). When the mixture in the flask was heated to reflux, the dropping funnel began to release diisopropyl diacetylene carboxylate dropwise. After 3 hours, all of the diisopropyl diacetylene carboxylate was transferred into the flask. Then, the whole reaction mixture was refluxed for another 16 hours. Toluene was removed by rotary evaporator under reduced pressure to give 80 g Example F (diisoproyl analog of molecule D).

Example K: Preparation of Imide-Containing Oxygen Scavenger

Molecule K

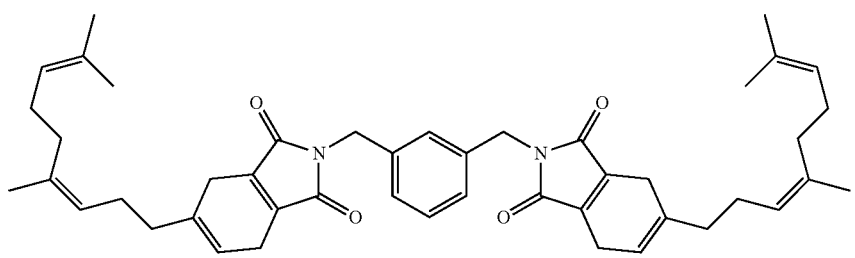

2,2'-(1,3-phenylenebis(methylene))bis(5-((Z)-4,8-dimethylnona-3,7-dien-1-yl)-4,7-dihydro-1H-isoindole-1,3(2H)-dione)

A 3-neck 250 mL round bottom flask was equipped with a Dean-Stark trap with a reflux condenser. One of the 3-necks of the flask was capped with a PTFE stopper and the remaining neck was sealed with a rubber septum. The reflux condenser was also sealed with a rubber septum. The acetylene dicarboxylic acid (12.50 g, 109.6 mmol) was suspended in 1,4-dioxane (25 mL) with stirring. The resulting mixture was placed under a flow of UHP nitrogen (cylinder)-gas in through the rubber septum in the neck of the flask and out the septum at the top of the reflux condenser. The mixture was heated (100° C.) in a heating cup on a hotplate stirrer. On heating, the mixture became homogeneous. Once the temperature reached 100° C., beta-farnesene (22.35 g, 109.4 mmol) was added via syringe through the septum in the neck of the flask. The solution was heated and stirred for 1 h at which time a small aliquot was taken for GC/MS analysis. This analysis showed good conversion to the anhydride and no aromatized (m/z 298) peaks were noted. Xylenes (50 mL) were added via syringe through the septum in the neck of the flask. The temperature of heating was increased to 160° C. and around 25 mL of solvent was collected in the sidearm. Almost 3 mL of this solvent separated at the bottom of the sidearm as a separate phase. The material in the sidearm was then removed by pipette and was discarded. The temperature was then increased to 185° C. (an hour had passed since the previous increase to 160° C.), and another 23 mL of distillate was collected in the sidearm. The m-xylylenediamine (5.78 mL, 5.97 g, 43.8 mmol) was added dropwise to the heated stirring mixture resulting in vigorous refluxing. The reaction was allowed to proceed at 185° C. for an additional 2 hours at which time TLC (1:1 hexane/EtOAc on silica gel; KMnO$_4$ stain) showed a nice conversion to product. Heating was turned off and the solution was stirred overnight under a stream of N$_2$ while cooling to ambient temperature. After cooling, the material was purified by flash column chromatography on silica gel (1000 mL 500 g) using the following stepped gradient as the eluent: 1 L hexanes, 1 L 5% EtOAc in hexanes, then 10% EtOAc in hexanes until the product was completely eluted from the column. The first fraction containing the product also contained some anhydride starting material as judged by TLC (anhydride remained at the baseline during TLC analysis). The fractions containing the purified product were combined and the volatiles were removed on a rotovap yielding the product as a thick slightly green/yellow oil (23.21 g; 76% of theoretical). $^1$H NMR (400 MHz, CDCl$_3$): δ 7.32 (s br, 1H), 7.19-7.24 (m, 3H), 5.55 (s br, 2H), 5.06-5.12 (m, 4H), 4.63 (s, 4H), 2.94-3.02 (m, 8H), 2.10-2.15 (m, 8H), 2.03-2.07 (m, 4H), 1.96-1.99 (m, 4H), 1.67 (s, 6H), 1.59 (s, 12H).

Example M: Preparation of Anti-Isomer of Compound II-24'

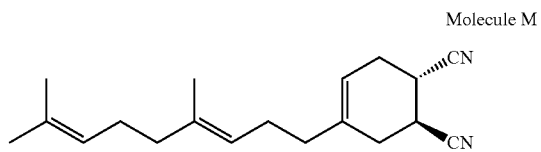 [SMILES: CC(C)=CCC/C(C)=C/CCC1=CC[C@H](C#N)[C@@H](C#N)C1]

Molecule M rac-1,2-anti-(4-(4,8-dimethylnonyl)-4-cyclohexene-1,2-dicarbonitrile)

Three sealed tube reaction flasks were each equipped with a magnetic stirring bar and were each charged with 13.84 g of fumaronitrile and 36.17 g of trans-beta-farnesene. The tubes were sealed and were heated in a temperature controlled sand bath (J-Kem Apollo setpoint 105° C.) with thermocouple between the glass holding the sand and the heating mantle. A second thermocouple was placed centrally between the three tubes in the sand bath for monitoring the temperature. The reaction was allowed to stir while heating for 66 hours. On system equilibration, the second thermocouple read 98° C. The reaction mixtures were removed from the sand bath and were allowed to cool to ambient temperature. The three reaction mixtures were combined and distilled from a 500 mL round bottom flask using a shortpath still head. The fumaronitrile was collected as a solid in the apparatus as the low boiling portion (195° C. mantle temp, 0.6 torr vacuum). The apparatus was periodically disassembled and rinsed with EtOAc to dissolve the unreacted fumaronitrile starting material. This process of removing the fumaronitrile was continued until no further solids condensed in the apparatus. The mantle temperature was then increased to 255° C. and the product was collected as the material distilling between 166° C. and 180° C. at 0.6 torr. The product was obtained in this manner as a colorless viscous liquid (135.5 g, 90.5% yield). GC-MS (m/z=282); $^1$H NMR (400 MHz, CDCl$_3$): δ 5.44-5.49 (m, br, 1H), 5.04-5.11 (m, 2H), 3.06-3.14 (m, 2H), 2.53-2.70 (m, 2H), 2.30-2.48 (m, 2H), 1.96-2.16 (m, 8H), 1.68 (s, 3H), 1.60 (s, 6H).

Example X19: Preparation of X19

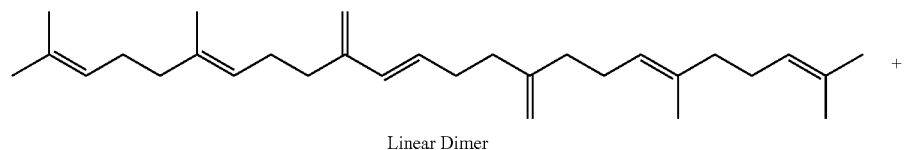

Linear Dimer

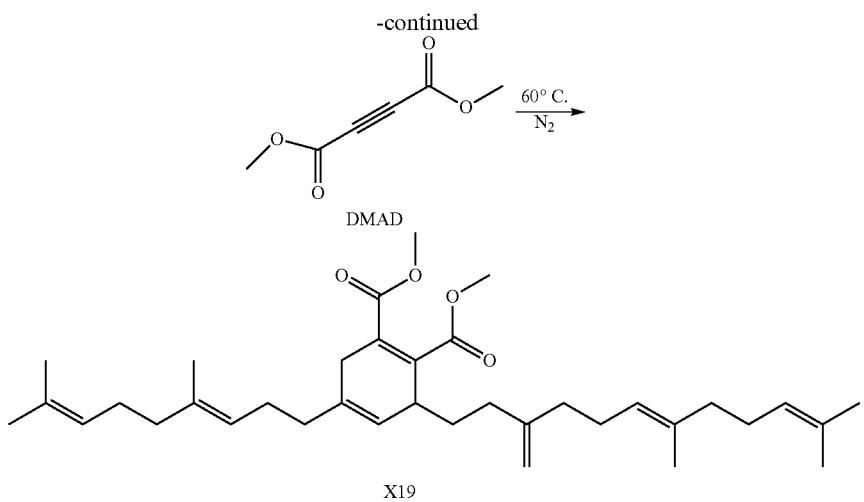

X19

| Reagent | MW | Mass | mmol | Equiv | Density | Volume | Source | Lot | Purity |
|---|---|---|---|---|---|---|---|---|---|
| Linear Dimer | 408.7 | 81.2g | 198.7 | 1 | | | Amyris | 497-11-7 | 100% |
| DMAD | 142.1 | 61.8g | 198.7 | 1 | 1.205 g/ml | 24.4 mL | TCI | BIPUF | 96% |

Example X19: Preparation of dimethyl 3-((E)-7,11-dimethyl-3-methylenedodeca-6,10-dien-1-yl)-5-(E)-4,8-dimethylnona-3,7-dien-1-yl) cyclohexa-1,4-diene-1,2-dicarboxylate (X19)

Linear dimer is prepared as described in U.S. patent publication 20110287988, which is incorporated by reference herein in its entirety. To an oven-dried 250 mL pressure vessel was added linear dimer (81.2 g, 198.7 mmol) and sparged with high purity nitrogen gas for 30 minutes, followed by the addition of DMAD (61.8 g, 198.7 mmol). Reaction vessel sealed and heated to 60° C. for 26 hours. The crude material was purified by silica gel chromatography (9:1 Hexanes/Ethyl Acetate) providing 50.0 grams (45.7% yield) of pure dimethyl 3-((E)-7,11-dimethyl-3-methylenedodeca-6,10-dien-1-yl)-5-(E)-4,8-dimethylnona-3,7-dien-1-yl)cyclohexa-1,4-diene-1,2-dicarboxylate as a clear liquid. Characterized by GC/MS MW=550.81, and $^1$H NMR.

Example X40: Preparation of Anti-Isomer of Compound II-3'

Molecule X40

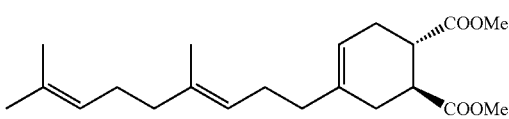

rac-1,2-anti-(dimethyl 4-(4,8-dimethylnonyl)cyclohexane-1,2-dicarboxylate)

In a 5 L Parr reactor, beta-farnesene (1768 g, 8.65 mol) was heated to 95° C. with stirring. Solid dimethylfumarate (1215 g, 8.43 mol, 0.97 equivalents) was added portionwise. The resulting mixture was allowed to stir at 95° C. overnight. The reaction mixture was then cooled and subjected to wiped film evaporation to remove the volatile components providing the product as a slightly yellow liquid (2837 g, 97% yield). HPLC Purity (>95%); LCMS (ESI: 349.0=M$^+$+1); $^1$H NMR (300 MHz, CDCl$_3$): δ 5.37 (s, br, 1H), 5.06 (m, 2H), 3.67 (s, 3H), 3.66 (s, 3H), 2.72-2.88 (m, 2H), 2.22-2.44 (m, 2H), 1.90-2.20 (m, 10H), 1.65 (s, 3H), 1.57 (s, 6H).

Example X41: Preparation of Syn-Isomer of Compound Having Formula II-7' with n=2

Molecule X41

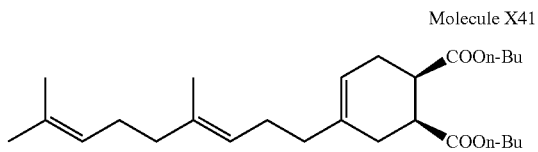

rac-1,2-syn-dibutyl 4-((E)-4,8-dimethylnona-3,7-dien-1-yl) cyclohex-4-ene-1,2-dicarboxylate In a 5 L Parr reactor, beta-farnesene (1166 g, 5.70 mol) was heated to 90° C. with stirring. Di-n-butylmaleate (1.245 L, 5.40 mol, 0.95 equivalents) was added dropwise over 4 hours. The resulting mixture was allowed to stir at 95° C. over a weekend followed by 120° C. for an additional 72 hours to drive the reaction to near completion. The reaction mixture was then cooled and subjected to wiped film evaporation to remove the volatile components providing the product as a slightly yellow liquid (2100 g, 90% yield). HPLC Purity (>95%); LCMS (ESI: 433.2=M$^+$+1); $^1$H NMR (300 MHz, CDCl$_3$): δ 5.36 (s, br, 1H), 5.03-5.10 (m, 2H), 4.03-4.10 (m, 4H), 2.93-3.4 (m, 2H), 2.40-2.58 (m, 2H), 2.20-2.37 (m, 2H), 1.90-2.12 (m, 10H), 1.66 (s, 3H), 1.52-1.62 (m, 8H), 1.28-1.41 (m, 4H), 0.90 (t, 6H).

Example CD: Blending of Example C and Example D to Form an Oxygen Scavenging Composition A container equipped with agitation (e.g., overhead mixer with impeller blades sized for quantity) is charged with a desired amount of Example D. Agitation is started. The amount of Example C required to make a desired blend (e.g., a 70:30 wt % (C:D) blend) is calculated. The appropriate amount of Example C is charged to the container. Agitation is continued for a minimum of 2 hours, maintaining a nitrogen blanket over the mixture. Agitation is stopped and samples are collected from at least 3 different locations in the mixture. Samples are analyzed by in process control GC-FID for homogeneity. If homogeneity is not observed, agitation is continued for another two hours, until homogeneity is achieved. The mixture is stored under nitrogen. Optionally, a desired amount of oxidation catalyst (e.g., cobalt neodecanoate) may be added to the mixture. The amount of oxidation catalyst (e.g., cobalt neodecanoate) may be determined by the final amount desired in a polymer blend, but may be in a range from about 5000 to about 10000 ppmw (e.g, 5000 ppmw, 7500 ppmw, or 10000 ppmw), based on the total weight of Example C and Example D.

For an approximately 450 kg batch of 70:30 wt % C:D blend, 12" impeller blades may be used for agitation. 135 kg Example D is charged to the mixer. Agitation is started. 315 kg Example C is charged to the mixer. Agitation and analysis are carried out as described above. Optionally, a desired amount of oxidation catalyst (e.g., cobalt neodecanoate) may be added to the mixture as described above.

Example CR: Blending of Example C and Maleic Anhydride Adducted Polybutadiene to Form an Oxygen Scavenging Composition A container equipped with agitation (e.g., overhead mixer with impeller blades sized for quantity) is charged with a desired amount of Ricon® 131MA5 maleic anhydride adducted polybutadiene, available from Cray Valley Polymers. Agitation is started. The amount of Example C required to make a desired blend (e.g., a 90:10 wt % (Example C:Ricon 131MA5) blend) is calculated. The appropriate amount of Example C is charged to the container. Agitation is continued for a minimum of 2 hours, maintaining a nitrogen blanket over the mixture. Agitation is stopped and samples are collected from at least 3 different locations in the mixture. Samples are analyzed by in process control GC-FID for homogeneity. If homogeneity is not observed, agitation is continued for another two hours, until homogeneity is achieved. The mixture is stored under nitrogen. Optionally, a desired amount of oxidation catalyst (e.g., cobalt neodecanoate) may be added to the mixture. The amount of oxidation catalyst (e.g., cobalt neodecanoate) may be determined by the final amount desired in a polymer blend, but may be in a range from about 5000 to about 10000 ppmw (e.g, 5000 ppmw, 7500 ppmw, or 10000 ppmw), based on the total weight of Example C and Ricon® 131MA5.

For an approximately 500 kg batch of 90:10 wt % C:D blend, 12" impeller blades may be used for agitation. 50 kg Ricon 131MA5 is charged to the mixer. Agitation is started. 450 kg Example C is charged to the mixer. Agitation and analysis are carried out as described above. Optionally, a desired amount of oxidation catalyst (e.g., cobalt neodecanoate) may be added to the mixture as described above.

Preparation of Oxygen Scavenging Oligomer

An example of an oxygen scavenging oligomer made by coupling together 3 oxgyen scavenging molecules as described herein is carried out as shown in Scheme A.1.1.

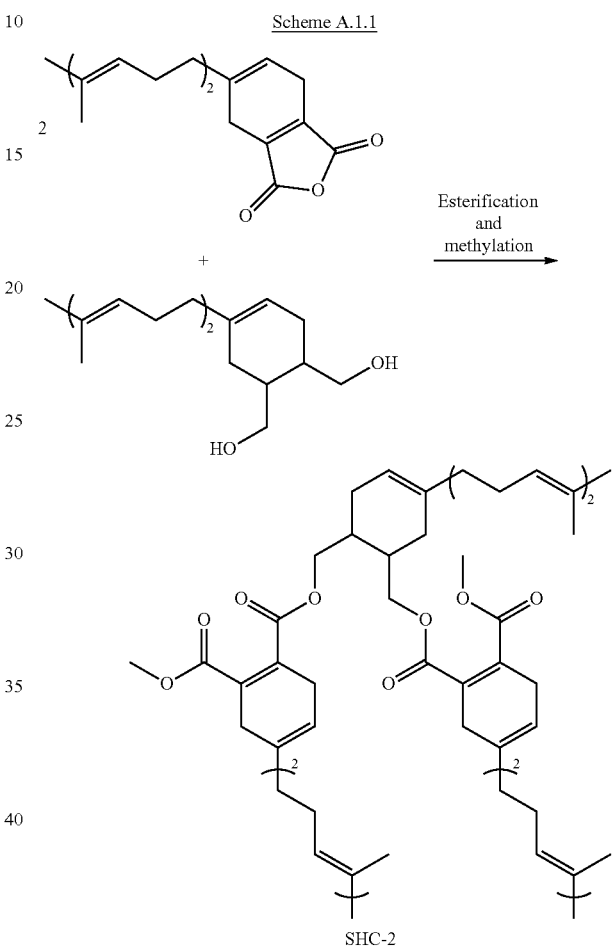

Step One: Preparation of Diol

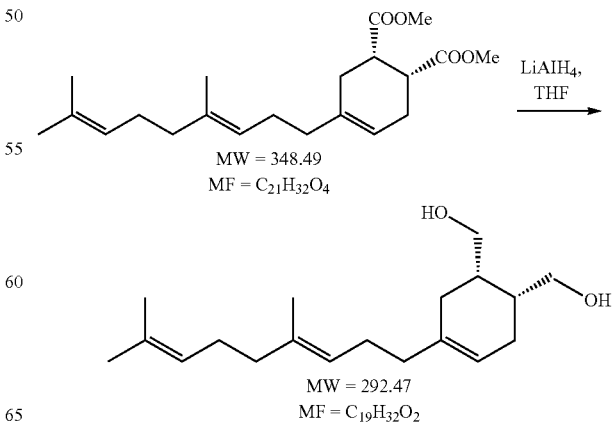

| Reagent/solvent | Supplier | cat # | Lot # | P (g/mL) | MW (g/mol) | mmol | mass (g) | volume (mL) | equiv. |
|---|---|---|---|---|---|---|---|---|---|
| farnesene maleic acid dimethyl ester adduct | Mark Micklatcher | | 559-19; 559-20; 559-22 | | 348.49 | 500 | 174.24 | | 1.00 |
| LiAlH$_4$ | Alfa Aesar | 89643 | I09W007 | | 37.95 | 555 | 21.05 | | 1.11 |
| tetrahydrofuran | Acros | 61045-0010 | | | | | | 400 | |
| Na$_2$SO$_4$•10H$_2$O | Alfa Aesar | A15702 | 10151157 | | 322.20 | 576 | 185.60 | | 1.15 |

A 2000 mL 4-neck flask was dried in an oven for 1 h prior to use. A pressure equalizing addition funnel was also dried in an oven for 1 h prior to use. The reaction vessel was equipped with a reflux condenser and a mechanical stirrer. The LiAlH$_4$ (21.05 g, 555 mmol) was added to anhydrous THF (600 mL). Once transfer was complete, the reaction vessel was equipped with the oven dried addition funnel. The diester (Example C above) (174.24 g, 500 mmol, recovered from the petroleum ether washes of 559-19, 559-20 and 559-22) was weighed into an oven dried 500 mL round bottom flask. The diester was taken up in anhydrous THF (200 mL) and the resulting solution was added to an addition funnel on top of the reaction vessel. The diester solution was added dropwise at a rate such that a gentle reflux of THF was maintained. Once addition was complete, the reaction mixture was stirred without external heating or cooling for an additional 3 hours. Sodium sulfate decahydrate (185.6 g, 576 mmol) was added portionwise cautiously to the mixture to quench the unreacted LiAlH$_4$. Vigorous gas evolution was noted initially with foam formation. Mixing speed was increased in order to insure proper mixing. Mixing was continued overnight. The following morning, celite (500 mL) was added to the reaction mixture. The resulting slurry was poured through a thin pad of celite (200 mL) on a sintered glass funnel. The filter cake was washed by passing an additional quantity of EtOAc (1000 mL) through the filter cake. The volatiles were removed from the solution on a rotovap. The crude product was then transferred to a 500 mL RB flask equipped with a shortpath distillation head. The material was distilled (1.6 torr; J-Kem controller reading). The fraction boiling between 196° C. and 201° C. was collected as the product (141.4 g, 97% of theoretical).

Step Two: Coupling Reaction to Make Di-Acid Precursor to SCH-2.

Under nitrogen, at −40° C., a mixture of molecule B (24 g, 80 mmol) and quinine (23.60 g, 72.80 mmol) in a mixed solvent of toluene and carbon tetrachloride (200 mL, 1:1) was added with the diol illustrated in Scheme A.1.1. (10.65 g, 36.40 mmol) in portions. The whole mixture was kept stirring at −40° C. for 2 hours. Then the reaction proceeded at room temperature for another 48 hours. The reaction was warmed from −40° C. to room temperature naturally without extra heating. Then, the resultant mixture was condensed under reduced pressure. After that, the residue was dissolved in ethyl acetate (1 L). The solution was washed with cold 5% HCl, cold water and brine. The combined organic layer was dried over anhydrous sodium sulfate and filtered. The filtrate was concentrated to give crude di-acid precursor of SHC-2 (22.80 g). This synthesis was scaled up by running parallel reactions for multiple times.

Step Three: Synthesis of SHC 2

Under nitrogen, at 0° C., to the solution of di-acid precursor of SHC 2 (89.73 g, 100 mmol) in methanol (200 mL) and toluene (500 mL), 2 M TMSCHN$_2$ (diazomethyl (trimethyl)silane) in hexanes (39 mL, 78 mmol) was added drop-wise over 30 min. The water-ice bath was removed to allow the reaction to proceed at room temperature for another 2 hours. Then the excess of the TMSCHN$_2$ and the rest of the unreacted volatile reagents were removed by rotary evaporator. After that, the crude compound was purified by silica gel chromatography with the eluents of ethyl acetate:hexane=1:9 to give pure SHC 2 (39 g, 42%).

Farnesene Oligomer Preparation

Numerous oxygen scavenging oligomers/polymers made by polymerizing one or more farnesene-derived oxygen scavenging monomers as described herein with ethylene glycol were made. In some cases, a glycol comonomer (e.g., polypropylene glycol (PPG) or polyethylene glycol (PEG) was incorporated into the polymerization reaction. In some cases, an ester comonomer (LiSIPA-DME or DMT) was incorporated into the polymerization reaction. A representative listing of oxygen scavenging polymers/oligomers and their respective compositions is provided in Table D.1 below. Also provided in Table D.1 is information regarding the catalyst used and molecular weight (Mn, GPC). Representative synthetic techniques for the oxygen scavenging oligomers/polymers are provided below.

TABLE D.1.

Material Charges and Procedures:

| Run ID | Compound A (mole %) | Compound C (mole %) | LiSIPA-DME (mole %) | Dimethyl Terep-hthalate (mole %) | Ethylene Glycol (mole %) | Polyethylene Clycol ($M_n$~600) (mole %) | Catalyst ID* | Catalyst Amount (Ti, ppm) | Triethyl Phosphate (P, ppm) | Mole Ratio Glycols/Acids Stechiometric excess is EG | GPC Mn |
|---|---|---|---|---|---|---|---|---|---|---|---|
| 110040-02-05 | 100 | | | | 95.8 | 4.2 | T | 200 | 193 | 2.2 | 9761 |
| 110040-02-06 | 98 | | 2 | | 100 | | 460 | 150 | 393 | 2.2 | 5404 |
| 110040-02-07 | 95 | | 5 | | 100 | | 460 | 150 | | 2.2 | 3342 |
| 110040-02-08 | 100 | | | | 50.0 | 50.0 | 460 | 150 | 385 | 2.2 | 1255 |
| 110040-02-12 | 100 | | | | 100 | | T | 60 | | 2.2 | 2404 |
| 110040-02-13 | 100 | | | | 100 | | T | 60 | | 2.2 | 2369 |
| 110040-02-15 | 100 | | | | 100 | | 460 | 150 | 186 | 2.2 | 2471 |
| 110040-02-16 | 100 | | | | 100 | | 460 | 150 | 186 | 2.2 | 3579 |
| 110040-02-17 | 98 | | 2 | | 100 | | 460 | 150 | 191 | 2.2 | 2327 |

TABLE D.1.-continued

Material Charges and Procedures:

| Run ID | Compound A (mole %) | Compound C (mole %) | LiSIPA-DME (mole %) | Dimethyl Terephthalate (mole %) | Ethylene Glycol (mole %) | Polyethylene Glycol ($M_n$~600) (mole %) | Catalyst ID* | Catalyst Amount (Ti, ppm) | Triethyl Phosphate (P, ppm) | Mole Ratio Glycols/Acids Stechiometric excess is EG | GPC Mn |
|---|---|---|---|---|---|---|---|---|---|---|---|
| 110040-02-18 | 98 | | 2 | | 100 | | 460 | 150 | 191 | 2.2 | 1844 |
| 110040-02-19 | 100 | | | | 96.6 | 3.4 | 460 | 150 | 186 | 2.2 | 4760 |
| 110040-02-20 | 100 | | | | 96.6 | 3.4 | 460 | 150 | 186 | 2.2 | 2674 |
| 110040-02-21 | 100 | | | | 100 | | 460 | 150 | 186 | 2.2 | 4625 |
| 110040-02-22 | | 100 | | | 100 | | 460 | 200 | 373 | 7.5 | 5557 |
| 110040-02-23 | | 80 | | 20 | 100 | | 460 | 100 | 356 | 5 | 6230 |

*: T = TnBT; 460 = Johnson Matthey AC 460

Ethylene glycol, Co-monomers (glycol or acid-based), Compound A or C, a boiling stone, and catalyst were charged under a purge of $N_2$ to glass reactor fitted with a $N_2$ gas inlet, mechanical helical agitator, and a condenser/liquid trap connected to a vacuum system. The mixtures were then heated to 180° C. under a gentle purge of $N_2$ and agitated by hand until liquid. Reactions were then agitated at 350 RPM. Temperature was slowly increased to 210° C. over 2-3 hours to drive the reaction to completion, as evidenced by bubbling ceasing in the reactor. In the cases of 110040-02-22 and 110040-02-23, instead of 2-3 hours, this was 36 hours, due to slow reaction. After esterification was complete the vacuum was slowly applied to the system to achieve a final vacuum of <1 mm Hg over 1-2 hours. Agitation was slowed to 150 RPM and the reaction was held <1 mm Hg for 2.25 hours. If no TEP (triethyl phosphate) was used, the reaction was discharged hot into a $N_2$ purged jar and cooled in an $N_2$ glove box. If TEP was used, the reaction was cooled to 125° C., TEP charged, mixed 10 minutes, and discharged hot into a $N_2$ purged jar and cooled in an $N_2$ glove box. The oligomers were then compounded without further modification into PET as described elsewhere.

Raw Material Information:
Ethylene Glycol (EG) was polymer grade from MEGlobal and used as received.
Compounds A & C were used as received from Amyris.
Propylene Glycol ($M_n$~600) was used as received from Aldrich.
LiSIPA-DME (Lithium sulfoisophthalic acid dimethyl ester) was used as received from Vitona.
Dimethyl Terephthalate (DMT) was used as received from Invista.
TnBT (titanium butoxide) was used as received from Aldrich. JM AC 460 was used as received from Johnson Matthey.

Preparation of Oxygen Scavenger Bottles

Oxygen scavenging compositions are prepared by blending host polymer, oxygen scavenger, accelerator (if applicable), and oxidation catalyst. Two general blending methods are used: a masterbatch procedure, and a solid state polymerization procedure. The PET is CLEARTUF® 8006S polyester resin, available from M&G Polymers USA, LLC. CLEARTUF® 8006S polyester resin is a 98.5 mole percent terephthalic acid, 1.5 mole percent isophthalic copolymer of polyethylene terephthalate resin. Cobalt neodecanoate pastilles, 20.5% Cobalt, is obtained from Shepherd Chemicals, Cincinnati, Ohio (product number 1354), containing up to 70 wt % cobalt neodecanoate and up to 30 wt % cobalt propionate. Manganese stearate is obtained from Shepherd Chemicals. A general masterbatch procedure that may be used for preparing oxygen scavenging bottles is as follows. Dried PET pellets and master batch pellets containing PET and cobalt neodecanoate may be mixed together in a bucket to achieve a polymer composition with 100 ppm cobalt from cobalt neodecanoate. The mixture of pellets is fed into an extruder, and a suitable amount of oxygen scavenger compound is pumped into an injection port located at the throat of the extruder, and the mixture is melt blended in the extruder to achieve a composition suitable for forming a bottle preform by injection molding.

A general solid state polymerization (SSP) procedure is as follows. A feed resin is extruded with cobalt neodecanoate powder and pelletized. The pelletized feed resin has an intrinsic viscosity of about 0.51 dl/g. The pellets are collected and heated under vacuum in a solid state polymerization process. The SSP process is monitored and allowed to continue until the IV reached about 0.85-0.86 dl/g. The resulting cobalt containing resin is dried and the oxygen scavenger is added, as described above, to form a composition suitable for forming a bottle preform by injection molding.

Preforms are formed by injection molding, which may be subsequently blow molded into 500 ml monolayer bottles.

In some cases, it may be desired that for the oxygen scavengers or compositions comprising oxygen scavengers, the water content be limited to about 500 ppm or less and/or the total acid and anhydride content be limited to about 0.1 mg KOH/g or less to limit reduction in intrinsic viscosity. Total acid number may be measured by any suitable technique, e.g., according to ASTM D974 "Standard Test Method for Acid and Base Number by Color-Indicator Titration," which is incorporated herein by reference in its entirety. Water content may be measured by any suitable method, e.g., by Karl Fischer titration.

The performance of the oxygen scavenger was evaluated by measuring the oxygen ingress into sealed bottles filled with deoxygenated water.

All the oxygen ingress measurements reported in the ensuing examples were made using a nominal 500 ml carbonated soft drink type bottle (530 mL overall volume, filled with 500 mL of liquid) blow molded from a 28 g preform which was filled and tested using the equipment and procedure described below.

The oxygen ingress was measured with a Fibox 4-Trace Fiber Optic Trace Oxygen Meter (Model Oxy-4-Trace-04-006) made by PreSens GmbH (www.presens.de, Regensburg, Germany). The meter reads a sensor dot which has been placed inside the sealed bottle. The principle of sensor operation is based on the quenching of luminescence caused by the collision between molecular oxygen and luminescent dye molecules in the excited state. The sensor dots and meter were calibrated according to the standards and procedures given by the manufacturer. The amount of dissolved oxygen in the liquid sealed inside the bottle is calculated by the Fibox software.

In a continuously purged nitrogen box, freshly blow molded bottles (three per formulation) are conditioned for 18-24 hours and then filled with 500 ml of deoxygenated water and carbonated by the addition of citric acid (5.54 g) and sodium bicarbonate (5.81 g) to give the desired degree of carbonation (3.1 volumes of $CO_2$). After filling, a transparent gas-tight plastic insert, which has a Fibox sensor affixed to the interior top of the insert, is fitted into the mouth of a bottle. The top exterior of the plastic insert has a threaded hole for the attachment of the fiber optic coupler used to read the Fibox sensor. The filled bottle with gas-tight insert is sealed with a metal retainer cap. The metal cap has an opening to permit reading of the Fibox sensor by the meter.

To take a reading, the bottles are shaken for 10 minutes (Eberbach Reciprocating Shaker, Model 6000) to insure equilibration between the oxygen dissolved in the liquid and the oxygen in the bottle headspace. The fiber optic cable is attached to the top of the gas-tight plastic bottle insert. The meter reads the sensor dot and calculates the dissolved $O_2$ concentration while the bottle is gently shaken while lying on its side.

An initial baseline oxygen reading (should be <50 ppb $O_2$) is made on each newly filled bottle. The bottles are aged under low light conditions in a room controlled at 71.6±1° F. (22±0.5° C.) and 43±2% RH. The dissolved $O_2$ concentration readings (ppm $O_2$, mg/L) are taken at regular time intervals until test is terminated.

The graphs in FIGS. 1 through 14 express the change of the dissolved oxygen concentration in the liquid as a function of time. ($\Delta$ ppm $O_2$ at a given time t relative to an initial time $t_0 = O_2(t) - O_2(t_0)$). The change is the average of three bottles. For the vertical axes, ppm=mg/L, and unless stated otherwise, the curves are collected at ambient conditions under low light conditions as described above.

Most of the oxygen in a sealed container resides in the headspace above the liquid rather than in the liquid itself. The total oxygen concentration (dissolved+headspace) inside a sealed container can be calculated from the following equation:

$$\text{Total } O_2 \text{ concentration (in ppm, mg } O_2/L) = \{C_{aq} * (33.7 * V_h + V_l)\}/(V_l + V_h),$$

where $C_{aq}$ is the dissolved oxygen concentration in ppm as measured by Fibox and the quantities $V_h$ and $V_l$ are the headspace and liquid volumes, respectively (in liters).

For each of Examples 1-67, the oxygen scavenger composition is identified in Tables E.1-E.7 below.

Examples 1-19. Oxygen Scavenging by Oxygen Scavengers of Formula II" Having Bisallylic Hydrogens Oxygen scavenging performance by a PET copolymer composition comprising an oxidation catalyst and oxygen scavenger molecules of formula II" are shown by Examples 1-19. Compositions and test conditions are tabulated in Table E.1. None of the compositions of Examples 1-19 contained an accelerator. For each of the compositions, the oxidation catalyst was 100-120 ppm cobalt metal from cobalt neodecanoate, introduced into the composition via masterbatch in CLEARTUF® 8006S resin, except for Examples 16 and 17 in which cobalt is introduced using SSP.

For Examples 1-15, the oxygen scavenger is compound (II-4") (Example D) which has 4 bisallylic hydrogens bonded to the 1,4-cyclohexadiene ring. For Examples 16-17, the oxygen scavenger is compound II-11" (Example E) and has 4 bisallylic hydrogens bonded to the 1,4-cyclohexadiene ring. For Example 18, the oxygen scavenger is Example K which has 4 bisallylic hydrogens bonded to each of the 1,4-cyclohexadiene rings. For Example 19, the oxygen scavenger is Example X19, in which the 1,4-cyclohexadiene ring has 3 bisallylic hydrogens bonded thereto, and 2 terpenoid tails bonded thereto.

For Examples 1-5, the host polymer is CLEARTUF® TURBO LT polyester resin, a copolymer of terephthalate, isophthalate and ethylene glycol having an intrinsic viscosity of 0.84 dl/g, available from M&G Polymers. The control is CLEARTUF® 8006S polyester resin, a copolymer of terephthalate, isophthalate and ethylene glycol, having an intrinsic viscosity of 0.80 dl/g. For Examples 1-5, the oxidation catalyst is 120 ppm cobalt metal from cobalt neodecanoate, introduced via a masterbatch formulation in CLEARTUF® 8006 resin into the composition. FIG. 1 shows the dissolved oxygen concentration as a function of time for Examples 1-5 and for the control sample (8006S PET only). As shown in FIG. 1, no induction time and no increase in oxygen concentration is detected even after 270 days for concentrations of 1.5 wt %, 2.0 wt % and 2.5 wt % oxygen scavenger, no induction time and no increase in oxygen concentration is detected until 120 days for a concentration of 1.0 wt % oxygen scavenger, and a concentration of 0.5 wt % oxygen scavenger shows reduced oxygen concentrations compared to the control. The bottles for each of Examples 1-5 are colorless, exhibiting L*=86, a*=0.4, b*=2, and haze value of 2.7%. Even after 270 days, bottles made according to Examples 3, 4, and 5 could meet useful targets for juice and beer bottle applications (dissolved oxygen concentration juice target 0.5 ppm $O_2$ and dissolved oxygen concentration beer target 0.15 ppm $O_2$), while exhibiting excellent color and low haze properties.

Figure 2:
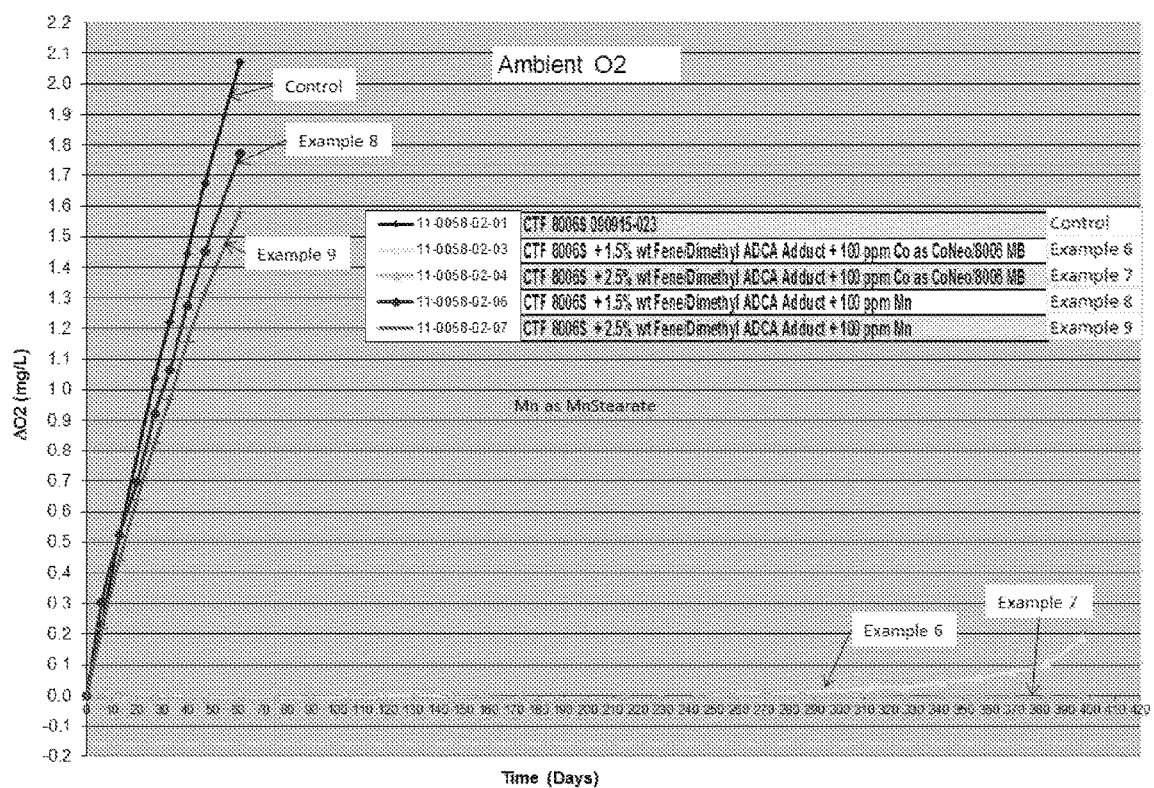
FIG. 2 provides a graph of dissolved oxygen concentration as a function of time for liquid in the interior of the capped blow molded bottles of Examples 6-9 under ambient conditions. The oxygen scavenger is Example D used at 1.5 wt % and 2.5 wt %, and the oxidation catalyst is cobalt neodecanoate as described for FIG. 1 or manganese stearate (available from Shepherd Chemical).
Figure 3:
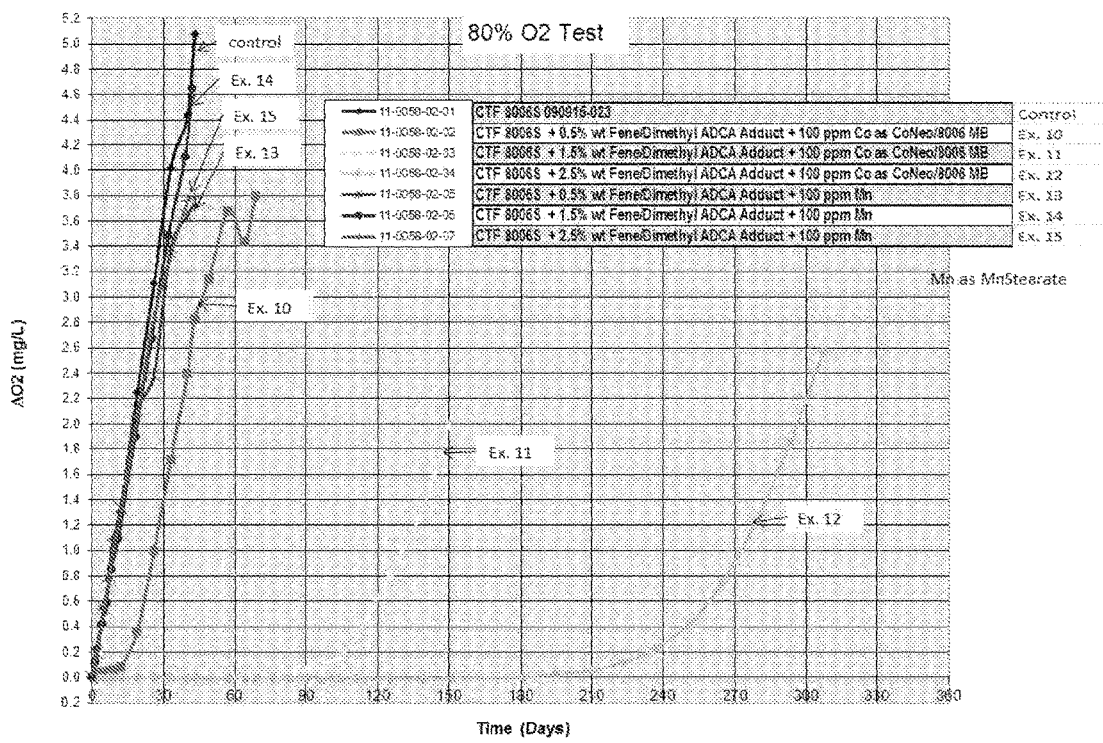
FIG. 3 provides a graph of dissolved oxygen concentration as a function of time for liquid in the interior of the capped blow molded bottles of Examples 10-15 under accelerated conditions (80% oxygen atmosphere). The oxygen scavenger is Example D used at 0.5 wt %-2.5 wt %, and the oxidation catalyst is cobalt neodecanoate or manganese stearate as described for FIG. 1.

For Examples 6-15, the effect of oxidation catalyst is investigated. For Examples 6-15, the host polymer is CLEARTUF® 8006S polyester resin and the oxygen scavenger is Example D. For Examples 6-9, bottles are tested in an ambient oxygen atmosphere (20% oxygen), and for Examples 10-15, bottles are tested in an enriched oxygen atmosphere (80% oxygen) for accelerated testing. For Examples 6-7 and 10-12, the oxidation catalyst is 100 ppm cobalt metal from cobalt neodecanoate, introduced via a masterbatch formulation in CLEARTUF® 8006 resin into the composition. For Examples 8-9 and Examples 13-15, the oxidation catalyst is 100 ppm manganese metal from Mn stearate. Results are shown in FIG. 2 (ambient testing) and FIG. 3 (accelerated testing). As shown, manganese (II) is a less effective oxidation catalyst than cobalt (II) for this oxygen scavenging composition under these conditions.

Figure 4:
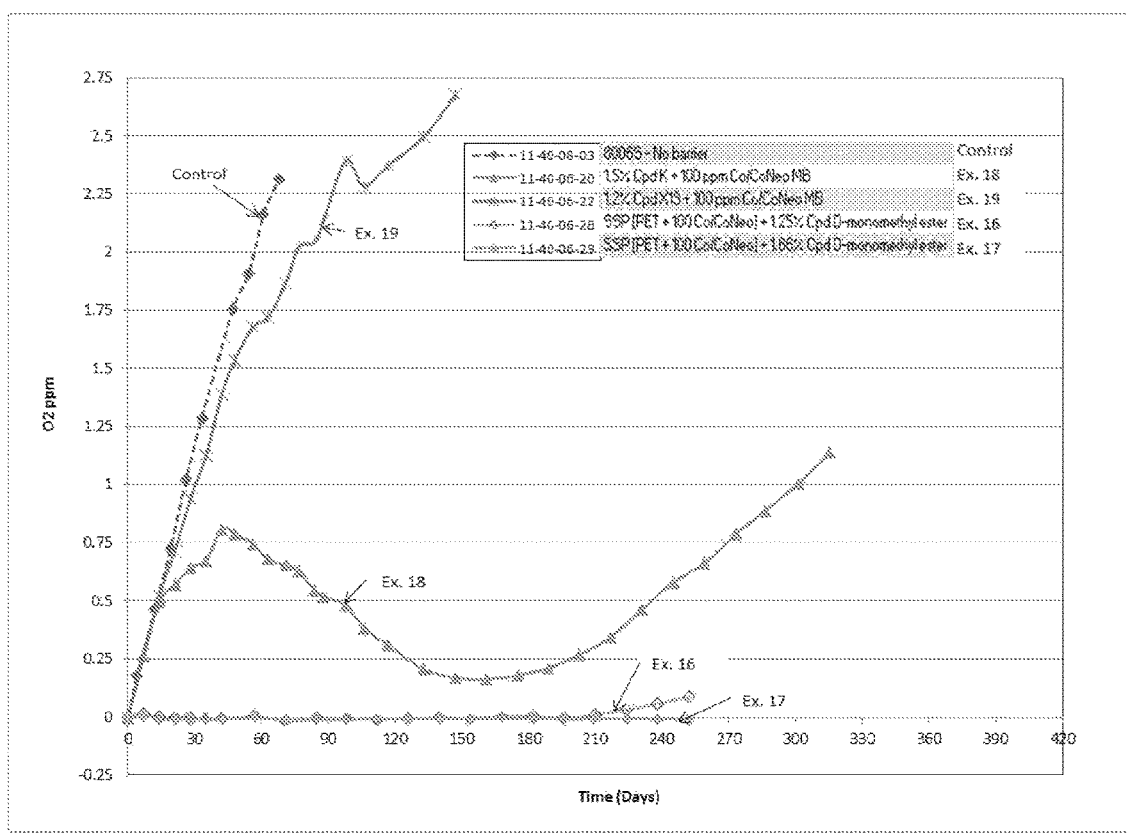
FIG. 4 provides a graph of dissolved oxygen concentration as a function of time for liquid in the interior of the capped blow molded bottles of Examples 16-19 under ambient conditions. The oxygen scavengers are Examples E, K, and X19, and the oxidation catalyst is cobalt neodecanoate as described for FIG. 1.

Examples 16-19 show oxygen scavenging by bottles made with compositions having oxygen scavenging molecules of formula (II") other than Example D. FIG. 4 shows dissolved oxygen concentration as a function of time for the bottles of Examples 16-19.

For Examples 16 and 17, the oxygen scavenger is Example E, which contains 4 bisallylic hydrogens bonded to the 1,4-cyclohexadiene ring. For Examples 16-17, no induction time is observed and no increase in dissolved oxygen content after about 95 days.

For Example 18, the oxygen scavenger is Example K which comprises 4 bisallylic hydrogens bonded to the each of the 1,4-cyclohexadiene rings. Bottles made using Example K were clear (no observable haze) and yellow (color may be due to impurities). After the induction time of about 45 days during which the dissolved oxygen concentration increased to about 800 ppb, the system scavenges oxygen vigorously depleting the oxygen concentration inside the container. For Example 18, the oxygen scavenger of Example K at 1.5 wt % exhibits an induction time of about 40-50 days. For Example 19, the oxygen scavenger is Example X19, in which the 1,4-cyclohexadiene ring comprises 3 bisallylic hydrogens bonded thereto, and 2 terpenoid tails bonded thereto. Bottles made using Example X19 were clear (no observable haze) and yellow. For Example 19, at 1.2 wt % the oxygen scavenger of Example X19 shows some oxygen uptake relative to the control, showing minimal reactivity for this loading.

TABLE E.1

Oxygen scavengers having formula II″ with bisallylic hydrogens bonded to 1,4-cyclohexadiene ring

| Ex. | Oxygen Scavenger | Accelerator | Oxidation catalyst | Environment |
|---|---|---|---|---|
| 1 | 0.5 wt % Example D | none | 120 ppm cobalt metal from cobalt neodecanoate | Ambient |
| 2 | 1.0 wt % Example D | none | 120 ppm Cobalt metal from cobalt neodecanoate | Ambient |
| 3 | 1.5 wt % Example D | none | 120 ppm Cobalt metal from cobalt neodecanoate | Ambient |
| 4 | 2.0 wt % Example D | none | 120 ppm Cobalt metal from cobalt neodecanoate | Ambient |
| 5 | 2.5 wt % Example D | none | 120 ppm Cobalt metal from cobalt neodecanoate | Ambient |
| 6 | 1.5 wt % Example D | none | 100 ppm cobalt metal from cobalt neodecanoate | Ambient |
| 7 | 2.5 wt % Example D | None | 100 ppm cobalt metal from cobalt neodecanoate | Ambient |
| 8 | 1.5 wt % Example D | none | 100 ppm Mn from manganese stearate | Ambient |
| 9 | 2.5 wt % Example D | none | 100 ppm Mn from manganese stearate | Ambient |
| 10 | 0.5 wt % Example D | none | 100 ppm Cobalt metal from cobalt neodecanoate | Accelerated (60% O$_2$) |
| 11 | 1.0 wt % Example D | none | 100 ppm Cobalt metal from cobalt neodecanoate | Accelerated |
| 12 | 2.5 wt % Example D | none | 100 ppm Cobalt metal from cobalt neodecanoate | Accelerated |
| 13 | 0.5 wt % Example D | none | 100 ppm Mn from manganese stearate | Accelerated |

TABLE E.1-continued

Oxygen scavengers having formula II" with bisallylic hydrogens bonded to 1,4-cyclohexadiene ring

| Ex. | Oxygen Scavenger | Accelerator | Oxidation catalyst | Environment |
|---|---|---|---|---|
| 14 | 1.5 wt % Example D | none | 100 ppm Mn from manganese stearate | Accelerated |
| 15 | 2.5 wt % Example D | none | 100 ppm Mn from manganese stearate | Accelerated |
| 16 | 1.25 wt % Example E 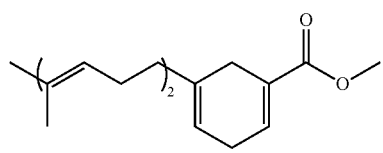 | none | 100 ppm Cobalt metal from cobalt neodecanoate | ambient |
| 17 | 1.66 wt % Example E | none | 100 ppm Cobalt metal from cobalt neodecanoate | ambient |
| 18 | 1.5 wt % Example K 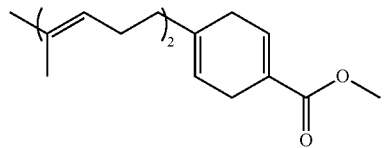 | None | 100 ppm Cobalt metal from cobalt neodecanoate | ambient |
| 19 | 1.2 wt % Example X19 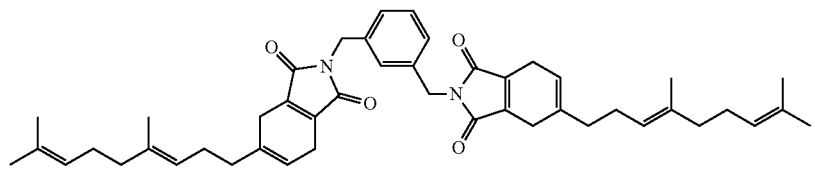 | none | 100 ppm Cobalt metal from cobalt neodecanoate | Ambient |

Figure 5A:
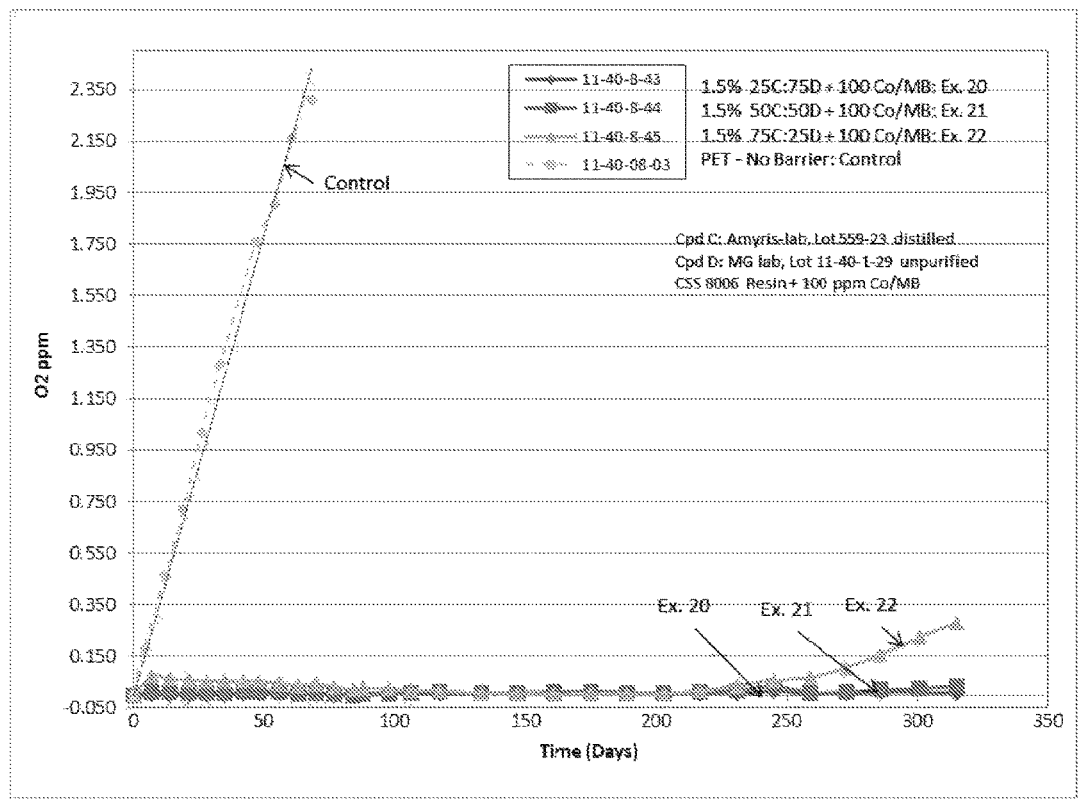
FIGS. 5A-5B provides a graph of dissolved oxygen concentration as a function of time for liquid in the interior of the capped blow molded bottles of Examples 20-22 under ambient conditions. The oxygen scavenger is Example C and the oxidation catalyst is cobalt neodecanoate as described for FIG. 1. Examples 20-22 include the accelerator oxygen scavenger of Example D.
Figure 5B:
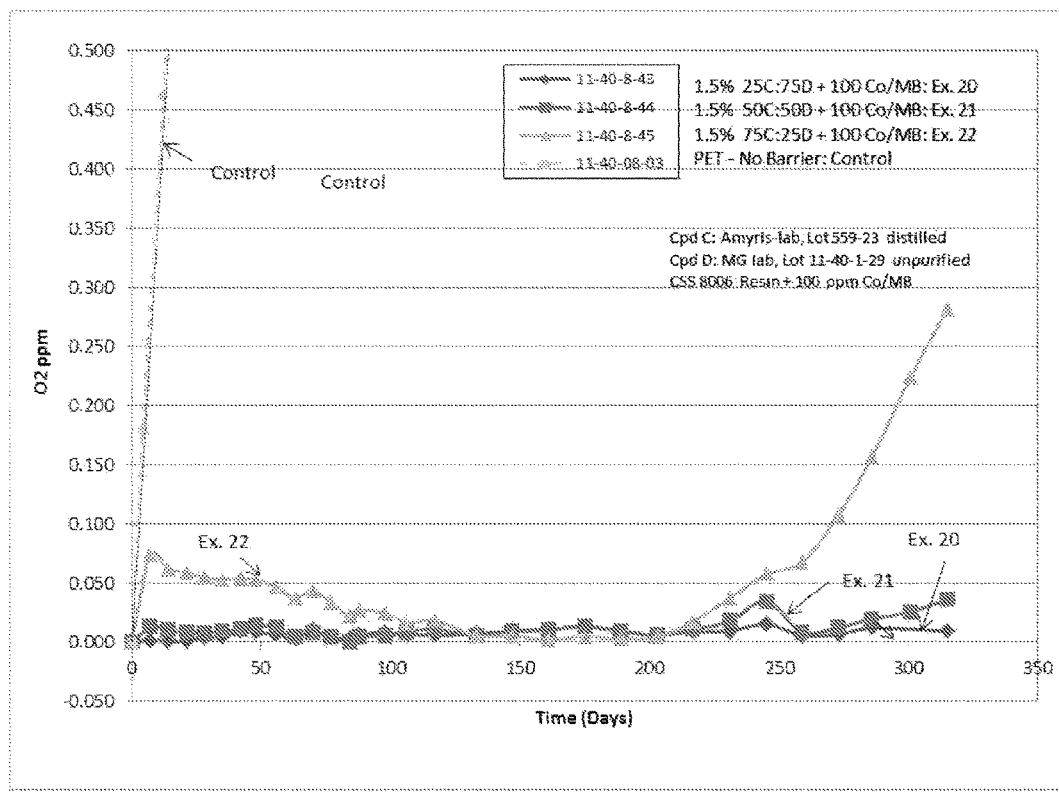

Examples 20-36. Oxygen Scavenging by Oxygen Scavengers of Formula II' Having Allylic Hydrogens and No Bisallylic Hydrogens Compositions Including Accelerator Oxygen scavenging activity by a PET copolymer composition comprising a cobalt neodecanoate oxidation catalyst, oxygen scavenger molecules of formula II', and an accelerator oxygen scavenger of formula II" is shown by Examples 20-22. Compositions and test conditions are tabulated in Table E.2. In these particular Examples 20-22, the oxygen scavenger is compound (II-4') (Example C) which comprises 4 allylic and no bisallylic hydrogens bonded to the cyclohexene ring, and the accelerator oxygen scavenger is compound (II-4") (Example D) which comprises 4 bisallylic hydrogens bonded to the 1,4-cyclohexadiene ring. For each of Examples 20-22, the oxidation catalyst is 100 ppm cobalt metal from cobalt neodecanoate, supplied as cobalt neodecanoate masterbatch. As illustrated in FIGS. 5A-5B, for Example 20-22, oxygen scavenging activity is observed using 1.5 wt % oxygen scavenger+accelerator, where the mass ratio (Ex. C):(Ex. D) is about 3:1 or less. As shown by Example 22, an induction time of a few days is observed when the mass ratio (Ex. C):(Ex. D) is about 75:25.

Figure 5C:
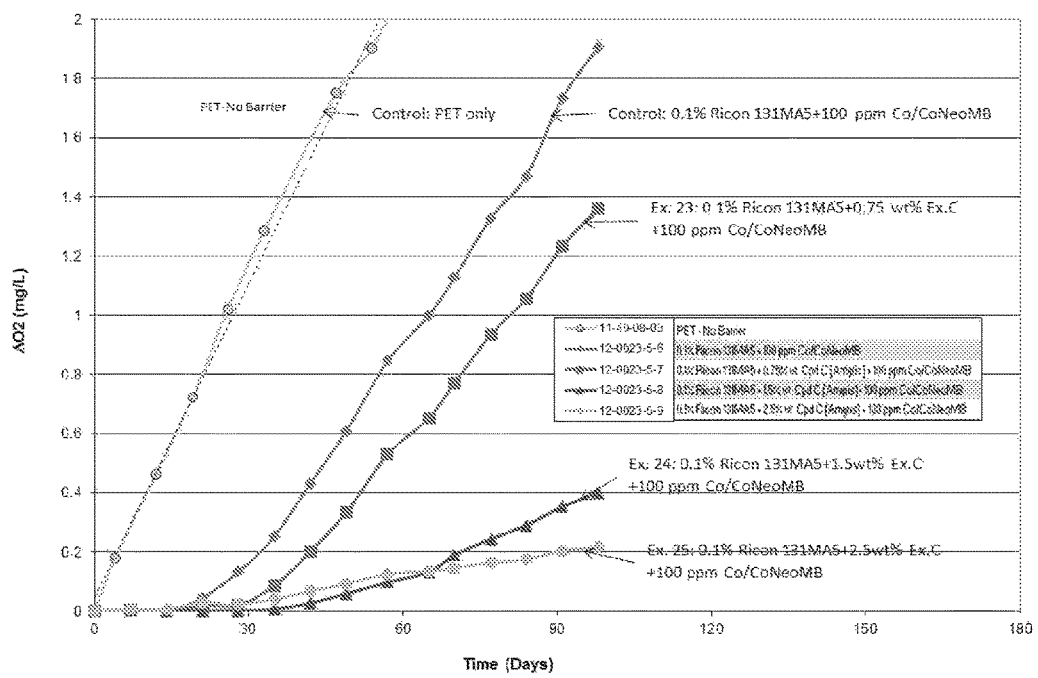
FIGS. 5C-5D provide graphs of dissolved oxygen concentration as a function of time for liquid in the interior of the capped blow molded bottles of Examples 23-25 and 26-28. The oxygen scavenger is Example C and the oxidation catalyst is cobalt neodecanoate as described for FIG. 1. Examples 23-25 and 26-38 include an accelerator oxygen scavenger that is a maleic anhydride adducted polybutadiene, RICON® 131MA5.
Figure 5D:
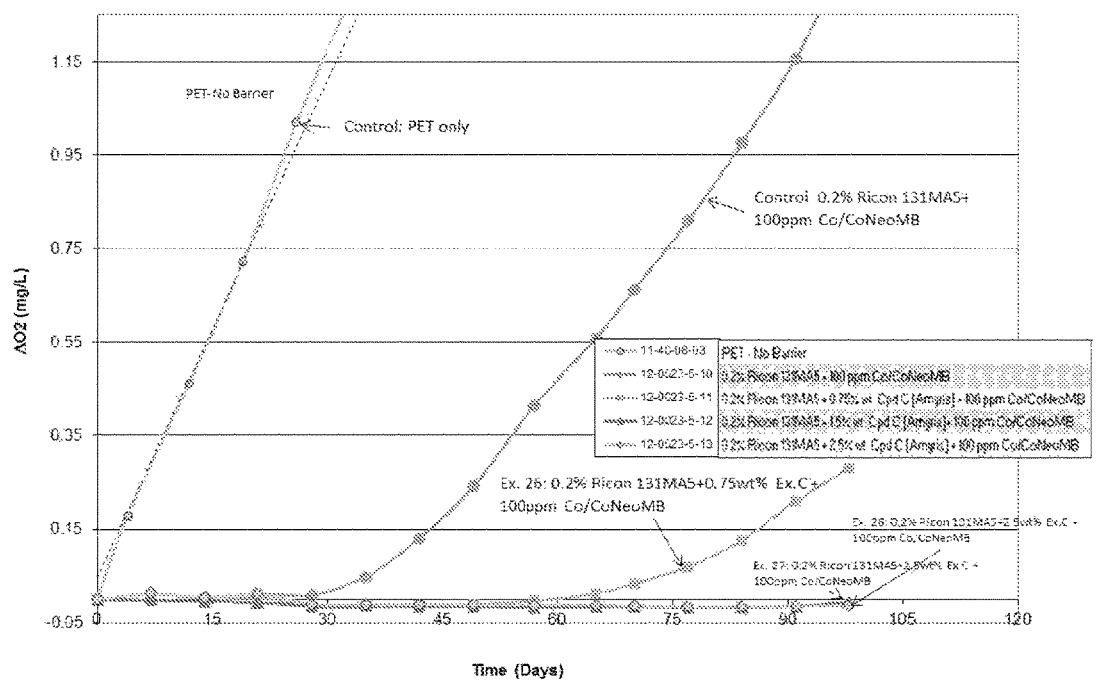

Oxygen scavenging by a PET copolymer composition comprising a cobalt neodecanoate oxidation catalyst, oxygen scavenger molecules of formula II', and a maleic anhydride adducted polybutadiene (Ricon 131MA5, available from Cray Valley Polymers) that acts as an oxygen scavenging accelerator is shown by Examples 23-28. For these Examples, the polybutadiene (Ricon 131) on which Ricon 131MA5 is based contains about 23% 1,2-vinyl content (see U.S. Pat. No. 5,300,569, which is incorporated herein by reference in its entirety). For each of Examples 23-28, the oxidation catalyst is 100 ppm cobalt metal from cobalt neodecanoate, which is incorporated as a cobalt neodecanoate/8006S masterbatch as described above. Bottles are blown as described above. A control sample comprising no oxygen scavenger, as well as a control sample comprising only 0.1 wt % Ricon 131 MA5 and 100 ppm cobalt metal from cobalt neodecanoate and a control sample comprising only 0.2 wt % Ricon 131MA5 and 100 ppm cobalt metal from cobalt neodecanoate are prepared. As illustrated in FIG. 5C, oxygen concentration for the control sample comprising only 0.1 wt % Ricon 131MA5 begins to increase after approximately two weeks, whereas Examples 23-25 show continued oxygen scavenging activity due to the presence of the oxygen scavenger of Example C. As illustrated in FIG. 5D, oxygen concentration for the control sample comprising only 0.2 wt % Ricon 131MA5 begins to increase after about 30 days, whereas Examples 26-28 show continued oxygen scavenging activity due to the presence of the oxygen scavenger of Example C.

Compositions not Including Accelerator

Figure 6A:
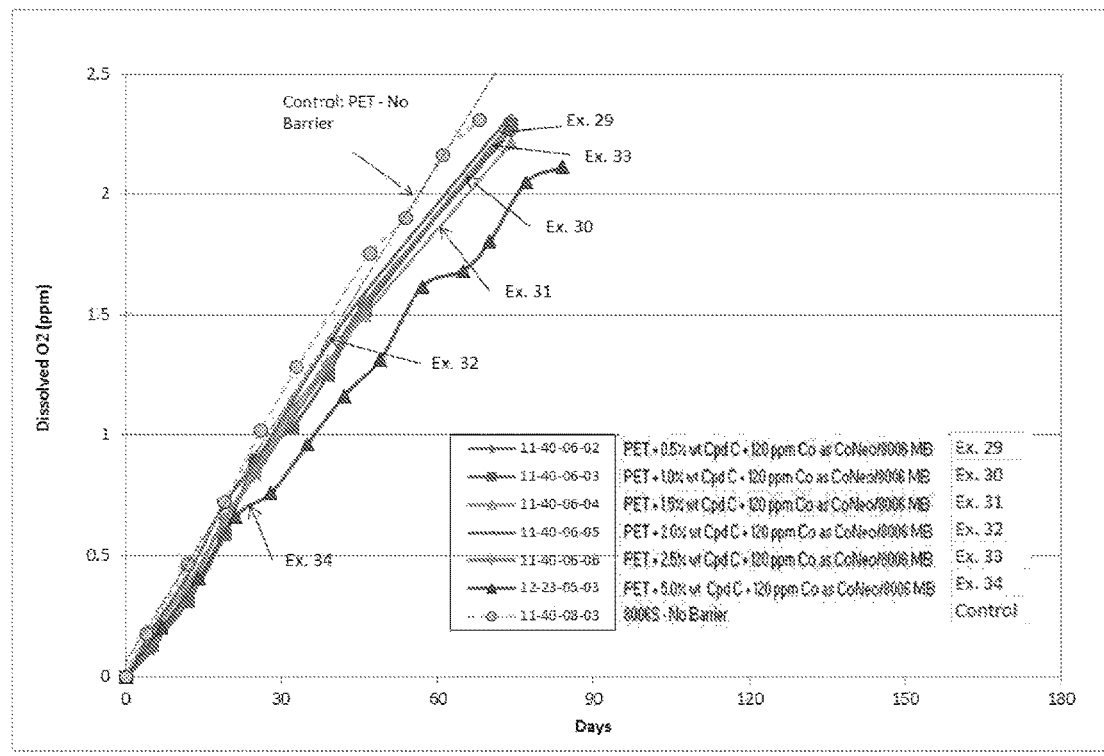
FIG. 6A provides a graph of dissolved oxygen concentration as a function of time for liquid in the interior of the capped blow molded bottles of Examples 29-34 under ambient conditions. The oxygen scavenger is Example C, the oxidation catalyst is cobalt neodecanoate as described for FIG. 1, and no accelerator is used.
Figure 6B:
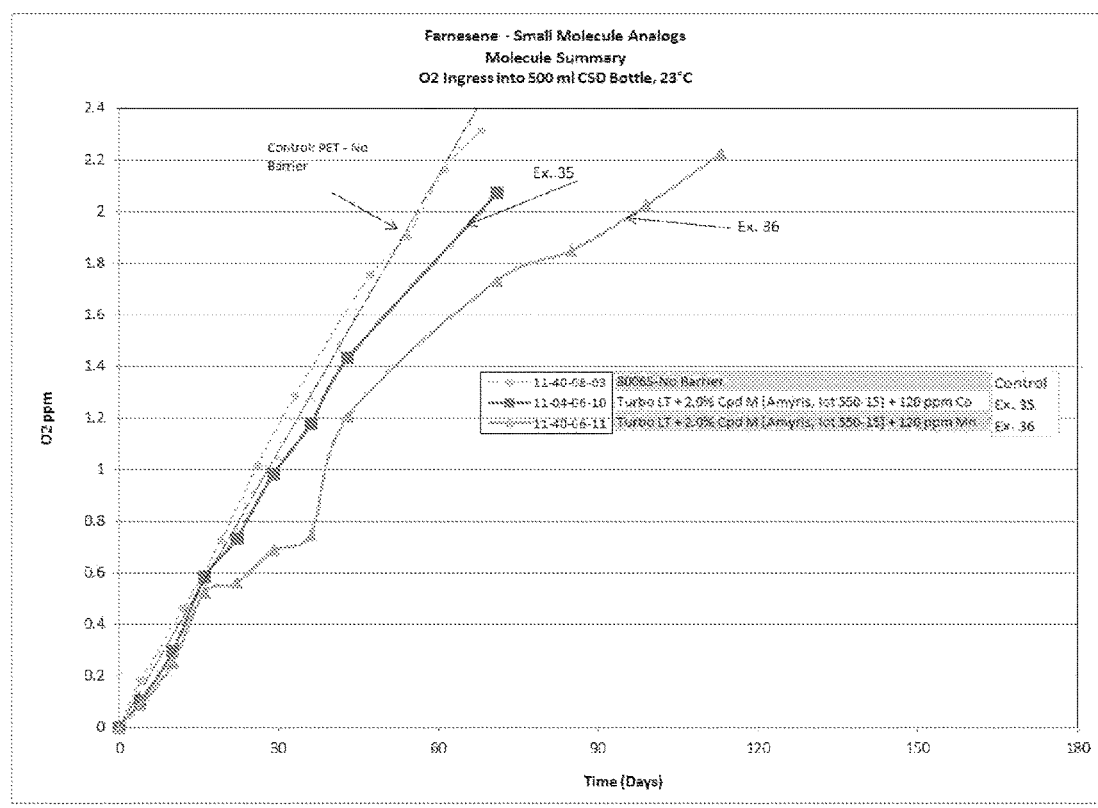
FIG. 6B provides a graph of dissolved oxygen concentration as a function of time for liquid in the interior of the capped blow molded bottles of Examples 35-36. The oxygen scavenger is Example M and the oxidation catalyst is cobalt neodecanoate or manganese stearate as described for FIGS. 1 and 2.

Examples 29-36 show oxygen scavenging activity by bottles formed from a PET copolymer composition in which a cobalt neodecanoate oxidation catalyst and an oxygen scavenger molecule of formula II' (having 4 allylic hydrogens and no bisallylic hydrogens) and have been blended, but no accelerator has been included (in contrast to Examples 20-28). In Examples 29-34, the oxygen scavenger is Example C. For Example 35-36, the oxygen scavenger is Example M. Compositions and test conditions are tabulated in Table E.2. For Examples 29-34, the oxidation catalyst is cobalt metal from cobalt neodecanoate, supplied as cobalt neodecanoate/80065 masterbatch. For Examples 29-33 and 35, 120 ppm cobalt metal from cobalt neodecanoate is used. For Example 34, 100 ppm cobalt metal from cobalt neodecanoate is used. For Example 36, 120 ppm manganese metal from manganese stearate is used. Results for Examples 29-34 are shown in FIG. 6A. Results for Examples 35-35 are shown in FIG. 6B.

TABLE E.2

Oxygen scavengers having formula II' with allylic hydrogens bonded to cyclohexene ring and no bisallylic hydrogens, with and without accelerator

| Ex. | Oxygen Scavenger | Accelerator | Scavenger: accelerator ratio |
|---|---|---|---|
| 20 | 1.5 wt % of a mixture of Example C scavenger and Example D accelerator, where the ratio of Example C to Example D is 25:75 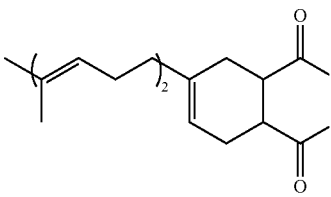 | Example D 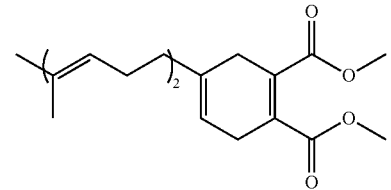 | 25:75 |
| 21 | 1.5 wt % of a mixture of Example C scavenger and Example D, where the ratio of Example C to Example D is 50:50 | Example D | 50:50 |
| 22 | 1.5 wt % of a mixture of Example C and Example D, where ratio of Example C to Example D is 75:25 | Example D | 75:25 |
| 23 | 0.75 wt % Example C | 0.1 wt % Ricon 131MA5 | 7.5:1 (by weight) |
| 24 | 1.5 wt % Example C | 0.1 wt % Ricon 131MA5 | 15:1 (by weight) |
| 25 | 2.5 wt % Example C | 0.1 wt % Ricon 131MA5 | 25:1 (by weight) |
| 26 | 0.75 wt % Example C | 0.2 wt % Ricon 131MA5 | 7.5:2 (by weight) |
| 27 | 1.5 wt % Example C | 0.2 wt % Ricon 131MA5 | 15:2 (by weight0 |
| 28 | 2.5 wt % Example C | 0.2 wt % Ricon 131MA5 | 25:2 (by weight) |
| 29 | 0.5 wt % Example C | none | N/A |
| 30 | 1.0 wt % Example C | none | N/A |
| 31 | 1.5 wt % Example C | none | N/A |
| 32 | 2.0 wt % Example C | none | N/A |
| 33 | 2.5 wt % Example C | none | N/A |
| 34 | 5.0 wt % Example C | none | N/A |

TABLE E.2-continued

Oxygen scavengers having formula II' with allylic hydrogens bonded to cyclohexene ring and no bisallylic hydrogens, with and without accelerator

| Ex. | Oxygen Scavenger | Accelerator | Scavenger: accelerator ratio |
|---|---|---|---|
| 35 | 2.0 wt % Example M + 120 ppm cobalt metal from cobalt neodecanoate | none | N/A |
| 36 | 2.0 wt % Example M + 120 ppm Mn metal from manganese stearate | none | N/A |

Figure 7A:
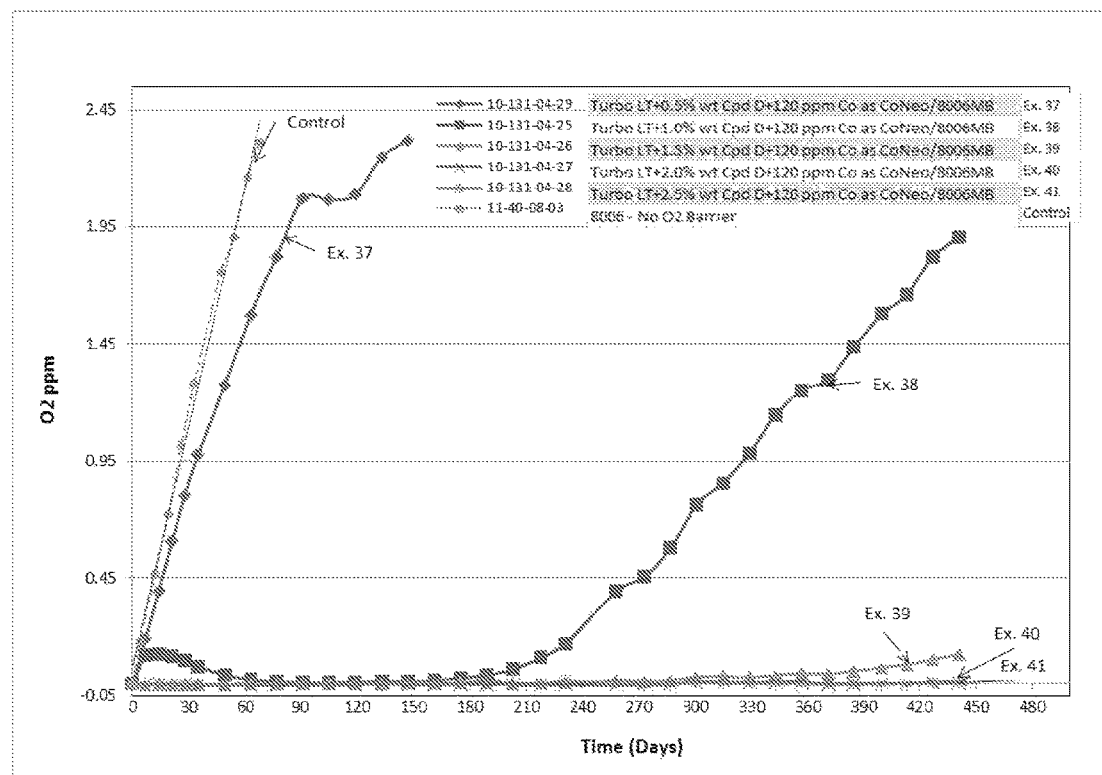
FIGS. 7A-7B provide graphs of dissolved oxygen concentration as a function of time for liquid in the interior of the capped blow molded bottles of Examples 37-41. The oxygen scavenger is Example B and the oxidation catalyst is cobalt neodecanoate as described for FIG. 1.
Figure 7B:
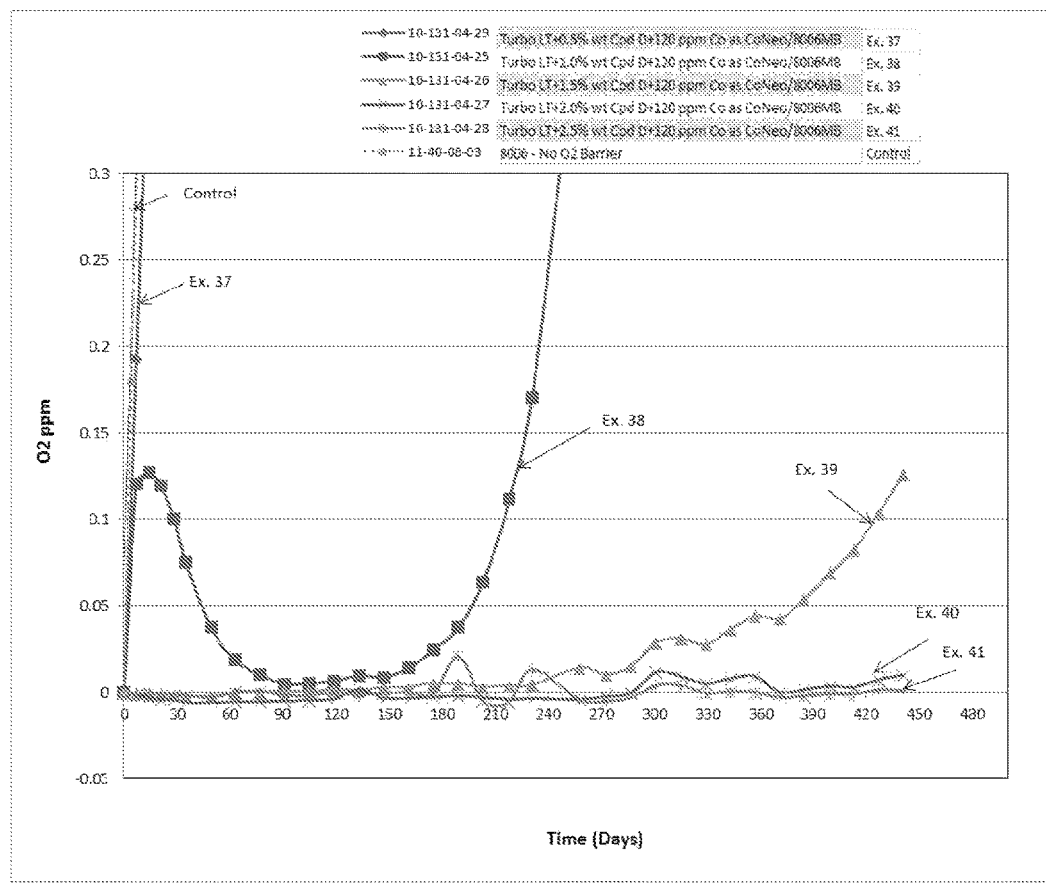

Examples 37-41. Oxygen Scavenging by Molecules of Formula III" Having Bisallylic Hydrogens Oxygen scavenging activity by a PET copolymer composition in which a cobalt neodecanoate oxidation catalyst and an oxygen scavenger molecule of formula III" are dispersed is shown by Examples 37-41. The oxygen scavenger is Example B and has four bisallylic hydrogens bonded to the 1,4-cyclohexadiene ring. Composition and test conditions are tabulated in Table E.3. Results are shown in FIGS. 7A-7B. It is possible that Example B reacted with the host polymer. As shown, at oxygen scavenger concentration of 1 wt % an induction time of a couple days is observed, and no induction time is observed for 1.5-2.5 wt %. Oxygen scavenging activity is substantially reduced when the oxygen scavenger concentration is 0.5 wt %.

In comparing oxygen scavenging capacity of oxygen scavengers of Example D to those of Example B, a composition comprising 1.0 wt % Example D appears to begin to lose activity after about 120 days (See Example 2, FIG. 1), whereas a composition comprising 1.0 wt % Example B shows no steep decrease in activity at 150 days (Example 38, FIGS. 7A-7B).

TABLE E.3

Oxygen scavenging compositions comprising oxygen scavengers of formula III" having bisallylic hydrogens

| Ex. | Oxygen Scavenger | Accelerator | Oxidation catalyst | Environment |
|---|---|---|---|---|
| 37 | 0.5 wt % Example B | none | 120 ppm Cobalt metal from cobalt neodecanoate as CoNeo/8006 masterbatch | Ambient |
| 38 | 1.0 wt % Example B | none | 120 ppm Cobalt metal from cobalt neodecanoate as CoNeo/8006 masterbatch | Ambient |
| 39 | 1.5 wt % Example B | none | 120 ppm Cobalt metal from cobalt neodecanoate as CoNeO/8006 masterbatch | Ambient |
| 40 | 2.0 wt % Example B | none | 120 ppm Cobalt metal from cobalt neodecanoate as CoNeo/8006 masterbatch | Ambient |
| 41 | 2.5 wt % Example B | none | 120 ppm Cobalt metal from cobalt neodecanoate as CoNeo/8006 masterbatch | Ambient |

Figure 8:
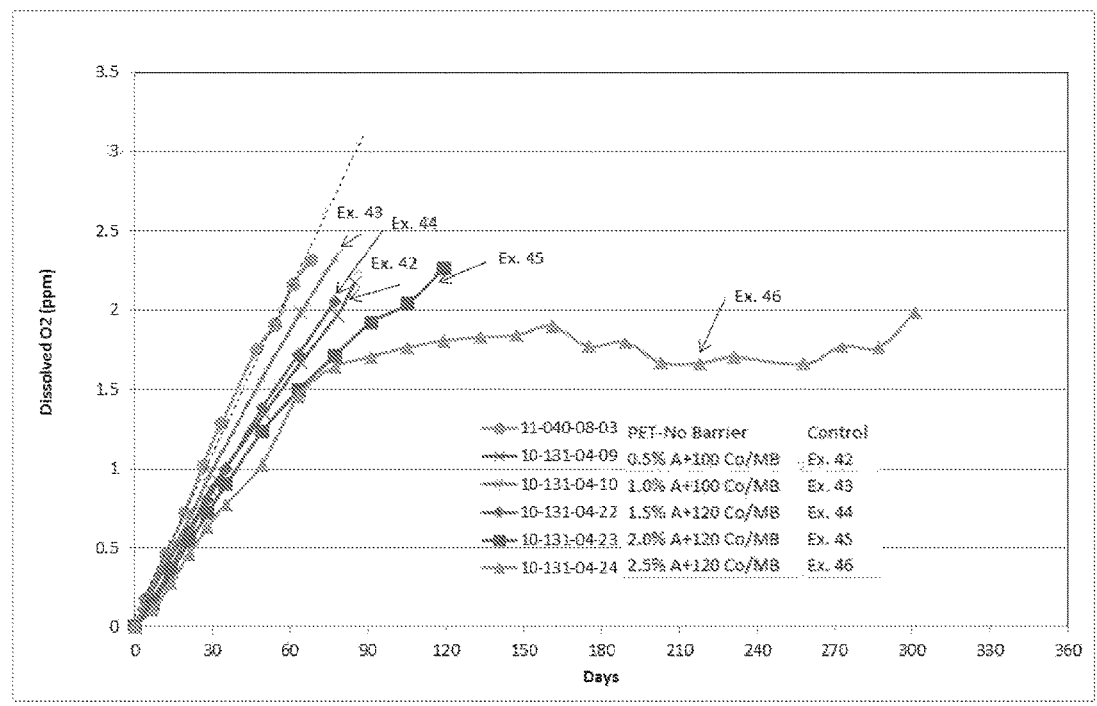
FIG. 8 provides a graph of dissolved oxygen concentration as a function of time for liquid in the interior of the capped blow molded bottles of Examples 42-46. For Examples 42-46, the oxygen scavenger is Example A and the oxidation catalyst is cobalt neodecanoate as described for FIG. 1.

Examples 42-46. Oxygen Scavenging by Molecules of Formula III' Having Allylic Hydrogens and no Bisallylic Hydrogens Oxygen scavenging activity by a PET copolymer composition in which a cobalt neodecanoate oxidation catalyst as described above for Example 1 and an oxygen scavenger molecule of formula III' (having 4 allylic hydrogens and no bisallylic hydrogens) have been blended are shown by Examples 42-46. Composition and test conditions are tabulated in Table E.4. In Examples 42-46, the oxygen scavenger is Example A. The bottles formed using 1.5 wt % Example A were optically clear, with higher concentrations exhibiting some haziness (indicative of phase separation). As shown, the oxygen scavenging activity at 2.5 wt % concentration shows an induction time of approximately 90 days. Results for Examples 42-46 are shown in FIG. 8.

TABLE E.4

Oxygen scavenging by molecules of formula III' having allylic hydrogens and no bisallylic hydrogens

| Ex. | Oxygen Scavenger | Accelerator | Oxidation catalyst | Environment |
|---|---|---|---|---|
| 42 | 0.5 wt % Example A | none | 120 ppm Cobalt metal from cobalt neodecanoate as CoNeo/8006 masterbatch | Ambient |
| 43 | 1.0 wt % Example A | none | 120 ppm Cobalt metal from cobalt neodecanoate as CoNeo/8006 masterbatch | Ambient |
| 44 | 1.5 wt % Example A | none | 120 ppm Cobalt metal from cobalt neodecanoate as CoNeo/8006 masterbatch | Ambient |
| 45 | 2.0 wt % Example A | none | 120 ppm Cobalt metal from cobalt neodecanoate as CoNeo/8006 masterbatch | Ambient |
| 46 | 2.5 wt % Example A | none | 120 ppm Cobalt metal from cobalt neodecanoate as CoNeo/8006 masterbatch | Ambient |

Figure 9A:
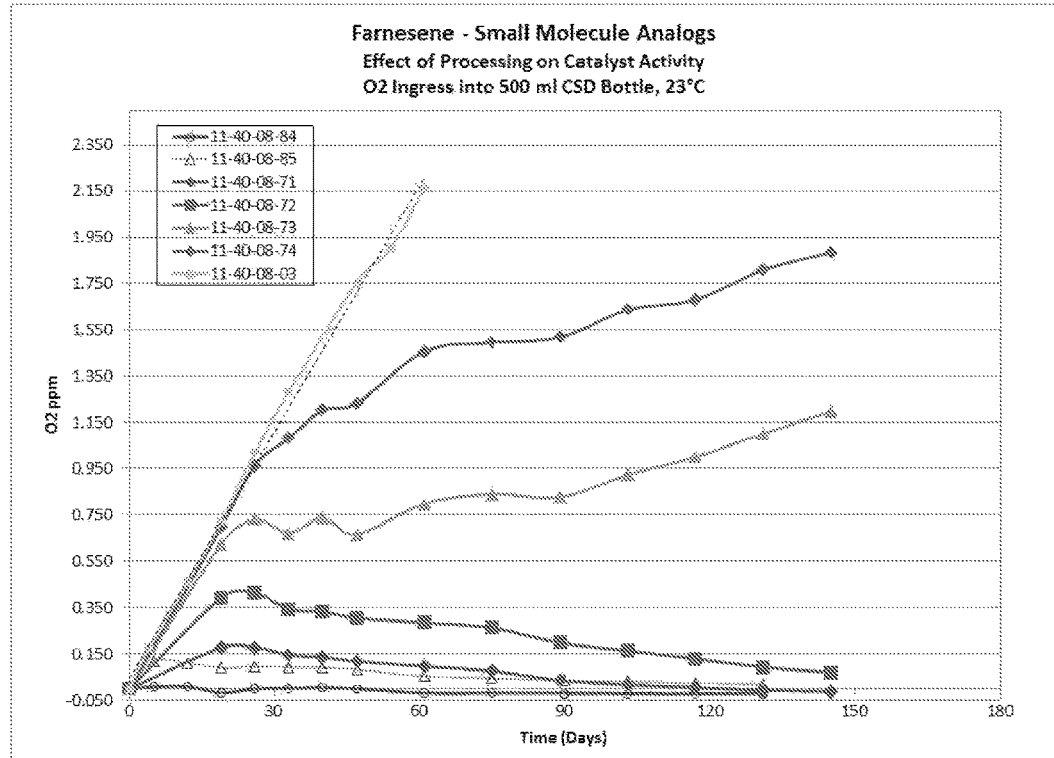
FIG. 9A provides a graph of dissolved oxygen concentration as a function of time for liquid in the interior of the capped blow molded bottles of Examples 48-53 and 56. For Examples 48-53, the bottles include an oxygen scavenging mixture of Example C and Example D and cobalt neodecanoate (as described for FIG. 1) as an oxidation catalyst. For Example 56, the oxygen scavenger is Example D and cobalt neodecanoate (as described for FIG. 1) is the oxidation catalyst. For Examples 48-49, the oxidation catalyst has been incorporated as a masterbatch. For Examples 50-53 and 56, the oxidation catalyst has been incorporated during a solid state polymerization process.
Figure 9B:
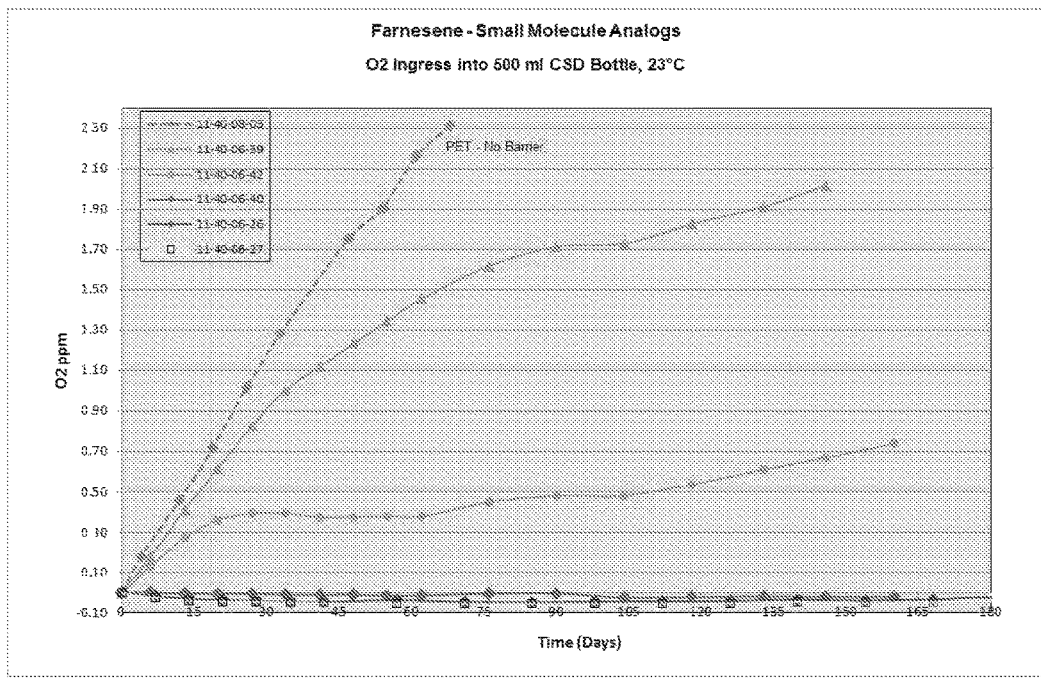
FIG. 9B provides a graph of dissolved oxygen concentration as a function of time for liquid in the interior of the capped blow molded bottles of Examples 54-57. For Examples 54-55, the oxygen scavenger is Example X41 and the oxidation catalyst is cobalt neodecanoate (as described for FIG. 1). Example 54 includes no accelerator and Example 55 includes Example D as an accelerator. For Example 56, the oxygen scavenger is Example D and cobalt neodecanoate (as described for FIG. 1) is the oxidation catalyst. For Examples 57-58, the oxygen scavenger is Example F and cobalt neodecanoate (as described for FIG. 1) is the oxidation catalyst. For all Examples illustrated in FIG. 9B, the oxidation catalyst has been incorporated during a solid state polymerization process.
Figure 9B:
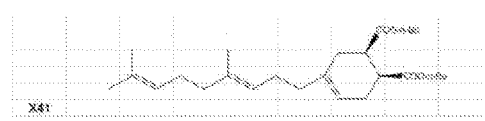

Examples 48-58. Incorporation of Oxidation Catalyst Using Solid Stating Polymerization For Examples 48-58, oxygen scavenging compositions in which a cobalt neodecanoate oxidation catalyst is incorporated into a PET copolymer matrix via a master batch addition are compared with oxygen scavenging compositions in which a cobalt neodecanoate oxidation catalyst is incorporated into a PET copolymer matrix using a solid stating polymerization step. Examples 48-49 were prepared using a masterbatch approach. Examples 50-58 were prepared using a solid state polymerization procedure. Compositions and test conditions are tabulated in Table E.5. All tests were done under ambient atmosphere. All compositions in Table E.5 include 100 ppm cobalt metal from cobalt neodecanoate. For Examples 48-53, the total combined amount of Example C and Example D is 1.5 wt %, with the relative amounts (mass ratio, [C]:[D]) indicated in Table E.5. Results for Examples 48-58 are shown in FIGS. 9A-9B.

In Examples 54-55, the oxygen scavenger is Example X41, which is an analog of Example C having n-butyl ester substituents instead of methyl ester substituents, resulting in higher molecular weight and increased hydrocarbon content for Example X41. Example 54 includes 1.9 wt % Example X41 and no accelerator. Example 55 includes the oxygen scavenger of Example X41 as well as an accelerator oxygen scavenger Example D, where the combined amount of Example X41 and Example D is 1.75 wt % and the mass ratio [N]:[D]=2:1. As shown, the oxygen scavenging activity in Example 54 shows an induction time of about 90 days, and Example 55 illustrates that including the accelerator of Example D in the composition shortens or eliminates the induction time. Example 56 shows oxygen scavenging activity of a composition including 1.5 wt % Example D, where the cobalt has been introduced in a solid stated formulation. For Examples 57 and 58, the oxygen scavenger is Example F, which is a diisopropyl analog of Example D having 4 bisallylic hydrogens bonded to the 1,4-cyclohexadiene ring. The oxygen scavenger of Example F is a higher molecular weight analog of Example D, and may exhibit lower volatility and/or lower tendency to migrate than the oxygen scavenger of Example D in some cases. For Examples 57-58, no induction time is observed and no increase in dissolved oxygen content is observed after about 95 days.

TABLE E.5

Incorporation of oxidation catalyst by master batch or solid state polymerization

| Ex. | Oxygen Scavenger | Accelerator | Scavenger: accelerator ratio | Process; oxidation catalyst |
|---|---|---|---|---|
| 48 | Ex. C 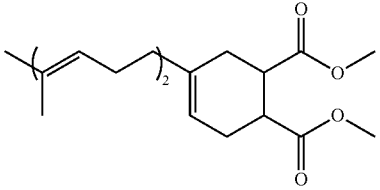 | Ex. D 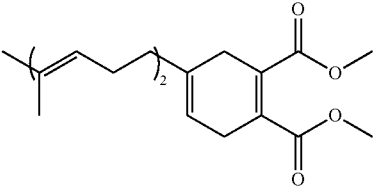 | 70:30 | Masterbatch; 100 ppm cobalt metal from cobalt neodecanoate |
| 49 | Ex. C | Ex. D | 50:50 | Masterbatch; 100 ppm cobalt metal from cobalt neodecanoate |
| 50 | Ex. C | Ex. D | 25:75 | SSP; 100 ppm cobalt metal from cobalt neodecanoate |
| 51 | Ex. C | Ex. D | 50:50 | SSP; 100 ppm cobalt metal from cobalt neodecanoate |
| 52 | Ex. C | Ex. D | 35:65 | SSP; 100 ppm cobalt metal from cobalt neodecanoate |
| 53 | Ex. C | Ex. D | 25:75 | SSP; 100 ppm cobalt metal from cobalt neodecanoate |
| 54 | 1.9 wt % Example X41 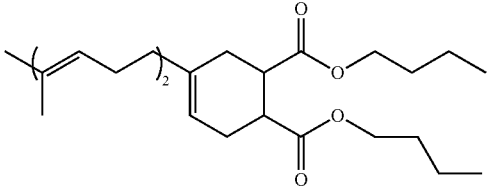 | none | N/A | SSP; 100 ppm cobalt metal from cobalt neodecanoate |
| 55 | 1.75 wt % [2 (Example X41):1 (Example D)] 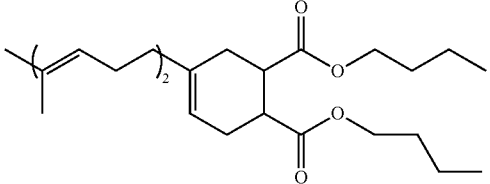 | Ex. D 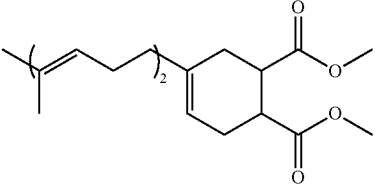 | 2:1 | SSP; 100 ppm metal from cobalt neodecanoate |
| 56 | 1.5 wt % Example D | none | N/A | SSP; 100 ppm cobalt metal from cobalt neodecanoate |

TABLE E.5-continued

Incorporation of oxidation catalyst by master batch or solid state polymerization

| Ex. | Oxygen Scavenger | Accelerator | Scavenger:accelerator ratio | Process; oxidation catalyst |
|---|---|---|---|---|
| 57 | 1.75 wt % Example F | none | N/A | SSP; 100 ppm cobalt metal from cobalt neodecanoate |
| 58 | 2.32 wt % Example F | none | N/A | SSP; 100 ppm cobalt metal from cobalt neodecanoate |

Examples 59-64: Addition of Chain Extender

Figure 10:
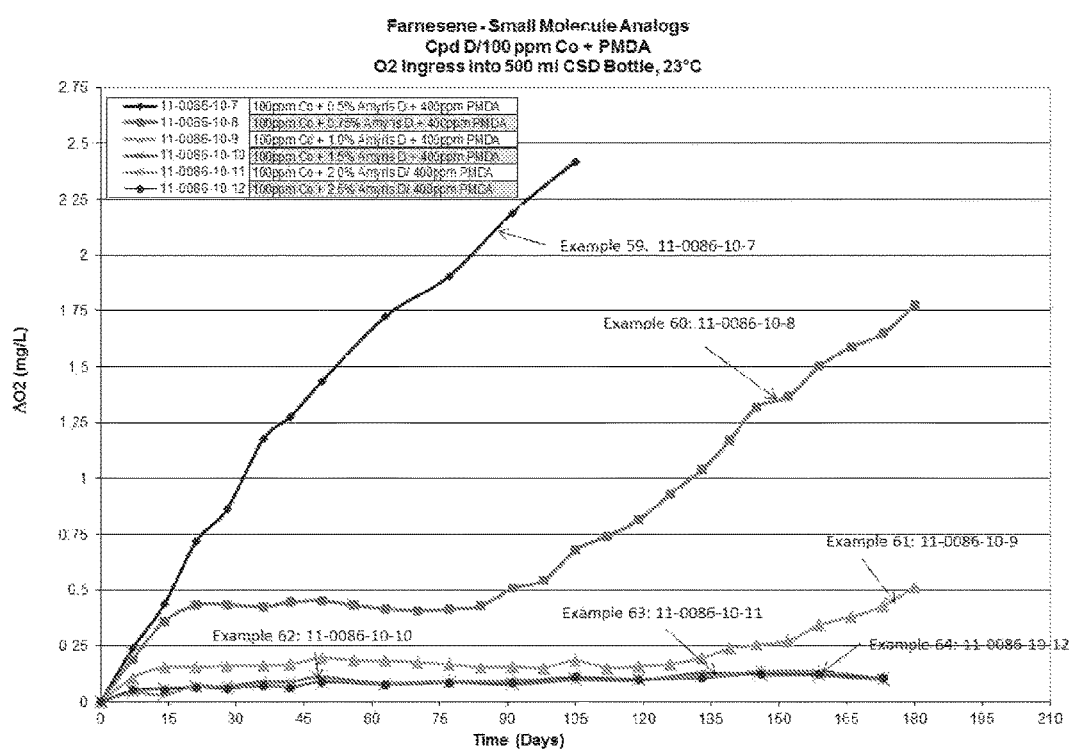
FIG. 10 provides a graph of dissolved oxygen concentration as a function of time for liquid in the interior of capped blow molded bottles of Examples 59-64. In each Example, the oxygen scavenger is Example D, the oxidation catalyst is cobalt neodecanoate (as described for FIG. 1), and a chain extender (PMDA) is used to increase intrinsic viscosity.

For Examples 59-64, oxygen scavenging compositions similar to those of Examples 1-5 and including a chain extender (pyromellitic dianhydride PMDA) to increase intrinsic viscosity are evaluated. The compositions are melt blended as described above, with the oxidation catalyst incorporated as a cobalt neodecanoate/8006S masterbatch. During the melt mixing process, the chain extender PMDA is added. Compositions are detailed in Table E.6. Bottles are formed and tested under ambient oxygen atmosphere as described for Example 1. Results are shown in FIG. 10.

Figure 11:
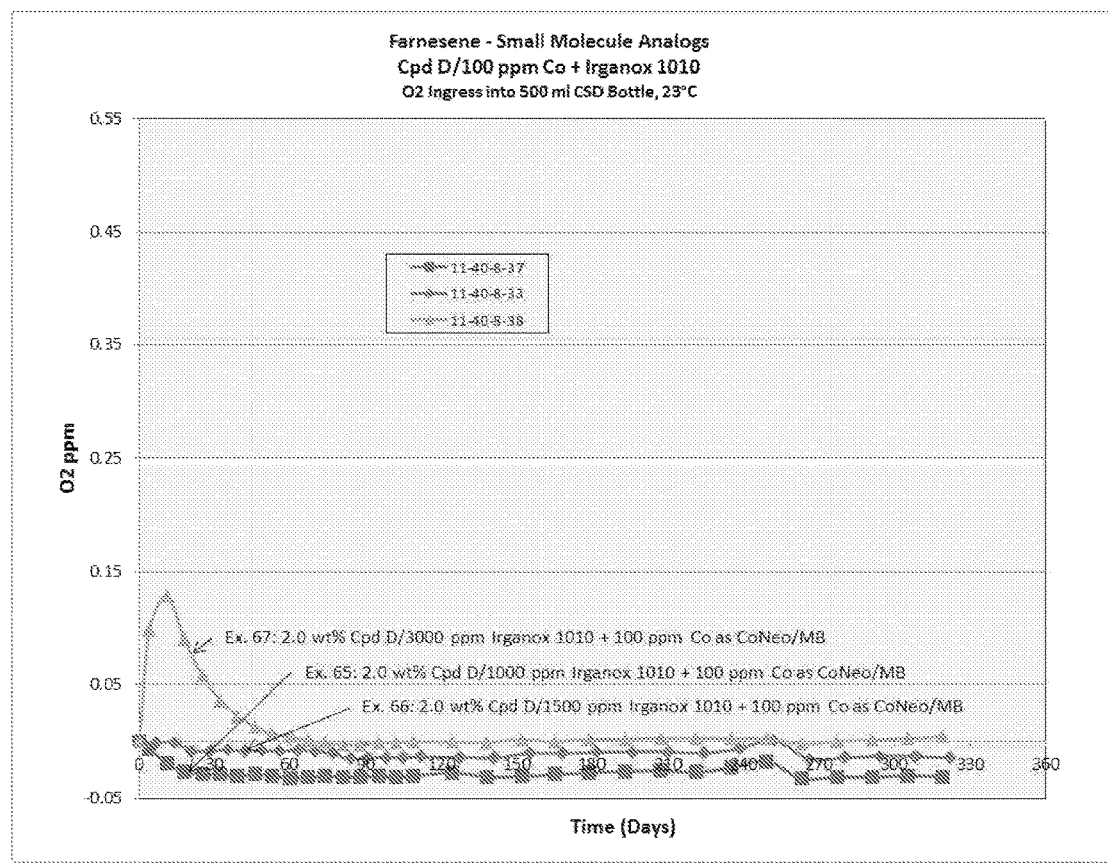
FIG. 11 provides a graph of dissolved oxygen concentration as a function of time for liquid in the interior of capped blow molded bottles of Examples 65-67. In each Example, the oxygen scavenger is Example D and the oxidation catalyst is cobalt neodecanoate (as described for FIG. 1). An antioxidant (IRGANOX® 1010) has been used to modulate oxygen scavenging activity.

Examples 65-67. Inhibition of Oxygen Scavenging Activity Using an Antioxidant For Examples 65-67, varying amounts of antioxidant were added to an oxygen scavenging composition to inhibit oxygen scavenging activity. The oxygen scavenging composition is made according to Example 1, except that the antioxidant was dissolved into the oxygen scavenger before melt blending with the host polymer. Composition and test conditions are tabulated in Table E.7. Note that no accelerators were used in Examples 65-67. As shown in FIG. 11, an induction time of about one week is induced with the addition of 3000 ppm Irganox 1010. No significant induction time is observed using 1000 ppm or 1500 ppm Irganox 1010.

TABLE E.6

Oxygen scavenging compositions comprising chain extender

| Ex. | Oxygen Scavenger | Oxidation catalyst | PMDA | Process |
|---|---|---|---|---|
| 59 | 0.5 wt % Ex. D | 100 ppm Cobalt metal from cobalt neodecanoate as CoNeo/8006 MB | 400 ppm | Masterbatch |
| 60 | 0.75 wt % Ex. D | 100 ppm Cobalt metal from cobalt neodecanoate as CoNeo/8006 MB | 400 ppm | Masterbatch |
| 61 | 1.0 wt % Ex. D | 100 ppm Cobalt metal from cobalt neodecanoate as CoNeo/8006 MB | 400 ppm | Masterbatch |
| 62 | 1.5 wt % Ex. D | 100 ppm Cobalt metal from cobalt neodecanoate as CoNeo/8006 MB | 400 ppm | Masterbatch |
| 63 | 2.0 wt % Ex. D | 100 ppm Cobalt metal from cobalt neodecanoate as CoNeo/8006 MB | 400 ppm | Masterbatch |
| 64 | 2.5 wt % Ex. D | 100 ppm Cobalt metal from cobalt neodecanoate as CoNeo/8006 MB | 400 ppm | Masterbatch |

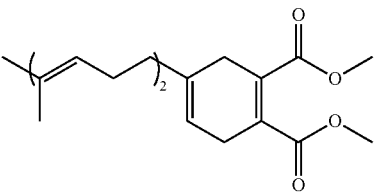

TABLE E.7

Oxygen scavenging activity inhibited by antioxidant.

| Ex. | Oxygen Scavenger | | Antioxidant | Oxidation catalyst | Environment |
|---|---|---|---|---|---|
| 65 | 2.0 wt % Example D | [structure] | 1000 ppm Iraganox 1010 | 100 ppm Cobalt metal from cobalt neodecanoate as CoNeo/8006 MB | Ambient |
| 66 | 2.0 wt % Example D | [structure] | 1500 ppm Irganox 1010 | 100 ppm Cobalt metal from cobalt neodecanoate as CoNeo/8006 MB | Ambient |
| 67 | 2.5 wt % Example D | [structure] | 3000 ppm Irganox 1010 | 120 ppm Cobalt metal from cobalt neodecanoate as CoNeo/8006 MB | Ambient |

Oxygen Scavenging Polymers/Oligomers

Performance of certain oxygen scavenging polymers/oligomers was evaluated. Oxygen scavenging polymers/oligomers made by copolymerizing the oxygen scavengers of Example A or Example C with one or more glycol co-monomers (and optionally one or more acid co-monomers) are shown in Table E.8 in FIGS. 15A-15B. Also provided in Table E.8 are catalyst, stabilizer, mole ratio, description of color and appearance, acid and alcohol content, and molecular weight (Mn, GPC). In Table E.8, EG refers to ethylene glycol, DMT refers to dimethyl terephthalate, PEG refers to polyethylene glycol (Mn about 600, stabilized with hindered phenols), and LiSIPA-DME refers to Lithium sulfoisophthalic acid dimethyl ester.

The oxygen scavenging polymers/oligomers were melt blended with 8006S or Turbo LT resin, and processed to make blow molded bottles as described above for Example 1.

Figure 12:
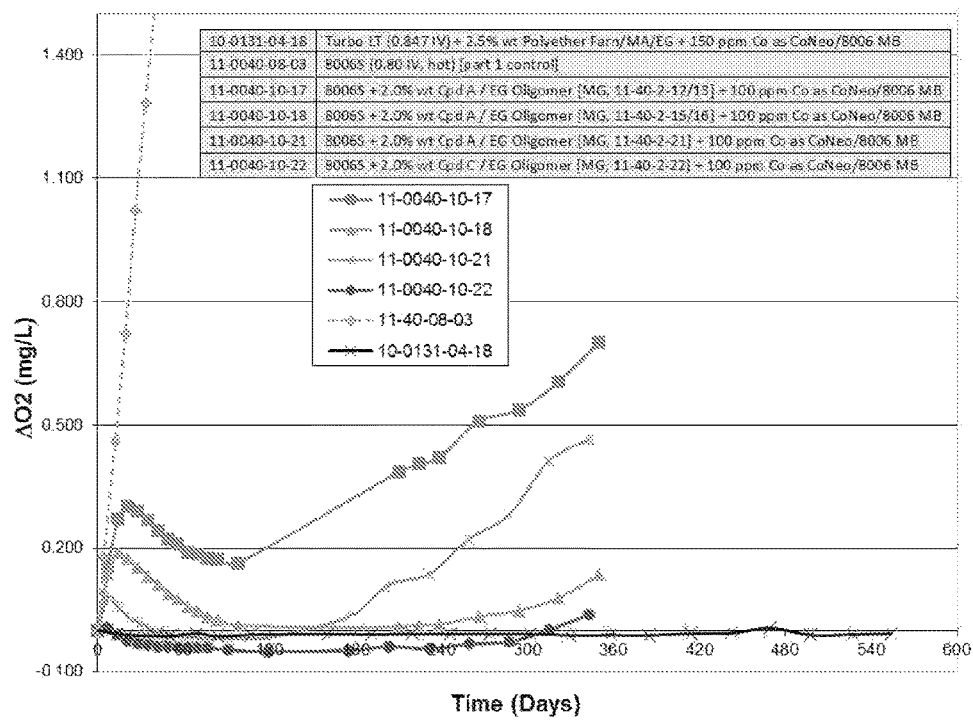
FIG. 12 provides a graph of dissolved oxygen concentration as a function of time in the interior of capped blow molded bottles incorporating oxygen scavenging polymers/oligomers formed by reacting the oxygen scavengers of Example A or Example C with ethylene glycol described in Table D.1 and in Table E.8.

FIG. 12 shows dissolved oxygen concentration as a function of time for certain representative samples from Table E.8 in FIGS. 15A-15B in which the oxygen scavengers of Example A or Example C are polymerized with ethylene glycol. The bottle resin compositions are described in the legend of the graph, and correspond to the composition shown in Table E.8.

Figure 13:
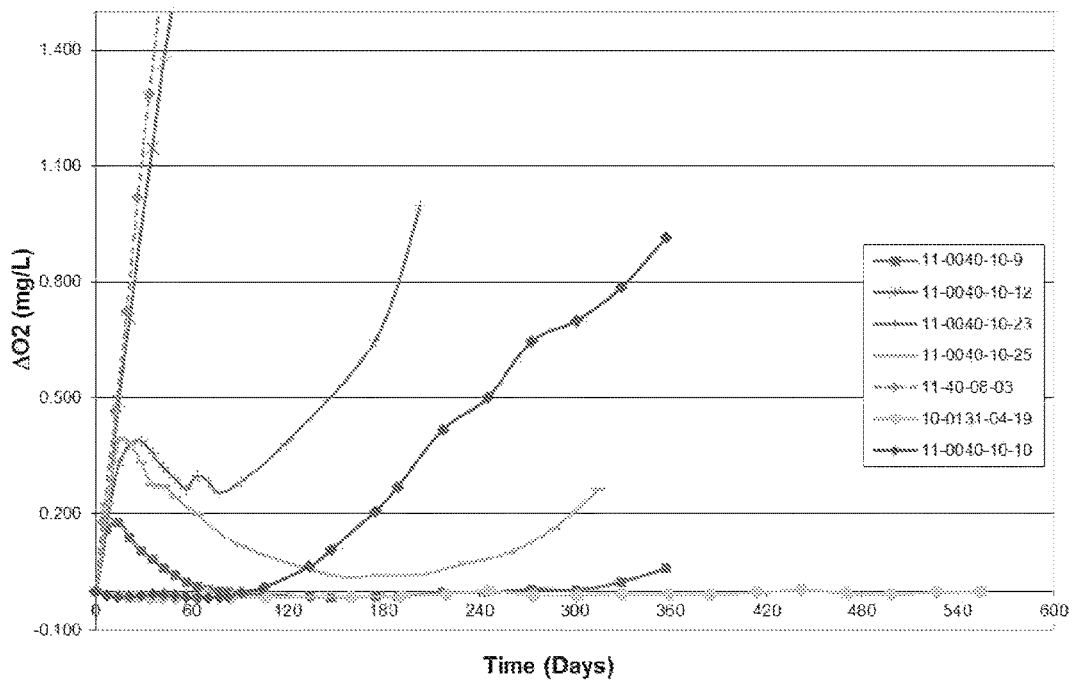
FIG. 13 provides a graph of dissolved oxygen concentration as a function of time in the interior of capped blow molded bottles incorporating certain representative oxygen scavenging polymers/oligomers formed by reacting the oxygen scavengers of Example A or Example C with ethylene glycol and one or more co-monomers as described in Table D.1 and Table E.8.

FIG. 13 shows dissolved oxygen concentration as a function of time for certain representative samples from Table E.8 in FIGS. 15A-15B in which the oxygen scavengers of Example A or Example C are polymerized with ethylene glycol, optionally polyethylene glycol as a co-monomer, and optionally an acid co-monomer. Co-monomers are selected to increase the dispersibility of the oxygen scavenger in the host polymer. PEG is well-tolerated as a co-monomer to EG in small amounts (up to about 4-5 mole %, so that the mole ratio PEG:EG is about 5:95 or less) but may deactivate the oxygen scavenger at high concentrations (about 50 mole %). As shown by sample 10-0131-04-19 in FIG. 13, compositions made using polypropylene glycol (PPG) in place of PEG shows similar behavior, where the molar ratio PPG:EG is approximately 5:95. A polymer made by polymerizing 80 mole % Example C/20 mole % DMT with ethylene glycol is an effective oxygen scavenger. Polymers made by polymerizing LiSIPA-DME and the oxygen scavenger of Example A with ethylene glycol showed variable oxygen scavenging performance, with those having a 98:2 molar ratio of Example A:LiSIPA-DME showing the best performance, and not exhibiting an induction time. A similar polymer having a 95:5 molar ratio of Example A:LiSIPA-DME showed very little or no activity. It is believed that variability of performance is due to non-optimized synthesis conditions (e.g., temperature). Althought not shown in Table E.8 or FIG. 13, polymers made by polymerizing the oxygen scavenger of Example B (at 10 mole % and above) with ethylene glycol under similar conditions were not effective oxygen scavengers. Again, the performance may be improved by optimizing synthesis conditions (e.g., temperature).

Figure 14:
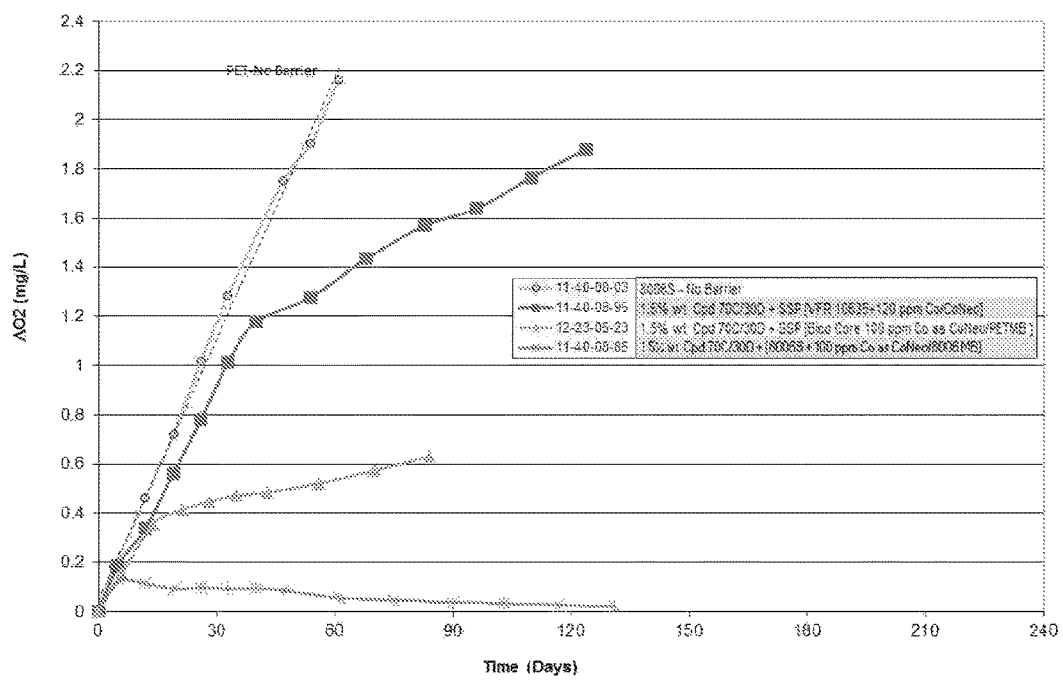
FIG. 14 provides a graph of dissolved oxygen concentration as a function of time in the interior of capped blow molded bottles. The bottles include an oxygen scavenging mixture of Example C and Example D (70:30 C:D by mass) and cobalt neodecanoate (as described for FIG. 1) as an oxidation catalyst. The oxidation catalyst has been incorporated and dispersed in the polymer matrix using different techniques.

Various methods were used to disperse the oxidation catalyst within the polymer composition, as illustrated in FIG. 14. In each case, the oxygen scavenger composition is 1.5 wt % of a mixture of Example C and Example D in a 70:30 C:D mass ratio. In one case (11-40-08-85), cobalt neodecanoate as described above was incorporated into a masterbatch pellet using known techniques. The masterbatch pellets containing the oxidation catalyst were then melt blended with the oxygen scavenger and the host polymer as described above for the general masterbatch technique, and bottles were formed. In one case (11-40-08-95) cobalt neodecanoate powder as described above was incorporated into the composition using the general solid state polymerization technique (SSP) as described above. In one case (12-23-05-23), cobalt neodecanoate is incorporated into the core of a BICO™ PET pellet using known techniques. A solid state polymerization process is carried out as described above, except incorporating the BICO™ PET pellet containing the cobalt neodecanoate in place of cobalt neodecanoate powder. In the case of the masterbatch dispersion technique (11-40-08-85), 100 ppm cobalt metal as cobalt neodecanoate was incorporated. In the case of the technique using an SSP process with cobalt neodecanoate powder (11-40-08-95), 120 ppm cobalt metal as cobalt neodecanoate was incorporated. In the case of the technique using an SSP process with BICO™ PET pellets containing the cobalt neodecanoate (12-23-05-23), 100 ppm cobalt metal as cobalt neodecanoate was incorporated. Note that for 11-40-08-85 and 11-40-08-95, Compound C was distilled prior to use. As shown in FIG. 14, the method used to disperse the oxidation catalyst may affect induction time and long term performance.

We claim:

1. An article having at least one wall, the at least one wall comprising a polyester host polymer made by reacting at least one acid selected from the group consisting of terephthalic acid and isophthalic acid or their dimethyl esters with at least one glycol selected from the group consisting of ethylene glycol, diethylene glycol, 1,4 butane diol and 1,3 butane diol, and 1,4-cyclohexanedimethanol (CHDM); and
an oxygen scavenging composition comprising
one or more compounds having formula

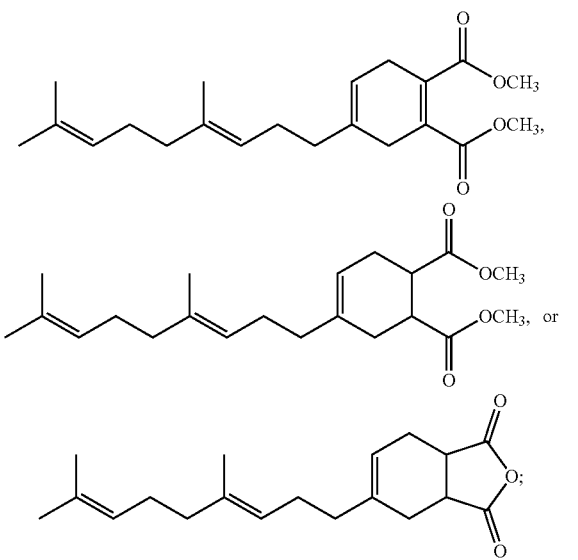

wherein the article is selected from the group consisting of a bottle and a preform.

2. The article of claim 1, wherein the oxygen scavenging composition further comprises an accelerator capable of initiating or accelerating oxygen uptake by the oxygen scavenging composition.

3. The article of claim 2, wherein the accelerator composes a compound selected from the group consisting of a polyethylene or a copolymer or adduct thereof, a polybutadiene or a copolymer or adduct thereof, a cyclohexene polymer or a copolymer or adduct thereof, a copolymer of polyethylene terephthalate with 5-sulfoisophthalic acid, a copolymer of polyethylene with polybutadiene, and a meta-xylamine-based polyamide or a copolymer or adduct thereof.

4. The article of claim 2, wherein the accelerator comprises a maleated polybutadiene or maleated polyisoprene.

5. The article of claim 2, wherein the accelerator comprises a compound having formula (I″), (II″) or (III″):

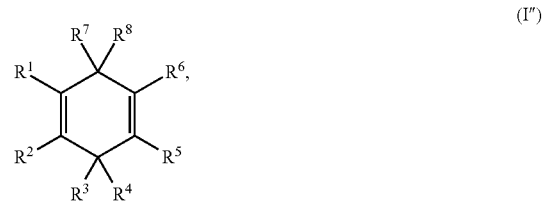

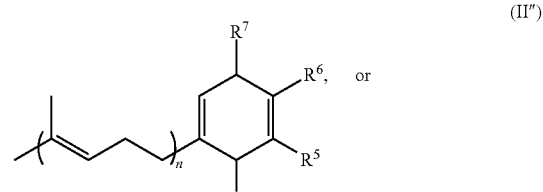

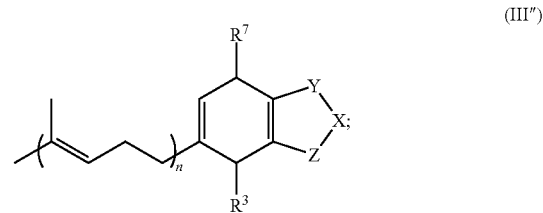

wherein X is O, one of Y and Z is C=O, the other of Y and Z is C=O or $CR^{10}R^{11}$ $R^1$, $R^2$, $R^3$, $R^4$, $R^5$, $R^6$, $R^7$, $R^8$, $R^{10}$ and $R^{11}$ are independently H, or a saturated or unseal rated, linear or branched, cyclic or acyclic, aliphatic or aryl, unsubstituted or substituted hydrocarbyl group, with the provisos that; i) at least one of $R^3$, $R^4$, $R^7$ and $R^8$ is hydrogen; and ii) at least one of $R^1$, $R^2$, $R^3$, $R^4$, $R^7$ and $R^8$ is an isoprenoid tad having formula

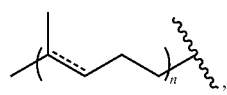

where n=1, 2, 3, 4, or 5.

6. The article of claim 5, wherein the at least one wall is a single layer comprising the oxygen scavenging composition.

7. The article of claim 5, wherein the at least one wall is a multilayer wall comprising the oxygen scavenging composition.

* * * * *